(12) United States Patent
Morales et al.

(10) Patent No.: US 11,472,814 B2
(45) Date of Patent: Oct. 18, 2022

(54) THIENOPYRANONES AND FURANOPYRANONES AS CHECKPOINT INHIBITORS AND MODULATORS OF ANTI-TUMOR IMMUNITY

(71) Applicant: SignalRx Pharmaceuticals, Inc., Omaha, NE (US)

(72) Inventors: Guillermo A. Morales, Oro Valley, AZ (US); Joseph R. Garlich, Fort Collins, CO (US); Donald L. Durden, Omaha, NE (US)

(73) Assignee: SignalRx Pharmaceuticals, Inc., Cumming, GA (US)

( * ) Notice: Subject to any disclaimer, the term of this patent is extended or adjusted under 35 U.S.C. 154(b) by 0 days.

(21) Appl. No.: 16/619,625

(22) PCT Filed: Jun. 5, 2018

(86) PCT No.: PCT/US2018/036122
§ 371 (c)(1),
(2) Date: Dec. 5, 2019

(87) PCT Pub. No.: WO2018/226739
PCT Pub. Date: Dec. 13, 2018

(65) Prior Publication Data
US 2020/0181164 A1 Jun. 11, 2020

Related U.S. Application Data

(60) Provisional application No. 62/515,627, filed on Jun. 6, 2017.

(51) Int. Cl.
| | | |
|---|---|---|
| *C07D 495/04* | (2006.01) | |
| *C07D 493/04* | (2006.01) | |
| *C07D 519/00* | (2006.01) | |
| *A61P 27/00* | (2006.01) | |
| *A61P 29/00* | (2006.01) | |
| *A61P 35/04* | (2006.01) | |
| *A61P 37/00* | (2006.01) | |
| *A61P 35/00* | (2006.01) | |
| *A61K 45/06* | (2006.01) | |

(52) U.S. Cl.
CPC ........... *C07D 495/04* (2013.01); *A61P 27/00* (2018.01); *A61P 29/00* (2018.01); *A61P 35/04* (2018.01); *A61P 37/00* (2018.01); *C07D 493/04* (2013.01); *C07D 519/00* (2013.01); *A61K 45/06* (2013.01)

(58) Field of Classification Search
CPC .. C07D 495/04; C07D 493/04; C07D 519/00; A61P 37/00; A61P 29/00; A61P 35/04; A61P 27/00; A61P 35/00; A61K 45/06
See application file for complete search history.

(56) References Cited

U.S. PATENT DOCUMENTS

| | | |
|---|---|---|
| 8,557,807 B2 | 10/2013 | Morales et al. |
| 9,505,780 B2 | 11/2016 | Morales et al. |
| 9,550,790 B2 | 1/2017 | Morales et al. |
| 9,981,983 B2 | 5/2018 | Morales et al. |
| 10,174,032 B2 | 1/2019 | Morales et al. |
| 10,308,662 B2 | 6/2019 | Morales et al. |
| 2015/0344494 A1* | 12/2015 | Durden ............... A61K 31/538 514/228.2 |

FOREIGN PATENT DOCUMENTS

| | | |
|---|---|---|
| WO | WO 2018/226739 | 12/2018 |
| WO | WO 2018/236971 | 12/2018 |

OTHER PUBLICATIONS

Alwithenani, A.I., and Mohammad A. Althubiti. "Systematic analysis of spleen tyrosine kinase expression and its clinical outcomes in various cancers." Saudi Journal of Medicine & Medical Sciences 8.2 (2020): 95.*
Barr, P.M., "Phase 2 study of idelalisib and entospletinib: pneumonitis limits combination therapy in relapsed refractory CLL and NHL." Blood, The Journal of the American Society of Hematology 127.20 (2016): 2411-2415.*
Cognitive Vitality Reports 2020 (Syk Inhibitors—Alzheimer's Drug Discovery Foundation p. 1-17.*
Peng, C., "Syk is low-expressed in non-small-cell lung cancer and inversely correlates with patient's survival." (2013): 149-151.*
Ulanova, M., "Spleen tyrosine kinase (Syk) as a novel target for allergic asthma and rhinitis." Expert opinion on therapeutic targets 9.5 (2005): 901-921.*
Verweij, Marcel. "Medical-Ethical Dimensions of Preventive Medicine." Preventive Medicine between Obligation and Aspiration. Springer, Dordrecht, 2000; excerpt p. 1-31.*

* cited by examiner

*Primary Examiner* — John M Mauro
(74) *Attorney, Agent, or Firm* — Thomas D. Webster; TDW Patents & Consulting LLC

(57) ABSTRACT

The invention relates to methods of treating diseases including but not limited to, cancer, non-cancer proliferative disease, sepsis, autoimmune disease, viral, bacterial or fungal infection, atherosclerosis, Type 1 or 2 diabetes, obesity, inflammatory disease, and/or SYK-associated disorder including by modulating biological processes through the inhibition of SYK alone, or in combination with inhibition of one or more of PI3 kinase including PI3K-gamma isoform, BET bromodomain proteins, CDK 4/6, and checkpoint proteins, comprising the administration of a compound (s) of Formula I-V (or pharmaceutically acceptable salts thereof) as defined herein.

18 Claims, No Drawings

THIENOPYRANONES AND FURANOPYRANONES AS CHECKPOINT INHIBITORS AND MODULATORS OF ANTI-TUMOR IMMUNITY

FIELD OF THE INVENTION

The present invention relates to thieno- and furano-pyranone compounds and methods of treating diseases in mammals including humans by administering a compound(s) of the invention. In one aspect, a compound or composition of the invention provides therapeutic benefit by inhibiting kinases, and/or Bromodomains, and/or immune-oncology checkpoints, and/or CDK4/6 including effecting treatment by re-activating anti-tumor immunity in the tumor microenvironment.

BACKGROUND

The need for better treatments for cancer and other diseases has led to combination therapies in which multiple anticancer agents are administered simultaneously to block more than one molecular or system target (see D. Melisi et al., Curr. Opin. Pharm., 2013, 13, 536-542; and L. Carlino et al., J. Med. Chem., 2016, 59, 9305-9320). An improvement on this basic strategy involves single molecule, multi-targeting agents by which combined simultaneous inhibition of multiple key signaling pathways can be achieved to regulate, for example, survival, cell cycle, and epigenetic adaptation in the treatment of cancer and other diseases. Noteworthy targets in this emerging area of investigation include kinases (e.g. PI3K), bromodomain proteins (e.g. BRD4), and checkpoint proteins such as but not limited to CDK4 and CDK6.

Activation of the immune response to yield durable antitumor immunity and anti-cancer activity via the checkpoint system is another emerging area of intense research interest. However, not all cancer patients respond to currently available checkpoint inhibitors such as anti PD1, and efforts are underway to identify other negative regulators of the innate and adaptive immune response for anti-cancer therapeutics. In this regard, a new target of interest for negative regulation of antitumor immunity is the PI3K signaling node, in particular p110γ and p110δ isoforms, in macrophages and T regulatory cells, respectively.

Another recently discovered target for control of the immune response is the nonreceptor protein tyrosine kinase "SYK" (or "Syk") which controls the immunosuppressive macrophage tumor microenvironment and metastasis in vivo. Inhibition of SYK induces apoptosis in multiple cancer types and also inhibits tumor formation. Known SYK inhibitors include fostamatinib (R788), BAY 61-3606, cerdulatinib (PRT062070), and entospletinib (GS-9973).

SYK and PI3K are involved in regulating macrophage M2 differentiation, the immunosuppressive tumor microenvironment, and metastasis. Thus, a single molecule inhibitor that targets PI3K and SYK is expected to augment activation of the anti-tumor immune response superior to that of a SYK inhibitor alone. A dual, single molecule PI3K/SYK kinase inhibitor is also expected to block macrophage M1-M2 transition, metastasis, and stimulate adaptive antitumor immunity above and beyond that achievable by SYK inhibition alone, or by a combination of SYK inhibitor with a separate PI3K inhibitor.

Protein kinases play an important role in regulating cell proliferation, cell cycle, cell metabolism, survival/apoptosis, DNA damage repair, cell motility, and response to the microenvironment. Not surprisingly kinases have been identified as oncogenes. For example, kinases such as c-Src, c-Abl, mitogen activated protein (MAP) kinase, phosphotidylinositol-3-kinase (PI3-K, PI3K, PI-3 kinase), AKT (also known as PKB), and the epidermal growth factor (EGF) receptor are commonly activated in cancer cells and are known to contribute to tumorigenesis.

PI-3 kinases comprise a large family of lipid kinases with roughly 16 members divided into 3 classes based on sequence homology and the particular product formed by enzyme catalysis. The class I PI-3 kinases are composed of 2 subunits: a 110 kd catalytic subunit and an 85 kd regulatory subunit. Class I PI-3 kinases are involved in important signal transduction events downstream of cytokines, integrins, growth factors and immunoreceptors, and control of this pathway may lead to important therapeutic effects. Inhibition of class I PI-3 kinase induces apoptosis, blocks tumor induced angiogenesis in vivo, and increases radiosensitivity in certain tumors.

Molecular and genetic studies have demonstrated a strong correlation between the PI-3 kinase pathway (also known as PI3K-AKT pathway) and a variety of diseases in humans such as inflammation, autoimmune conditions, and cancers (P. Workman et al., Nat. Biotechnol. 2006, 24, 794-796). Many types of cancer are thought to arise in response to abnormalities in signal transduction pathways of which the PI-3 kinase pathway is a major example.

Multiple studies have shown that p110a, which is a Class IA isoform of the regulatory subunit of PI-3 kinase, is frequently over-expressed and mutated in many cancers including gliomas, colon, brain, breast, lung, prostate, gynecological and other tumor types (Y. Samuels et al., *Science* 2004, 304, 554). Thus, a rational approach to treating cancer relates to developing drugs that act on kinases including those of the PI-3 kinase pathway.

Recent evidence from multiple laboratories points to a role for the gamma isoform of PI3K in the regulation of the immune response and antitumor immunity. A PI3K gamma-selective agent presently in clinical trials is IPI-549 (Infinity).

In addition to the important role of kinases such as PI3K in disease states, a growing list of diseases including cancer can arise by epigenetically-induced changes in gene expression and cellular phenotype by mechanisms other than changes in DNA nucleotide sequence. Epigenetic effects are controlled by three types of proteins: the writers (i.e., DNA methyltransferase which adds methyl groups to DNA), the erasers (i.e., histone deacetylase, HDAC, which removes acetyl groups from histones), and the readers (i.e., BET bromodomain proteins such as BRD2, BRD3, BRD4 and BRDT). Bromodomain proteins serve as "readers" for the chromatin to recruit regulatory enzymes such as the writers and erasers leading to regulation of gene expression. Inhibitors of bromodomain proteins are potentially useful in the treatment of diseases including obesity, inflammation, and cancer (A. C. Belkina et al., *Nat. Rev. Cancer* 2012, 12, 465-477).

BET inhibitors act as acetylated lysine mimetics that disrupt the binding interaction of BET proteins with acetylated lysine residues on histones (D. S. Hewings et al., *J. Med. Chem.* 2012, 55, 9393-9413). This leads to suppression of transcription of several key genes involved in cancer including c-MYC, MYCN, BCL-2, and some NF-kB-dependent genes (J. E. Delmore et al., *Cell* 2011, 146, 904-917) (A. Puissant et al., *Cancer Discov.* 2013, 3, 308-323). Most B-cell malignancies are associated with the activation of the c-MYC gene which is partially controlled by the PI-3 kinase-AKT-GSK3beta signaling axis (J. E. Delmore et al., *Cell* 2011, 146, 904-917). MYC (encompassing c-MYC and MYCN) is an oncoprotein that has been difficult to inhibit using small molecule approaches (E. V. Prochownik et al., *Genes Cancer* 2010, 1, 650-659). Recently it has been shown that BET inhibition prevents the transcription of MYCN, (A. Puissant et al., *Cancer Discov.* 2013, 3, 308-323), and blocking PI3K enhances MYC degradation (L. Chesler et al., *Cancer Res.* 2006, 66, 8139-8146). Therefore, single molecule inhibition of both PI3K and bromodomain proteins could provide a novel and more effective way to inhibit MYC activity. Several reported BET inhibitors contain the 3,5-dimethylisoxazole chemotype as the acetyl-lysine mimetic moiety (D. S. Hewings, *J. Med. Chem.* 2011, 54, 6761-6770) (D. S. Hewings et al., *J. Med. Chem.* 2012, 55, 9393-9413) (D. S. Hewings et al., *J. Med. Chem.* 2013, 56, 3217-3227).

Recent evidence from a number of laboratories has demonstrated that BET bromodomain inhibitors in different disease contexts can either block inflammation or activate the adaptive immune response including antitumor immunity and modulate viral infectivity e.g. HIV, HPV, RSV, etc. Moreover, recent reports provide evidence that BRD4 inhibitors activate antitumor immunity by suppression of checkpoint molecules such as PDL1 (Zhu et al, Cell Rep, 2016). Studies using JQ1 and Compound 0 have demonstrated that BET proteins are critical for macrophage immunomodulatory responses. BRD4 is now known to regulate M2 macrophage polarization and determine the potency of JQ 1 in IL4 induced gene expression. The functions of BET proteins in M2 macrophage response are regulated by direct contact with the promoter chromatin of Arginase/Arg, Chi313/YM1 and Retnla/Fizz1, and this interaction is blocked by JQ1 and the dual PI3K/BRD4 inhibitor Compound 0. Thus, inhibitors of BRD4 are potentially useful for blocking a detrimental M2 macrophage response. Such inhibitors would include dual and triple single molecule inhibitors of BRD4, and inhibitors that only target BRD4 including, for example, 1-BET-762; JQ-1; JQ-1 (+); CPI-203; OTX-015; GW-841819X; CP-0610; CPI-232; BET-BAY-002; 1-BET-151; RVX-208; 1-BET-726; N-(2-hydroxy-3-methylquinolin-6-yl) piperidine-1-sulfonamide; N-[4-(2,4-difluorophenoxy)-3-(6-methyl-7-oxo-6; 7-dihydro-1H-pyrrolo[2,3-c]pyridin-4-yl)phenyl]ethanesulfonamide; and N-{6-[methyl(propanoyl)amino]-3-oxo-4-[(1S)-1-phenylpropyl]-3,4-dihydropyrio[2,3b]pyrazin-2-yl}-beta-alanine.

Enzymes called cyclin dependent kinases (CDKs) play an important role in mitosis in normal cells and cancer cells. The cell cycle has four basic phases: S phase where DNA replication occurs; M phase (mitosis) where DNA and cellular components divide to form two daughter cells; G2 phase, between S and M, where cells prepare for mitosis; and G1 phase after mitosis, where cells commit and prepare for another round of DNA and cellular replication. The following seven CDKs have a demonstrated role in cell cycle progression: CDK1-4, 6,10, and 11. Cyclins are proteins that associate with CDKs (forming holoenzymes) to promote activity of the CDKs. Cyclin D is one of the major cyclins with three homologues (Cyclin D1, D2, and D3). Cyclin D interacts with four CDKs: CDK2, 4, 5, and 6. During cell proliferation accumulation of the cyclin D-Cdk4/6 complex is important for cell cycle progression. The cyclin D CDK4/6 complex phosphorylates retinoblastoma tumor suppressor protein (Rb) to form phosphorylated retinoblastoma tumor suppressor protein (pRb). Phosphorylated Rb (pRb) inactivates the cell cycle inhibiting the effect of Rb and allowing the cell cycle to proceed through cell division. Unphosphorylated Rb inhibits cell cycle progression by binding to E2F transcription factors which suppresses their activity and blocks proliferation. Phosphorylated Rb blocks E2F binding and allows expression of genes needed for cell cycling. It is estimated that the Rb pathway is deregulated in greater than 80% of human tumors (S. Ortega et al., *Biochim. Biophys. Acta* 2002, 1602, 73). Thus, CDK inhibitors could have significant therapeutic potential for treating several diseases including cancer, diabetes, renal disease, neurodegenerative disease, and infectious diseases.

SYK is a cytosolic nonreceptor protein tyrosine kinase expressed at high levels in hematopoietic and nonhematopoietic cells. Silencing SYK expression inhibits tumor formation and promotes apoptosis in a number of different cancers including B-cell lymphocytic leukemia, breast cancer, diffuse large B-cell lymphoma, follicular lymphoma, mantle cell lymphoma, pancreatic cancer, lung cancer, prostate cancer, retinoblastoma, ovarian cancer, and small cell lung cancer formation (Lee S J, Choi J S, Han B G, Kim H S, Song H J, Lee J, et al. Crystal structures of spleen tyrosine kinase in complex with novel inhibitors: structural insights for design of anticancer drugs, FEBS J. 2016 October; 283(19):3613-25).

SYK and PI3K are involved in regulating macrophage M2 differentiation, as well as immunosuppressive tumor microenvironment, and metastasis. Known SYK inhibitors, including fostamatinib (R788), BAY61-3606, cerdulatinib (PRT062070), and entospletinib (GS-9973) (See ref 17-19 of Lee et al., FEBS J. 2016, 283(19), 3613-25), bind tightly in the ATP-binding pocket of the enzyme. Another potent selective SYK inhibitor, Compound 0282, has recently been published with the crystal structures of analogs (Lee et al FEBS J. 2016 October; 283(19):3613-25). Genetic and pharmacologic evidence indicates that SYK is an immune checkpoint that controls the innate immunosuppressive macrophage immunomodulatory response in vitro and in vivo, at least in part by controlling macrophage M1 to M2 differentiation in a variety of cancer types.

The SYK and PI3K pathways represent a new focus for orthogonal inhibition by multi-target inhibitors to maximally block the M2 macrophage component that contributes to a tumor surviving in its microenvironment (See Hatton O et al. PLoS One. 2012; 7(8): e42610; Hatton O et al., Am J Transplant. 2013 April; 13(4):883-90; Hatton O et al., J Biol Chem. 2011 Oct. 28; 286(43):37368-78).

There is also growing interest in combining checkpoint inhibitors of CDK4 and CDK6 with inhibitors of the PI3K pathway. For example, Vora et al. (*Cancer Cell* 2014, 26, 136-149) describe how CDK4/6 inhibitors sensitize PIK3CA mutant (PI3K alpha gene) breast cancer to PI3K inhibitors such as BLY719 (selective PI3K alpha inhibitor). Another study showed that resistance to checkpoint blockage could be overcome by the PI3K gamma inhibitor IPI-549 (O. De Henau et al., *Nature* 2016, 539, 443-447). Thus, PI3K gamma inhibition may enhance the effects of checkpoint inhibitors by changing the immune-suppressive microenvironment around tumors.

Multi-targeted single molecule inhibitors are advantageous over combinations of single-target inhibitors for a number of reasons including: a) reduced development costs; b) lower toxicity; c) lower non-target side effects due to non-target drug interactions; d) simultaneous target inhibition in, for example, each cancer cell provides greater efficacy (combinations suffer from differing metabolism, distribution and pharmacokinetic dynamics); e) lower financial costs to patients and the healthcare system; f) increased efficacy and longer durations of response; and g) accelerated drug development. Single-molecule multi-target inhibition can avoid problems with differing ADME properties that can arise when administering separate inhibitors. Moreover, a significant limitation in using drug combinations in oncology is dose limiting toxicity which results from additive off-target toxicities from the individual drugs. This was proven by the recent clinical evaluation of the PI3K inhibitor BKM120 in combination with a PARP inhibitor (Olaparib) where, due to the toxicity of the 2 drugs, the maximum tolerated dose of the PI3K inhibitor was limited to half that as a single agent (See Matulonis U. et al. "Phase I of oral BLK120 or BLY719 and olaparib for high-grade serous ovarian cancer or triple-negative breast cancer: final results of the BMK120 plus olaparib cohort". 106th Annual Meeting of the American Association for Cancer Research; April 18-22: AACR; 2015). From the patient's perspective, a single molecule, multi-target inhibitor could dramatically simplify taking medications and improve patient compliance. For example, a patient requiring the inhibition of PI3K, BRD4, CDK4/6 and RAF kinase could be required to take four separate medicines to achieve inhibition of all four targets, whereas a single molecule triple inhibitor could allow the patient to take just two medications, for example Sorafinib (RAF Kinase inhibitor) and a single molecule triple inhibitor agent targeting PI3K, BRD4 and CDK4/6. This would also improve patient compliance to achieve full scheduled dosing to maximize the effectiveness of treatment.

There remains a need for single molecule, multi-target inhibitors of kinases, epigenetic modulators, checkpoint control proteins, CDKs, and SYK to provide effective treatments for diseases and anti-tumor immunity.

SUMMARY OF THE INVENTION

The present invention relates to thienopyranone and furanopyranone compounds that are useful in therapeutic methods including as inhibitors of SYK and/or PI3K and/or BRD4 and/or CDK4/6 and/or checkpoint proteins, or any combination thereof to provide superior therapeutic benefit including improved anti-tumor immunity.

The present invention also relates to compounds and compositions that inhibit SYK, and to multitarget, single molecule inhibitors of SYK and one or more of PI3K, BRD4, CDK4/6, and checkpoint proteins for the control of macrophage M1-M2 transition in vivo. Control of macrophage M1-M2 transition is expected to provide an effective means to treat diverse medical conditions including fibrosis, Parkinson's Disease, neurological disease, and cancer.

In particular, the present invention relates to new thienopyranone and furanopyranone compounds, conjugates thereof, pharmaceutical compositions containing the thienopyranones and furanopyranones or conjugates thereof as active ingredients, and use of the compounds as therapeutic agents including as antitumor agents for the treatment of disorders including but not limited to cancer. Some of the compounds disclosed in this application can be prepared by methods described in U.S. Pat. Nos. 8,557,807, 9,505,780, and Morales et al., *J. Med. Chem.* 2013, the entire contents of which are herein incorporated by reference.

The present invention relates in one aspect to methods for treating diseases in mammals including humans by administering a therapeutically effective amount of a thienopyranone (7H-thieno[3,2-b]pyran-7-ones) or furanopyranone compound of the general Formula I or a pharmaceutically acceptable salt thereof:

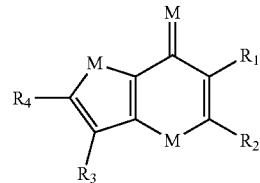

Formula I wherein M is independently oxygen (O) or sulfur (S);
R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is selected from R1 or morpholine or thiomorpholine or piperazine
R3 is selected from R1;
R4 is selected from R1.

These and other objects of the invention are evidenced by the summary of the invention, the description of the preferred embodiments and the claims.

DETAILED DESCRIPTION

A. Definitions

As used herein, the term "disease" or "condition" refers to various diseases and/or conditions in a mammal including a human as generally understood and as described herein. The term(s) may but not necessarily will refer to a disease or condition that is associated with aberrant activity or expression of a kinase (e.g. PI3K), and/or Bromodomain, and/or CDK4/6, and/or checkpoint protein, and/or SYK. In diseases characterized by tumor development, such as cancer, other aberrant changes may be present such as alterations in the tumor microenvironment.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilms' tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids, psoriasis; Adrenal Glands: neuroblastoma; and breast cancer.

The term "cancerous cell" as provided herein, includes a cell affected by any one of the above-identified cancers. The term "cancer stem cell" refers to a subpopulation of cells in a solid or non-solid tumor that demonstrate enhanced drug efflux properties, are lacking in cell cycle progression, and are resistant to anoikis.

As used herein, the term "branched" refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl, isopropyl, —CH$_2$CH$_2$CH(CH$_3$)CH$_2$CH$_3$, —CH$_2$CH (CH$_2$ CH$_3$)CH$_2$ CH$_3$, —CH$_2$CH$_2$C(CH$_3$)$_2$CH$_3$, —CH$_2$CH$_2$C(CH$_3$)$_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl, cyclohexyl, piperidine and the like.

The term "unsaturated" as used herein refers to a group where at least one available valence bond of two adjacent backbone atoms is not attached to other atoms. Representative examples of unsaturated groups include, but are not limited to, —CH$_2$ CH$_2$CH=CH$_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group which may be substituted or unsubstituted having 4n+2 delocalized π (pi) electrons, The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is)oxazoyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents. An atom with two substituents is denoted with "di," whereas an atom with more than two substituents is denoted by "poly." Representative examples of such substituents include, but are not limited to aliphatic groups, aromatic groups, alkyl, alkenyl, alkynyl, aryl, alkoxy, halo, aryloxy, carbonyl, acryl, cyano, amino, amide, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl", "optionally substituted alkenyl", "optionally substituted alkynyl", "optionally substituted carbocyclic", "optionally substituted aryl", "optionally substituted heteroaryl", "optionally substituted heterocyclic", and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, alkoxy, oxo, thiooxo, —NO2, —CN, —CF3, —N3, —NH2, protected amino, —NH— alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O— heteroaryl, —O-heterocyclic, —C(O)-alkyl, —C(O)-alkenyl, —C(O)-alkynyl, —C(O)— cycloalkyl, —C(O)-aryl, —C(O)-heteroaryl, —C(O)-heterocycloalkyl, —CONH2, —CONH-alkyl, —CONH-alkenyl, —CONH-alkynyl, —CONH-cycloalkyl, —CONH-aryl, —CONH-heteroaryl, —CONH— heterocycloalkyl, —OCO2-alkyl, —OCO2-alkenyl, —OCO2-alkynyl, —OCO2-cycloalkyl, —OCO2-aryl, —OCO2-heteroaryl, —OCO2-heterocycloalkyl, —OCONH2, —OCONH-alkyl, —OCONH-alkenyl, —OCONH-alkynyl, —OCONH-cycloalkyl, —OCONH-aryl, —OCONH-heteroaryl, —OCONH— heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —NHCO2-alkyl, —NHCO2-alkenyl, —NHCO2-alkynyl, —NHCO2-cycloalkyl, —NHCO2-aryl, —NHCO2-heteroaryl, —NHCO2-heterocycloalkyl, —NHC(O)NH2, —NHC(O)NH-alkyl, —NHC(O)NH-alkenyl, —NHC(O)NH-alkenyl, —NHC(O)NH— cycloalkyl, —NHC(O)NH-aryl, —NHC(O)NH-heteroaryl, —NHC(O) NH— heterocycloalkyl, —NHC(S)NH2, —NHC(S)NH-alkyl, —NHC(S)NH-alkenyl, —NHC(S)NH-alkynyl, —NHC(S)NH— cycloalkyl, —NHC(S)NH-aryl, —NHC(S)NH-heteroaryl, —NHC(S)NH— heterocycloalkyl, —NHC(NH)NH2, —NHC(NH)NH-alkyl, —NHC(NH)NH-alkenyl, —NHC(NH)NH— alkenyl, —NHC(NH)NH-cycloalkyl, —NHC(NH)NH-aryl, —NHC(NH)NH-heteroaryl, —NHC(NH)NH— heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH— alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)—alkynyl, —S(O)-cycloalkyl, —S(O)-aryl, —S(O)-heteroaryl, —S(O)-heterocycloalkyl-SO2NH2, —SO2NH-alkyl, —SO2NH-alkenyl, —SO2NH-alkynyl, —SO2NH-cycloalkyl, —SO2NH-aryl, —SO2NH-heteroaryl, —SO2NH-heterocycloalkyl, —NHSO2-alkyl, —NHSO2-alkenyl, —NHSO2-alkynyl, —NHSO2-cycloalkyl, —NHSO2-aryl, —NHSO2-heteroaryl, —NHSO2-heterocycloalkyl, —CH2NH2, —CH2SO2CH3, -alkyl, -alkenyl, -alkynyl, -aryl, -arylalkyl, -heteroaryl, -heteroarylalkyl, -heterocloalkyl, -cycloalkyl, -carbocyclic, -heterocyclic, polyalkoxyalkyl, polyalkoxy, methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

The term "unsubstituted" as used herein refers to a group that does not have any further groups attached thereto or substituted therefore.

The term "alkyl" as used herein, alone or in combination, refers to a branched or unbranched, saturated aliphatic group. The alkyl radical may be optionally substituted independently with one or more substituents described herein. Lower alkyl refers to alkyl groups of from one to six carbon atoms. Examples of lower alkyl groups include methyl, ethyl, propyl, isopropyl, butyl, s-butyl, t-butyl, isobutyl, pentyl, and the like. Higher alkyl refers to alkyl groups containing more than seven carbon atoms. A "Co" alkyl (as in "Co—Co-alkyl") is a covalent bond. Exemplary alkyl groups are those of $C_{20}$ or below. In this application, alkyl refers to alkanyl, alkenyl, and alkynyl residues (and combinations thereof); it is intended to include vinyl, allyl, isoprenyl, and the like. Thus, when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like. The terms "alkyl" or "alk" as used herein refer to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (1-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$ CH(CH$_3$)$_2$), 2-methyl-1-butyl (—CH$_2$CH(CH$_3$)CH$_2$ CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)$_2$), 2-methyl-2-pentyl (—C(CH$_3$)$_2$CH$_2$CH$_2$CH$_3$), 3-methyl-2-pentyl (—CH(CH$_3$) CH(CH$_3$)CH$_2$CH$_3$), 4-methyl-2-pentyl (—CH(CH$_3$)CH$_2$CH (CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. The cycloalkyl radical may be optionally substituted independently with one or more substituents described herein. Bicyclic carbocycles having 7 to 12 atoms can be arranged, for example, as a bicyclo[4,5], [5,5], [5,6]

or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "alkenyl" as used herein alone or in combination refers to a branched or unbranched, unsaturated aliphatic group containing at least one carbon-carbon double bond which may occur at any stable point along the chain. The alkenyl radical may be optionally substituted independently with one or more substituents described herein, and includes radicals having "cis" and "trans" orientations, or alternatively, "E" and "Z" orientations. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. The alkynyl radical may be optionally substituted independently with one or more substituents described herein. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or nonaromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heteroaryl" and "heteroar-", used alone or as part of a larger moiety, e.g., "heteroaralkyl", or "heteroaralkoxy", refer to groups having 5 to 18 ring atoms, preferably 5, 6, 7, 9, or 14 ring atoms; having 6, 10, or 14 (pi) electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The term "aryloxy" as used herein alone or in combination refers to an aryl group bound through a single terminal ether linkage.

The terms "halogen", "halo" and "hal" as used herein refer to monovalent atoms of fluorine, chlorine, bromine, iodine and astatine.

The term "hetero" or "heteroatom" as used herein combination refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle" or "heterocyclyl" or "heterocyclic ring" or "heterocyclic" as used herein refers to a cyclic group containing one or more heteroatoms. The heterocyclic radical may be optionally substituted independently with one or more substituents described herein.

Representative examples of heterocycles include, but are not limited to, pyridine, piperidine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical" are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "substituent" means any group selected from H, F, Cl, Br, I, alkyl, alkenyl, alkynyl, carbocycle, aryl, heterocycle, heteroaryl, formyl, nitro, cyano, amino, amide, carboxylic acid, carboxylic ester, carboxyl amide, reverse carboxyl amide, halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally' substituted aryl, optionally substituted heteroaryl, alkylaminoalkyl, dialkylaminoalkyl, carboxy, carboxy ester, —C(O)NR$^5$R" (where R$^5$ is hydrogen or alkyl and R" is hydrogen, alkyl, aryl, or heterocyclyl), —NRSC(O)R" (where R$^5$ is hydrogen or alkyl and R" is alkyl, aryl, or heterocyclyl), amino, alkylamino, dialkylamino, and —NHS(O)$_2$R' (where R' is alkyl, aryl, or heteroaryl).

The term "carbonyl" or "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "carbamate" as used herein alone or in combination refers to an ester group represented by the general structure —NH(CO)O—. Carbamate esters may have alkyl or aryl groups substituted on the nitrogen, or the amide function.

term "cyanate" "isocyanate", "thiocyanate", or "isothiocyanate" as used herein alone or in combination refers to an oxygen- or sulfur-carbon double bond carbon-nitrogen double bond.

Representative examples of cyano groups include, but are not limited to, isocyanate, isothiocyanate and the like.

The term "cyano", "cyanide", "isocyanide", "nitrile", or "isonitrile" as used herein alone or in combination refers to a carbon-nitrogen triple bond.

The term "amino" as used herein alone or in combination refers to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and substituted alkyl.

The term "targeting agent" as used herein means any moiety attached to a compound of the invention allowing an increase in concentration of the compound at a site of treatment, for example, a tumor site. Exemplary targeting agents include but are not limited to carbohydrates, peptides, vitamins, and antibodies.

As used herein, the term "multi-target inhibitor" or "multi-target agent" refers to a single molecule having the capacity to interact with at least two different protein targets in vitro or in vivo including the capacity to inhibit the activity or normal function of said targets, e.g., to inhibit binding or enzymatic activity. Multi-target inhibitors have the capacity to interact with two or more of the following targets: SYK, PI3K, Bromodomain, CDK 4/6, and checkpoint protein.

As used herein, the term "dual inhibitor" refers to the capacity of a single molecule to interact with and/or inhibit the activity or normal function of two different target proteins such as SYK, PI3K, bromodomain protein, CDK4 or CDK6, and checkpoint protein, to inhibit enzymatic activity or to prevent the interaction of the target protein with other proteins or molecules in vivo.

As used herein, the term "triple inhibitor" refers to the capacity of a single molecule to interact with and/or inhibit the activity or normal function of three different classes of target proteins, selected from PI3K, bromodomain protein, a CDK (such as CDK4 and/or CDK6), checkpoint protein, and SYK to inhibit enzymatic activity or to prevent the interaction of the target proteins with other proteins or molecules in vivo. Thus, by inhibiting two or three different classes of target proteins, a dual or triple inhibitor would be providing a plurality of disease-treating mechanisms including, for example, anticancer activity.

As used herein, the term "infection" or "infectious disease" means a disease or condition that arises due to the presence of a pathogen(s) including, for example, bacteria, viruses, fungi, prions, and the like.

The term "effective amount" or "effective concentration" when used in reference to a compound, product, or composition as provided herein, means a sufficient amount of the compound, product or composition to provide the desired pharmaceutical or therapeutic result.

The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

The term "hydrolyzable" as used herein refers to whether the group is capable of or prone to hydrolysis (i.e., splitting of the molecule or group into two or more new molecules or groups).

The term "pharmaceutically acceptable salt" of a compound of the instant invention (e.g., Formula I) is one which is the acid addition salt of a basic compound of the invention with an inorganic or organic acid which affords a physiologically acceptable anion or which is the salt formed by an acidic compound of the invention with a base which affords a physiologically acceptable cation.

The term "prodrug" or "procompound" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphatecontaining prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "conjugate" as used herein refers to a compound that has been formed by the joining of two or more compounds via either a covalent or non-covalent bond.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the terms "treatment", "treat", and "treating" refer to preventing, reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (i.e., in light of a history of symptoms and/or in light of genetic or other susceptibility factors). Treatment may also be continued after symptoms have resolved, for example to prevent or delay their recurrence.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethyl silyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" include compounds of Formulas I-V and stereoisomers, geometric isomers, tautomers, solvates, metabolites, and pharmaceutically acceptable salts, prodrugs, and conjugates thereof.

The term "TP scaffold" or "Thienopyranone scaffold" refers to a compound of general Formula I as described herein where M of the fused 5-membered ring is S. The term "Furanopyranone scaffold" refers to a compound of Formula I where M of the fused 5-membered ring is O.

As used herein, the term "CDK inhibiting" as applied to a compound of the invention means that a compound inhibits a normal or wild-type function of a CDK protein, in vivo and/or in vitro (e.g., CDK4 and/or CDK6) with an $IC_{50}$ value of less than or equal to 50 μM in an appropriate in vitro assay.

As used herein, the term "PI3K inhibiting" as applied to a compound of the invention means that a compound inhibits the normal or wild-type function of PI3K, i.e., enzymatic activity, in vivo and/or in vitro (e.g., PI3Kα, PI3Kβ, PI3Kγ) with an $IC_{50}$ value of less than or equal to 50 μM in an appropriate in vitro assay.

As used herein, the term "Bromodomain inhibiting" as applied to a compound of the invention means that a compound inhibits the normal or wild-type function of a Bromodomain protein, in vivo and/or in vitro (e.g., BRD4) with an $IC_{50}$ value of less than or equal to 50 μM in an appropriate in vitro assay.

As used herein, the term "SYK inhibiting" as applied to a compound of the invention means that a compound inhibits the normal or wild-type function of SYK in vivo and/or in vitro with an $IC_{50}$ value of less than or equal to 50 μM in an appropriate in vitro assay.

As used herein, the term "checkpoint inhibitor" or "immune oncology checkpoint inhibitor" or "immune checkpoint inhibitor" refers to a compound, including a compound of the invention, that inhibits a checkpoint protein including, for example, Ipilimumab (Yervoy®), Pembrolizumab (Keytruda®), Nivolumab (Opdivo®), PD-1, and CTLA-4, in vivo and/or in vitro with an IC50 value of less than or equal to 50 μM in an appropriate in vitro assay.

B. Compounds

The present invention relates in part to compounds and therapeutic methods of use of compounds of the Formula I including but not limited to compounds that inhibit SYK and compounds that inhibit SYK and at least one of PI3K, BRD4, CDK4/6, and checkpoint protein:

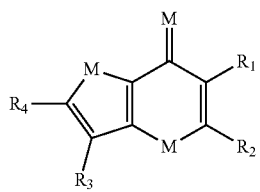

Formula I wherein M is independently O or S;
R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse carboxyl amide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is selected from R1 or morpholine or thiomorpholine or piperazine;
R3 is selected from R1; and
R4 is selected from R1.

A particular compound of Formula I is one wherein a substituent of R1 comprises a bone directing group such as, for example, amino phosphonic acid, bisphosphonate, or the like.

A particular subset of Formula I includes compounds wherein substituent R3 binds and potently (IC50<1000 nM) inhibits SYK protein.

The present invention also provides compounds of Formula II and methods of administering those compounds to a mammal in need thereof including, but not limited to, compounds that inhibit SYK or SYK and at least one of PI3K, BRD4, CDK4/6, and checkpoint protein:

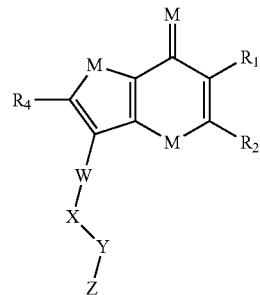

Formula II wherein M is independently O or S;
and wherein R1 and R2 and R4 are as described for Formula I, and wherein;
W is null, aryl, heteroaryl, or heterocyclic;
X is oxygen or amino wherein the amino group is either a secondary nitrogen or substituted tertiary nitrogen;
Y is a heteroaryl including pyrimidine;
Z is a heteroaryl such as but not limited to 5-membered aromatic rings containing one or two amino groups in the ring.

Representative examples of compounds of Formula II include but are not limited to:

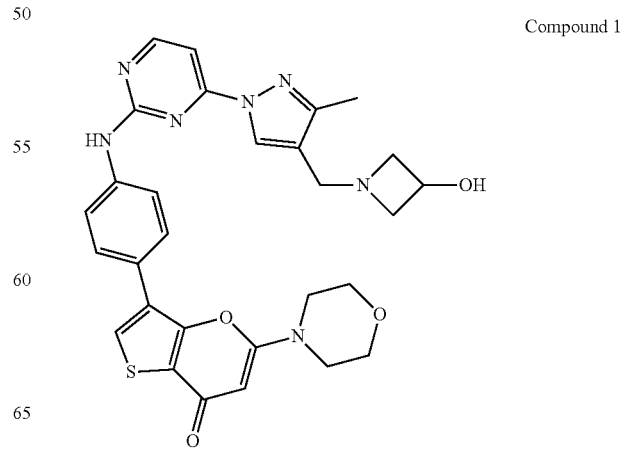

Compound 1

Compound 2

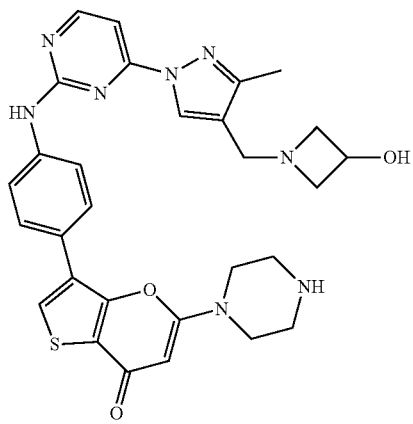

Formula III

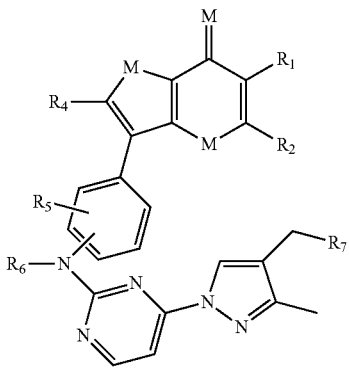

wherein M is independently O or S;

R1, R2, and R4 are as described for Formula I,

R5 is present in 1, 2,3, or 4 points of substitution on the aryl ring and is independently selected from R1;

R6 is independently selected from R1; and

R7 is independently selected from R1.

The present invention also provides compounds of Formula IV and methods of administering those compounds to a mammal in need thereof including, but not limited to, compounds that inhibit SYK, or SYK and at least one of PI3K, BRD4, CDK4/6, and checkpoint protein:

Compound 3

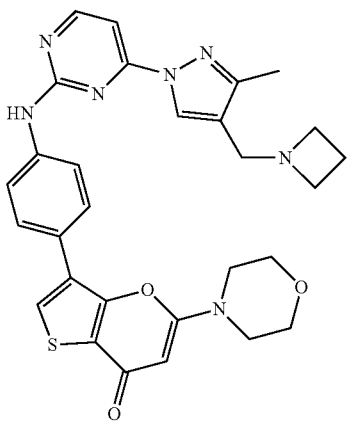

Formula IV

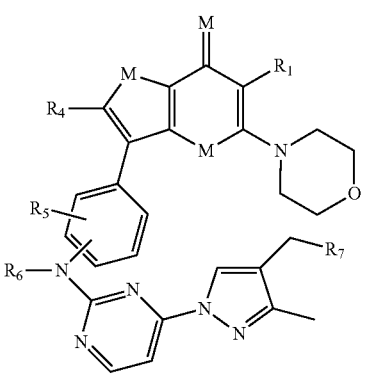

Compound 4

wherein M is independently O or S;

R1 and R4 are as described for Formula I,

R5 is present in 1, 2,3, or 4 points of substitution on the aryl ring and is independently selected from R1;

R6 is independently selected from R1; and

R7 is independently selected from R1.

The present invention also provides compounds of Formula III and methods of administering those compounds to a mammal in need thereof including, but not limited to, compounds that inhibit SYK, or SYK and at least one of PI3K, BRD4, CDK4/6, and checkpoint protein:

The present invention also provides compounds of Formula V and methods of administering the compounds to a mammal in need thereof including, but not limited to, compounds that inhibit SYK, or SYK and at least one of PI3K, BRD4, CDK4/6, and checkpoint protein:

Formula V

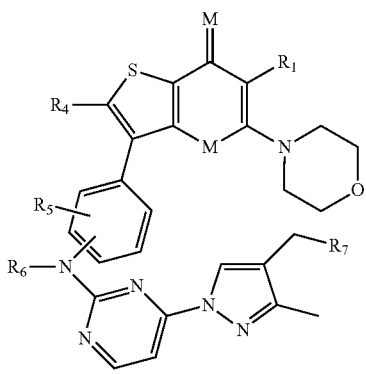

wherein R1 and R4 are as described for Formula I,
R5 is present in 1, 2, 3, or 4 points of substitution on the aryl ring and is independently selected from R1;
R6 is independently selected from R1; and
R7 is independently selected from R1.

A particular compound of the invention is one wherein a substituent at the R3 position of Formula I or a substituent at the R3-corresponding position of Formulas II-V comprises a bone directing group such as, for example, amino methylene phosphonic acids, bisphosphonates, or hydroxybisphosphonates and similar polyanionic moieties with affinity for calcific surfaces such as the bone.

A pharmaceutically acceptable salt of a compound of the invention is one which is the acid addition salt of a basic compound of Formula I-V with an inorganic or organic acid which affords a physiologically acceptable anion, or which is the salt formed by an acidic compound of Formula I-V with a base which affords a physiologically acceptable cation and provides a particular aspect of the invention. Examples of such acids and bases are provided hereinbelow.

Another aspect of the invention relates to methods of using a pharmaceutical formulation comprising in association with a pharmaceutically acceptable carrier, diluent or excipient, a compound of Formula I-V (or a pharmaceutically acceptable salt thereof) as provided in any of the descriptions herein.

In addition, compounds (or salts thereof) of the present invention are useful as an active ingredient in the manufacture of a medicament for use in inhibiting SYK, or SYK and at least one of PI3K, BRD4, CDK4/6, and checkpoint protein in vitro or in vivo.

The present invention also provides a method for treating a disease in a human or other mammal including, but not limited to, cancer, non-cancer proliferative disease, sepsis, autoimmune disease, viral infection, atherosclerosis, Type 1 or 2 diabetes, obesity, inflammatory disease, and Myc-dependent disorder by administering a therapeutically effective amount of a compound(s) or composition of Formula I-V or conjugate or prodrug thereof having any of the definitions herein. Compounds of Formula I-V may differ in their effectiveness to treat a disease described herein.

The present invention further provides a method for inhibiting SYK, or SYK and one or more of PI-3 kinase, bromodomain protein, CDK4/6, and checkpoint proteins in a mammal in need thereof by administering a therapeutically effective amount of a compound of Formula I-V, or conjugate or prodrug thereof having any of the definitions herein.

Further, the present invention provides a method of inhibiting tumor growth comprising administering to a mammal in need of treatment, an effective dose of a compound of Formula I-V, or conjugate or prodrug thereof.

Also, there is provided a compound of Formula I-V (or conjugate, prodrug, or salt thereof) having any of the definitions herein for use as an anticancer agent.

In addition, there is provided use of a compound of Formula I-V having any of the definitions herein for the manufacture of a medicament for the treatment of a disease described herein including, but not limited to, cancer.

As an additional feature of the invention there is provided a pharmaceutical formulation comprising in association with a pharmaceutically acceptable carrier, diluent or excipient, a conjugate of a compound of Formula I-V (or of a pharmaceutically acceptable salt thereof) as provided in any of the descriptions herein.

The present invention also includes methods of use of isotopically-labeled compounds, and pharmaceutically acceptable salts thereof, of compounds of Formulas I-V, but where one or more atoms are replaced by a corresponding isotope. Examples of isotopes that can be incorporated into compounds of the invention include isotopes of hydrogen, carbon, nitrogen, oxygen, phosphorous, fluorine and chlorine. Compounds of the present disclosure, conjugates thereof, and pharmaceutically acceptable salts of said compounds or of said conjugates which contain the aforementioned isotopes and/or other isotopes of other atoms are included within the scope of this disclosure. Certain isotopically-labeled compounds of the present disclosure, for example those into which radioactive isotopes, such as $^{2}$H, $^{3}$H, $^{14}$C, $^{15}$N, $^{32}$P and $^{131}$I are incorporated, are useful in drug and/or substrate tissue distribution assays for example when imaging tumors. Fluorine-18 ($^{18}$F) is particularly preferred for the ease of preparation and detectability it provides. Isotopically labeled compounds of the invention can generally be prepared by carrying out the procedures disclosed in the Schemes and/or in the Examples and Preparations below, by substituting a readily available isotopically labeled reagent for a non-isotopically labeled reagent.

It will be appreciated that certain compounds of Formula I-V (or salts, procompounds, conjugates, etc.) may exist in, and be isolated in, isomeric forms, including tautomeric forms, cis- or trans-isomers, as well as optically active, racemic, enantiomeric or diastereomeric forms. It is to be understood that the present invention encompasses a compound of Formula I-V in any of the tautomeric forms or as a mixture thereof; or as a mixture of diastereomers, as well as in the form of an individual diastereomer, and that the present invention encompasses a compound of Formula I-V as a mixture of enantiomers, as well as in the form of an individual enantiomer, any of which mixtures or form desirably possesses inhibitory properties against kinases including SYK kinase and/or PI3 kinase, it being well known in the art how to prepare or isolate particular forms and how to determine inhibitory properties against kinases by standard tests including those described herein below.

In addition, a compound of Formula I-V (or salt, procompound, conjugate thereof, etc.) used in the methods of the invention may exhibit polymorphism or may form a solvate with water or an organic solvent. The present invention also encompasses any such polymorphic form, any solvate or any mixture thereof.

The methods of using the invention includes a pharmaceutically acceptable salt of a compound defined by the above Formulas I-V. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

C.1. Synthesis of Compounds and Conjugates

The compounds of the present invention may be prepared according to the examples provided herein as well as by processes known in the chemical arts and described, for example, in U.S. Pat. No. 8,557,807 and references cited therein, as well as in G. A. Morales et al., J. Med. Chem. 2013, 56, 1922-1939, the entire contents of which are herein incorporated by reference. Of particular relevance are the methods described therein to synthesize Compound 0.

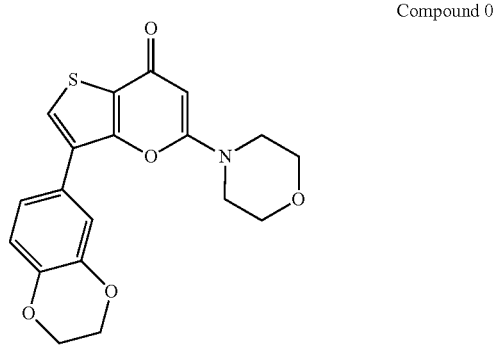 [SMILES: O=c1cc(N2CCOCC2)oc2c(-c3ccc4c(c3)OCCO4)csc12]

Compound 0

Starting materials and intermediates used to prepare a compound of the invention are either commercially available or can be easily prepared by one of ordinary skill in the art. Compounds and conjugates described herein and used in the therapeutic methods of the invention can be made, for example, by the procedures disclosed in U.S. Pat. Nos. 6,949,537; 7,662,977; 7,396,828; 8,557,807; and 9,505780; and in U.S. patent application Ser. Nos. 14/702,816, and 15/297,293, the entire contents of which are herein incorporated by reference. Compounds of the present invention may also be prepared by methods described in, for example, US20100160340 (LY2835219/Abemaciclib), WO2010020675 (PD-0332991/Palbociclib), WO2010020675 (LEE-011/Ribociclib), WO200803215 (Palbociclib) and U.S. Pat. No. 7,781,583 (Palbociclib) which are herein incorporated by reference. Thio compounds can be made from oxygen analogs as described in the art, for example by using Lawesson's reagent as described in Morales et al., J. Med. Chem. 2013. Furan analogs of the thiophene-pyranone compounds (termed thienopyranones) can be made, for example, by the general schemes outlined below where the key intermediate "g" is prepared and utilized. Intermediate "g" is then further elaborated to the oxygen analog of "compound 6" as described in Morales et al., J. Med. Chem. 2013 (reference incorporated herein) which is designated below as compound "i". Compound "i" can then be reacted via couplings with boronates to make the final substituted furanopyranones of the invention. Alternatively, the bromine atom in compound "i" can be converted to a boron derivative and then coupled with aryl or heteroaryl bromides or iodides to make furanopyranones of the invention.

A reaction scheme is shown below for preparing furanopyranones of the invention via the key furan intermediate "g" and subsequent conversion to compound "i" which is then further reacted to produce compounds of the invention:

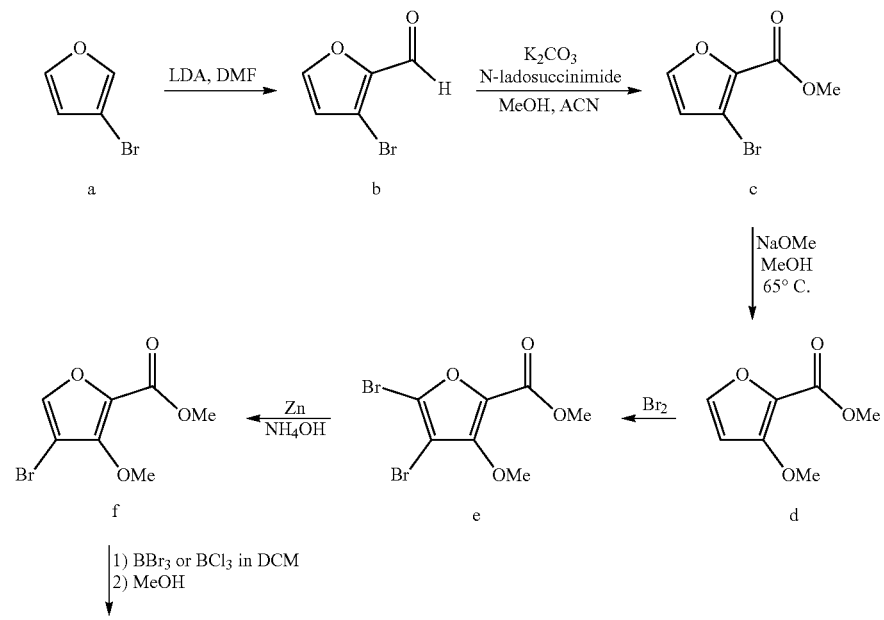

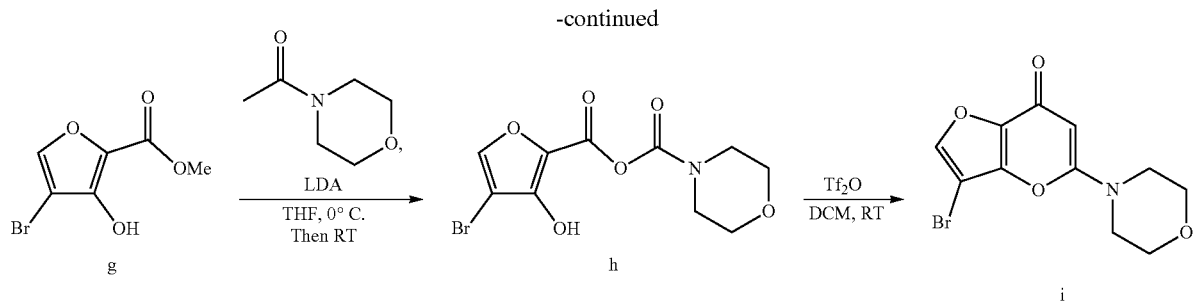

Expanded reaction scheme for introducing substituents at R4 of furan based compounds of the invention are based on methods described in US20120022059-A1 which are herein incorporated by reference and shown below:

And to add $R_4$ groups

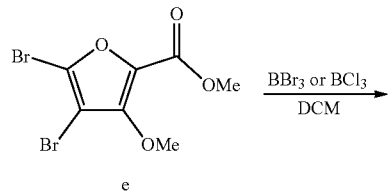

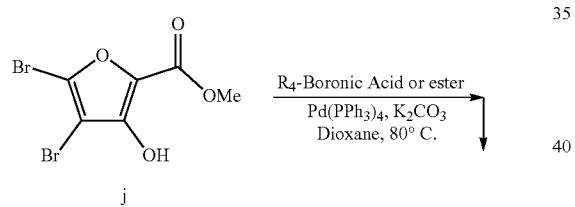

And to add $R_4$ groups

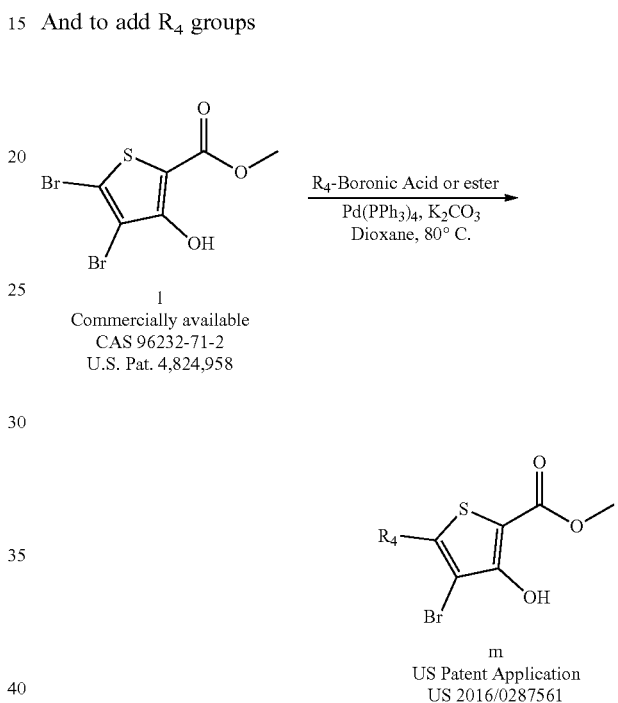

Scheme for introducing substituents at R4 of TP scaffold core.

The selective introduction of substituents at the R4 position of thiophene containing compounds of the invention is based on the synthesis of molecule "m" (R4 is pyrazole) starting from molecule "l" as disclosed in published US Patent Application 2016/0287561, the entire contents of which is herein incorporated by reference.

An additional scheme to obtain furanopyranones is shown below using $NaN_3$ to arrive at the key bromo-hydroxy-furan "g" which can then be used to make intermediate "i" and subsequent elaboration to compounds of the invention:

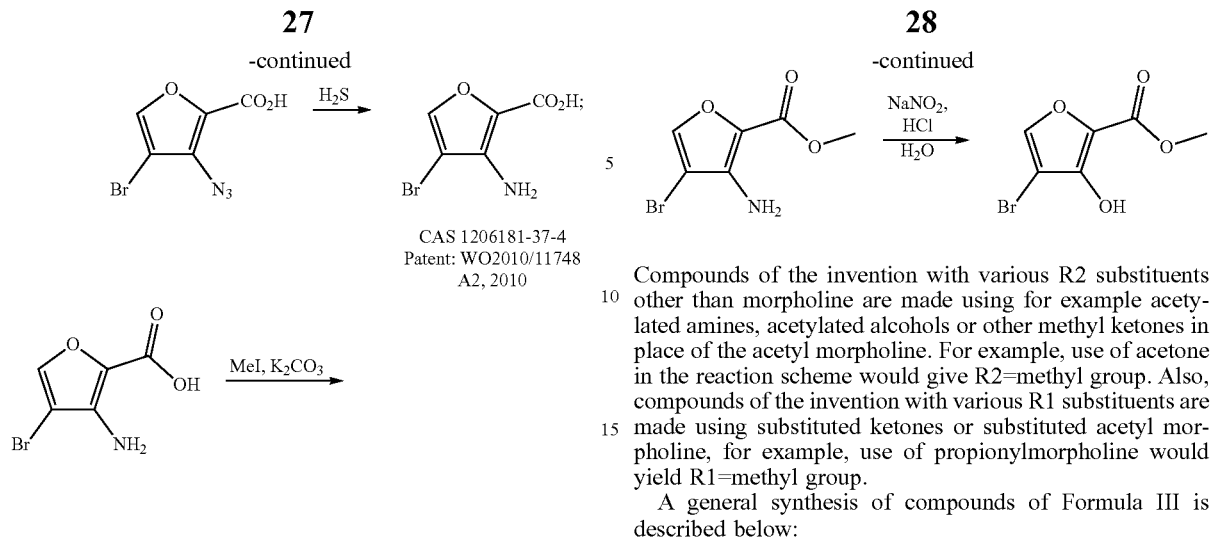

Compounds of the invention with various R2 substituents other than morpholine are made using for example acetylated amines, acetylated alcohols or other methyl ketones in place of the acetyl morpholine. For example, use of acetone in the reaction scheme would give R2=methyl group. Also, compounds of the invention with various R1 substituents are made using substituted ketones or substituted acetyl morpholine, for example, use of propionylmorpholine would yield R1=methyl group.

A general synthesis of compounds of Formula III is described below:

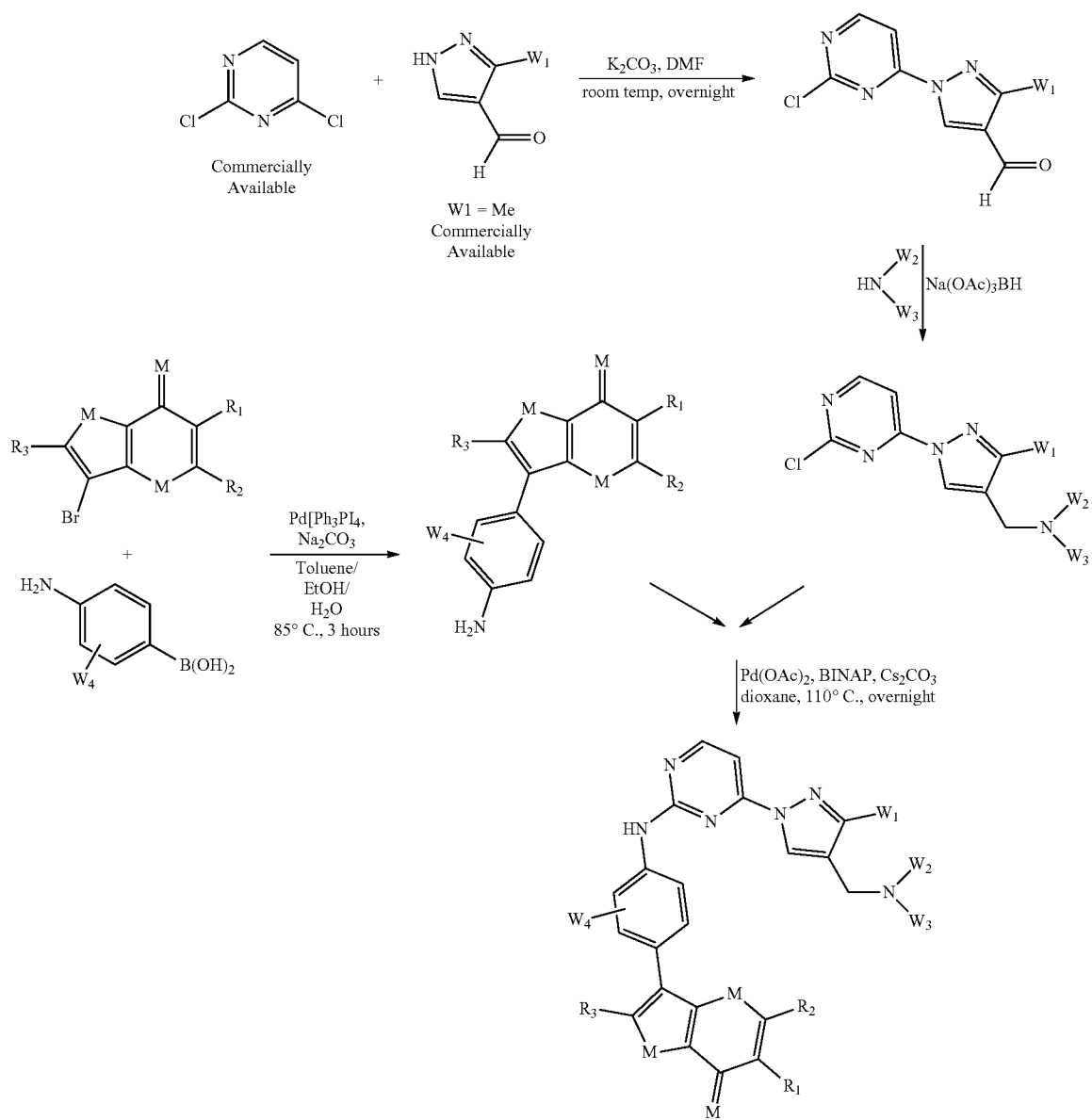

Where M is independently O or S;
W1 and W2 are independently selected from R1 of Formula I;
W2 and W3 are independently selected from R1 of Formula I; and
W2 and W3 can be connected by a covalent bond forming a nitrogen containing cyclic ring.

It should be appreciated that other heterocycles and substitution patterns of the various rings can be substituted into this general synthetic preparation.

Additionally, compounds of Formula I can be synthesized via the stepwise assembly shown in the scheme below (and further elaborated to specific species in Example 3) along the certain preferred building blocks listed below the scheme:

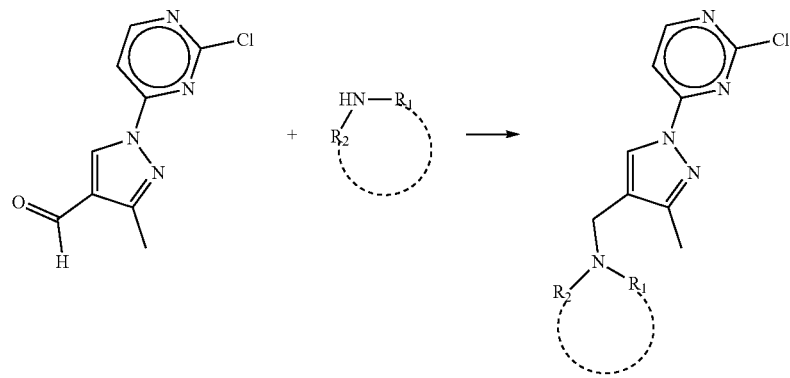

A

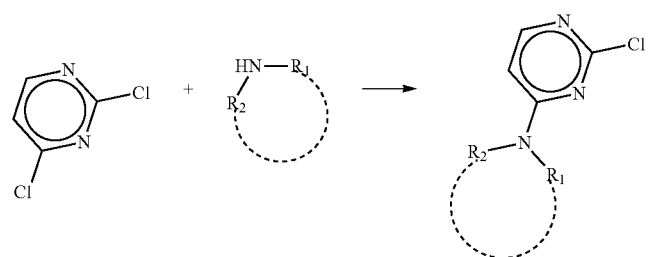

B

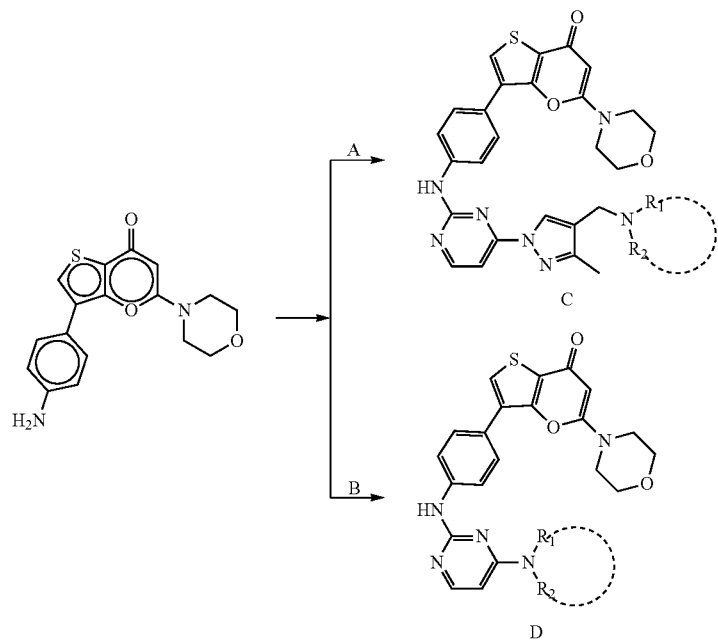

-continued

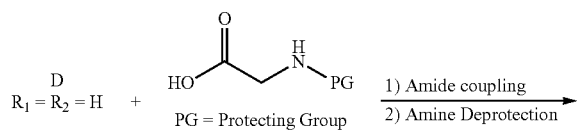
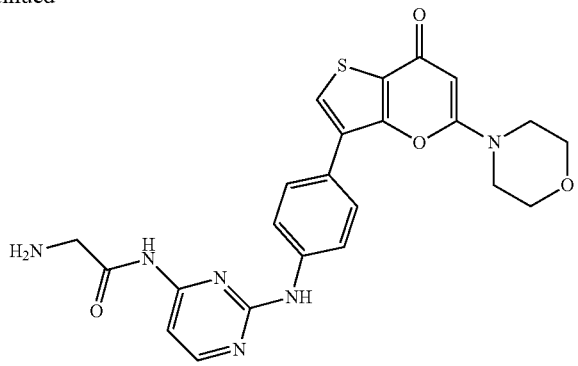

A preferred collection of amines to produce products C and D are shown below:

A preferred list of acids for synthesizing products such as E are listed below:

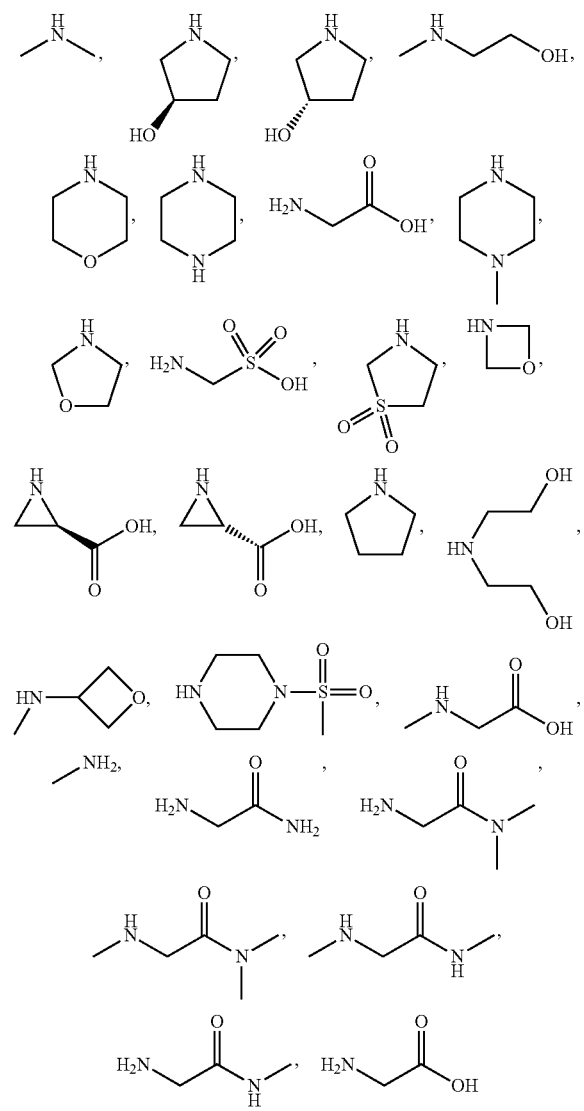
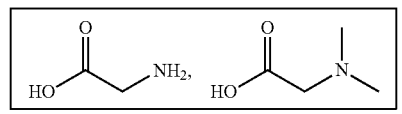

The compounds used in the methods of the invention, or their pharmaceutically acceptable salts, may have asymmetric carbon atoms or quaternized nitrogen atoms in their structure. It will be appreciated that certain compounds of Formula I (or salts, conjugates, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as a mixture thereof or as a mixture of diastereomers, as well as in the form of an individual diastereomer, and that the present invention encompasses a compound of Formula I as a mixture of enantiomers, as well as in the form of an individual enantiomer, any of which mixtures or form possesses inhibitory properties against kinases, for example PI-3 kinases. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of the invention.

Additional synthetic methodologies to prepare the compounds of the invention are described in the compound preparations described in the Examples.

The compounds used in the methods of the invention, or their pharmaceutically acceptable salts, may have asymmetric carbon atoms or quaternized nitrogen atoms in their structure. It will be appreciated that certain compounds of Formula I-V (or salts, conjugates, etc.) may exist in, and be isolated in, isomeric forms, including tautomeric forms, cis- or trans-isomers, as well as optically active, racemic, enantiomeric, or diastereomeric forms. It is to be understood that the present invention encompasses a compound of Formula I-V in any of the tautomeric forms or as a mixture thereof; or as a mixture of diastereomers, as well as in the form of an individual diastereomer, and that the present invention encompasses a compound of Formula I-V as a mixture of enantiomers, as well as in the form of an individual enantiomer, any of which mixtures or form possesses inhibitory properties against kinases, for example PI3 kinases. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of the compounds used in the methods of the invention. The carbonyl of the chromone is converted to the thione moiety as we describe earlier by reaction with Lawesson's reagent or other ketone to thioketone conversion conditions known to those skilled in the art.

D. Formulations

As an additional aspect of the invention there is provided a pharmaceutical formulation or composition comprising in association with a pharmaceutically acceptable carrier, diluent or excipient, a compound of the invention, e.g., Formula I-V (or a pharmaceutically acceptable salt or procompound or conjugate thereof) as provided in any of the descriptions herein for use in a method of the invention. Compositions of the present invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions used in the methods of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions used in the methods of the present invention may also be formulated as suppositories, which may contain suppository bases including, but not limited to, cocoa butter or glycerides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane.

Compositions of the present invention may also be formulated transdermal formulations comprising aqueous or nonaqueous vehicles including, but not limited to, creams, ointments, lotions, pastes, medicated plaster, patch, or membrane.

Compositions used in the methods of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions used in the methods of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions used in the methods of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh et al., U.S. Pat. No. 4,621,023 of Redziniak et al., or U.S. Pat. No. 4,508,703 of Redziniak et al., can be used. Other suitable formulations can employ niosomes. Niosomes are lipid vesicles similar to liposomes, with membranes consisting largely of non-ionic lipids, some forms of which are effective for transporting compounds across the stratum corneum.

The following formulation examples are illustrative only and are not intended to limit the scope of the compounds used in the methods of the invention in any way. The phrase "active ingredient" refers herein to a compound according to Formula I-IX or a pharmaceutically acceptable salt, procompound, conjugate, or solvate thereof.

| Formulation 1: Tablet containing the following components: | |
|---|---|
| Ingredient | Amount (mg/tablet) |
| Active ingredient | 250 |
| Dried starch | 200 |
| Magnesium stearate | 10 |
| Total | 460 mg |

| Formulation 2: Capsules containing the following components: | |
|---|---|
| Ingredient | Amount (mg/tablet) |
| Active ingredient | 60 |
| Dried starch | 44 |
| Magnesium stearate | 1.5 |
| Microcrystalline cellulose | 44 |
| Total | 150 mg |

Parenteral dosage forms for administration to patients by various routes including, but not limited to, subcutaneous, intravenous (including bolus injection), intramuscular, and intra-arterial are also contemplated by the present invention. Parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

An example parenteral composition used in the method of the invention would be intended for dilution with aqueous solution(s) comprising for example 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

E. Therapeutic Use

In one embodiment of the present invention, a compound(s) and composition(s) of the invention is administered to a mammal in need thereof including a human to treat or prevent a disease or disorder including, but not limited to, cancer, non-cancer proliferative disease, sepsis, autoimmune disease, viral infection, atherosclerosis, Type 2 diabetes, obesity, inflammatory disease, fibrotic disease, or Myc-dependent disorder by administering a therapeutically effective dose of a compound of Formula I-V. In some aspects of this embodiment, a compound of the invention provides therapeutic benefit by inhibiting SYK, or SYK and at least one of bromodomain (e.g. BRD4), PI3K, CDK4/6 and checkpoint protein. Without intending to be bound by theory, the therapeutic effectiveness of a compound of the invention may involve inhibition of SYK and/or SYK and at least one of PI3K, bromodomain proteins, checkpoint proteins, CDK4/6 and SYK. Inhibiting SYK and/or SYK and one or more of the aforementioned targets with a single drug provides a sophisticated combination therapy for patients resulting in more effective and durable clinical benefits. With dual or triple or more inhibitory activity in a single drug, more cost-effective treatments can be provided, benefiting patients and the healthcare system.

In one aspect, the invention relates to a method for inhibiting PI3K in a mammal by administering a compound of the invention.

In another aspect, the invention relates to a method for modulating Bromodomain protein regulated processes by inhibiting BRD4 in a mammal by administering a compound of the invention.

In another aspect, the invention relates to a method for inhibiting SYK in a mammal by administering a compound of the invention.

In another aspect, the invention relates to a method for modulating PI3K and/or BRD4 protein, and/or SYK protein, and/or CDKs, and/or checkpoint proteins in a mammal by administering one or more compound(s) of the invention.

In another aspect, the invention relates to a method of modulating MYC dependent processes by inhibiting PI3K and/or BRD4 in a mammal by administering a compound of the invention.

In another aspect, the invention relates to a method for modulating the fibrosis process in a mammal by administering a compound of the invention.

In another aspect, the invention relates to a method for modulating macrophage transitions in a mammal, for example, in the tumor microenvironment by administering a compound of the invention.

In another aspect, the invention relates to a method for inhibiting one or more targets in one cell at the same time in a mammal by administering a compound of the invention wherein the targets are selected from PI3K, BRD4, SYK, CDK4/6, and checkpoint proteins including inhibiting SYK and/or SYK and at least one of PI3K, BRD4, CDK4/6, and checkpoint protein.

In another aspect, the invention relates to a method for inhibiting multiple targets in one cell at the same time wherein the inhibition is superior (i.e. greater than) to a combination of inhibitors of those same targets.

In another aspect, the invention relates to a method for inhibiting multiple targets with a single compound (e.g. dual inhibitor such as a PI3K/BRD4 inhibitor) in each cell at the same time wherein the inhibition achieved is superior in a greater percentage of cells than that achieved by a combination of inhibitors of those same targets.

In another aspect, the invention relates to a method to modulate epigenetic regulation in a cell by inhibiting a bromodomain protein (e.g., BET proteins, such as BRD2, BRD3, BRD4, and/or BRDT, and non-BET proteins, such as CBP, ATAD2A, GCN5L, BAZ2B, FALZ, TAF1 and/or BRPF1), by administering a compound of the invention. In some embodiments, a compound of the invention is capable of inhibiting the activity of a bromodomain-containing protein, such as a BET protein (e.g., BRD2, BRD3, BRD4 and/or BRDT), non-BET proteins (e.g., CBP, ATAD2A, GCN5L, BAZ2B, FALZ, TAF1, and/or BRPF1) or a mutant thereof, in a biological sample useful for purposes including, but not limited to, blood transfusion, organ-transplantation, biological specimen storage, and biological assays.

In some embodiments, the present invention provides a method for inhibiting the activity of a bromodomain-containing protein, such as a BET protein (e.g., BRD2, BRD3, BRD4 and/or BRDT), non-BET proteins (e.g., CBP, ATAD2A, GCN5L, BAZ2B, FALZ, TAF1, and/or BRPF1) or a mutant thereof, in a patient comprising administering to said patient an effective amount of a compound or composition of the invention.

The present invention encompasses methods of treatment comprising administration of a compound(s) of Formula I-V including methods of treatment of a patient suffering from a condition or disease associated with one or more of aberrant kinase activity including PI3 kinase, aberrant SYK activity, aberrant bromodomain protein activity, aberrant CDK 4/6 activity, aberrant checkpoint protein activity, or associated with MYC (c-MYC or MYCN) driven disease. In one aspect, the activity may be abnormal, excessive, or constitutively active in a patient in need of such treatment.

The present invention also relates to a method for treating inflammatory disease comprising administering to a patient in need thereof a therapeutically effective amount of compound(s) of Formula I-V. Exemplary, but non-exclusive diseases and adverse health conditions attributable to kinase activity, in particular inappropriate PI-3 kinase signaling activity, have been disclosed in the art, for example U.S.

2002/0150954A1; U.S. Pat. Nos. 5,504,103; 6,518,277B1; 6,403,588; 6,482,623; 6,518,277; 6,667,300; U.S. 20030216389; U.S. 20030195211; U.S. 20020037276 and U.S. Pat. No. 5,703,075 the contents of which are herein incorporated by reference.

The methods of the invention also include treatment of CNS disorders, including schizophrenia, episodic paroxysmal anxiety (EPA) disorders such as obsessive compulsive disorder (OCD), post-traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourette's syndrome, tics, tremor, dystonia, spasms, anorexia, bulimia, stroke, addiction/dependency/craving, sleep disorder, epilepsy, migraine; and attention deficit/hyperactivity disorder (ADHD).

In another aspect, the present invention provides a method for treating Alzheimer's Disease or other neurological diseases including but not limited to Parkinson's Disease comprising administering to a patient in need thereof a therapeutically effective amount of a compound of Formula I-V. It has been reported that increasing PIP2 concentrations by, for example, inhibiting PI-3 kinase decreases levels of neurotoxins associated with Alzheimer's Disease (US 2008/0312187; incorporated herein by reference).

In another aspect, the present invention provides a method for enhancing the chemosensitivity of tumor cells comprising administering to a patient in need thereof a therapeutically effective amount of a compound of Formula I-V.

In another aspect, the present invention provides a method for enhancing the radiosensitivity of tumor cells comprising administering to a patient in need thereof a therapeutically effective amount of a compound of Formula I-V.

In another aspect, the present invention provides a method for inhibiting or reducing tumor growth comprising administering to a patient in need thereof a therapeutically effective amount of a compound of a compound of Formula I-V.

In another aspect, the present invention provides a method for inducing oxidative stress in tumor cells comprising administering to a patient in need thereof a therapeutically effective amount of a compound of Formula I-V.

In another aspect, the present invention provides a method for inhibiting or reducing tumor growth by inhibiting cancer stem cell growth and/or proliferation comprising administering to a patient in need thereof a therapeutically effective amount of a compound of Formula I-V.

In another aspect, the present invention provides a method for inhibiting tumor induced angiogenesis comprising administering to a patient in need thereof a therapeutically effective amount of a compound of Formula I-V.

Further, the present invention provides a method for inhibiting angiogenesis associated with non-cancer diseases comprising administering to a patient in need thereof a therapeutically effective amount of a compound of Formula I-V.

In yet another aspect, the present invention provides a therapeutic method for increasing apoptosis in cancer cells and cancerous tumors comprising administering to a patient in need thereof a therapeutically effective amount of a compound of Formula I-V.

The present invention also provides a method of treating cancer comprising administering to a patient in need thereof a therapeutically effective amount of a compound of Formula I-V.

In yet another aspect, the present invention provides a therapeutic method wherein a compound or composition of the invention having SYK and/or BRD4 and/or PI3K inhibitory activity, or combinations thereof, is administered to block the macrophage M1-M2 transition and therefore block pathophysiologic pathways by which M2 macrophages induce tumor immunosuppression, fibrosis, and suppress immunity to pathogens including bacteria, viruses, fungi and parasites.

In another aspect the invention provides a compound having single, dual or triple inhibitory activity against SYK, PI3K and/or BRD4 in a single small molecule.

In another aspect, a compound of the invention provides single, dual or triple or more inhibitory activity against SYK, PI3K and/or BRD4 to treat a fibrotic disease.

In another aspect, a compound of the invention provides single, dual or triple or more inhibitory activity against SYK, PI3K and/or BRD4 to treat a disease associated with aberrant angiogenesis or vasculogenesis.

In another aspect, a compound of the invention provides single, dual or triple or more inhibitory activity against SYK, PI3K and/or BRD4 to treat and block the immunosuppressive macrophage dependent tumor microenvironment, termed the M2 macrophage response and activate antitumor immunity in cancer.

In another aspect, a chemotype of the invention provides single, dual or triple or more inhibitory activity against SYK, PI3K and/or BRD4 to treat a disease associated with M2 macrophages in which said macrophages drive fibrotic or aberrant angiogenesis.

In another aspect, a compound of the invention provides single, dual or triple or more inhibitory activity against SYK, PI3K and/or BRD4 to treat a disease associated with the hypoxic activation of HIF1α and HIF1α-VEGF signaling axis which regulates M2 macrophage immunosuppression, fibrotic and aberrant angiogenic diseases.

In another aspect, a compound of the invention provides single, dual or triple or more inhibitory activity against SYK, PI3K and/or BRD4 to treat a disease associated with viral infection and replication e.g. HPV, HIV, etc. requiring BRD4.

In another aspect, a compound of the invention provides single, dual or triple or more inhibitory activity against SYK, PI3K and/or BRD4 to treat a disease associated with immune suppression or immunodeficiency caused by the activation of M2 macrophages or immunosuppressive macrophages e.g. MDSCs.

In another aspect, a compound of the invention provides single, dual or triple or more inhibitory activity against SYK, PI3K and/or BRD4 to treat a disease associated with need to augment immunity to control infection from virus, bacteria or fungi by the control of immunosuppressive effects of BRD4 or SYK or PI3K.

In another aspect, a compound of the invention provides single, dual or triple or more inhibitory activity against SYK, PI3K and/or BRD4 to treat a disease associated with T cell immunodeficiency or exhaustion associated with chronic infection or cancer.

In another aspect, a compound of the invention provides single, dual or triple or more inhibitory activity against SYK, PI3K and/or BRD4 to treat a disease associated with allergic, anaphylactic or autoimmune disease associated with activation of PI3K and role of BRD4 or SYK regulation.

In another aspect, a compound of the invention provides single, dual or triple or more inhibitory activity against SYK, PI3K and/or BRD4 to treat a disease associated with mast cell or basophil activation including but not restricted to allergic, anaphylactic or autoimmune disease.

In another aspect, a compound of the invention provides single, dual or triple or more inhibitory activity against SYK, PI3K and/or BRD4 to treat a disease associated with a resistance to a SYK inhibitory chemotype.

In another aspect, a compound of the invention provides single, dual or triple or more inhibitory activity against SYK, PI3K and/or BRD4 to treat a disease associated with resistance to a CDK4/6/9 inhibitor.

In another aspect, a compound of the invention provides single, dual or triple or more inhibitory activity against SYK, PI3K and/or BRD4 to treat a disease associated with resistance to a BRD4 inhibitory chemotype.

In another aspect, a compound of the invention provides single, dual or triple or more inhibitory activity against SYK, PI3K and/or BRD4 to treat a disease associated with need for vaccination therapy to augment the adaptive immune response.

In another aspect, a compound of the invention provides single, dual or triple or more inhibitory activity against SYK, PI3K and/or BRD4 to treat a disease associated with the use of cell-based immunotherapy e.g. CAR T cells to augment antitumor response.

In another aspect, a chemotype of the invention provides single, dual or triple or more inhibitory activity against SYK, PI3K and/or BRD4 to treat a disease associated with the use of chemotherapy or monoclonal antibody administration to augment therapy and block resistance.

In another aspect, a compound of the invention provides single, dual or triple or more inhibitory activity against SYK, PI3K and/or BRD4 to treat a disease associated with the need to activate the TH1/TH17 adaptive T cell immune response.

In another aspect, a compound of the invention provides single, dual or triple or more inhibitory activity against SYK, PI3K and/or BRD4 to treat a disease associated with parasitic infection to block the immunosuppressive macrophage, myeloid M2 response to activate adaptive immunity.

In another aspect, a compound of the invention provides single, dual or triple or more inhibitory activity against SYK, PI3K and/or BRD4 to treat a disease associated with vascular disease including vasculopathies and diseases known to be caused by aberrant integrin adhesion e.g. sickle cell disease (SCD).

In another aspect, a compound of the invention provides single, dual or triple or more inhibitory activity against SYK, PI3K and/or BRD4 to treat a disease associated with aberrant cytokine signaling related to immunotherapy induced "cytokine storm".

In another aspect, a compound of the invention provides single, dual or triple or more inhibitory activity against SYK, PI3K and/or BRD4 to treat a disease associated with activation of TH2 cytokines to include but not restricted to IL-10, IL-4 which result in immunosuppression and suppression of antitumor immunity.

In another aspect, a compound of the invention provides single, dual or triple or more inhibitory activity against SYK, PI3K and/or BRD4 to treat a disease associated with the activation of the interaction between red blood cells, leukocytes and endothelium e.g. sickle cell disease, other hemoglobinopathies.

In another aspect, a compound of the invention provides single, dual or triple or more inhibitory activity against SYK, PI3K and/or BRD4 to treat a disease associated with thrombosis, stroke (CVA) and myocardial infarction.

In another aspect, a compound of the invention provides single, dual or triple or more inhibitory activity against SYK, PI3K and/or BRD4 to treat a disease associated with metastasis driven through the activation of immunosuppressive macrophages and/or M2 macrophages in all cancers.

In another aspect, a compound of the invention provides single, dual or triple or more inhibitory activity against SYK, PI3K and/or BRD4 to treat a disease associated with need to augment immune checkpoint inhibitor therapeutic activity e.g. includes PD1 and PDL1 blockade and all other immune checkpoints for activation of immunity.

In another aspect, a compound of the invention provides single, dual or triple or more inhibitory activity against SYK, PI3K and/or BRD4 to treat a disease where said disease in an eye or skin related disorder associated with autoimmunity, immune suppression, fibrosis, proliferation, inflammation, angiogenesis or thrombosis.

In another aspect, a compound of the invention provides single, dual or triple or more inhibitory activity against SYK, PI3K and/or BRD4 to treat a disease associated with platelet activation, thrombosis, stroke (CVA) and myocardial infarction (MI).

In another aspect, a compound of the invention provides single, dual or triple or more inhibitory activity against SYK, PI3K and/or BRD4 to treat a disease associated with aberrant transcription associated with tissue/organ damage to control inflammation, fibrosis, apoptosis and organ dysfunction following cellular injury.

In another aspect, a compound of the invention provides single, dual or triple or more inhibitory activity against SYK, PI3K and/or BRD4 to treat a disease associated with resistance to PD-1 or PD-L1 monoclonal antibody therapy to block PD-1 and/or PD-L1 expression in tumor or immune compartment.

In another aspect, a compound of the invention provides single, dual or triple or more inhibitory activity against SYK, PI3K and/or BRD4 to treat a disease associated with autoimmunity, graft vs host disease or organ graft rejection.

In another aspect, a compound of the invention provides single, dual or triple or more inhibitory activity against SYK, PI3K and/or BRD4 to treat a disease associated with cancer stem cell activity as mechanism for resistance to standard of care.

In another aspect, a compound of the invention provides single, dual or triple or more inhibitory activity against SYK, PI3K and/or BRD4 to treat a disease associated with bone related pain from metastatic disease activation of osteoclasts and osteoblasts In another aspect, a compound of the invention provides single, dual or triple or more inhibitory activity against SYK, PI3K and/or BRD4 to treat a disease associated with vascular leakage and edema related diseases e.g. ARDS.

In another aspect, a compound of the invention provides single, dual or triple or more inhibitory activity against SYK, PI3K and/or BRD4 to treat all lymphoid malignancy in particular B cell driven lymphoma and leukemias.

In another aspect, a compound of the invention provides single, dual or triple or more inhibitory activity against SYK, PI3K and/or BRD4 to treat a disease associated with immune complex accumulation including but not restricted to arthritis, nephritis, serum sickness, etc.

In another aspect, a compound of the invention provides single, dual or triple or more inhibitory activity against SYK, PI3K and/or BRD4 to treat a disease associated with activation of B cell receptor (BCR), Fc receptors (FcRs; FcεR, FcγRs, FcαR) and T cell receptor (TCR) or any immunoreceptor activation motif (YxxL x$_6$YxxL) (ITAM) mediated pathophysiologic state.

In another aspect, a compound of the invention provides single, dual or triple or more inhibitory activity against SYK, PI3K and/or BRD4 to treat a disease associated with fibrosis of an organ system where the PI3K-SYK-Rac2 signal axis controls M2 macrophage response and fibrosis; PI3K and/or SYK inhibitor blocks or prevents fibrosis.

In another aspect, a compound of the invention provides single, dual or triple or more inhibitory activity against SYK, PI3K and/or BRD4 to treat a disease associated with fibrosis of an organ system where the PI3K-BRD4-MYC signal axis controls M2 macrophage response and fibrosis; PI3K and/or SYK, BRD4 bromodomain inhibitor blocks or prevents fibrosis.

In another aspect, a compound of the invention provides single, dual or triple or more inhibitory activity against SYK, PI3K and/or BRD4 to treat an infectious disease of neurodegenerative disease.

In another aspect, a compound of the invention provides single, dual or triple or more inhibitory activity against SYK, PI3K and/or BRD4 to control M1 to M2 transition and hence the immune response as it relates to antitumor immunity, fibrosis and immunosuppression in diseases in need of immune stimulation e.g. vaccination, cell-based immunotherapy, CAR, etc.

In another aspect, a compound of the invention provides single, dual or triple or more inhibitory activity against SYK, PI3K and/or BRD4 to control the M2 to M1 response and hence the activation of the immune response in diseases in need of suppressing aberrant immunity i.e. autoimmunity, immunotherapy related immunotoxicity syndromes.

In another aspect, a compound of the invention provides single, dual or triple or more inhibitory activity against SYK, PI3K and/or BRD4 to control the process of neurodegeneration as result of abnormal processing of protein and/or activation of immunity to include ALS, Parkinson's disease, Alzheimer's disease and others.

In another aspect, a compound of the invention provides single, dual or triple or more inhibitory activity against SYK, PI3K and/or BRD4 to control and treat any disease associated with dominant aberrant pathophysiologic transcription including, but not restricted to, fibrosis in any organ system, hypertrophy following injury as in myocardial infarction of cerebrovascular accident (stroke) or other acute events which activate aberrant transcription.

In another aspect, a compound of the invention provides single, dual or triple or more inhibitory activity against SYK, PI3K and/or BRD4 to control viral infection by virtue of capacity to control replication of latency states as for HIV, HPV, HSV and other viral processes.

In another aspect, a compound of the invention provides single, dual or triple or more inhibitory activity against SYK, PI3K and/or BRD4 to control infection with viruses, bacteria, fungi or parasites via the induction of autophagy and the activation of host immunity.

In another aspect, a compound of the invention provides single, dual or triple or more inhibitory activity against SYK, PI3K and/or BRD4 to control DNA repair and hence will augment radiation oncology therapy.

In another aspect, a compound of the invention provides single, dual or triple or more inhibitory activity against SYK, PI3K and/or BRD4 to control an aberrant disease-causing disease modifying epigenome and/or transcriptome to include but not restricted to autoimmunity, immunosuppression, hypertrophy, metabolic syndromes, apoptosis, autophagy, cell death and inflammation.

In another aspect, a compound of the invention provides single, dual or triple or more inhibitory activity against SYK, PI3K and/or BRD4 to control an aberrant disease causing or disease modifying metabolome or metabolism to include but not restricted to diabetes, steatohepatitis, endocrine disorders, obesity, etc.

In another aspect, a compound of the invention provides single, dual or triple or more inhibitory activity against SYK, PI3K and/or BRD4 to control diseases associated with aberrant angiogenesis to include but not restricted to eye diseases, macular degeneration, retinopathy, etc.

In yet another aspect, the present invention provides a therapeutic method wherein a compound or composition of the invention having dual or triple or quadruple inhibitory activity against SYK and/or BRD4 and/or CDK4-6, and/or PI3K is administered to block pathophysiologic pathways by which M2 macrophages induce tumor immunosuppression, fibrosis and suppress immunity to pathogens including bacteria, viruses, fungi and parasites.

The inhibitory activity of a compound of the invention against PI3K and/or BRD4 and/or SYK and/or CDK4/6 can be readily determined using methods known to the skilled artisan, or by commercial vendors offering such services. For example, in vitro kinase inhibition (e.g., PI3K or SYK inhibition) can be determined by a standard kinase inhibition assay using labeled ATP to determine if a test compound inhibits the transfer of phosphate from ATP to the kinase substrate. In vivo, PI3K inhibition can be determined from target tissue biopsies by standard tissue processing to disrupt cells and then performing Western Blot analysis to determine the presence or absence of pAKT (substrate of PI3K) relative to a control sample. The activity of a compound of the invention as an inhibitor of a bromodomain-containing protein, such as a BET protein, such as BRD2, BRD3, BRD4, and/or BRDT, or an isoform or mutant thereof, may be determined in vitro, in vivo, or in a cell line. In vitro assays include assays that determine inhibition of bromodomain-containing proteins. Alternatively, inhibitor binding may be determined by running a competition experiment where a provided compound is incubated with a bromodomain-containing protein, such as a BET protein bound to known ligands, labeled or unlabeled. For example, bromodomain inhibition can be determined in vitro using Alpha Screen Technology (http://www.reactionbiology.com/webapps/site/NewsPDFs/Bromodomain%20Assay%20Platform%20for%20Drug%20Screening%20and%20Discovery.pdf). In vivo bromodomain inhibition can be determined indirectly by evaluating the amount of protein present of proteins whose genes' transcription is influenced or controlled by the bromodomain protein, for example, the MYCN protein transcription is controlled by BRD4 (J. E. Delmore et al., *Cell* 2011, 146, 904-917; A. Puissant, *Cancer Discov.* 2013, 3, 308-323). Bromodomain inhibition may also be predicted by in silico modeling as described below in the Examples. Additionally, the company Promega offers a SYK luminescent assay to determine a compound's ability to inhibit the SYK protein (https://www.promega.com/-/media/files/resources/protocols/kinase-enzyme-appnotes/syk-kinase-assay-protocol.pdf?la=en).

In certain embodiments, the invention provides a method of treating a disorder (as described above) in a mammal subject, comprising administering to the subject identified as in need thereof, a compound of the invention. The identification of those patients who are in need of treatment for the disorders described herein is within the ability and knowledge of one skilled in the art. Certain of the methods for identification of patients who are at risk of developing the above disorders which can be treated by the subject method are appreciated in the medical arts, such as family history, and the presence of risk factors associated with the development of that disease state in the subject patient.

Assessing the efficacy of a treatment in a patient includes determining the pre-treatment extent of a disorder by methods known in the art (i.e., determining tumor size or screening for tumor markers where the cell proliferative disorder is cancer), then administering a therapeutically effective amount of a compound of the invention, to the patient. After an appropriate period of time after administration (e.g., 1 day, 1 week, 2 weeks, one month, six months), the extent of the disorder is again determined. Modulation (e.g., decrease) of the extent or invasiveness of the disorder (i.e., reduced tumor size) would indicate efficacy of the treatment. The extent or invasiveness of the disorder may be determined periodically throughout treatment. For example, the extent or invasiveness of the disorder may be assessed every few hours, days or weeks to assess the further efficacy of the treatment. A decrease in extent or invasiveness of the disorder indicates that the treatment is efficacious. The methods described may be used to screen or select patients that may benefit from treatment with a compound of the invention.

A variety of cancers may be treated according to the methods of the present invention including, but not limited to: carcinoma of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; and other tumors including melanoma, xeroderma pigmentosum, keratoacanthoma, seminoma, thyroid follicular cancer, and teratocarcinoma. The methods of the invention may also be used to treat accelerated or metastatic cancers of the bladder, pancreatic cancer, prostate cancer, non-small cell lung cancer, colorectal cancer, and breast cancer.

A method of the invention may be administered simultaneously or metronomically with other anti-cancer treatments such as chemotherapy and radiation therapy. The term "simultaneous" or "simultaneously" as used herein, means that the other anti-cancer treatment and the compound of the present invention are administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at a certain frequency relative to repeat administration and/or the chemotherapy regimen.

The chemotherapy treatment may comprise administration of a cytotoxic agent or cytostatic agent, or combination thereof. Cytotoxic agents prevent cancer cells from multiplying by: (1) interfering with the cell's ability to replicate DNA, and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include but are not limited to the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethi ophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-.alpha.), etoposide, and teniposide. Other proliferative cytotoxic agents are navelbene, CPT-11, anastrozole, letrozole, capecitabine, raloxifene, cyclophosphamide, iodamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see R. F. Service, *Science* 1996, 274, 2009) estramustine, nocodazole, MAP4, and the like. Examples of such agents are also described in J. C. Bulinski et al., *J. Cell Sci.* 1997, 110, 3055-3064; D. Panda et al., *Proc. Natl. Acad. Sci. USA* 1997, 94, 10560-10564; P. F. Mtihlradt et al., *Cancer Res.* 1997, 57, 3344-3346; K. C. Nicolaou et al., *Nature* 1997, 387, 268-272; R. J. Vasquez et al., *Mol. Biol. Cell.* 1997, 8, 973-985; and D. Panda et al., *J. Biol. Chem.* 1996, 271, 29807-29812.

Other suitable cytotoxic agents include but are not limited to epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used according to the methods of the invention include, but are not limited to, hormones and steroids (including synthetic analogs): 17 alpha-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, zoladex. Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and Src inhibitors. Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include but are not limited to epidermal growth factor inhibitors, Her-2 inhibitors, MEK-1 kinase inhibitors, MAPK kinase inhibitors, PI3K inhibitors, Src kinase inhibitors, and PDGF inhibitors.

The present invention also encompasses a method for treating pancreatitis comprising administering to a patient in need thereof a therapeutically effective amount of a compound or compounds of Formula I-V. As discussed in I. Gukovsky et al., *Gastroenterology* 2004, 126, 554-566, inhibition of PI-3 kinase may prevent pancreatitis.

The present invention also encompasses a method for treating ulcers comprising administering to a patient in need thereof a therapeutically effective amount of a compound of Formula I-V. The present invention also encompasses a method for treating gastric cancer, such as stomach cancer, comprising administering to a patient in need thereof a therapeutically effective amount of a compound of the present invention. As discussed in Bacon et al., Digestive Disease Week Abstracts and Itinerary Planner, Vol. 2003, Abstract No. M921 (2003) and Rokutan et al., Digestive Disease Week Abstracts and Itinerary Planner, Vol. 2003, Abstract No. 354 (2003), PI-3 kinase is involved in the adhesion of *Helicobacter pylori* to gastric cells.

The present invention also encompasses a method for treating age-related macular degeneration (AMD) comprising administering to a patient in need thereof a therapeutically effective amount of a compound of Formula I-VI. As discussed in M. R. Barakat et al., *Expert Opin. Investig. Drugs* 2009, 18, 637-646, inhibition of VEGF inhibits blood vessel overgrowth associated with AMD. The methods of the invention may also treat AMD by inhibiting angiogenesis.

The present invention also encompasses a method for treating conditions associated with a mutant PTEN comprising administering to a patient in need thereof a therapeutically effective amount of a compound of Formula I-V. PTEN is a tumor suppressor gene located on chromosome 10q23, in which mutations have been identified in patients with Cowden disease. As discussed in A. Vega et al., *J Invest. Dermatol.* 2003, 121, 1356-1359, mutations in PTEN have reduced ability to inhibit the activation of the proto-oncogene AKT. Inhibitors of PI-3 kinase may inhibit phosphorylation of AKT, thereby reducing the deleterious effect of mutant PTEN.

Tat is the human immunodeficiency virus type 1 (HIV-1) trans-activator protein and is known to be tightly regulated by lysine acetylation (R. E. Kiernan et al., *EMBO Journal* 1999, 18, 6106-6118). It is also known that HIV-1 Tat transcriptional activity is absolutely required for productive HIV viral replication (K. T. Jeang et al., *Curr. Top. Microbiol. Immunol.* 1994, 188, 123-144). Thus, the interaction of the acetyl-lysine of the protein Tat with one or more bromodomain-containing proteins (which are associated with chromatin remodeling) could mediate gene transcription allowing viral replication. Blocking bromodomain-containing proteins can thus serve to inhibit HIV viral replication and act as a therapeutic treatment for diseases involving HIV viral replication such as AIDS. The present invention encompasses a method for treating diseases involving HIV viral replication such as but not limited to AIDS comprising administering to a patient in need thereof a therapeutically effective amount of a compound of Formula I-V. The methods of this invention comprised of administering one or more compounds of Formula I-V are useful for treating viral infections such as but not limited to human papillomavirus, Herpesvirus, Epstein-Barr virus, human immunodeficiency virus, hepatitis B virus, and hepatitis C virus.

In another aspect, the invention provides a method for inhibiting activity of a bromodomain-containing protein in a patient comprising the step of administering to said patient a compound or compounds of Formula I-V either alone or in combination with other treatment agents.

In another aspect, the invention provides a method for treating bromodomain-containing protein-mediated disorders in a patient in need thereof, comprising administering to said patient a compound of Formula I-V.

The methods of the invention also include treating a subject with a MYC-dependent cancer, comprising administration of a compound of Formula I-VI. Subjects with MYC-dependent cancer can be determined by several ways including but not limited to determining MYC mRNA expression levels in the tumor and/or MYC protein expression in the tumor.

Preferred subjects for treatment with the methods of the invention can be identified by historical experience or known prevalence of MYC activation in certain cancers such as multiple myeloma (J. E. Delmore, Cell 2011, 146, 904-917), CLL (J. R. Brown et al., *Clin. Cancer Res.* 2012, 18, 3791-3802), leukemia (M. A. Dawson et al., *Nature* 2013, 478, 529-533), neuroblastoma (A. Puissant et al., *Cancer Discov.* 2013, 3, 308-323), or medulloblastoma (Y. J. Cho et al., *J. Clin. Oncol.* 2010, 29, 1424-1430).

Other diseases and conditions treatable according to the methods of this invention include, but are not limited to, other proliferative disorders, sepsis, autoimmune disease, infections including but not limited to viral infections. Diseases such as atherosclerosis and type 2 diabetes (V. A. DeWaskin et al., *Nature Rev. Drug Disc.* 2013, 12, 661-662) and obesity and inflammation (A. C. Belkina et al., *Nature Rev. Cancer* 2012, 12, 465-474) are also treatable according to the methods of the invention.

The invention further provides methods for treating or ameliorating cancer or other proliferative disorder by administration of an effective amount of a compound of Formula I-V to a mammal including a human in need of such treatment. Examples of cancers treatable using an effective amount of a compound of Formula I-V include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, Merkle cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

The methods of this invention further include administering one or more compounds of Formula I-V for treating benign proliferative disorders such as, but are not limited to, meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

The methods of this invention further comprise administering one or more compounds of Formula I-V for treating infectious and noninfectious inflammatory events and autoimmune and other inflammatory diseases. Examples of autoimmune and inflammatory diseases, disorders, and syndromes treated using the compounds and methods described herein include but are not limited to: appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis, Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I or 2 diabetes, septic shock, systemic lupus erythematosus, rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierma, mycosis fungoides, acute respiratory distress syndrome and ischemia/reperfusion injury. In some embodiments, the present invention provides a method of treating systemic inflammatory response syndromes such as LPS-induced endotoxic shock and/or bacteria-induced sepsis by administration of an effective amount of a compound of Formula I-V to a mammal in need of such treatment.

F. Administration and Dosage

Compounds of Formula I-V for use in a method of the present invention can be administered in any manner including but not limited to orally, parenterally, sublingually, transdermally, rectally, transmucosally, topically, pulmonarily, nasally, or bucally. Parenteral administration includes but is not limited to intravenous, intraarterial, intraperitoneal, subcutaneous, intramuscular, intrathecal, and intraarticular. Compounds or compositions of the invention may also be administered via slow controlled i.v. infusion or by release from an implant device.

A therapeutically effective amount of a compound of Formula I-V for use in a method of the invention varies with the nature of the condition being treated, the length of treatment time desired, the age and the condition of the patient, and is ultimately determined by the attending physician. In general, however, doses employed for adult human treatment typically are in a range of about 0.001 mg/kg to about 200 mg/kg per day, or about 1 µg/kg to about 100 µg/kg per day. The desired dose may be conveniently administered in a single dose, or as multiple doses administered at appropriate intervals, for example, as two, three, four or more sub-doses per day. Multiple doses over a 24-hour period may be desired or required.

A number of factors may lead to the compounds of Formula I-V being administered according to the methods of the invention over a wide range of dosages. When given in combination with other therapeutic agents, compounds of the present invention may be provided at relatively lower dosages. As a result, the daily dosage of a combination administered according to the methods of the present invention may be from about 1 ng/kg to about 100 mg/kg. The dosage of a compound of Formula I-V according to the methods of the present invention may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

The present invention has multiple aspects, illustrated by the following non-limiting examples. The examples are merely illustrative and are not intended to limit the scope of the invention in any way.

EXAMPLES

HPLC traces for example compounds synthesized were recorded using a HPLC consisting of Shimadzu or Agilent HPLC pumps, degasser and UV detector, equipped with an Agilent 1100 series auto-sampler. The UV detection provided a measure of purity by percent peak area. A MS detector (APCI) PE Sciex API 150 EX was incorporated for purposes of recording mass spectral data providing compound identification. HPLC/mass traces were obtained using one of three chromatographic methods. If a method is not specifically listed in the example then method A was utilized. The three methods are listed below:

Method A: Column SunFire™ (Waters) C18, size 2.1 mm×50 mm;
Solvent A: 0.05% TFA in water, Solvent B: 0.05% TFA in acetonitrile;
Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.
Method B: Column Aquasil™ (Thermo) C18, size 2.1 mm×150 mm; particle size 5. Solvent A: 0.05% TFA in water, Solvent B: 0.05% TFA in acetonitrile;
Flow rate—0.3 mL/min; Gradient: 10% B to 95% B in 2.4 min, hold at 95% B for 6.25 min and 95% B to 10% B in 0.2 min, hold at 10% B for 1.5 min.; UV detector—channel 1=220 nm, channel 2=254 nm.
Method C: Column Phenomenex C18, size 2 mm×50 mm; particle size 5µ. Solvent A: 0.05% TFA in water, Solvent B: 0.05% TFA in acetonitrile; Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Example 1. Preparation of Compound 1 (Small Scale)

(Note that the key starting material 3-Bromo-5-morpholino-4-oxa-1-thia-7-indenone preparation is described in the references in the specification for example Morales et al *J. Med. Chem.* 2013).

Step 1: Preparation of 3-(p-Aminophenyl)-5-morpholino-4-oxa-1-thia-7-indenone 3-Bromo-5-morpholino-4-oxa-1-thia-7-indenone (3.16 g, 10.0 mmol) and 4-aminophenylboronic acid hydrochloride (2.00 g, 11.5 mmol, 1.1 eq.) were dissolved in a 2:1 v/v mixture of toluene and ethanol (100 mL). The mixture was treated with $Na_2CO_3$ 2M aqueous solution (33 mL) and deoxygenated by bubbling $N_2$ for 30 minutes. $Pd[PPh_3]_4$ (578 mg, 0.5 mmol) was added and the mixture was heated to 85° C. for 16 hours. LCMS indicated complete conversion to product. The cooled reaction mixture was diluted with EtOAc (300 mL) washed with water and brine. The organics were dried over anhydrous $MgSO_4$, filtered and concentrated in vacuo. The crude residue was triturated with MeOH/$Et_2O$ mixture and filtered to yield the pure title compound as a tan solid. Yield=1.15 g (3.51 mmol, 35%).

LC/MS—HPLC (254 nm)—Rt 2.11 min. MS (ESI) m/z 329.1 [$M^+$+$H^+$]. Purity=98.0% by UV (254 nm).

Step 2: Preparation of 1-{[1-(2-Chloro-4-pyrimidinyl)-3-methyl-H-pyrazol-4-yl]methyl}-3-azetidinol A stirred suspension of commercially available 1-(2-chloro-4-pyrimidinyl)-3-methyl-1H-pyrazole-4-carbaldehyde (222 mg, 1.0 mmol) and 3-azetidinol hydrochloride (219 mg, 2.0 mmol) in dichloromethane (10 mL) was treated with triethylamine (700 µL, 5.0 mmol) followed by portionwise addition of $Na(OAc)_3BH$ (636 mg, 3.0 mmol). The resulting mixture was stirred at room temperature overnight. Next morning, LCMS indicated clean conversion to product. The reaction mixture was transferred to a separatory funnel, diluted with dichloromethane, washed with saturated aqueous $NaHCO_3$ solution. The organic layer was dried over anhydrous $MgSO_4$, filtered and concentrated in vacuo. The crude product was obtained as a white foam (185 mg, 0.66 mmol, 66%) and used directly in the next step.

LC/MS—HPLC (254 nm)—Rt 1.04 min. MS (ESI) m/z 280.5 [$M^+$+$H^+$]. Purity=95% by UV (254 nm).

Step 3: Preparation of 3-[p-(4-{4-[(3-Hydroxy-1-azetidinyl)methyl]-3-methyl-1H-pyrazol-1-yl}-2-pyrimidinylamino)phenyl]-5-morpholino-4-oxa-1-thia-7-indenone (Compound 1)

In a 8 mL vial, 1-{[1-(2-Chloro-4-pyrimidinyl)-3-methyl-1H-pyrazol-4-yl]methyl}-3-azetidinol (84 mg, 0.3 mmol), 3-(p-aminophenyl)-5-morpholino-4-oxa-1-thia-7-indenone (66 mg, 0.2 mmol), $Cs_2CO_3$ (195 mg, 0.6 mmol), Xantphos (46 mg, 0.08 mmol) and $Pd(OAc)_2$ (9 mg, 0.04 mmol) were degassed under $N_2$ for 10 minutes. Degassed 1,4-dioxane (4 mL) was added and the resulting mixture was stirred at 110° C. for 6 hours. LCMS indicated approximately 50% conversion to product. At this point, the reaction was cooled and filtered. Solids were rinsed with a 9:1 v/v $CH_2Cl_2$/MeOH mixture. The filtrates were concentrated and the crude residue was purified by preparative TLC plate on silica-gel (20×20 cm, 1 m thickness) eluting with a 400:50:2 v/v mixture of $CH_2Cl_2$/MeOH/$NH_4OH$. The product was obtained as a tan solid. Yield=14 mg (0.025 mmol, 12%).

LC/MS—HPLC (254 nm)—Rt 2.18 min. MS (ESI) m/z 572.4 [M$^+$+H$^+$]. Purity=97.0% by UV (254 nm).

Example 2. Preparation of Compound 1 (Large Scale)

Step 2: Preparation of 1-{[1-(2-Chloro-4-pyrimidinyl)-3-methyl-1H-pyrazol-4-yl]methyl}-3-azetidinol A stirred suspension of 1-(2-chloro-4-pyrimidinyl)-3-methyl-1H-pyrazole-4-carbaldehyde (1.11 g, 5.0 mmol) prepared in Step 1 of Example 1 and 3-azetidinol hydrochloride (1.1 g, 10.0 mmol) in dichloromethane (50 mL) was treated with triethylamine (3.5 mL, 25.0 mmol) followed by portionwise addition of $Na(OAc)_3BH$ (3.18 g, 15.0 mmol). The resulting mixture was stirred at room temperature overnight. Next morning, LCMS indicated clean conversion to product. The reaction mixture was transferred to a separatory funnel, diluted with 95:5 v/v mixture of dichloromethane/iPrOH, washed with saturated aqueous $NaHCO_3$ solution. The organic layer was dried over anhydrous $MgSO_4$, filtered and concentrated in vacuo. The crude product was obtained as a white foam (1.5 g, ~quant.) and used directly in the next step.

LC/MS—HPLC (254 nm)—Rt 0.84 min. MS (ESI) m/z 280.4 [M$^+$+H$^+$]. Purity=92% by UV (254 nm).

Step 3: Preparation of 3-[p-(4-{4-[(3-Hydroxy-1-azetidinyl)methyl]-3-methyl-1H-pyrazol-1-yl}-2-pyrimidinylamino)phenyl]-5-morpholino-4-oxa-1-thia-7-indenone (Compound 1)

In a 100 mL round bottom flask, 1-{[1-(2-chloro-4-pyrimidinyl)-3-methyl-1H-pyrazol-4-yl]methyl})-3-azetidinol (694 mg, 2.49 mmol), 3-(p-aminophenyl)-5-morpholino-4-oxa-1-thia-7-indenone (740 mg, 2.26 mmol), $Cs_2CO_3$ (1.47 g, 4.52 mmol), BINAP (563 mg, 0.904 mmol) and $Pd(OAc)_2$ (101 mg, 0.452 mmol) were degassed under $N_2$ for 30 minutes. Degassed 1,4-dioxane (45 mL) was added and the resulting mixture was stirred at 110° C. for 6 hours. LCMS indicated approximately 50% conversion to product. At this point, the reaction was cooled and filtered. Solids were rinsed with a 9:1 v/v $CH_2Cl_2$/MeOH mixture and then 1:1 v/v DMF/MeOH mixture at 60° C. The filtrates were concentrated and the crude residue, which was initially purified by reverse phase C-18 column chromatography, followed by purification by preparative TLC plate on silica-gel (20×20 cm, 1 m thickness) eluting with a 400:50:2 v/v mixture of $CH_2Cl_2$/MeOH/$NH_4OH$. The product was obtained as a light yellow solid. Yield=147 mg (0.258 mmol, 11%).

LC/MS—HPLC (254 nm)—Rt 2.48 min. MS (ESI) m/z 572.4 [M$^+$+H$^+$]. Purity=95.6% by UV (254 nm).

Example 3. Molecular Design and Docking Scores of Dual SYK-PI3K(Alpha) and Triple SYK-PI3K(Alpha)-BRD4-1 Inhibitors Potential dual SYK-PI3K(alpha) and triple SYK-PI3K (alpha)-BRD4-1 inhibitors based on Compound 3 were devised according to the following procedure.

The main core of Compound 3, namely 3-(4-((4-(3,4-dimethyl-1H-pyrazol-1-yl)pyrimidin-2-yl)amino)phenyl)-5-morpholino-7H-thieno[3,2-b]pyran-7-one, was kept constant and the amino group on the 4-methylene unit of the 1H-pyrazol-1-yl group was exchanged with other small amino-containing groups. In addition, the pyrazole group was removed and substituted with amino groups to produce 4-amino-containing pyrimidin-2-yl analogs. This process afforded a Compound 3-based virtual library of 42 analogs.

The 42 analogs of Compound 3 were drawn in 2D, the compounds were then ionized based on their calculated ionization state at physiological pH 7.4, and their structures minimized to output a 3-dimensional virtual library containing 42 structures with 3-dimensional coordinates.

To determine the potential inhibitory affinity of these 42 analogs against SYK, PI3K-alpha and BRD4-BD1, in silico models of these proteins were built using the human-derived crystal structures of the biological targets found and retrieved from the Protein Data Bank (PDB codes 4XG9, 4JPS and 5U28, respectively). The 3 crystal structures contain a co-crystallized small-molecule inhibitor placed at the biological target's active site.

The in silico models for the biological targets were created by removing the atomic coordinates of the co-crystallized small molecules, water molecules, salts and co-crystallization factors. Then, charges were calculated and applied to atoms and ionizable amino acid residues (e.g., lysine, arginine), and the 3-dimensional coordinates of each biological target was saved for in silico docking studies. The location of a co-crystallized small molecule in the original crystal structure was used as the binding site. Amino acid residues around the co-crystallized small molecule (6 Å to 10 Å) were selected for docking (binding site). For a compound to be considered a viable potential inhibitor, it must fit in the binding site of the biological target and interact with key amino acid residues required for binding (SYK: GLU449, MET450, ALA451; PI3K-alpha: VAL851; BRD4-BD1: ASN140).

All compounds tested were docked 150 times in the binding site. The binding affinity for a compound was determined by calculating the free docking energy (also known as affinity energy expressed as ΔG in kcal/mol) where the more negative the ΔG value the more potency/affinity a compound is predicted to have for the biological target. The best docking pose for each compound that matches the binding criteria for each target as described above was selected.

The Table below shows all 42 compounds numbered sequentially with their molecular weight (g/mol) and calculated binding affinity (kcal/mol) for SYK, BRD4-1 (BRD4-BD1), and PI3K-alpha.

TABLE 1

| | | | | | PI3K- |
| | | Mol | SYK | BRD4-1 | alpha |
| Cd | Structure | Weight | Score | Score | Score |
|---|---|---|---|---|---|
| 5 | 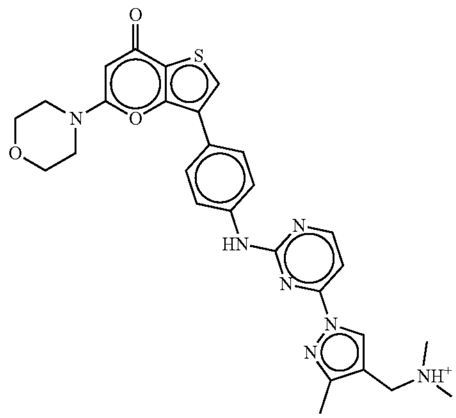 | 544.65 | −45.08 | −12.92 | −18.46 |
| 6 | 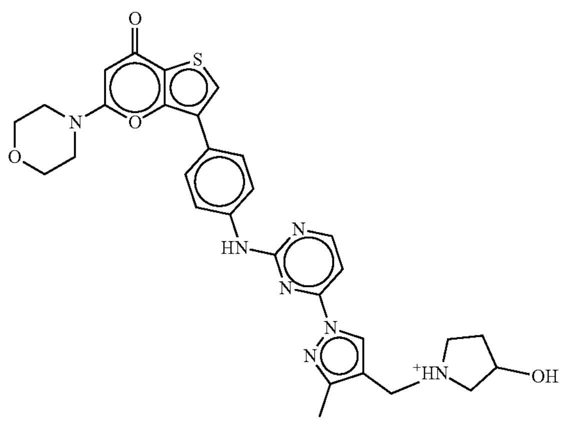 | 586.69 | −44.16 | −3.49 | −31.05 |
| 7 | 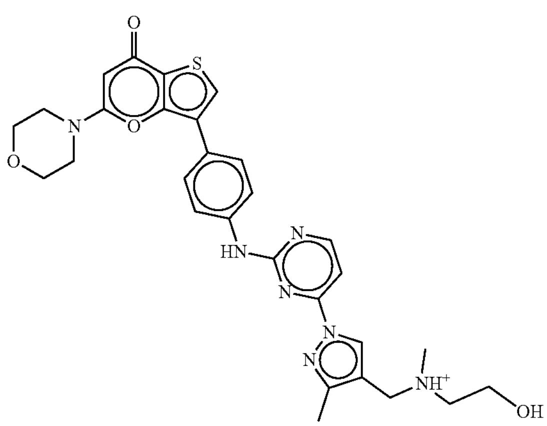 | 574.67 | −43.91 | −7.00 | −18.11 |

Compounds predicted to bind with Syk, BRD4-1, and PI3K.

TABLE 1-continued

Compounds predicted to bind with Syk, BRD4-1, and PI3K.

| Cd | Structure | Mol Weight | SYK Score | BRD4-1 Score | PI3K-alpha Score |
|----|-----------|------------|-----------|--------------|------------------|
| 8  | 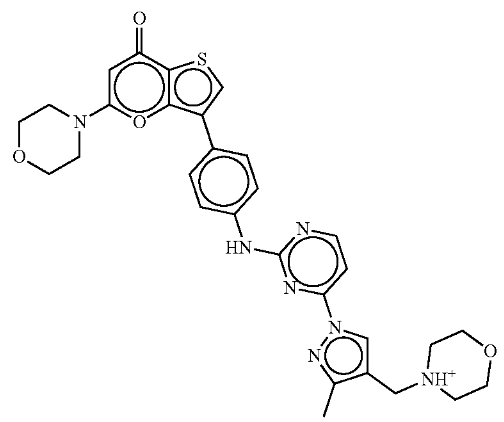          | 586.69     | −43.05    | −7.15        | −20.14           |
| 9  | 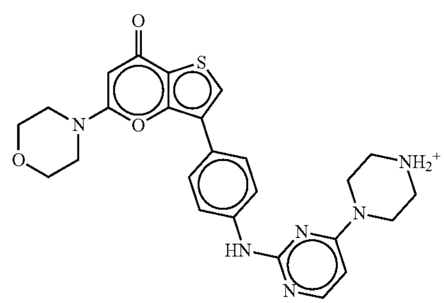          | 491.59     | −42.67    | −14.79       | −26.19           |
| 10 | 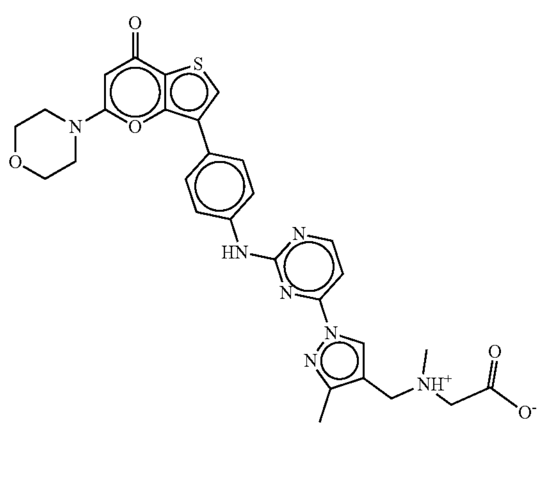          | 587.65     | −42.07    | −1.55        | −17.24           |

TABLE 1-continued

Compounds predicted to bind with Syk, BRD4-1, and PI3K.

| Cd | Structure | Mol Weight | SYK Score | BRD4-1 Score | PI3K-alpha Score |
|---|---|---|---|---|---|
| 11 | 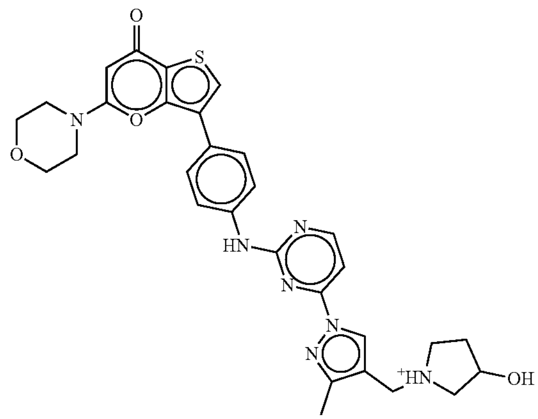 | 586.69 | −40.99 | −16.21 | −33.54 |
| 12 | 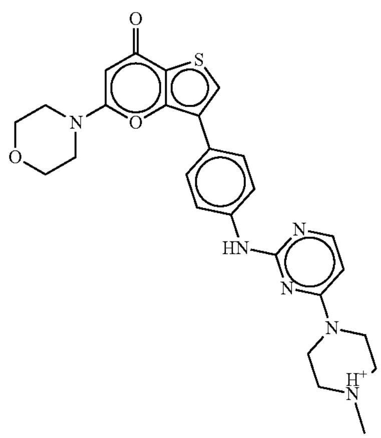 | 505.61 | −40.50 | −4.79 | −20.21 |
| 13 | 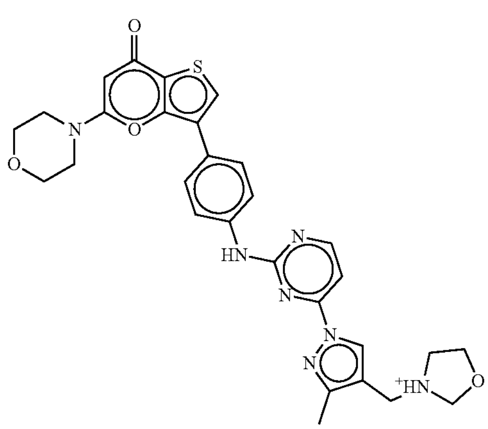 | 572.66 | −40.35 | −2.51 | −18.67 |

TABLE 1-continued
Compounds predicted to bind with Syk, BRD4-1, and PI3K.
| Cd | Structure | Mol Weight | SYK Score | BRD4-1 Score | PI3K-alpha Score |
| --- | --- | --- | --- | --- | --- |
| 14 | 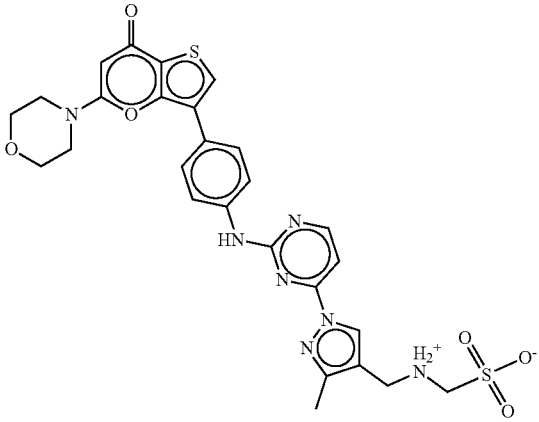 | 609.68 | −40.28 | −5.97 | −12.47 |
| 15 | 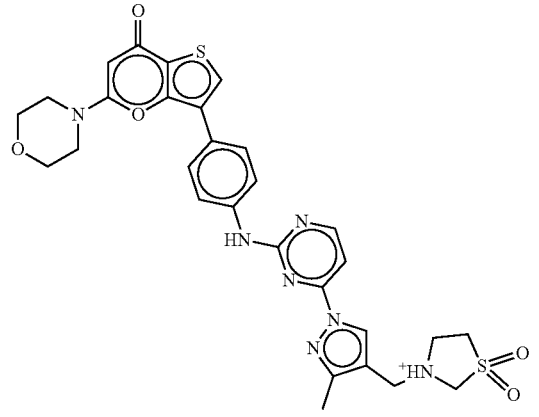 | 620.72 | −40.21 | −10.58 | −25.08 |
| 16 | 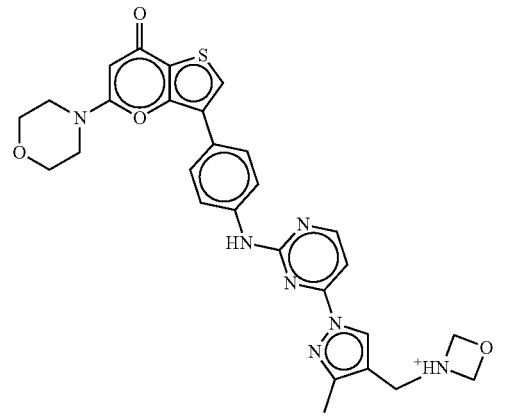 | 558.63 | −40.09 | −14.40 | −20.21 |

TABLE 1-continued
Compounds predicted to bind with Syk, BRD4-1, and PI3K.
| Cd | Structure | Mol Weight | SYK Score | BRD4-1 Score | PI3K-alpha Score |
|---|---|---|---|---|---|
| 17 | 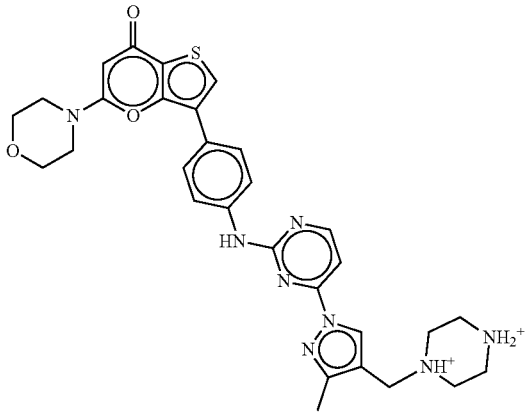 | 586.71 | −38.69 | −10.23 | −15.05 |
| 18 | 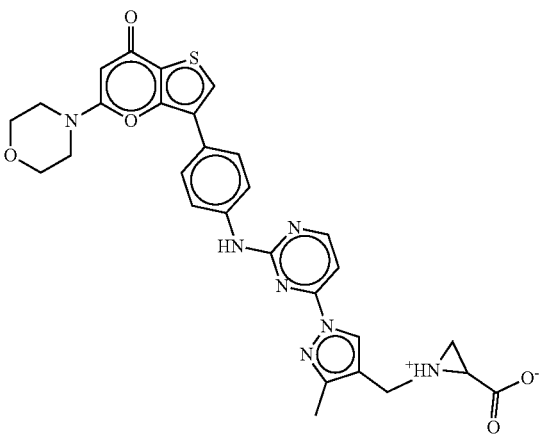 | 585.63 | −38.68 | −13.11 | −23.88 |
| 19 | 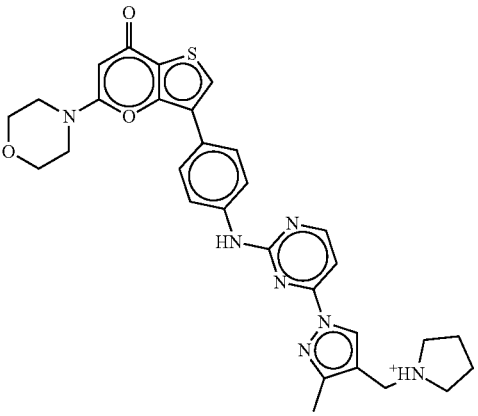 | 570.69 | −38.45 | −12.47 | −29.96 |

TABLE 1-continued

Compounds predicted to bind with Syk, BRD4-1, and PI3K.

| Cd | Structure | Mol Weight | SYK Score | BRD4-1 Score | PI3K-alpha Score |
|---|---|---|---|---|---|
| 20 | 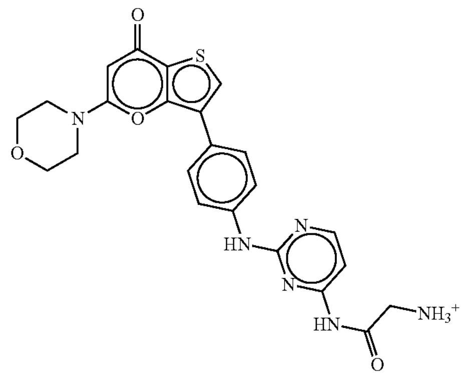 | 479.53 | −37.85 | −10.80 | −29.89 |
| 21 | 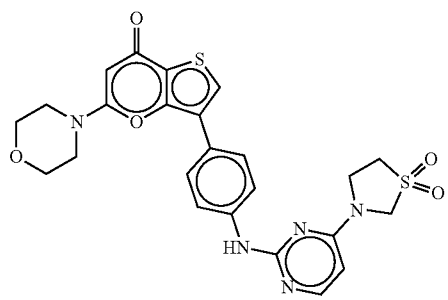 | 525.60 | −37.75 | −9.08 | −29.60 |
| 22 | 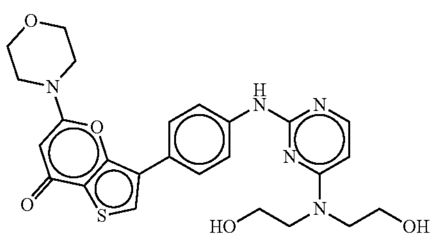 | 509.58 | −37.65 | −6.99 | −14.31 |
| 23 | 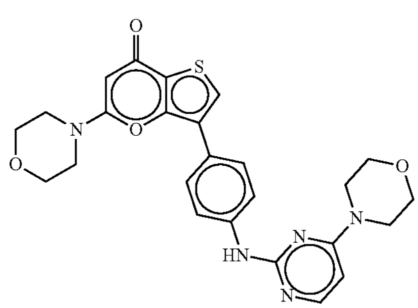 | 491.56 | −37.65 | −20.32 | −18.14 |

TABLE 1-continued
Compounds predicted to bind with Syk, BRD4-1, and PI3K.
| Cd | Structure | Mol Weight | SYK Score | BRD4-1 Score | PI3K-alpha Score |
|---|---|---|---|---|---|
| 24 | 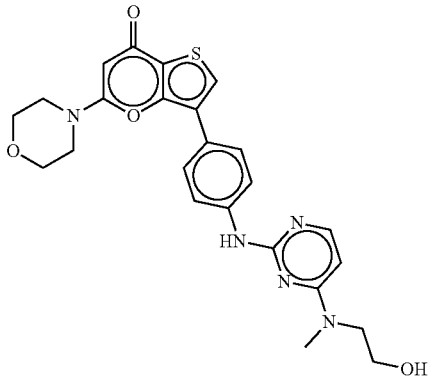 | 479.55 | −37.42 | 3.82 | −25.23 |
| 25 | 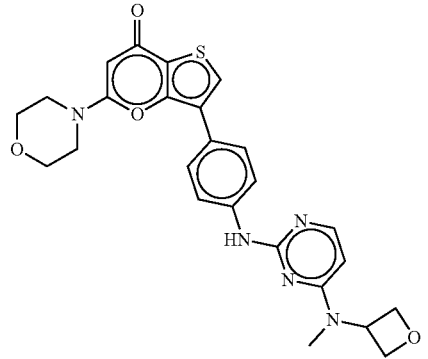 | 491.56 | −37.31 | −7.51 | −21.23 |
| 26 | 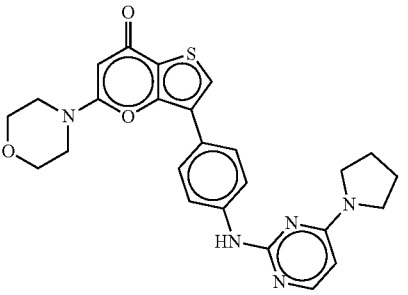 | 475.56 | −36.82 | −14.34 | −28.68 |
| 27 | 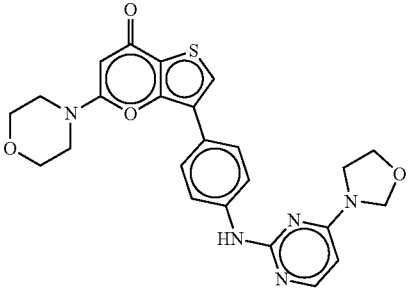 | 477.54 | −36.19 | −9.22 | −22.34 |

TABLE 1-continued
Compounds predicted to bind with Syk, BRD4-1, and PI3K.
| Cd | Structure | Mol Weight | SYK Score | BRD4-1 Score | PI3K-alpha Score |
|---|---|---|---|---|---|
| 28 | 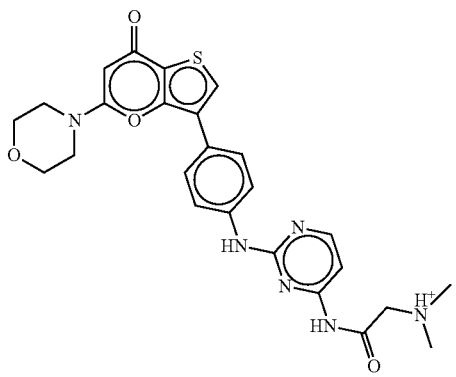 | 507.59 | −35.82 | −5.06 | −18.58 |
| 29 | 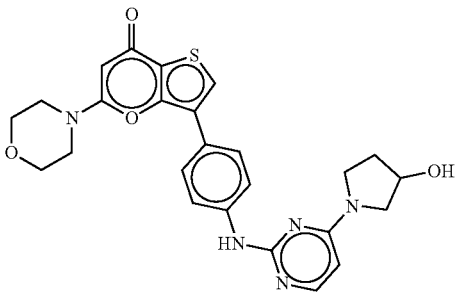 | 491.56 | −35.79 | −18.67 | −23.92 |
| 30 | 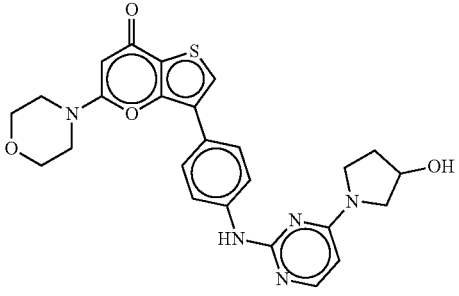 | 491.56 | −35.44 | −13.80 | −29.56 |
| 31 | 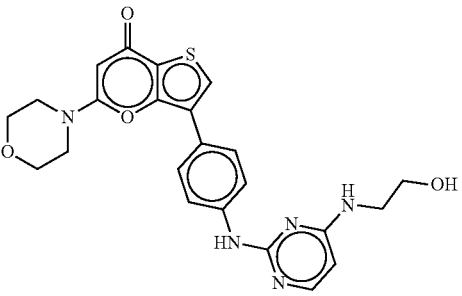 | 465.53 | −35.37 | −18.75 | −17.13 |

TABLE 1-continued

Compounds predicted to bind with Syk, BRD4-1, and PI3K.

| Cd | Structure | Mol Weight | SYK Score | BRD4-1 Score | PI3K-alpha Score |
|---|---|---|---|---|---|
| 32 | 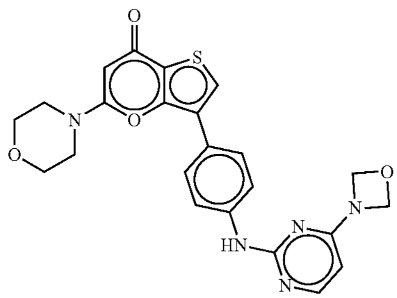 | 463.51 | −34.94 | −18.28 | −23.00 |
| 33 | 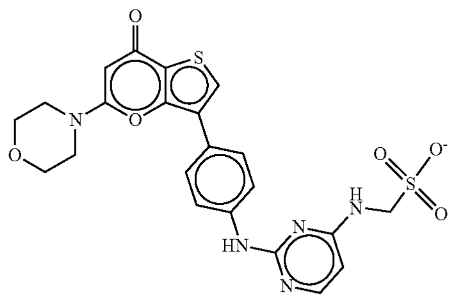 | 514.55 | −34.75 | −13.03 | −28.45 |
| 34 | 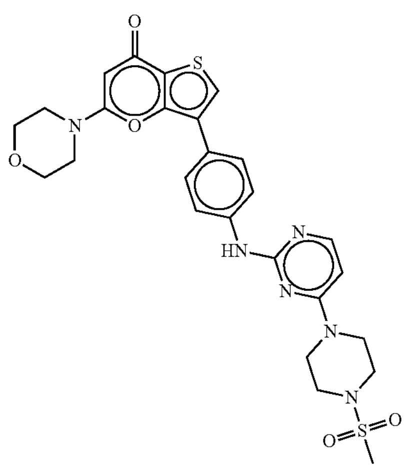 | 568.67 | −34.68 | −7.77 | −14.14 |
| 35 | 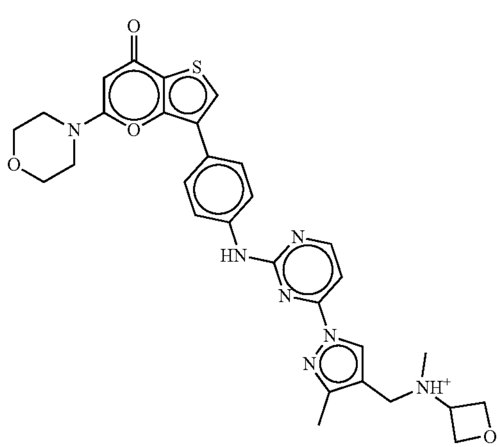 | 586.69 | −34.68 | −14.52 | −24.09 |

TABLE 1-continued

Compounds predicted to bind with Syk, BRD4-1, and PI3K.

| Cd | Structure | Mol Weight | SYK Score | BRD4-1 Score | PI3K-alpha Score |
|---|---|---|---|---|---|
| 36 | 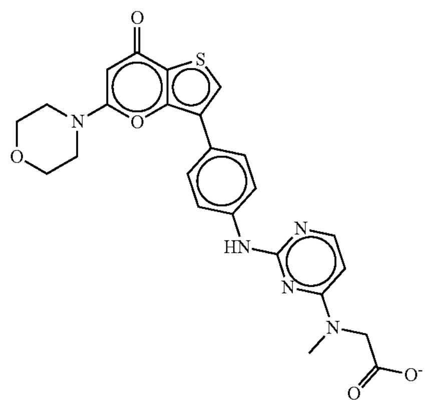 | 492.53 | −34.16 | −14.07 | −28.56 |
| 37 | 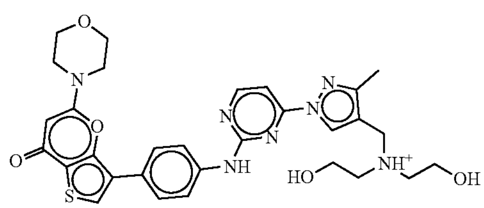 | 604.70 | −33.99 | 4.76 | −20.56 |
| 38 | 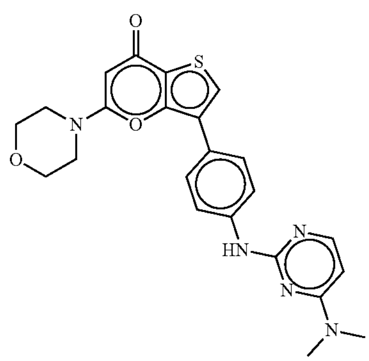 | 449.53 | −33.90 | −17.00 | −28.09 |
| 39 | 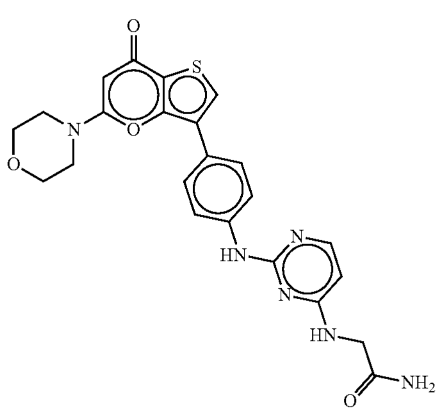 | 478.52 | −33.38 | −7.43 | −24.37 |

TABLE 1-continued

Compounds predicted to bind with Syk, BRD4-1, and PI3K.

| Cd | Structure | Mol Weight | SYK Score | BRD4-1 Score | PI3K-alpha Score |
|---|---|---|---|---|---|
| 40 | 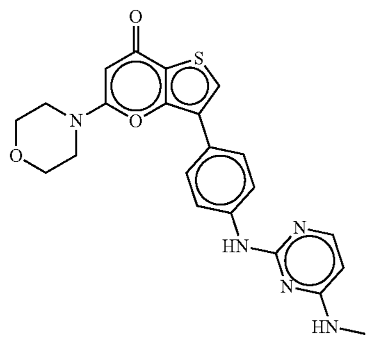 | 435.50 | −33.25 | −7.54 | −21.90 |
| 41 | 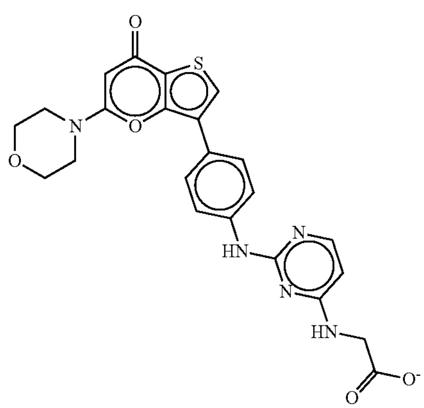 | 478.50 | −32.90 | −13.12 | −15.10 |
| 42 | 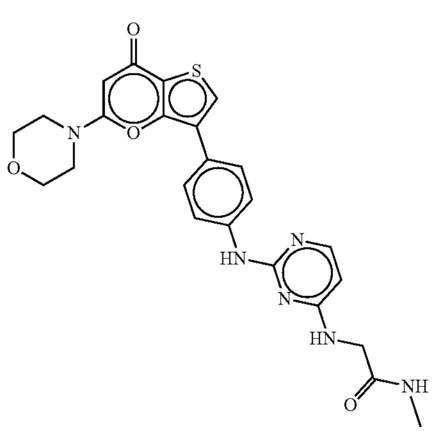 | 492.55 | −32.85 | −8.94 | −27.21 |

TABLE 1-continued
Compounds predicted to bind with Syk, BRD4-1, and PI3K.
| Cd | Structure | Mol Weight | SYK Score | BRD4-1 Score | PI3K-alpha Score |
|---|---|---|---|---|---|
| 43 | 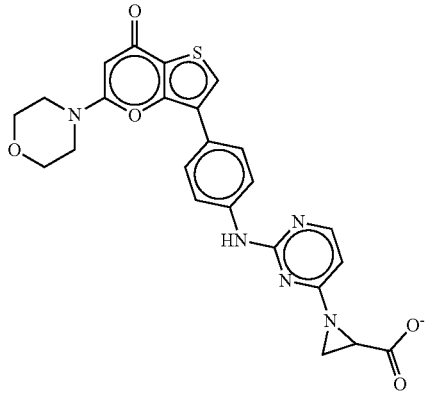 | 490.51 | −32.53 | −9.75 | −19.40 |
| 44 | 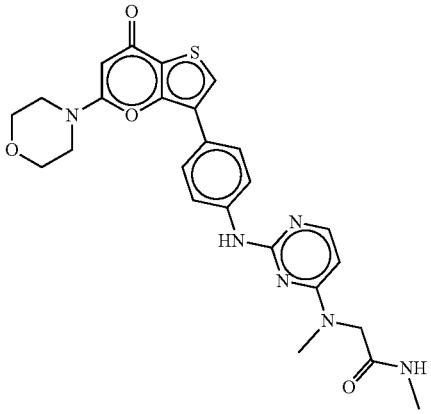 | 506.58 | −32.35 | −12.14 | −25.32 |
| 45 | 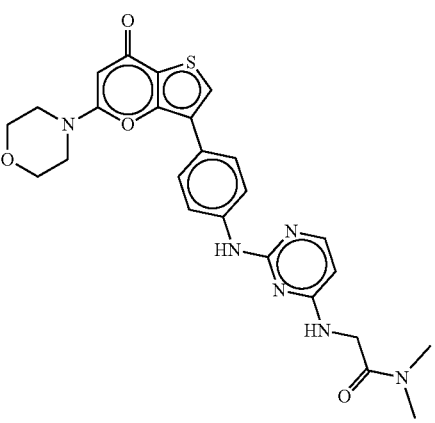 | 506.58 | −32.20 | −11.54 | −28.17 |

TABLE 1-continued

Compounds predicted to bind with Syk, BRD4-1, and PI3K.

| Cd | Structure | Mol Weight | SYK Score | BRD4-1 Score | PI3K-alpha Score |
|----|-----------|------------|-----------|--------------|------------------|
| 46 | 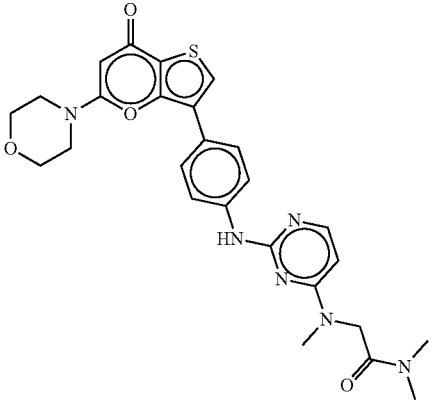 | 520.60 | −31.97 | −8.70 | −23.26 |

Example 4. Molecular Design and Docking Scores of Dual SYK-PI3K(Gamma) Inhibitors Potential dual SYK-PI3K inhibitors were devised according to the following procedure: To construct a virtual library of potential dual SYK-PI3K inhibitors, a literature search was conducted and moieties identified to exhibit SYK affinity were selected as SKY-recognition building blocks (47 SYK building blocks). For PI3K recognition, 82 TP-based building blocks were used where the aromatic units linked to the thiophene group of the TP core included with 5-membered and 6-membered rings (benzene and heterocyclic rings). Each of these 82 TP-based building blocks is further diversified by changing oxygen for sulfur in the thiophene to give a furan ring (benzofuran); exchanging sulfur for the divalent oxygen in the pyran ring (thiochromone); and doing both substitutions (benzofuran/thiochromone) yielding a total of 328 TP-based building blocks. These PI3K recognition units contained a single attachment point (permutated on the benzene or heterocycle) for the linkage with the SYK recognition fragment. The 82 TP-based blocks (all with oxygen) are shown in Table 3 below along with the 47 SYK-recognition unit building blocks in Table 2.

These SYK and PI3K recognition structures were combined combinatorially creating a virtual library of 15,416 compounds (47×328) as shown in the scheme below:

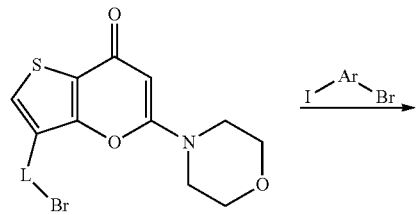

L = Nothing, CH$_2$, N, O, S

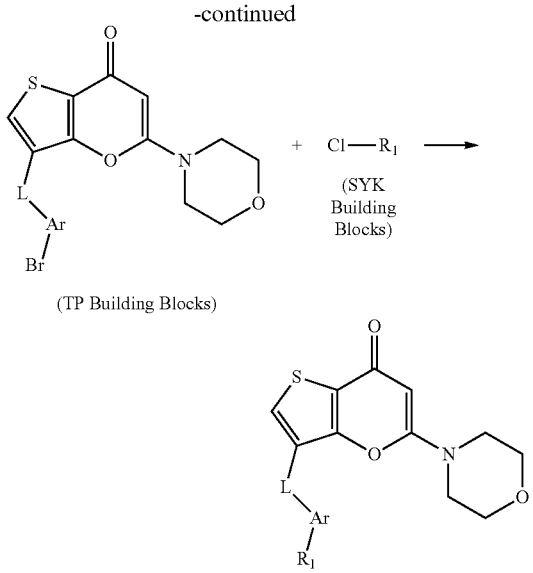

It should be noted that the I, Br, and Cl are not chemically reacting but are placeholders for where the points of attachment are made in silico to combinatorially create a virtual library. The actual synthesis of these compounds can be achieved using the methods described in the specification and other examples.

All hydrogen atoms were added to the compounds. Since these compounds are expected to ultimately be in the blood stream if/when administered to a living organism or animal (i.e., primates, non-primates), the ionized species of the compounds in such environment will be calculated for our in silico studies. Therefore, the compounds were then ionized based on their calculated ionization state at physiological pH 7.4, and their structures minimized to output a virtual library of 15,416 compounds each with a 3-dimensional structure and 3-dimensional coordinates, herein referred to as 3D virtual library.

To determine what compounds from this 3D virtual library could have high inhibitory affinity against SYK and PI3K, in silico models based on these kinases were built using the 3-dimensional coordinates of the kinases. For this, the crystal structures of human-derived SYK and PI3K-gamma were obtained from the Protein Data Bank (PDB codes 4XG9 and 4XZ4, respectively). The crystal structures of these kinases contain a co-crystallized small-molecule inhibitor placed at the ATP site (kinase activity site).

To construct in silico models for SYK and PI3K-gamma, the atomic coordinates of the co-crystallized small molecules, water molecules, salts and co-crystallization factors were removed from the 3D coordinates of the kinases, charges were calculated and applied to atoms and ionizable amino acid residues (e.g., lysine, arginine), and the 3-dimensional coordinates of each kinase was saved for in silico docking studies.

For the identification of potential dual SYK and PI3K-gamma inhibitors, the compounds in the 3D virtual library were docked first against SYK at its kinase activity site. For a compound to be considered a viable potential inhibitor, such compound must fit in the kinase activity site (binding site) and interact with the backbone of SYK (i.e., GLU449, MET450, ALA451). All the compounds were docked at least 100 times in the binding site. The binding affinity for a compound was determined by calculating the free docking energy (also known as and referred to as affinity energy expressed as ΔG in kcal/mol) where the more negative the ΔG value is the more potency/affinity a compound has for the biological target, in this case SYK.

The top-best docking pose for each compound was selected based on the best calculated binding affinity. From the docking results, the top 200 compounds predicted to bind the strongest to SYK were selected to be docked against PI3K-gamma.

PI3K has 4 isoforms, namely alpha, beta, delta and gamma, and their ATP kinase recognition site is highly homologous. PI3K inhibitors are known for making a key hydrogen-bond interaction with a valine residue, in the case of PI3K-gamma it is VAL882. To identify compounds with higher selectivity towards the PI3K gamma isoform, we identified 2 unique amino acid residues in the PI3K-gamma ATP catalytic pocket: LYS802 and LYS890. For a small compound to be considered a PI3K kinase inhibitor such compound must fit in the ATP kinase catalytic pocket (also referred to as recognition site) and engage in a hydrogen-bond interaction with VAL882.

Additional interactions with LYS802 and LYS890 are expected to increase selectivity towards PI3K-gamma.

The top 200 SYK inhibitors were docked against PI3K-gamma at the ATP kinase recognition site. As done for SYK, each compound was docked at least 100 times and their predicted binding affinity calculated. This process was also performed for PI3K-alpha and PI3K-delta.

The top 200 SYK inhibitors along with their PI3K alpha, delta, and gamma scores are shown in the Table that follows below (200 entries in 50 pages) ordered by best SYK scores first.

TABLE 2

47 SYK BUILDING BLOCKS

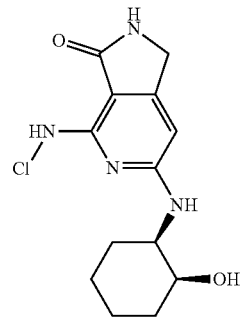 [SMILES: O=C1NCc2cc(N[C@@H]3CCCC[C@@H]3O)nc(NCl)c21]

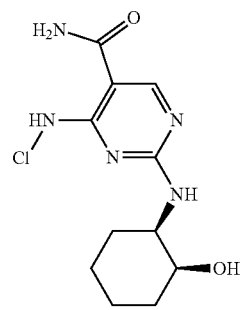 [SMILES: NC(=O)c1cnc(N[C@@H]2CCCC[C@@H]2O)nc1NCl]

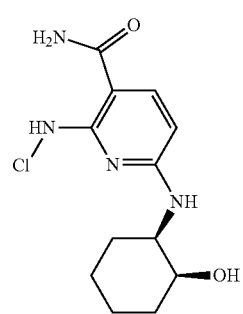 [SMILES: NC(=O)c1ccc(N[C@@H]2CCCC[C@@H]2O)nc1NCl]

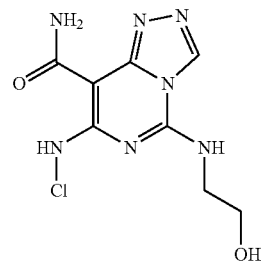 [SMILES: NC(=O)c1c(NCl)nc(NCCO)n2cnnc12]

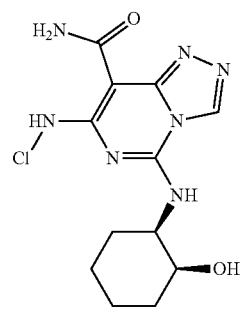 [SMILES: NC(=O)c1c(NCl)nc(N[C@@H]2CCCC[C@@H]2O)n2cnnc12]

TABLE 2-continued
47 SYK BUILDING BLOCKS
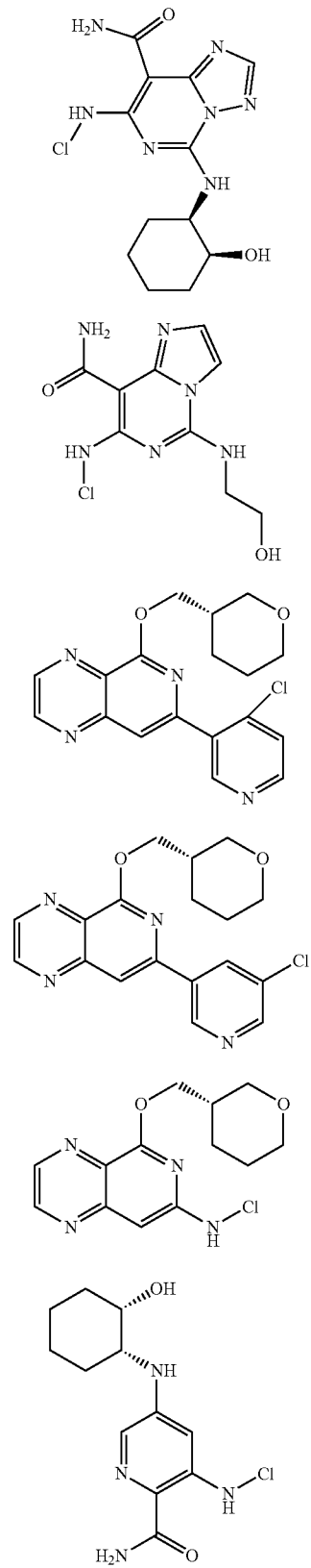
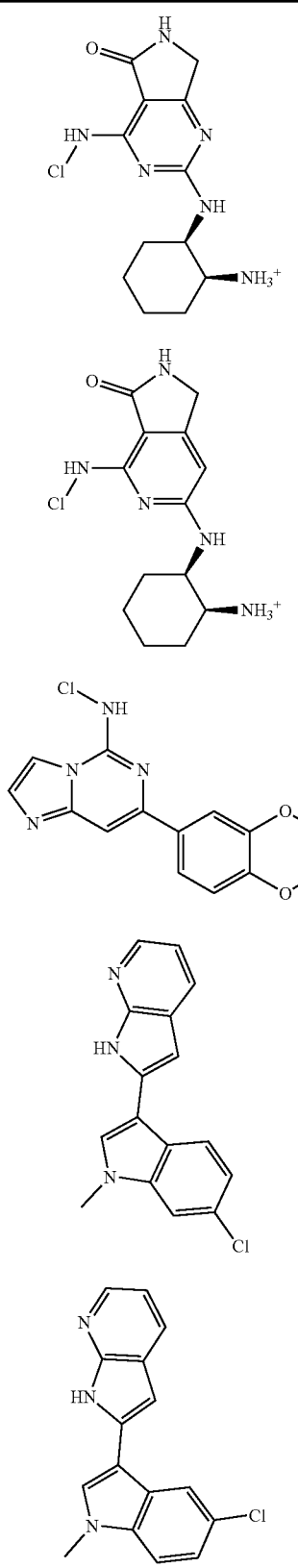

TABLE 2-continued
47 SYK BUILDING BLOCKS
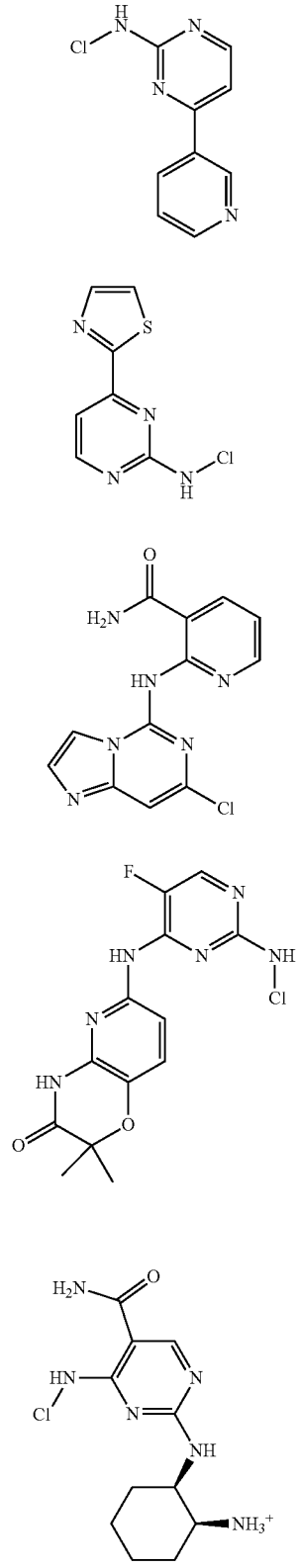
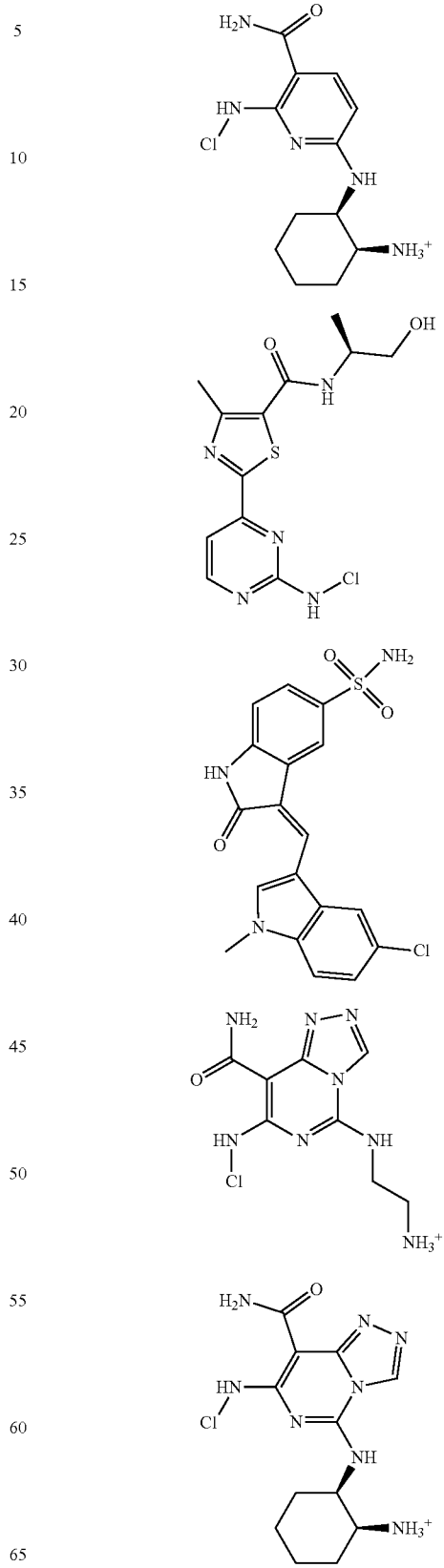

TABLE 2-continued

47 SYK BUILDING BLOCKS

TABLE 2-continued
47 SYK BUILDING BLOCKS
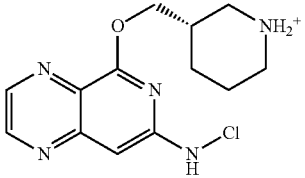 [SMILES: ClNc1cc2nccnc2c(OC[C@H]2CCC[NH2+]C2)n1]
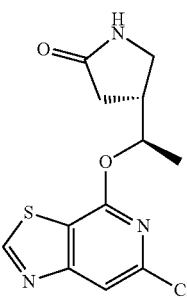
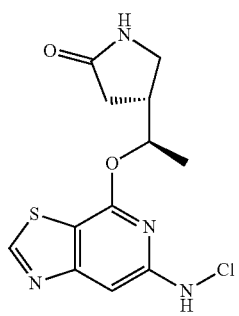 [SMILES: C[C@@H](Oc1nc(NCl)cc2ncsc12)[C@H]1CNC(=O)C1]
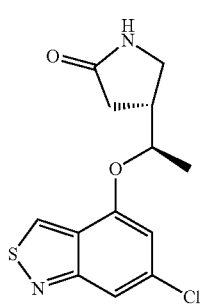 [SMILES: C[C@@H](Oc1cc(Cl)cc2nscc12)[C@H]1CNC(=O)C1]
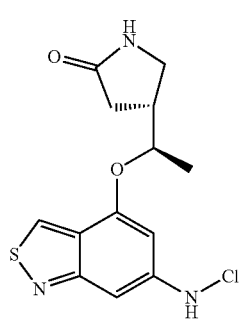 [SMILES: C[C@@H](Oc1cc(NCl)cc2nscc12)[C@H]1CNC(=O)C1]
TABLE 2-continued
47 SYK BUILDING BLOCKS
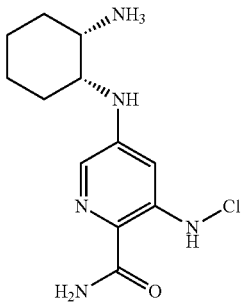 [SMILES: NC(=O)c1ncc(N[C@@H]2CCCC[C@@H]2N)cc1NCl]
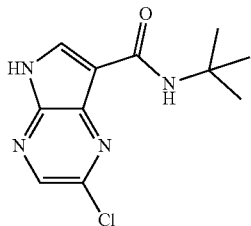 [SMILES: CC(C)(C)NC(=O)c1c[nH]c2ncc(Cl)nc12]
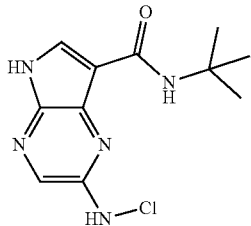 [SMILES: CC(C)(C)NC(=O)c1c[nH]c2ncc(NCl)nc12]
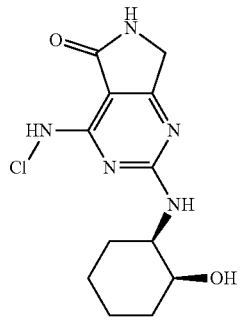 [SMILES: O=C1NCc2nc(N[C@@H]3CCCC[C@@H]3O)nc(NCl)c21]
TABLE 3
82 TP-BASED BUILDING BLOCKS
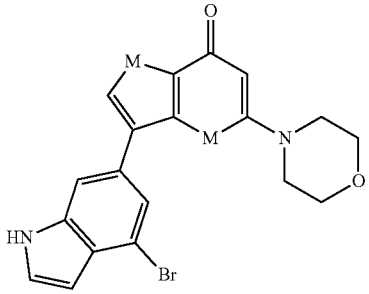

TABLE 3-continued
82 TP-BASED BUILDING BLOCKS
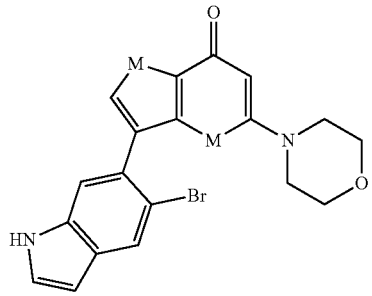
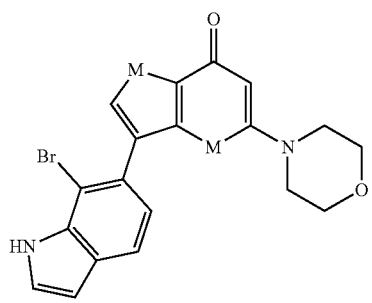
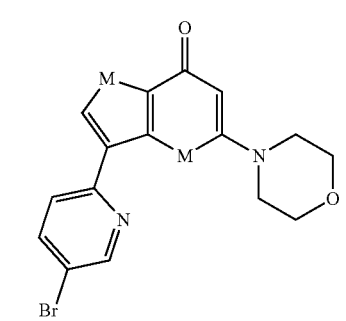
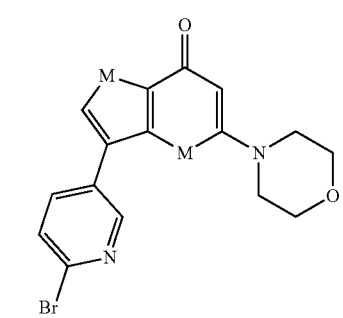
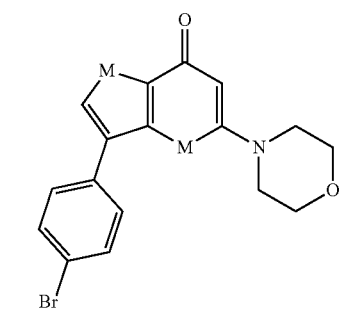
TABLE 3-continued
82 TP-BASED BUILDING BLOCKS
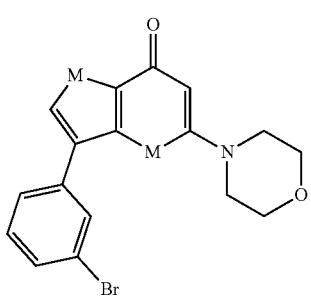
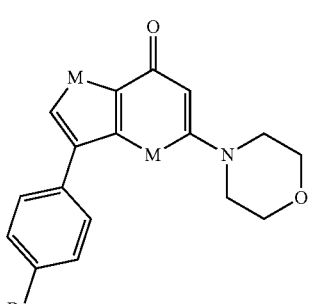
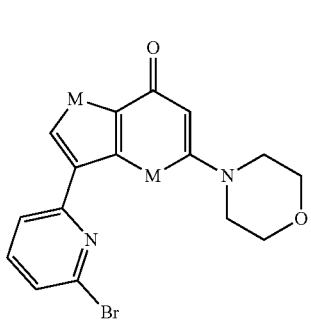
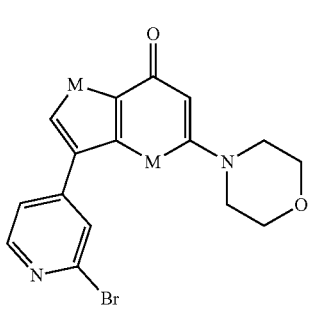
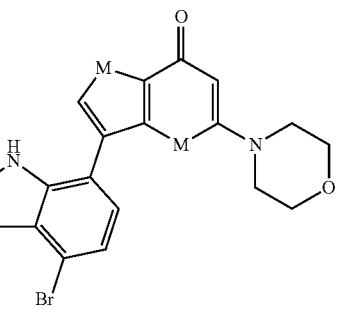

TABLE 3-continued
82 TP-BASED BUILDING BLOCKS
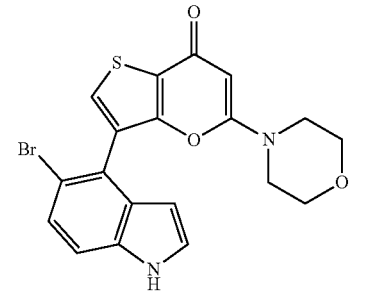 [SMILES: O=c1cc(N2CCOCC2)oc2c(-c3c(Br)ccc4[nH]ccc34)csc12]
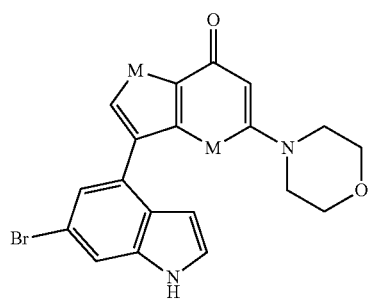
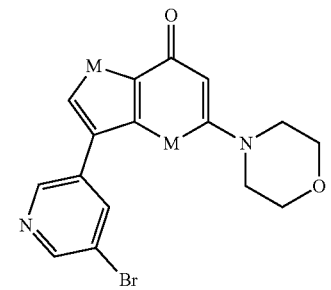
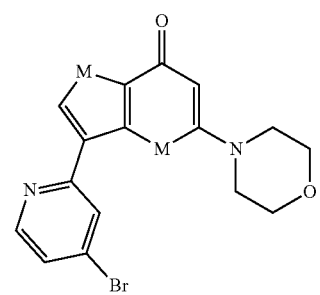
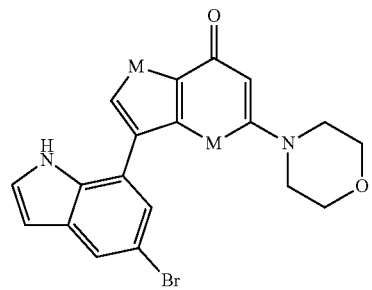
TABLE 3-continued
82 TP-BASED BUILDING BLOCKS
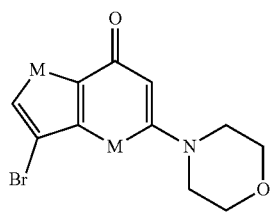
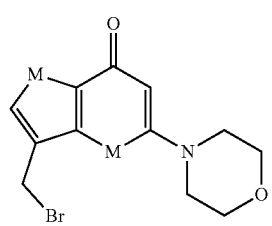
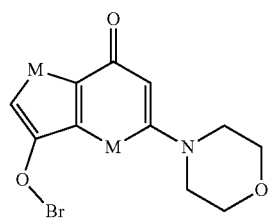
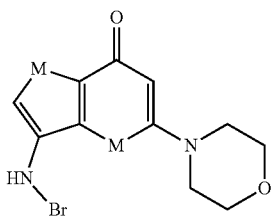
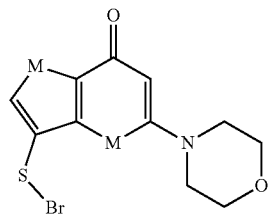
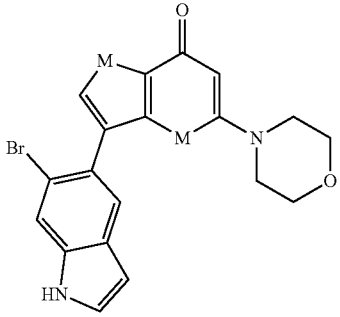

TABLE 3-continued
82 TP-BASED BUILDING BLOCKS
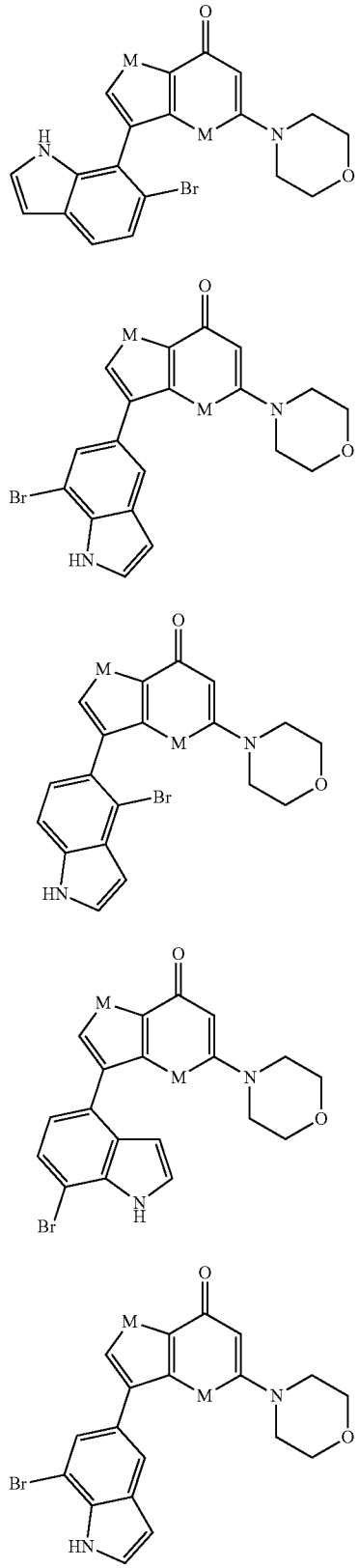
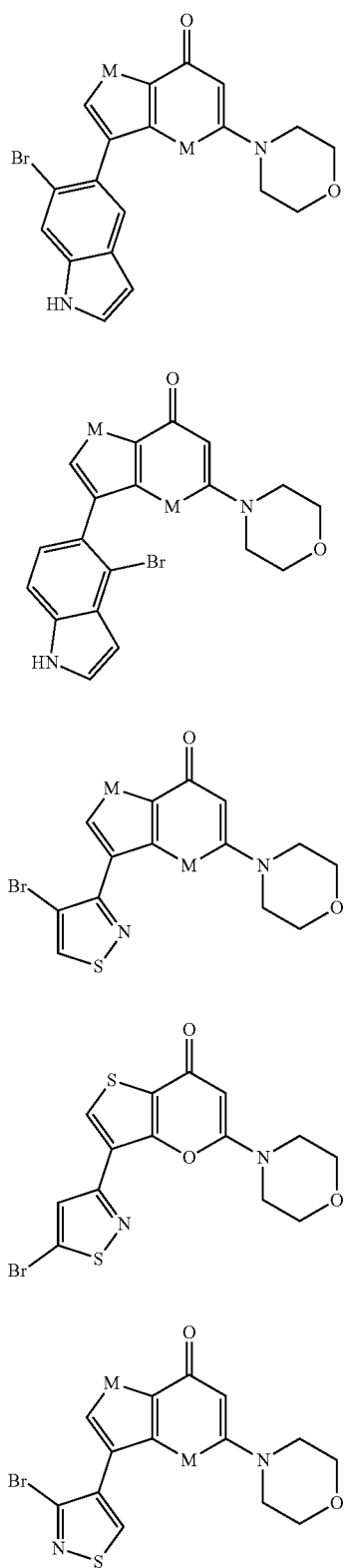

TABLE 3-continued
82 TP-BASED BUILDING BLOCKS
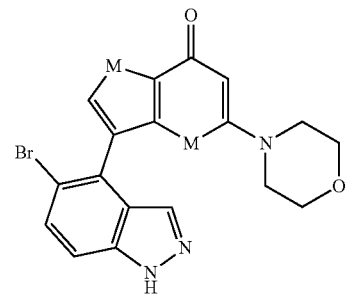
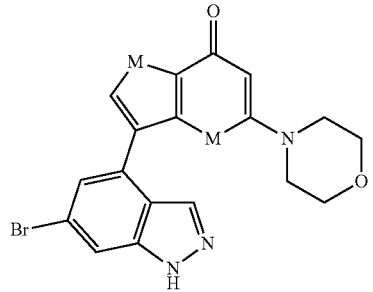
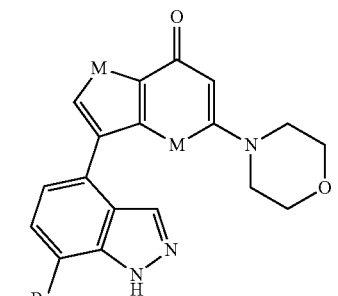
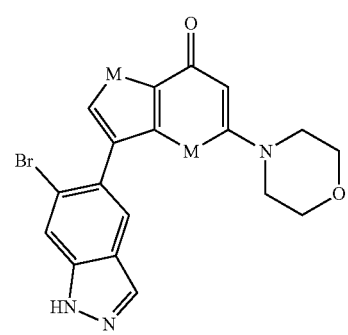
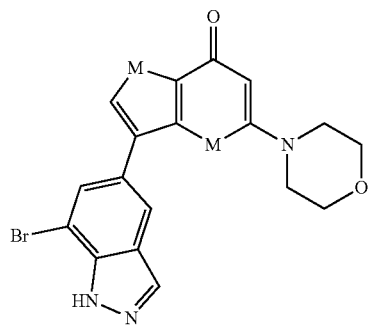
TABLE 3-continued
82 TP-BASED BUILDING BLOCKS
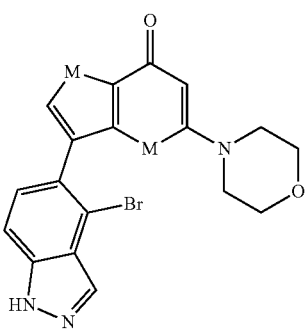
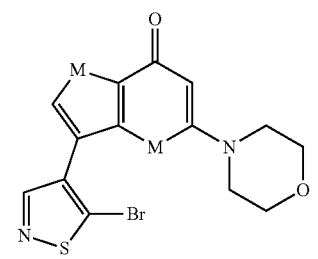
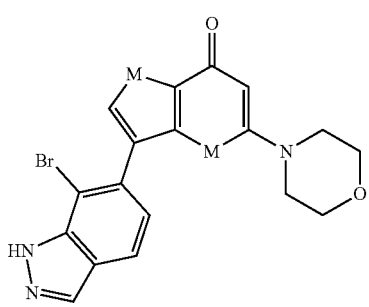
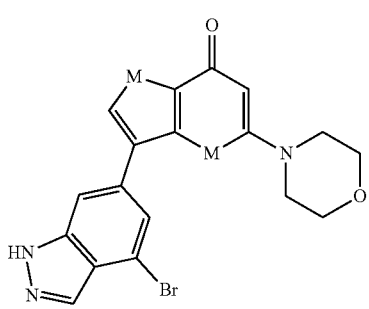
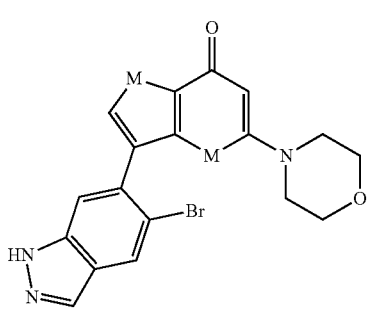

TABLE 3-continued
82 TP-BASED BUILDING BLOCKS
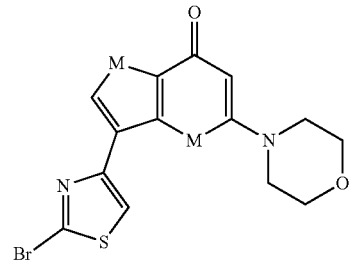
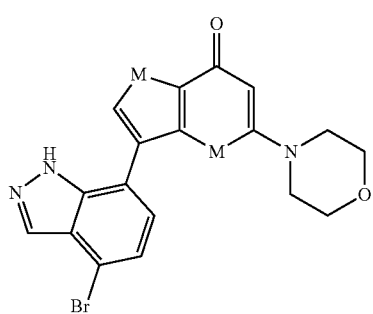
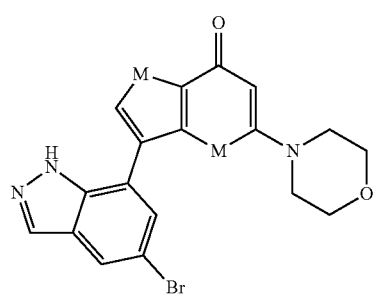
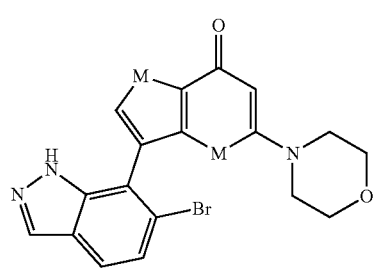
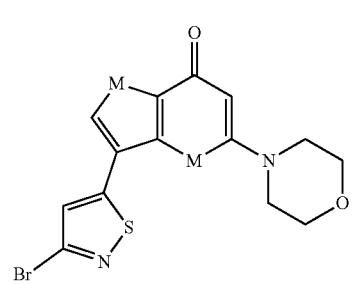
TABLE 3-continued
82 TP-BASED BUILDING BLOCKS
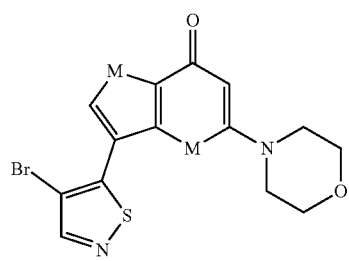
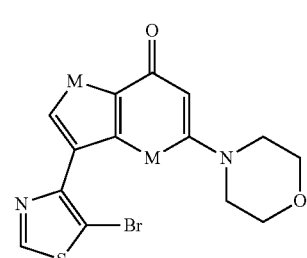
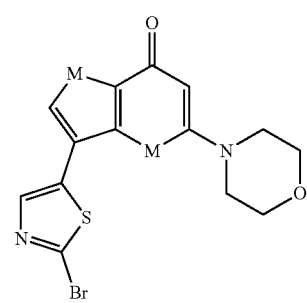
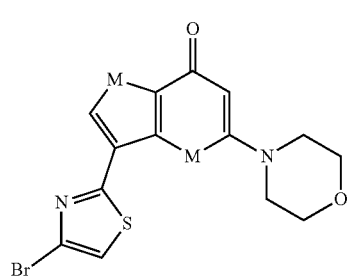
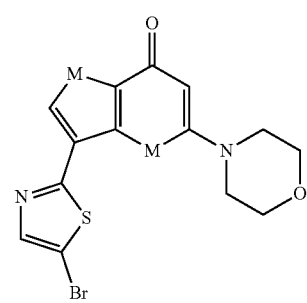

TABLE 3-continued
82 TP-BASED BUILDING BLOCKS
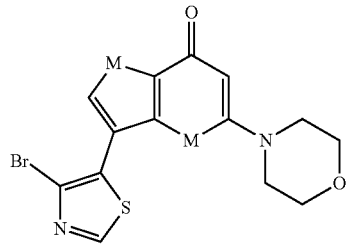
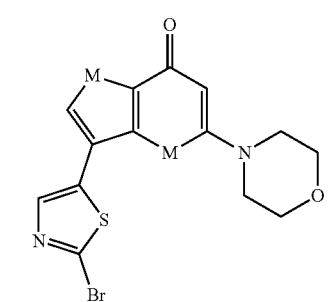
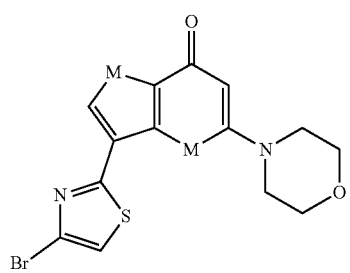
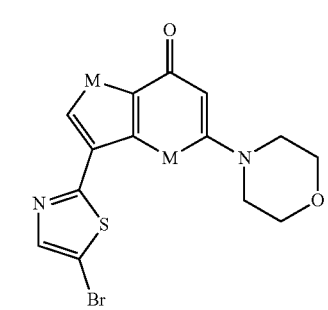
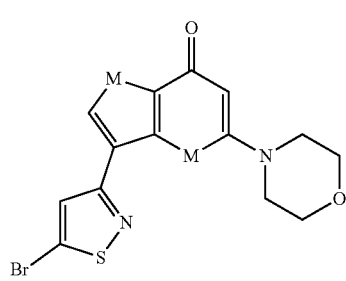
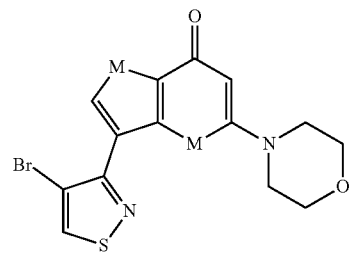
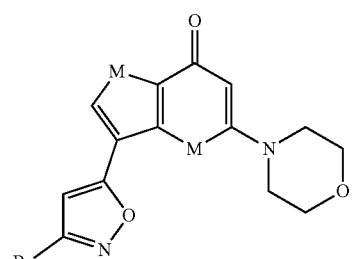
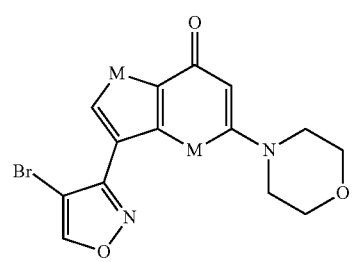
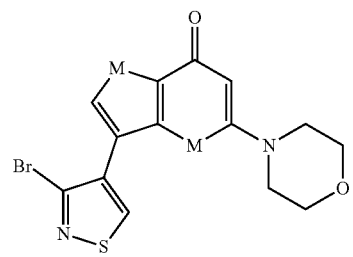
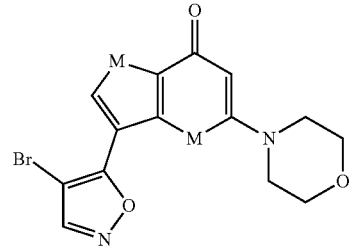
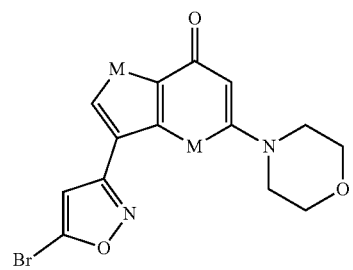

TABLE 3-continued
82 TP-BASED BUILDING BLOCKS
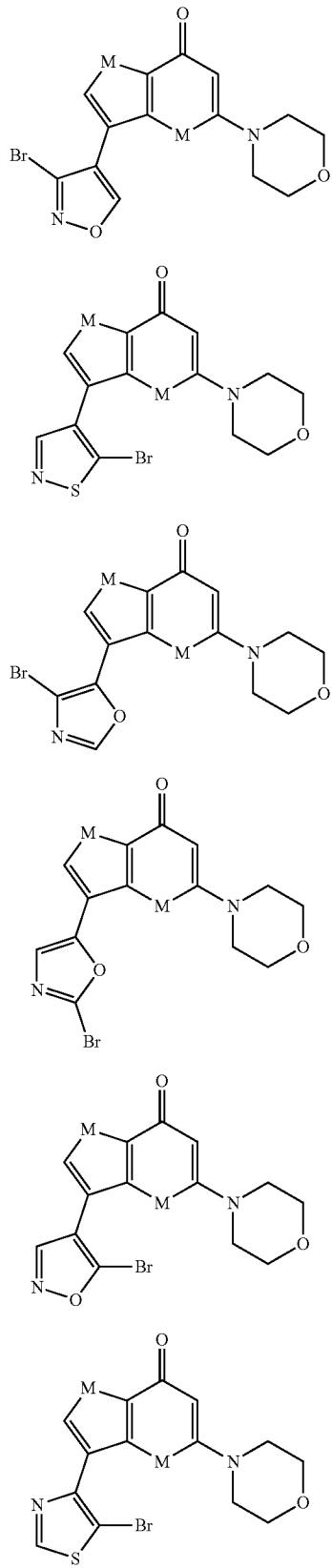
TABLE 3-continued
82 TP-BASED BUILDING BLOCKS
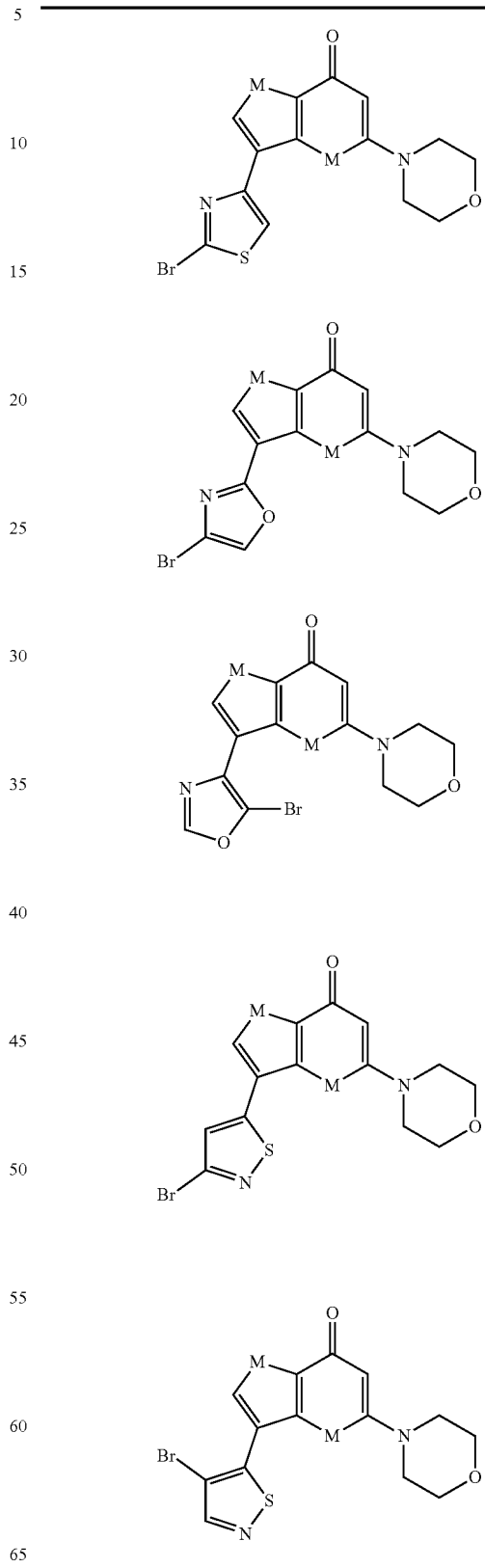

TABLE 3-continued
82 TP-BASED BUILDING BLOCKS
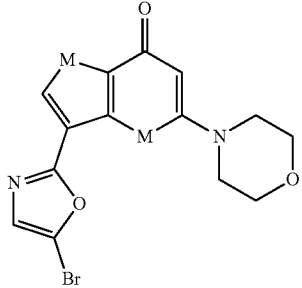
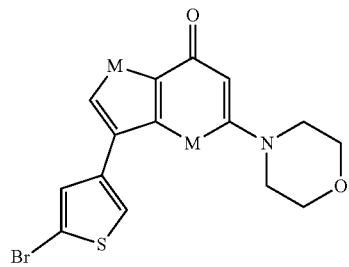
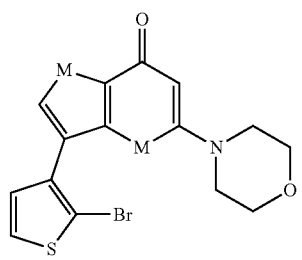
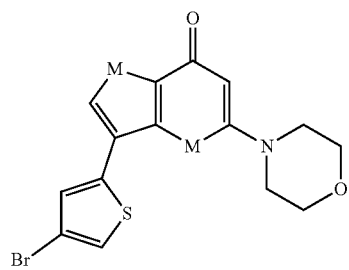
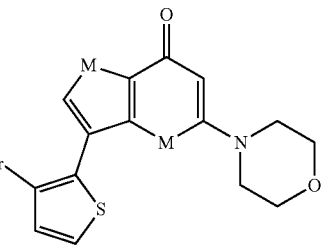
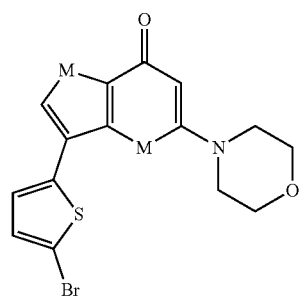
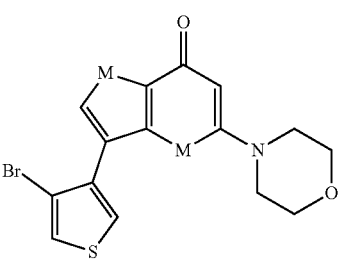
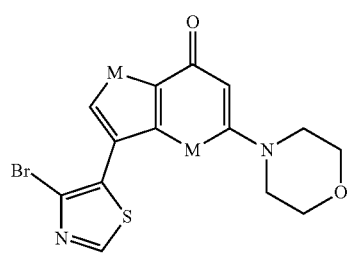

TABLE 4

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 47 | 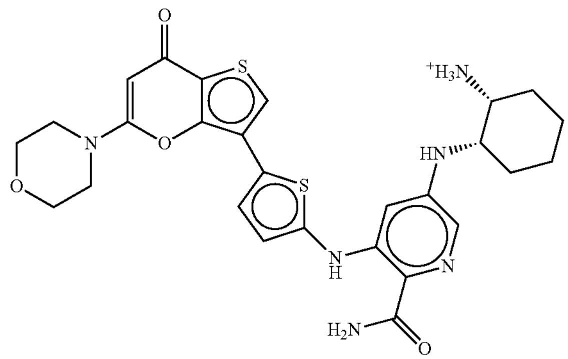 | 567.70 | −89.72 | −69.92 | −66.39 | −68.32 |
| 48 | 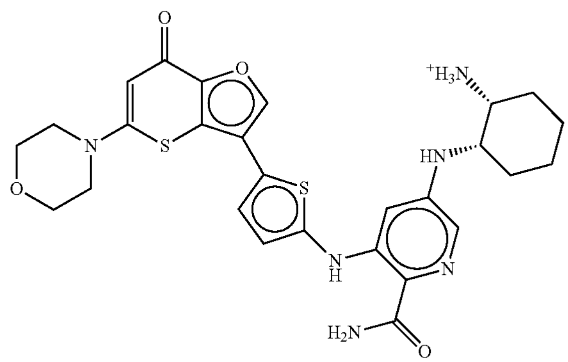 | 567.70 | −89.63 | −68.33 | −55.69 | −75.11 |
| 49 | 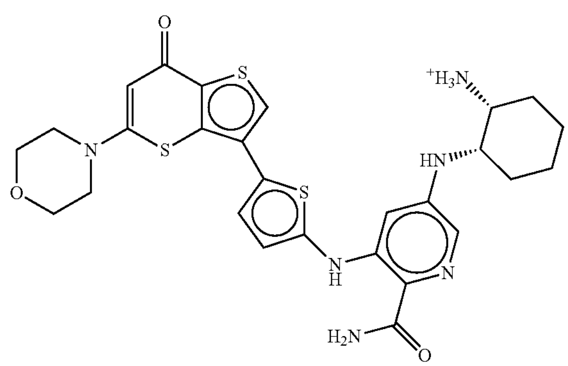 | 583.77 | −88.95 | −76.61 | −46.64 | −76.71 |
| 50 | 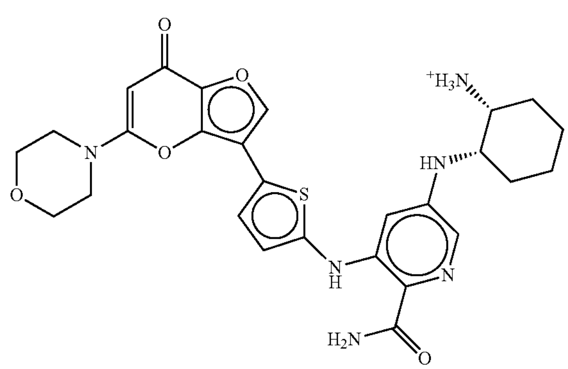 | 551.64 | −88.50 | −77.89 | −70.51 | −71.51 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 51 | 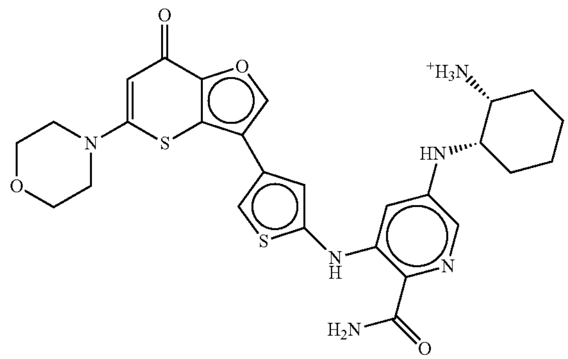 | 567.70 | −81.97 | −62.54 | −55.79 | −77.22 |
| 52 | 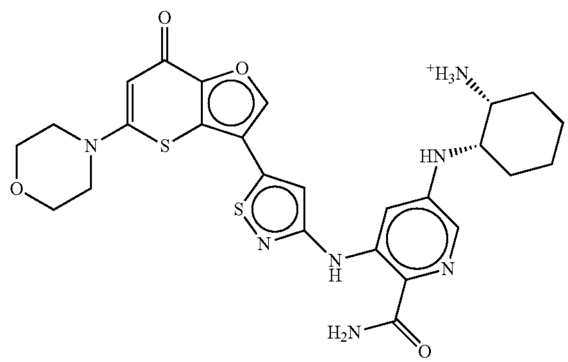 | 568.69 | −81.29 | −69.38 | −60.95 | −69.22 |
| 53 | 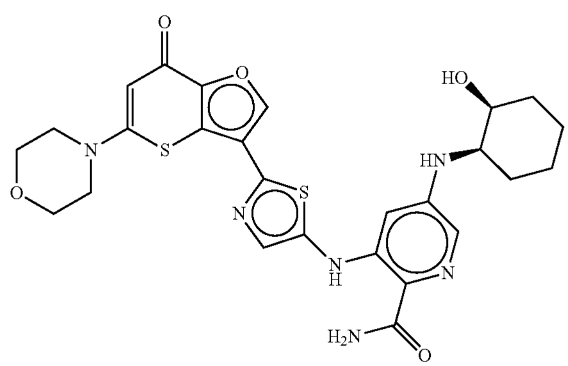 | 568.67 | −80.56 | −74.08 | −65.89 | −68.82 |
| 54 | 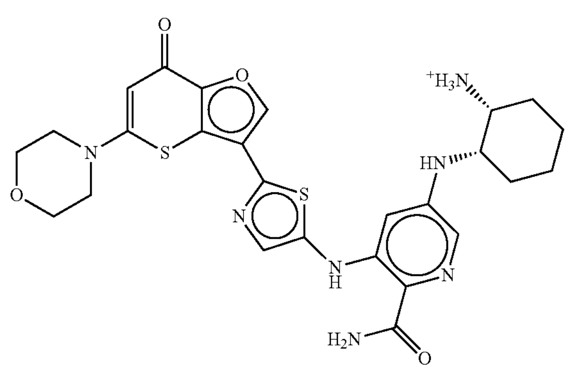 | 568.69 | −80.14 | −62.25 | −65.73 | −45.08 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 55 | 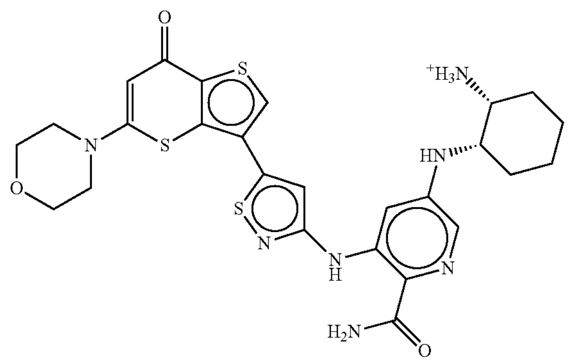 | 584.76 | −79.21 | −64.00 | −60.73 | −65.52 |
| 56 | 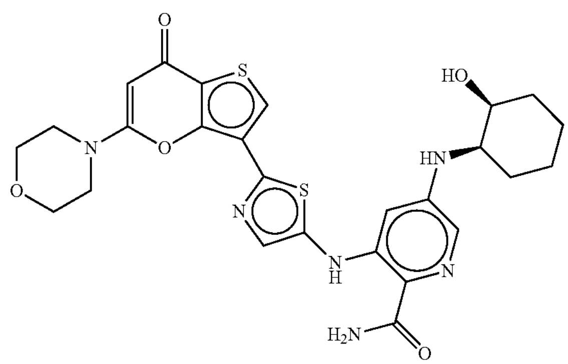 | 568.67 | −79.20 | −73.45 | −70.03 | −72.16 |
| 57 | 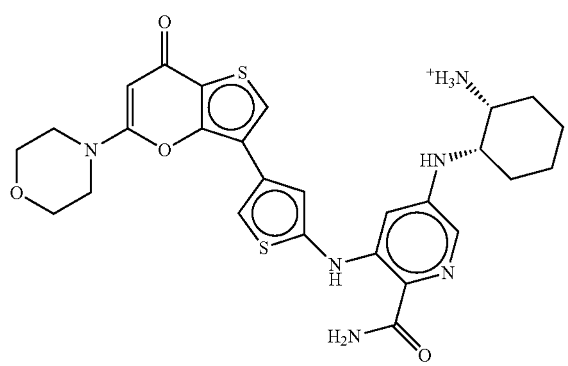 | 567.70 | −78.57 | −74.14 | −60.74 | −65.89 |
| 58 | 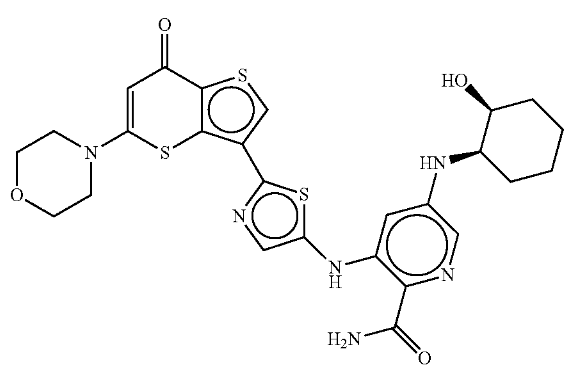 | 584.73 | −76.16 | −74.34 | −56.51 | −63.42 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 59 | 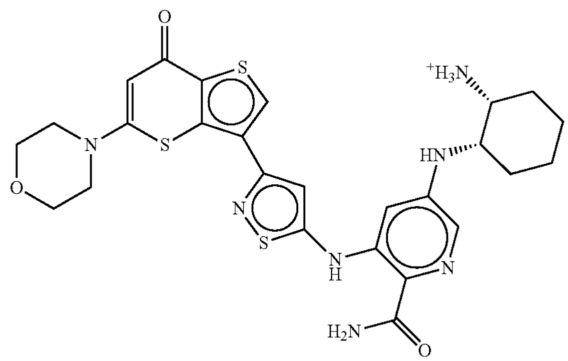 | 584.76 | −75.68 | −62.34 | −53.55 | −74.15 |
| 60 | 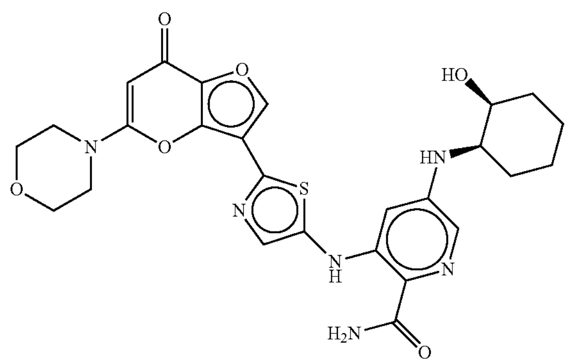 | 552.60 | −74.90 | −76.66 | −62.77 | −76.64 |
| 61 | 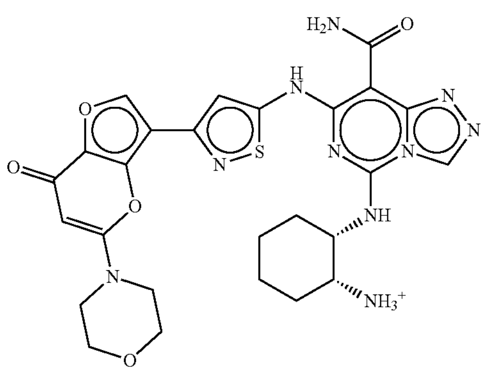 | 593.64 | −74.22 | −61.26 | −49.36 | −60.73 |
| 62 | 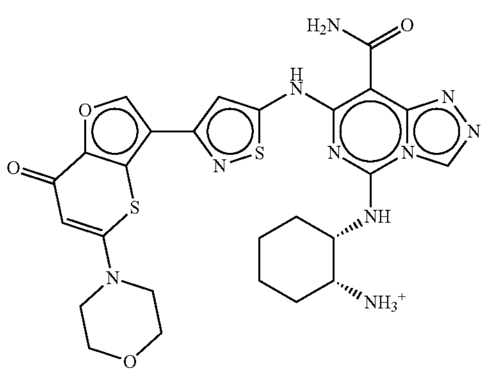 | 609.70 | −73.78 | −61.83 | −59.44 | −53.88 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 63 | 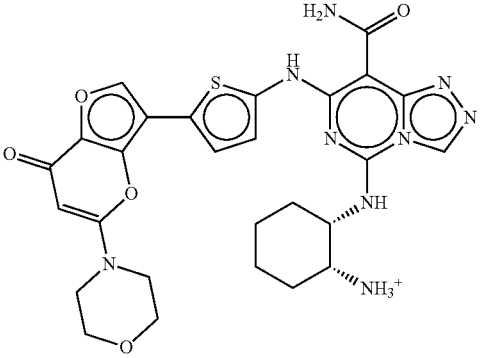 | 592.65 | −73.11 | −50.53 | −56.41 | −49.43 |
| 64 | 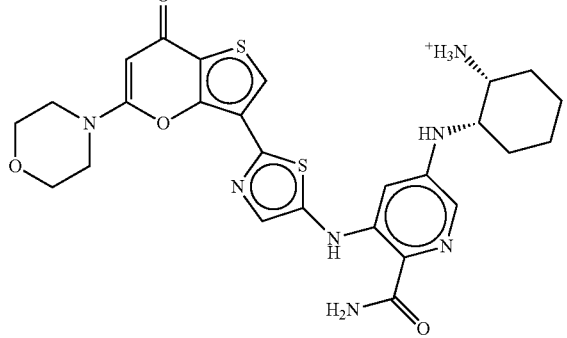 | 568.69 | −72.13 | −64.31 | −68.75 | −68.23 |
| 65 | 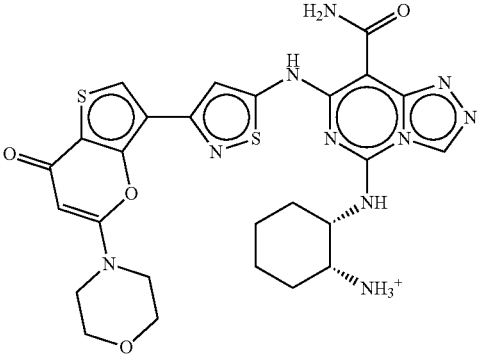 | 609.70 | −72.01 | −43.27 | −40.77 | −72.45 |
| 66 | 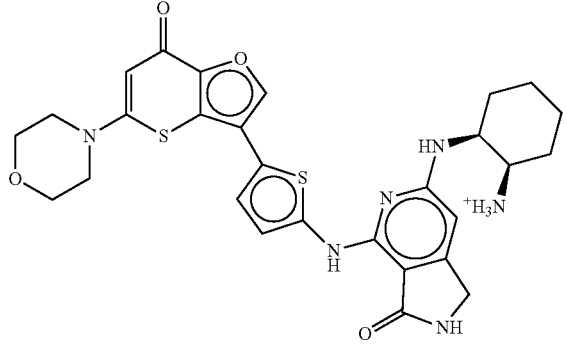 | 579.71 | −71.63 | −56.41 | −55.37 | −58.34 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 67 | 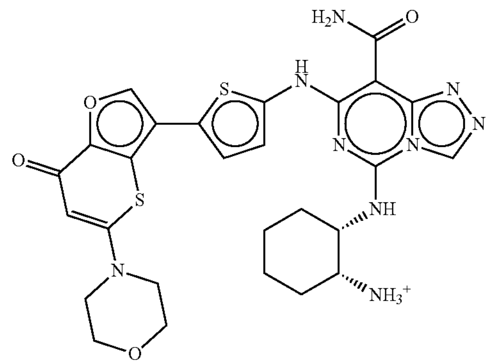 | 608.72 | −70.90 | −52.16 | −41.40 | −49.61 |
| 68 | 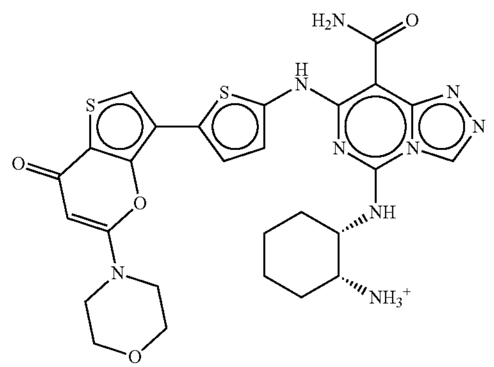 | 608.72 | −70.85 | −57.87 | −56.92 | −58.56 |
| 69 | 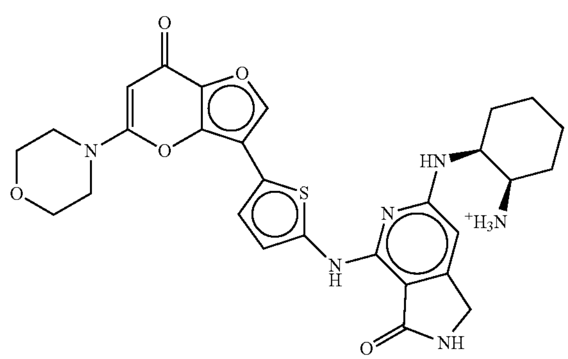 | 563.65 | −69.93 | −65.03 | −55.66 | −65.90 |
| 70 | 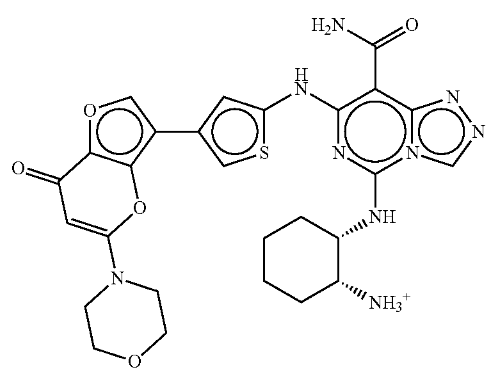 | 592.65 | −69.52 | −60.31 | −49.68 | −57.31 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 71 | 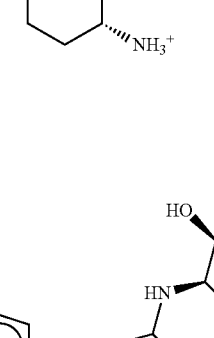 | 624.78 | −68.97 | −55.96 | −46.24 | −52.14 |
| 72 | 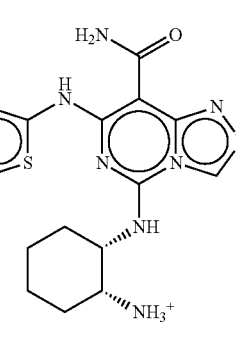 | 551.61 | −68.10 | −60.94 | −56.01 | −55.55 |
| 73 | 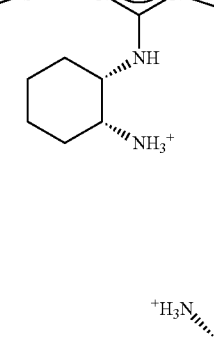 | 624.78 | −67.57 | −44.08 | −52.96 | −50.92 |
| 74 | 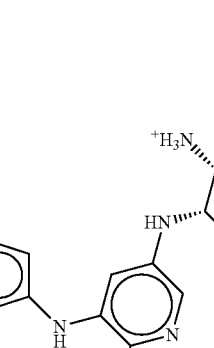 | 552.63 | −67.51 | −45.96 | −46.06 | −59.95 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 75 | 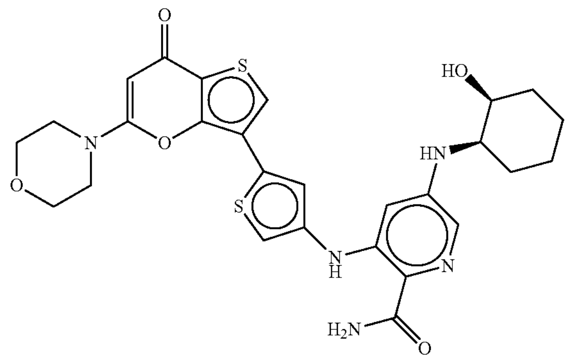 | 567.68 | −67.03 | −47.57 | −55.13 | −56.72 |
| 76 | 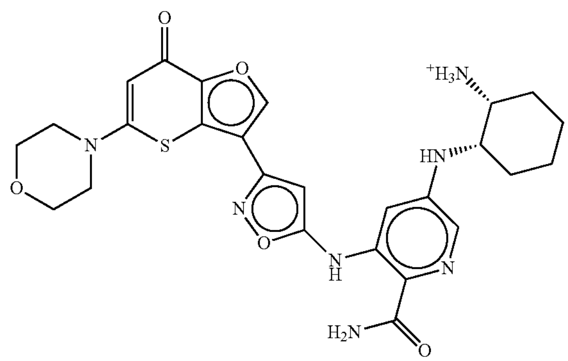 | 552.63 | −67.00 | −55.13 | −44.59 | −56.02 |
| 77 | 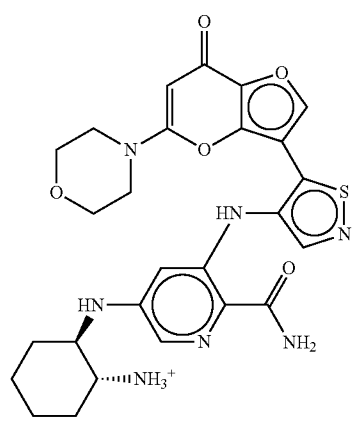 | 552.63 | −66.22 | −66.02 | −54.43 | −68.99 |
| 78 | 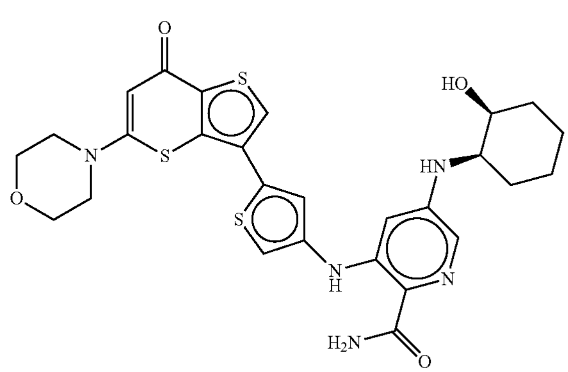 | 583.75 | −65.99 | −56.73 | −52.98 | −61.30 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 79 | 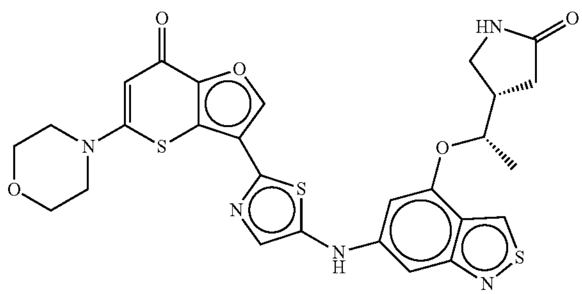 | 595.71 | −64.29 | −61.52 | −52.37 | −70.60 |
| 80 | 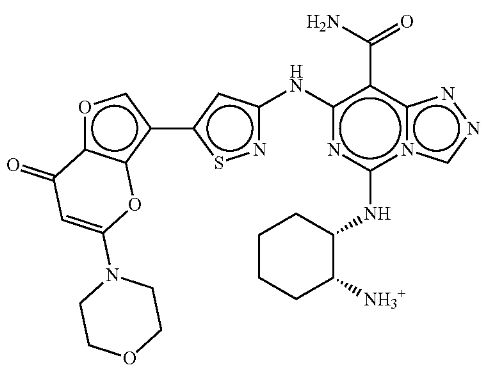 | 593.64 | −63.19 | −62.12 | −40.65 | −50.92 |
| 81 | 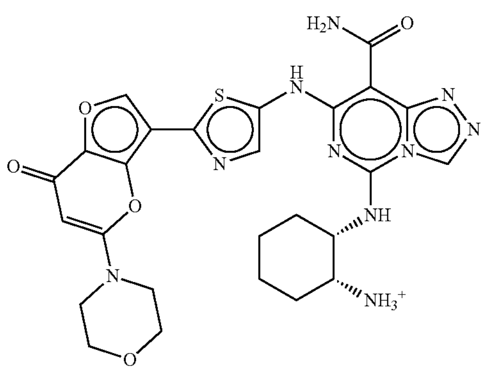 | 593.64 | −62.80 | −44.85 | −36.44 | −50.17 |
| 82 | 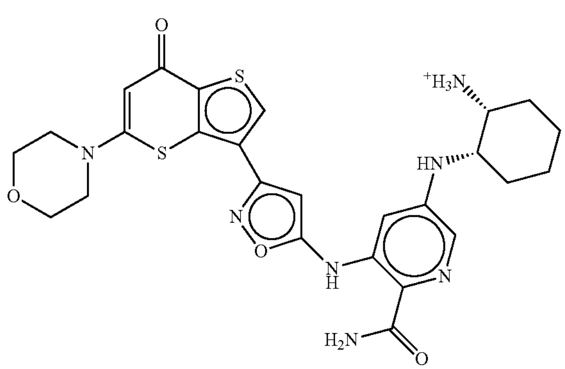 | 568.69 | −62.74 | −51.03 | −33.53 | −40.80 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 83 | 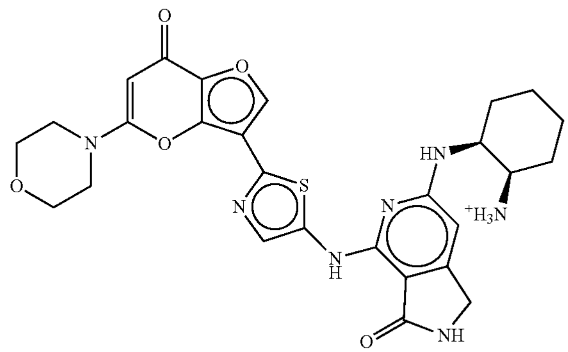 | 564.64 | −62.62 | −55.21 | −48.74 | −58.10 |
| 84 | 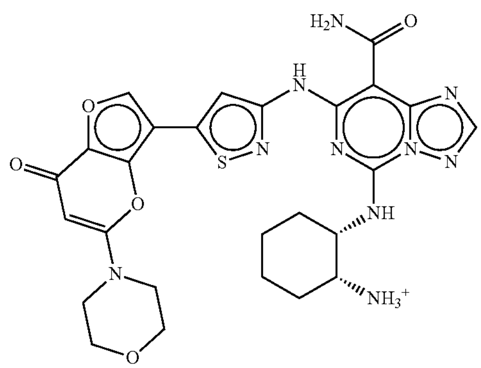 | 593.64 | −62.50 | −45.10 | −37.65 | −52.13 |
| 85 | 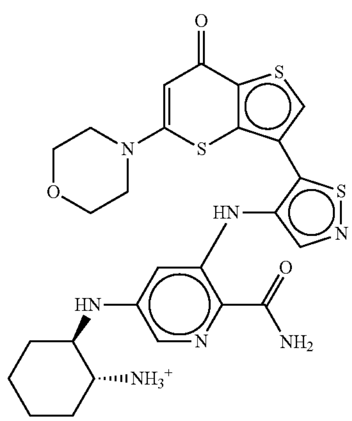 | 584.76 | −61.69 | −59.21 | −54.91 | −67.91 |
| 86 | 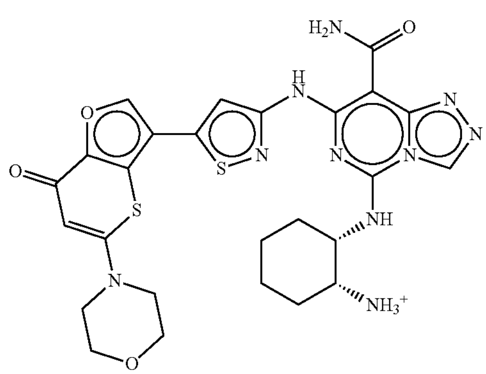 | 609.70 | −61.60 | −43.61 | −45.94 | −39.78 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 87 | 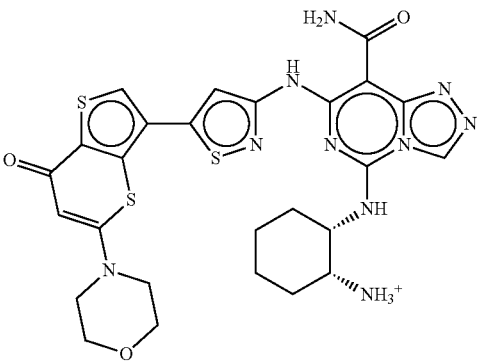 | 625.77 | −61.52 | −46.07 | −48.88 | −47.16 |
| 88 | 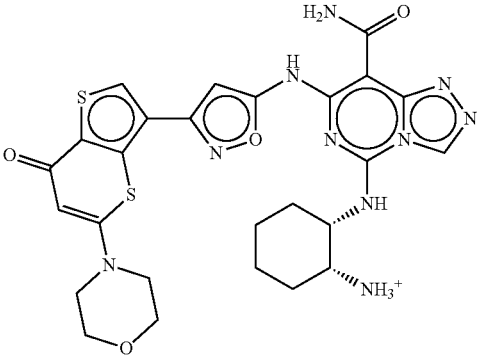 | 609.70 | −61.07 | −37.68 | −38.63 | −45.60 |
| 89 | 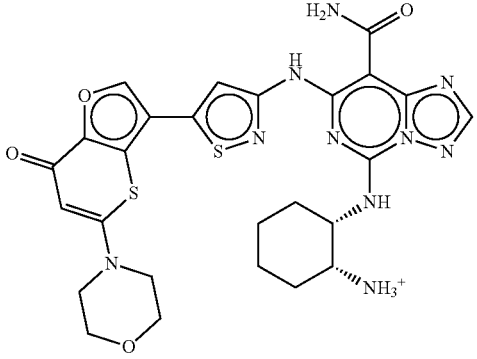 | 609.70 | −60.66 | −43.80 | −35.71 | −48.32 |
| 90 | 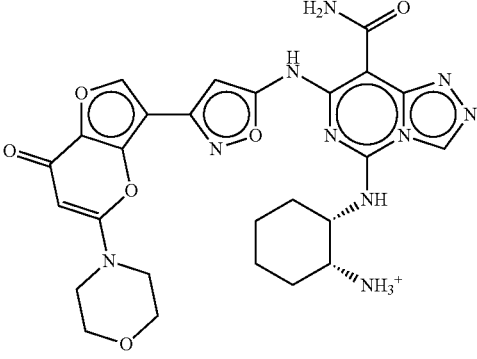 | 577.57 | −60.64 | −46.76 | −44.06 | −49.09 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 91 | 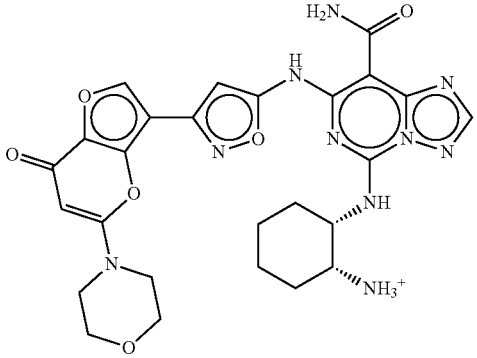 | 577.57 | −60.53 | −46.90 | −51.79 | −57.04 |
| 92 | 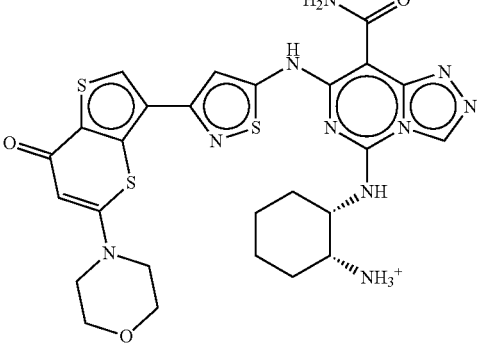 | 625.77 | −60.44 | −51.57 | −33.12 | −49.16 |
| 93 | 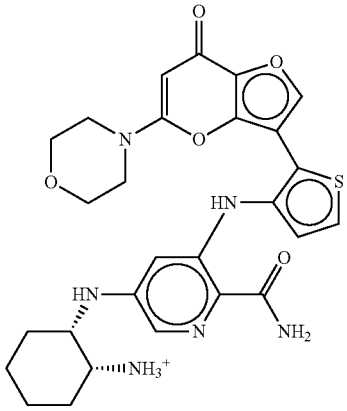 | 551.64 | −60.09 | −43.90 | −56.34 | −54.01 |
| 94 | 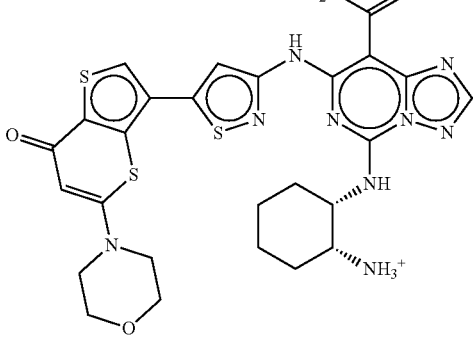 | 625.77 | −59.91 | −39.80 | −36.80 | −56.01 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 95 | 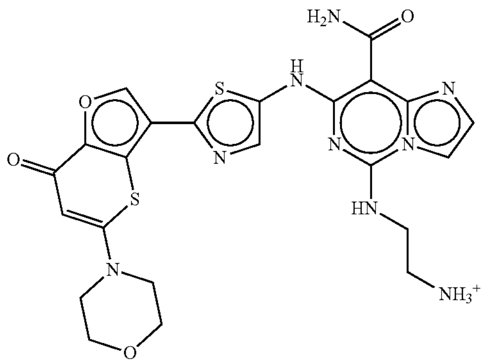 | 554.63 | −59.77 | −46.75 | −35.52 | −57.53 |
| 96 | 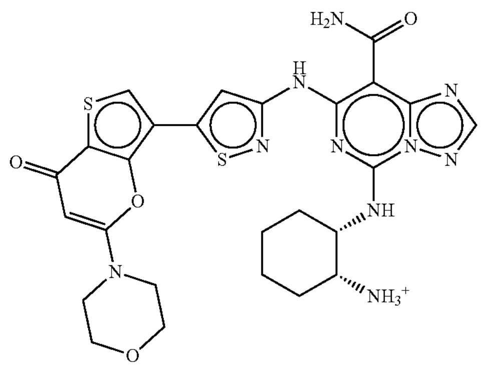 | 609.70 | −59.64 | −48.88 | −27.52 | −59.23 |
| 97 | 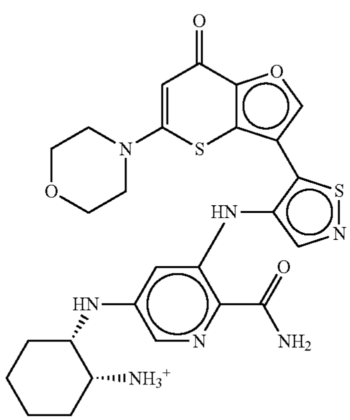 | 568.69 | −59.42 | −62.21 | −46.65 | −57.55 |
| 98 | 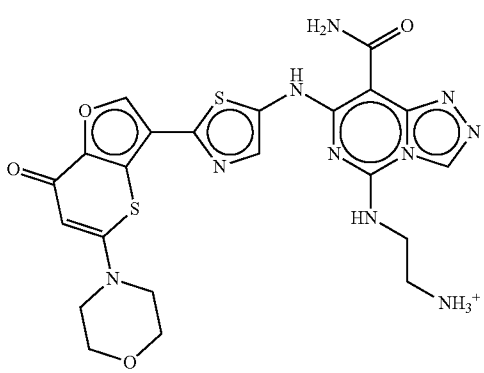 | 555.61 | −59.22 | −46.75 | −43.38 | −47.20 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 99 | 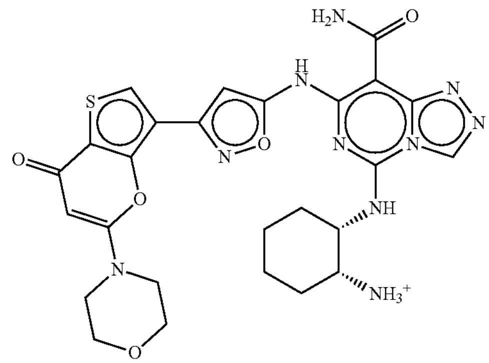 | 593.64 | −59.12 | −50.69 | −45.14 | −42.60 |
| 100 | 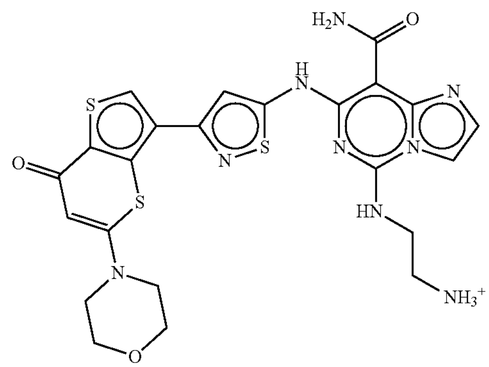 | 570.69 | −59.04 | −43.10 | −37.64 | −34.62 |
| 101 | 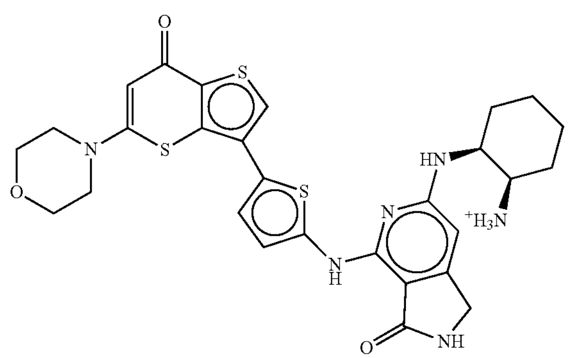 | 595.78 | −59.00 | −50.86 | −49.44 | −49.03 |
| 102 | 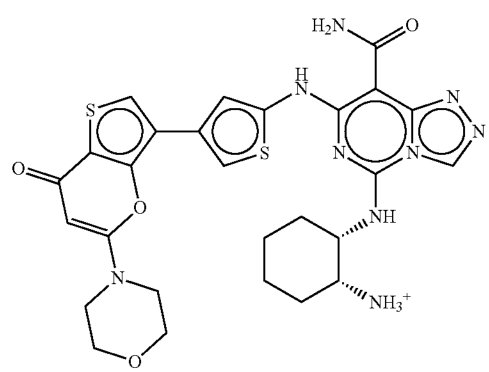 | 608.72 | −58.92 | −49.89 | −40.88 | −48.29 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 103 | 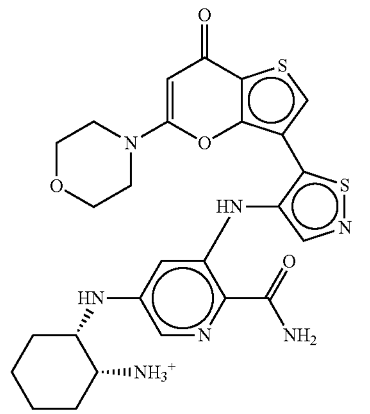 | 568.69 | −58.68 | −54.13 | −43.03 | −52.28 |
| 104 | 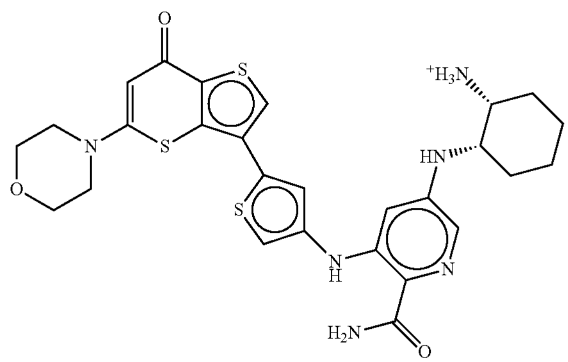 | 583.77 | −58.59 | −41.01 | −43.40 | −50.26 |
| 105 | 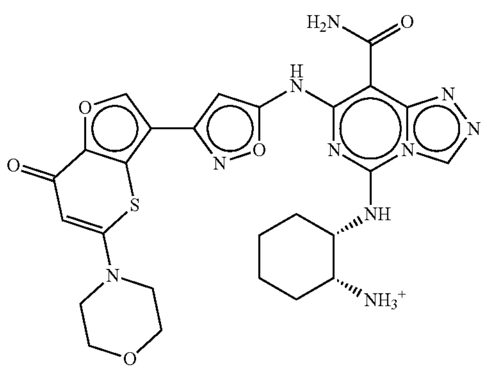 | 593.64 | −58.55 | −34.04 | −27.93 | −42.68 |
| 106 | 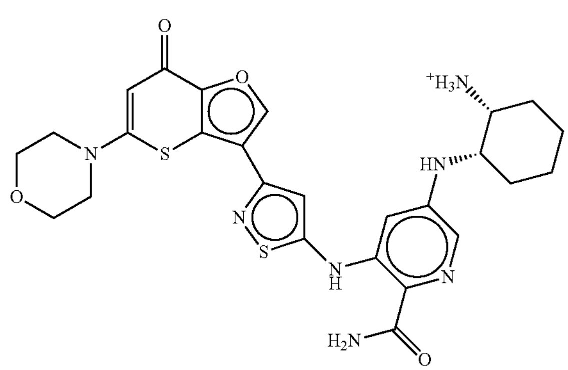 | 568.69 | −58.54 | −25.49 | −47.05 | −50.78 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 107 | 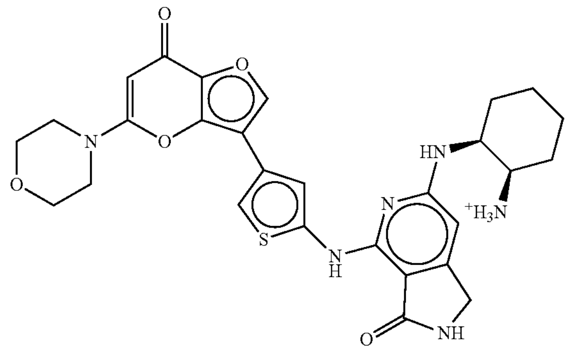 | 563.65 | −58.38 | −45.80 | −41.56 | −55.30 |
| 108 | 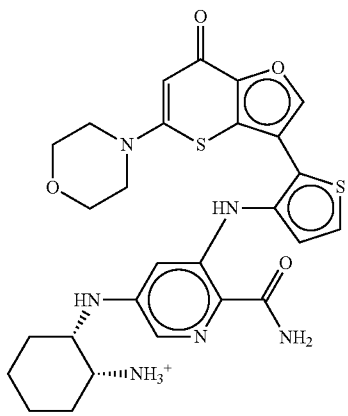 | 567.70 | −58.34 | −52.40 | −48.81 | −58.38 |
| 109 | 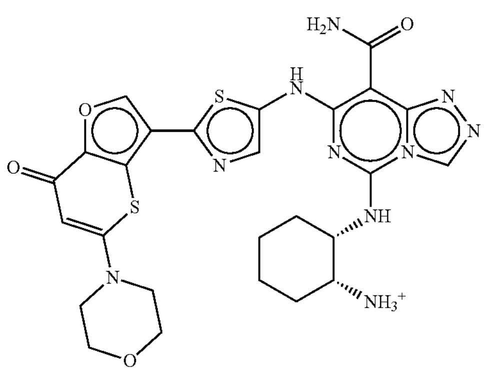 | 609.70 | −58.17 | −36.99 | −39.23 | −32.73 |
| 110 | 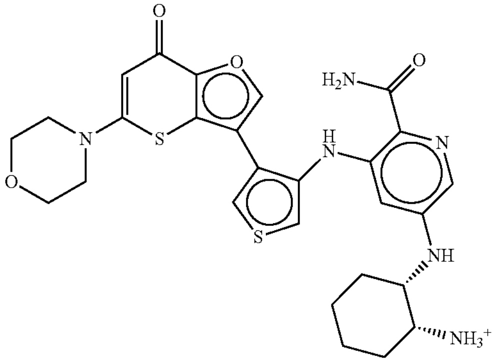 | 567.70 | −57.98 | −55.53 | −37.82 | −53.83 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 111 | 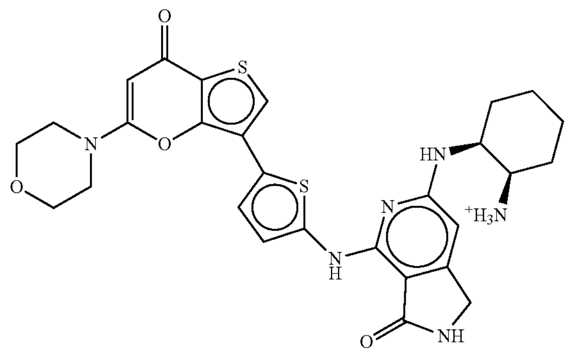 | 579.71 | −57.93 | 14.91 | −45.51 | −50.19 |
| 112 | 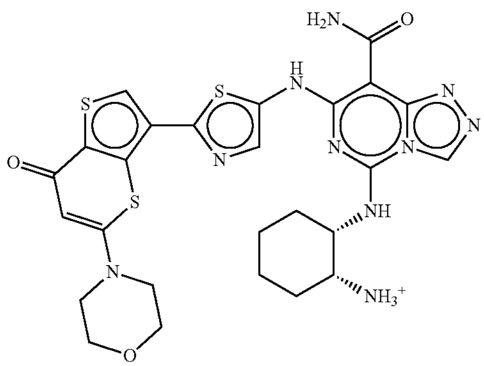 | 625.77 | −57.91 | −37.27 | −31.94 | −49.75 |
| 113 | 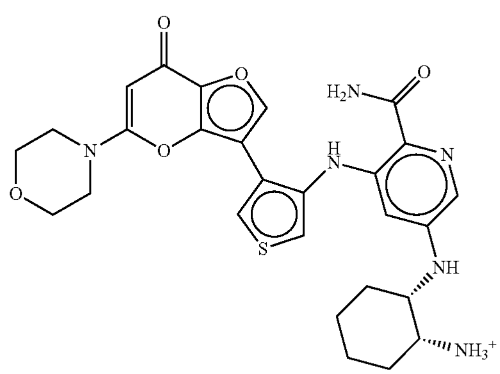 | 551.64 | −57.78 | −58.81 | −57.69 | −58.57 |
| 114 | 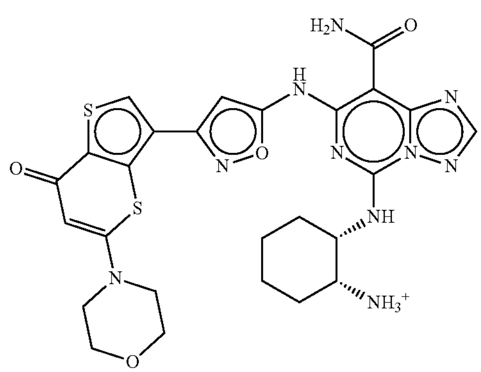 | 609.70 | −57.75 | −42.14 | −34.18 | −42.44 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 115 | 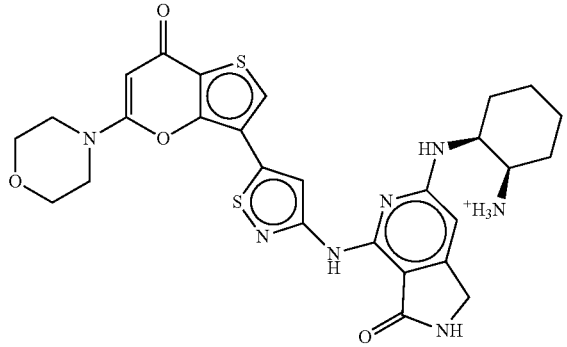 | 580.70 | −57.63 | −57.98 | −51.25 | −58.98 |
| 116 | 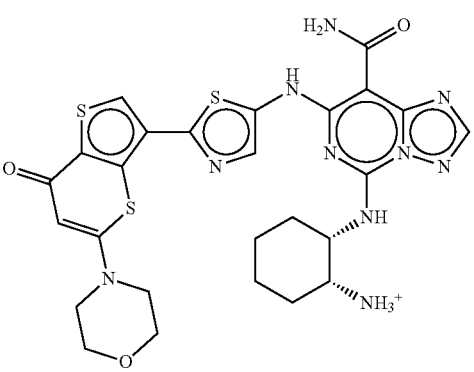 | 625.77 | −57.44 | −44.72 | −23.90 | −38.30 |
| 117 | 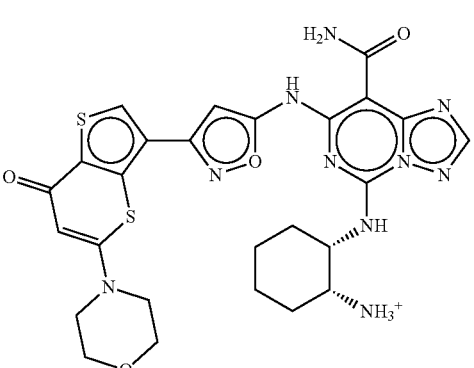 | 593.64 | −57.41 | −36.94 | −41.53 | −39.77 |
| 118 | 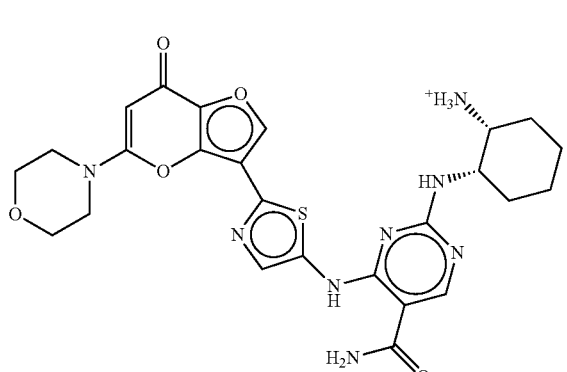 | 553.61 | −57.40 | −44.00 | −31.23 | −53.43 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 119 | 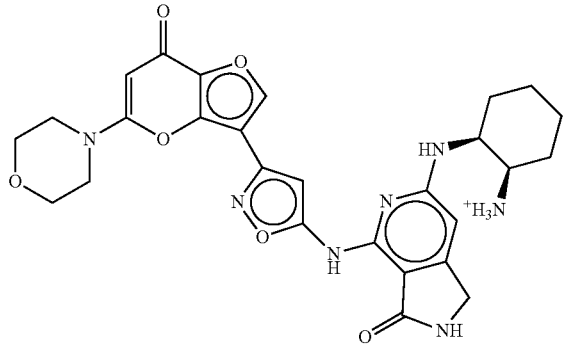 | 548.57 | −57.33 | −44.29 | −45.55 | −58.90 |
| 120 | 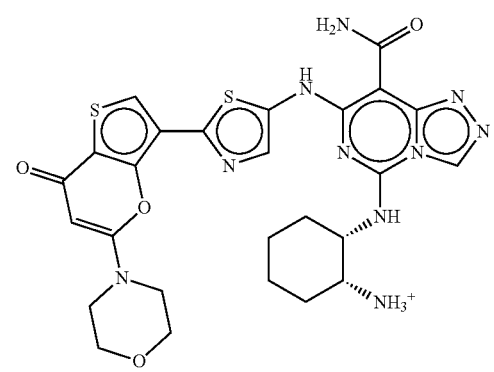 | 609.70 | −57.25 | −39.60 | −36.76 | −62.99 |
| 121 | 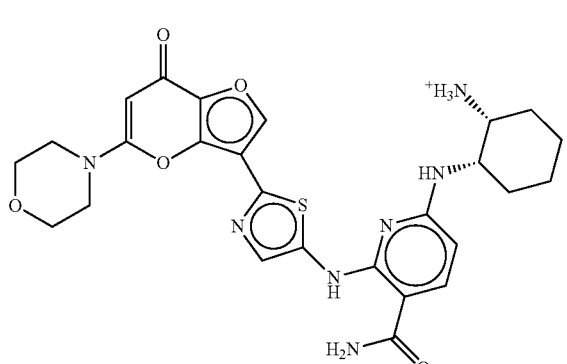 | 552.63 | −57.07 | −49.81 | −36.45 | −51.21 |
| 122 | 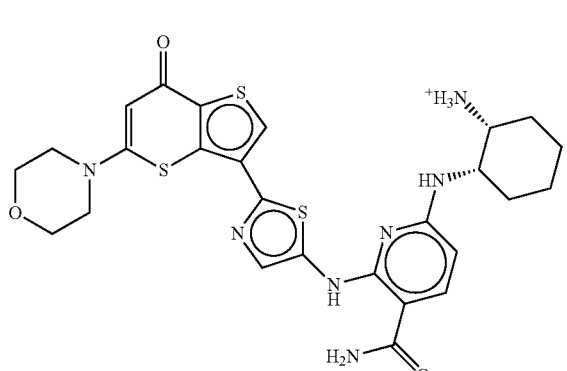 | 584.76 | −57.01 | −48.05 | −41.31 | −47.87 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 123 | 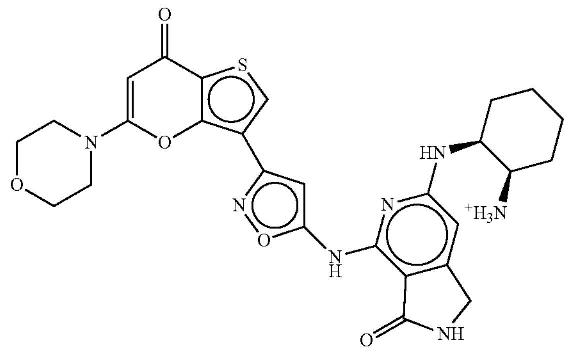 | 564.64 | −56.98 | −40.60 | −48.86 | −48.41 |
| 124 | 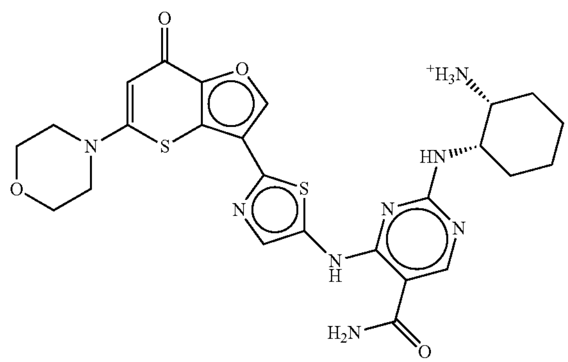 | 569.68 | −56.96 | −50.55 | −42.93 | −39.78 |
| 125 | 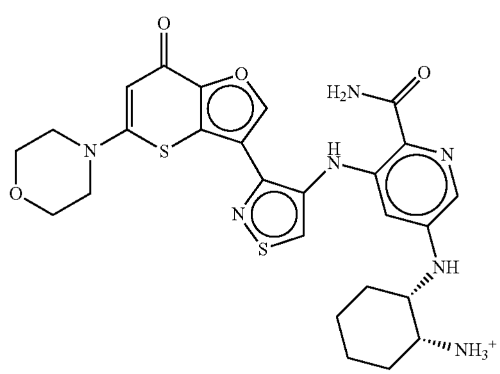 | 568.69 | −56.74 | −55.19 | −54.79 | −55.50 |
| 126 | 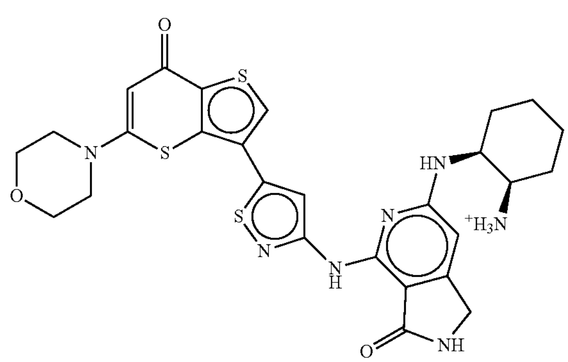 | 596.77 | −56.69 | −45.25 | −52.67 | −44.51 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 127 | 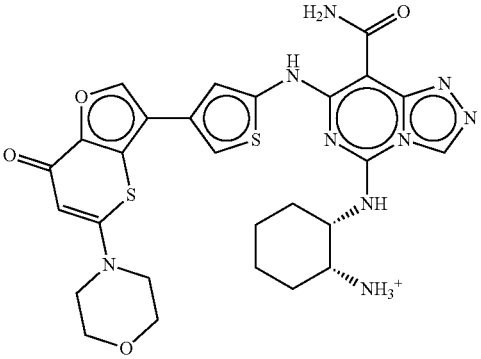 | 608.72 | −56.66 | −43.96 | −26.20 | −25.22 |
| 128 | 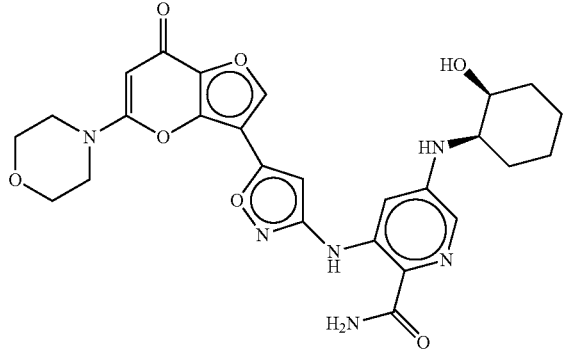 | 536.54 | −56.63 | −51.53 | −46.34 | −56.23 |
| 129 | 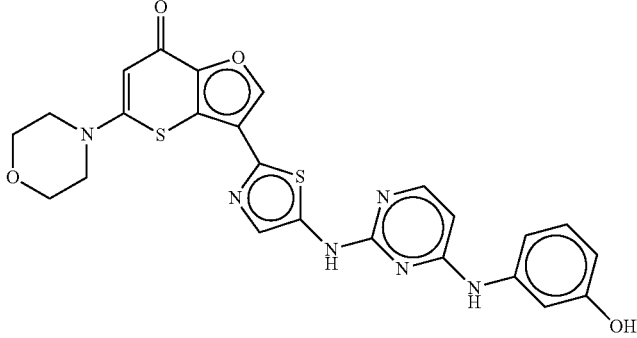 | 520.58 | −56.54 | −50.99 | −35.79 | −50.01 |
| 130 | 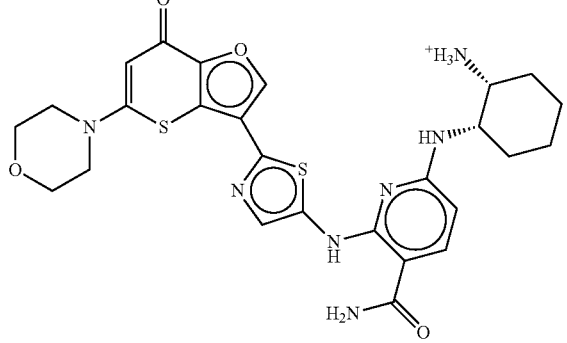 | 568.69 | −56.47 | −42.18 | −31.79 | −38.51 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 131 | 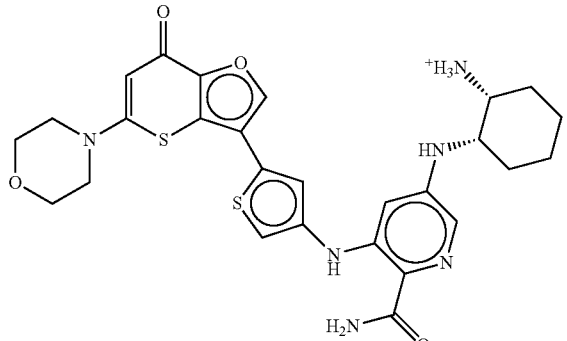 | 567.70 | −56.46 | −51.47 | −39.92 | −58.57 |
| 132 | 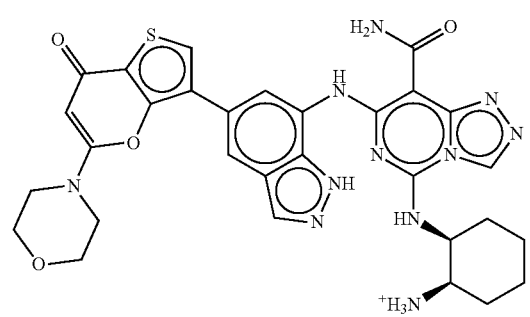 | 642.71 | −56.43 | −39.47 | −38.35 | −39.00 |
| 133 | 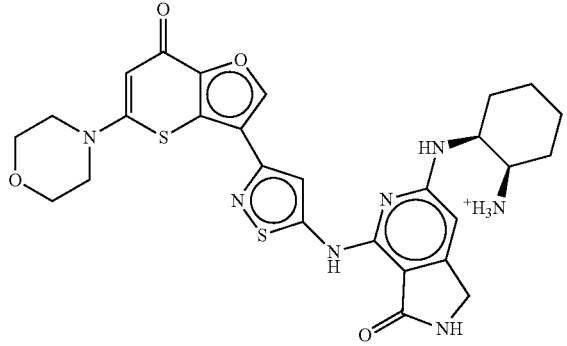 | 580.70 | −56.32 | −43.65 | −46.57 | −54.63 |
| 134 | 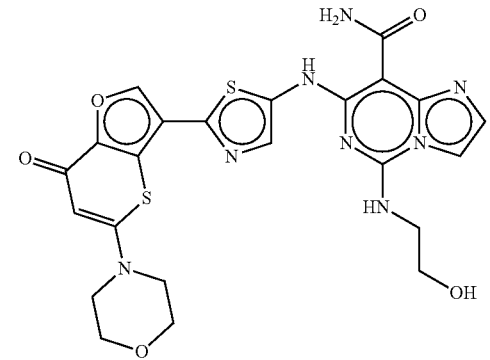 | 554.60 | −56.29 | −41.84 | −40.44 | −60.20 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 135 | 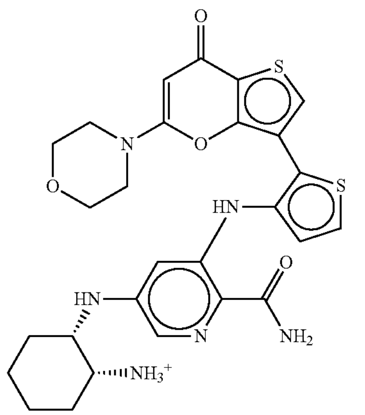 | 567.70 | −56.26 | −46.94 | −50.06 | −44.81 |
| 136 | 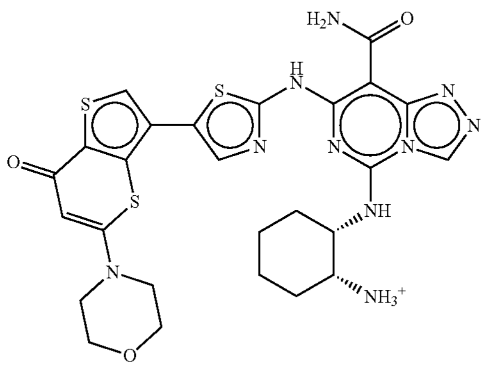 | 625.77 | −56.24 | −38.01 | −42.06 | −45.80 |
| 137 | 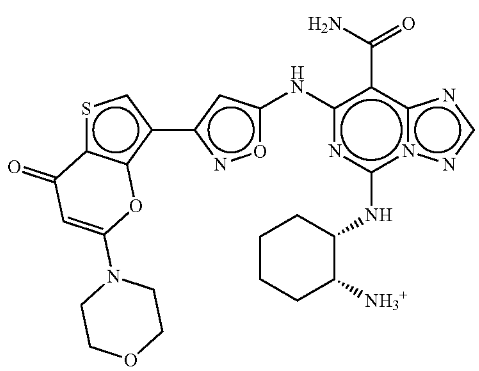 | 593.64 | −56.17 | −38.62 | −45.64 | −54.05 |
| 138 | 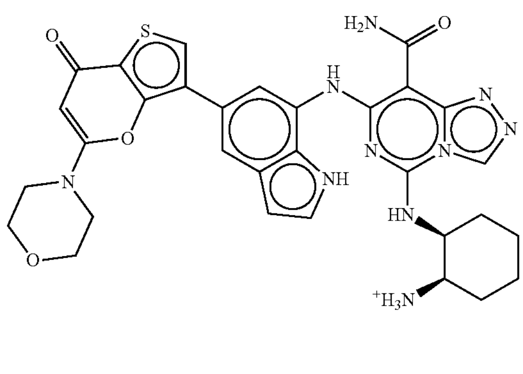 | 641.72 | −56.09 | −35.84 | −26.39 | −20.31 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 139 | 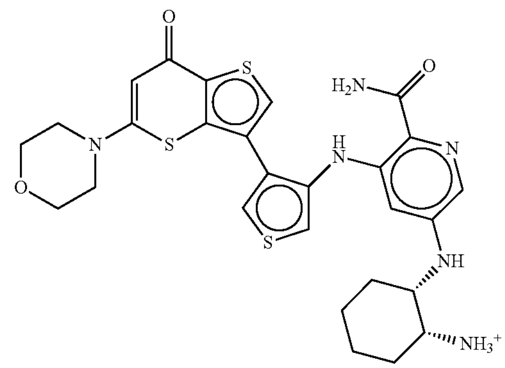 | 583.77 | −56.06 | −41.93 | −43.11 | −50.92 |
| 140 | 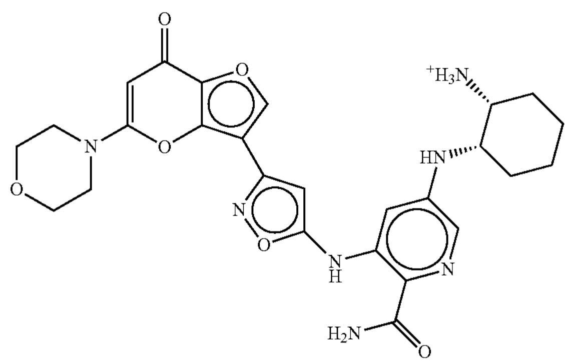 | 536.56 | −55.98 | −35.95 | −38.36 | −37.10 |
| 141 | 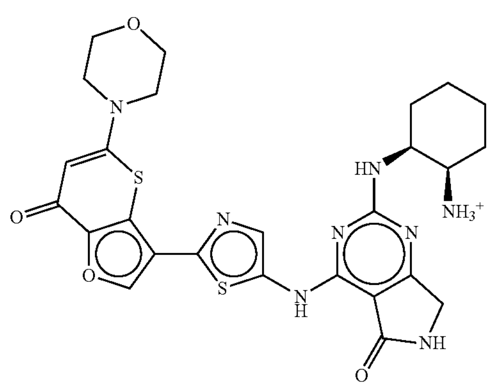 | 581.69 | −55.87 | −40.68 | −39.64 | −41.70 |
| 142 | 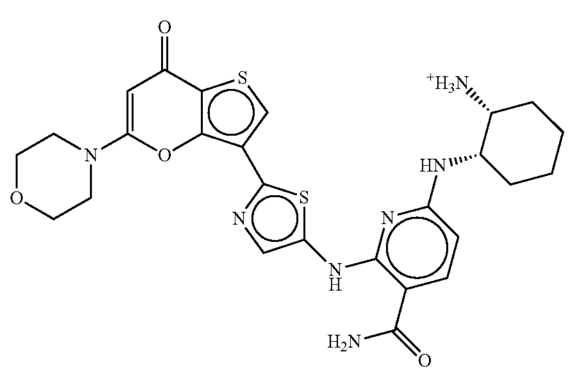 | 568.69 | −55.79 | −37.40 | −30.22 | −38.21 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 143 | 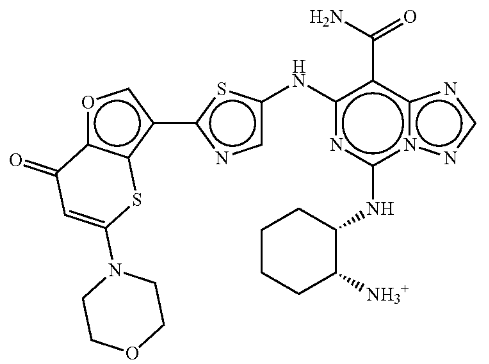 | 609.70 | −55.75 | −37.65 | −41.11 | −47.65 |
| 144 | 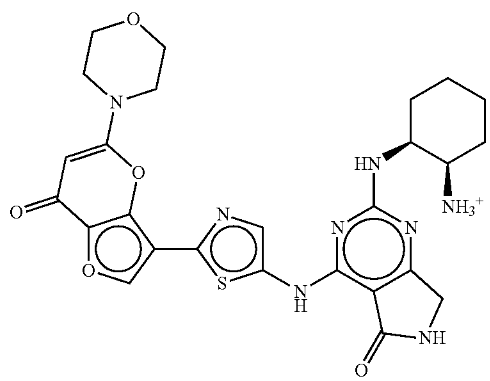 | 565.62 | −55.65 | −51.27 | −39.25 | −56.20 |
| 145 | 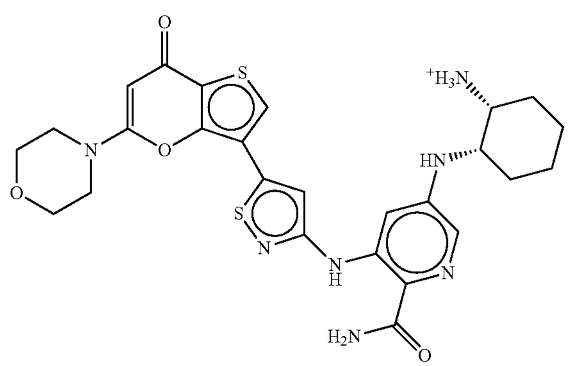 | 568.69 | −55.64 | −42.18 | −40.12 | −41.92 |
| 146 | 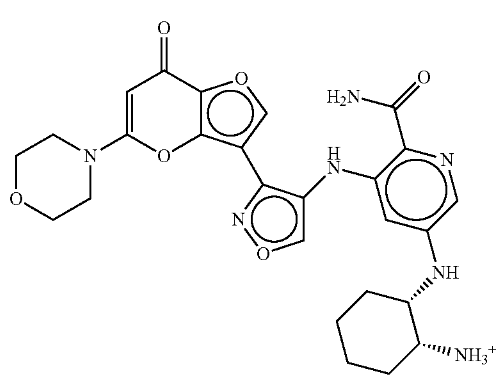 | 536.56 | −55.61 | −50.94 | −54.46 | −53.24 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 147 | 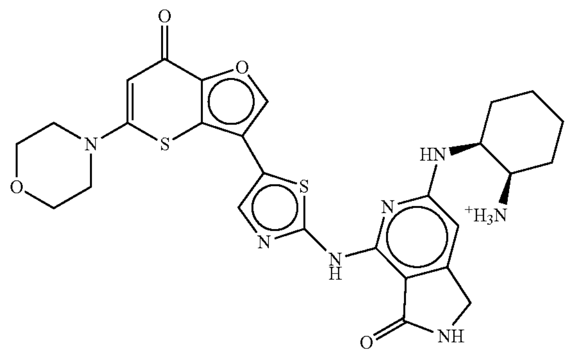 | 580.70 | −55.49 | −47.62 | −32.57 | −51.17 |
| 148 | 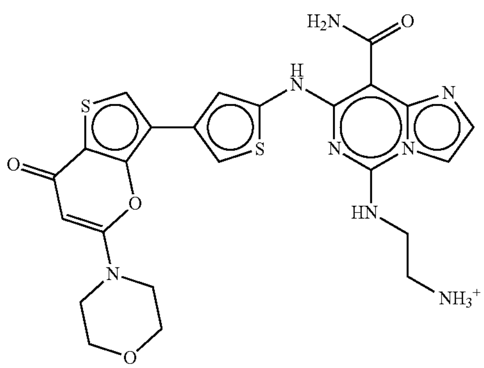 | 553.64 | −55.47 | −37.60 | −31.84 | −41.74 |
| 149 | 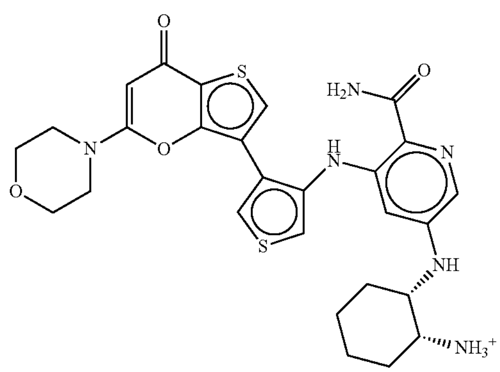 | 567.70 | −55.40 | −53.11 | −51.11 | −50.44 |
| 150 | 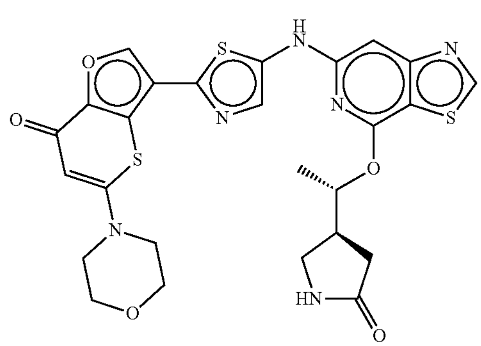 | 596.70 | −55.34 | −48.90 | −43.19 | −47.16 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 151 | 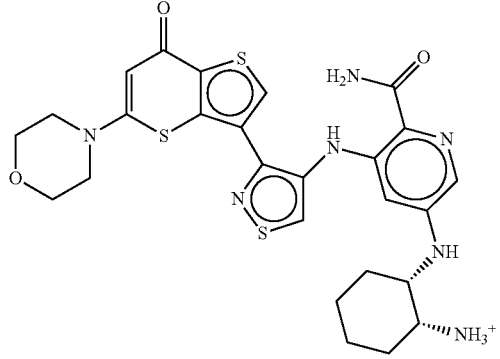 | 584.76 | −55.33 | −51.83 | −35.70 | −46.20 |
| 152 | 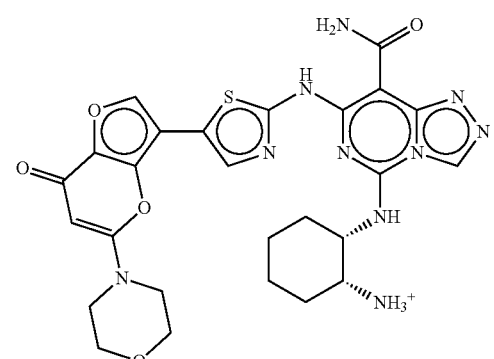 | 593.64 | −55.19 | −37.08 | −27.64 | −41.43 |
| 153 | 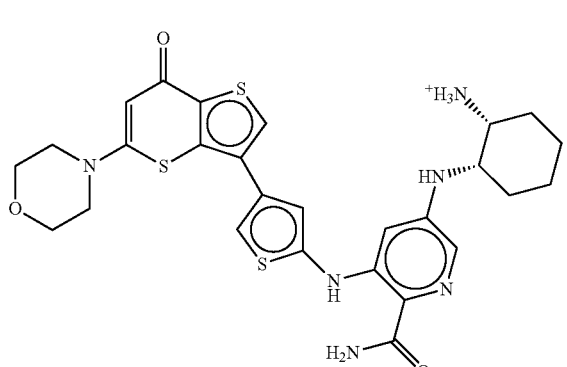 | 583.77 | −55.17 | −39.63 | −37.81 | −33.13 |
| 154 | 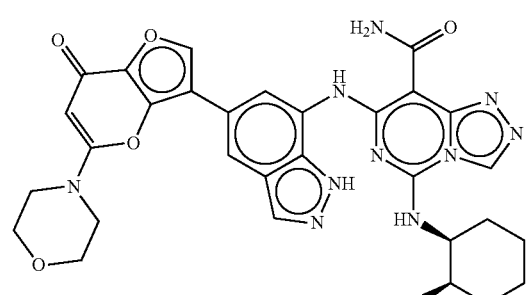 | 626.65 | −55.13 | −43.30 | −40.71 | −38.64 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 155 | 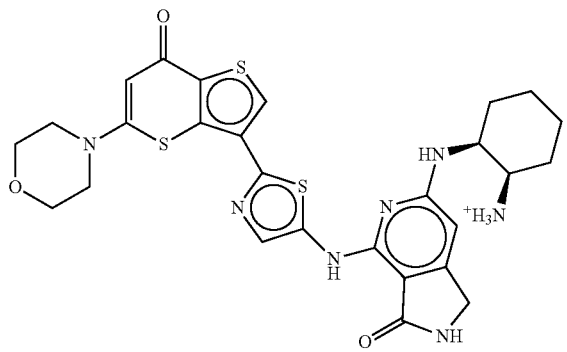 | 596.77 | −55.13 | −50.54 | −35.12 | −50.72 |
| 156 | 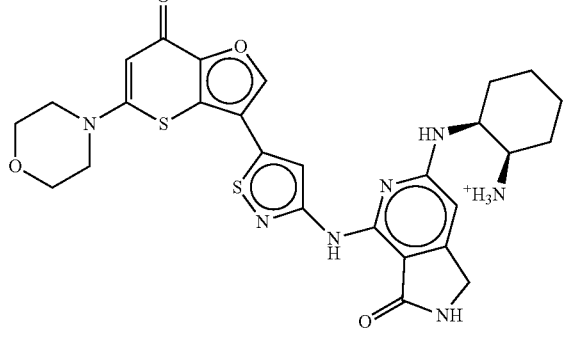 | 580.70 | −55.10 | −40.76 | −49.74 | −47.87 |
| 157 | 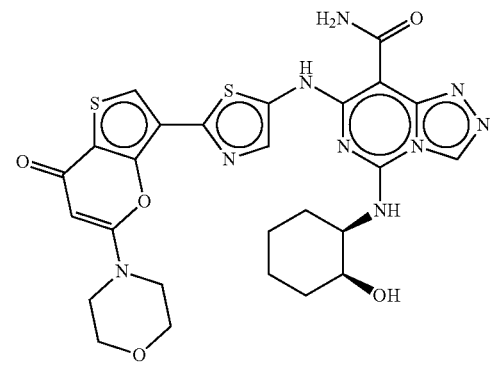 | 609.68 | −55.00 | −58.86 | −41.79 | −40.73 |
| 158 | 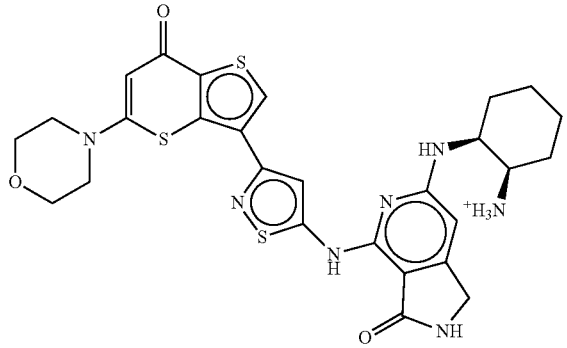 | 596.77 | −54.95 | −50.01 | −33.15 | −55.68 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 159 | 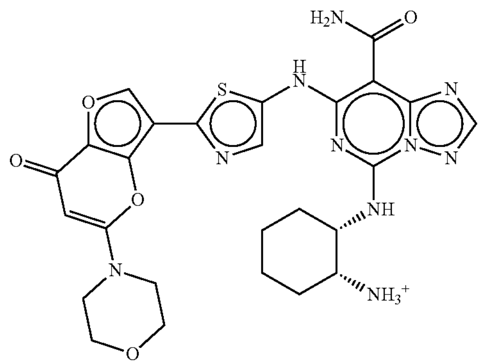 | 593.64 | −54.89 | −31.76 | −28.31 | −40.44 |
| 160 | 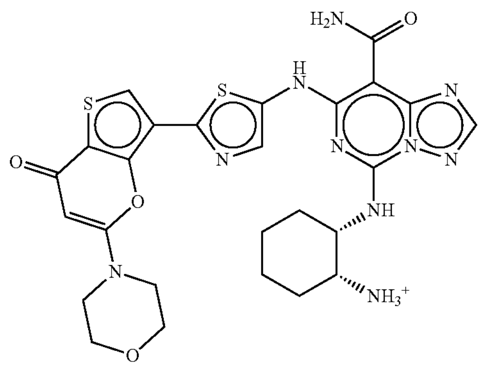 | 609.70 | −54.84 | −42.49 | −33.53 | −43.16 |
| 161 | 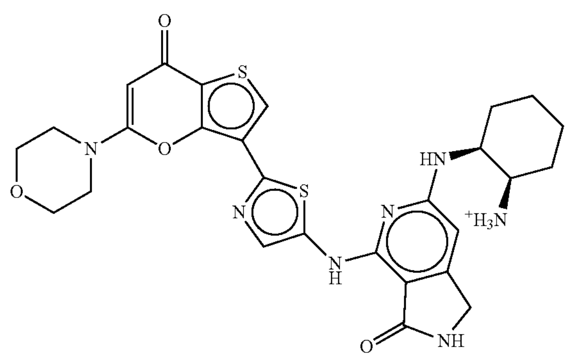 | 580.70 | −54.81 | −47.98 | −38.96 | −53.65 |
| 162 | 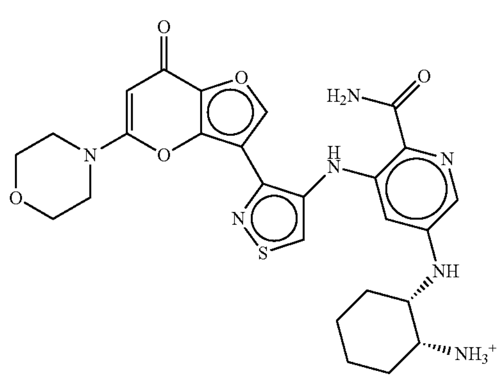 | 552.63 | −54.81 | −54.17 | −41.94 | −53.15 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 163 | 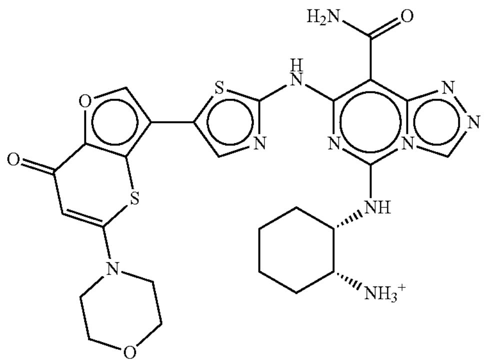 | 609.70 | −54.77 | −50.13 | −16.49 | −46.98 |
| 164 | 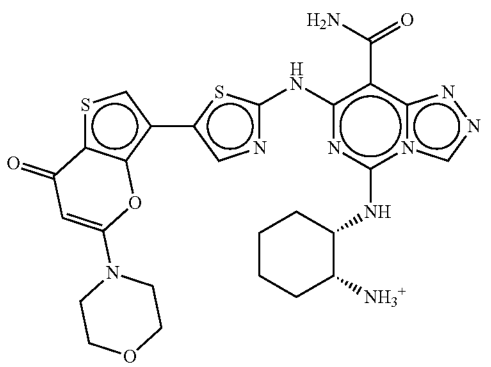 | 609.70 | −54.56 | −45.59 | −43.28 | −45.48 |
| 165 | 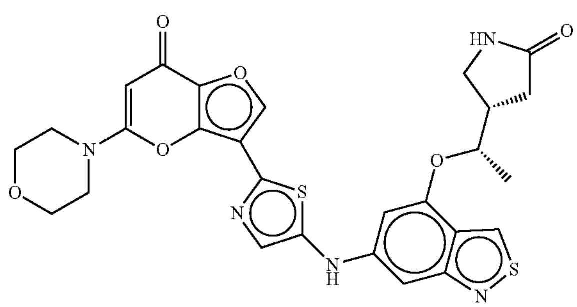 | 579.65 | −54.55 | −48.88 | −44.12 | −53.44 |
| 166 | 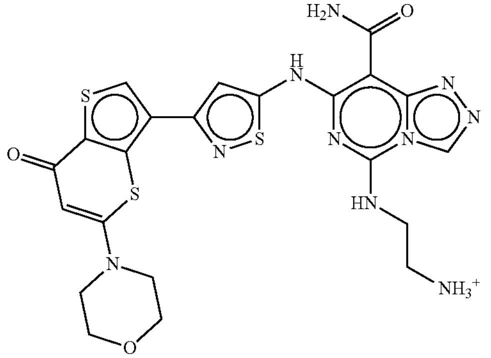 | 571.68 | −54.54 | −40.33 | −37.49 | −38.17 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 167 | 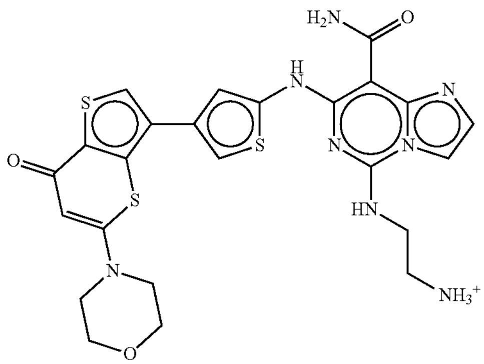 | 569.70 | −54.48 | −37.89 | −30.67 | −32.76 |
| 168 | 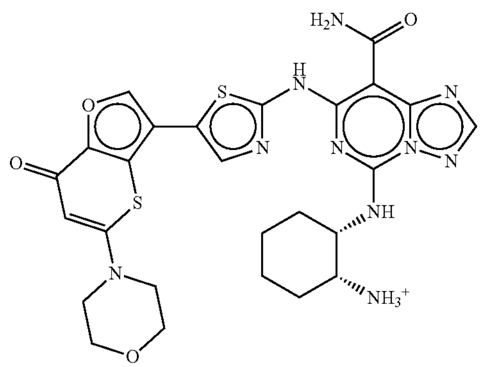 | 609.70 | −54.35 | −34.24 | −32.05 | −40.47 |
| 169 | 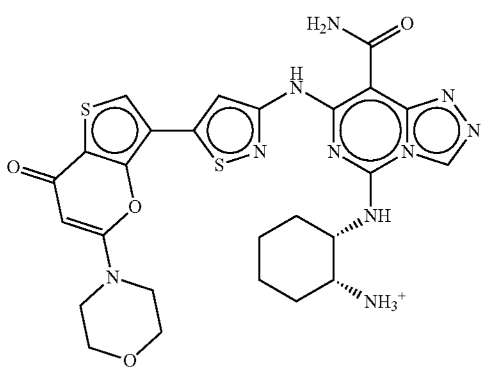 | 609.70 | −54.28 | −50.50 | −26.98 | −33.26 |
| 170 | 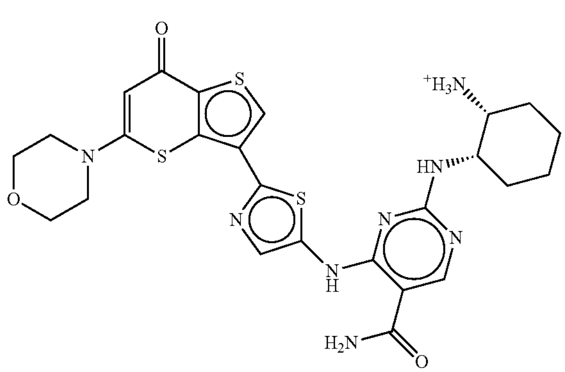 | 585.75 | −54.27 | −50.79 | −40.25 | −45.77 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 171 | 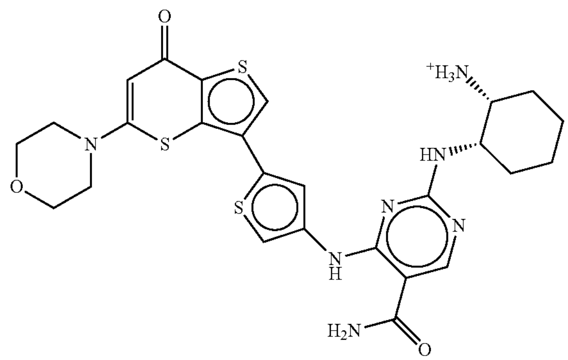 | 584.76 | −54.25 | −56.37 | −25.58 | −44.13 |
| 172 | 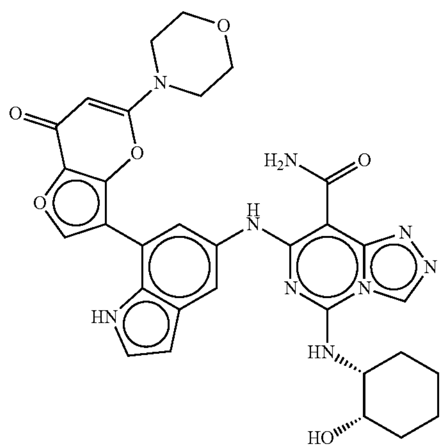 | 625.63 | −54.21 | −46.31 | −27.46 | −28.59 |
| 173 | 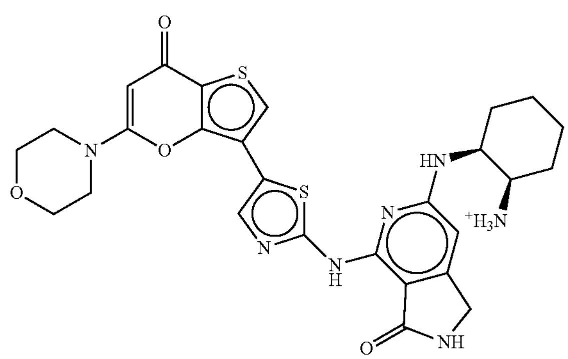 | 580.70 | −54.21 | −45.85 | −41.56 | −52.11 |
| 174 | 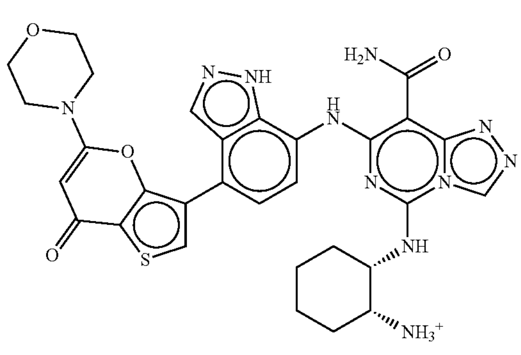 | 642.71 | −54.16 | −32.33 | −32.72 | −31.72 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 175 | 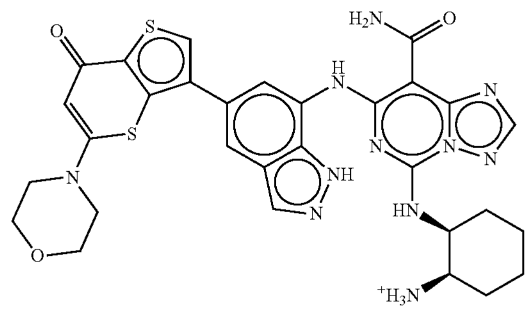 | 658.78 | −54.12 | −42.78 | −37.02 | −35.11 |
| 176 | 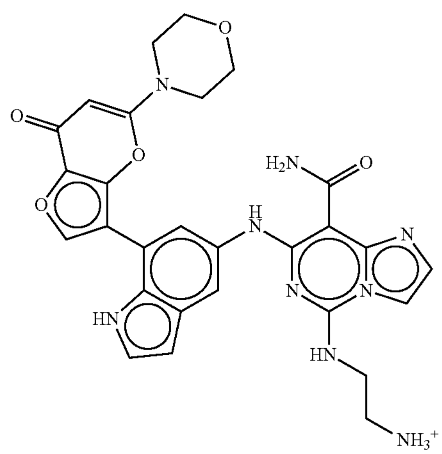 | 570.58 | −54.05 | −41.70 | −37.49 | −34.18 |
| 177 | 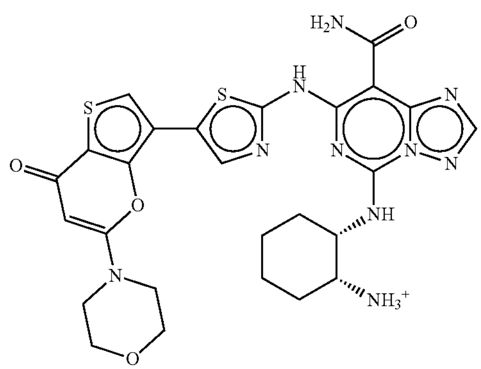 | 609.70 | −54.04 | −42.55 | −35.10 | −20.13 |
| 178 | 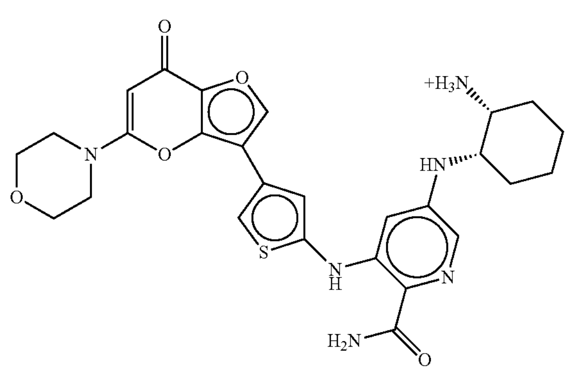 | 551.64 | −53.97 | −46.77 | −35.80 | −47.94 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 179 | 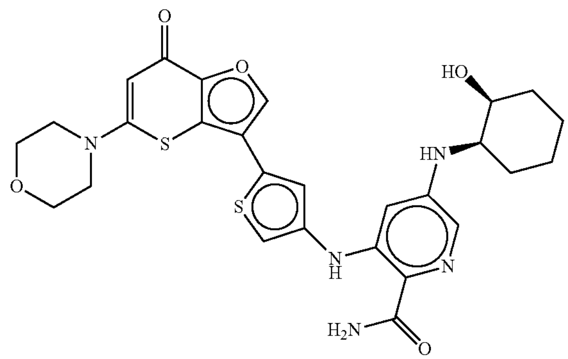 | 567.68 | −53.93 | −44.70 | −32.43 | −47.99 |
| 180 | 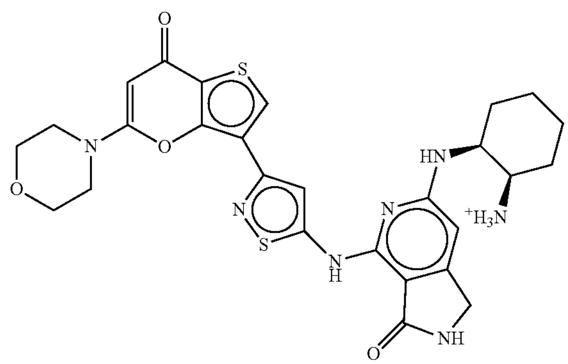 | 580.70 | −53.91 | −46.89 | −36.93 | −47.04 |
| 181 | 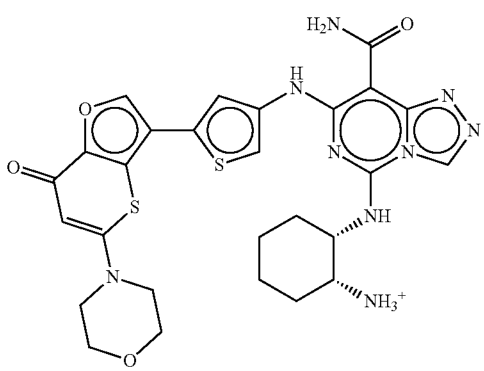 | 608.72 | −53.86 | 297.12 | −18.77 | −30.14 |
| 182 | 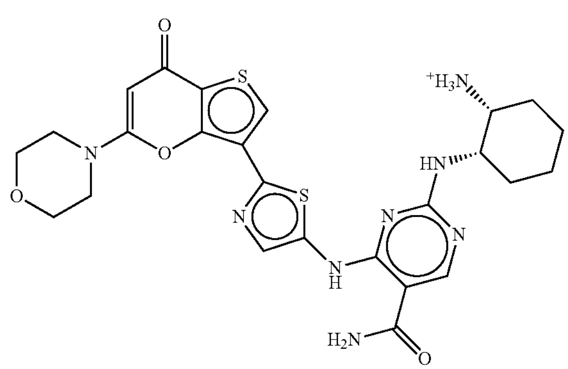 | 569.68 | −53.83 | −36.45 | −40.07 | −42.38 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 183 | 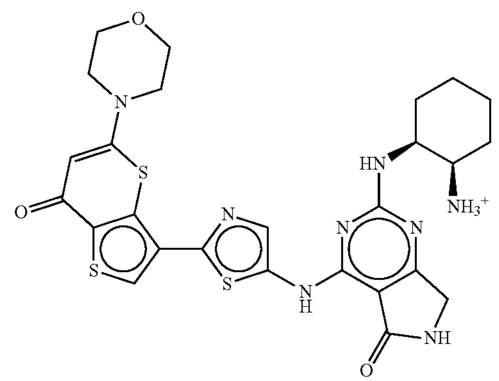 | 597.76 | −53.81 | −51.30 | −31.30 | −47.20 |
| 184 | 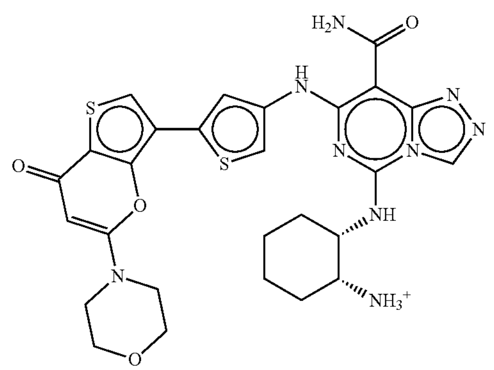 | 608.72 | −53.78 | −38.97 | −33.87 | −47.88 |
| 185 | 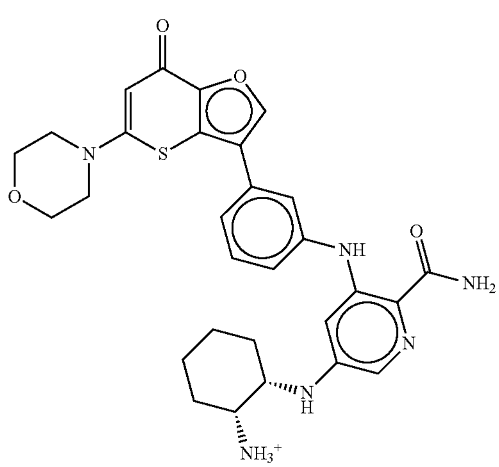 | 561.68 | −53.75 | −34.00 | −25.85 | −46.78 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 186 | 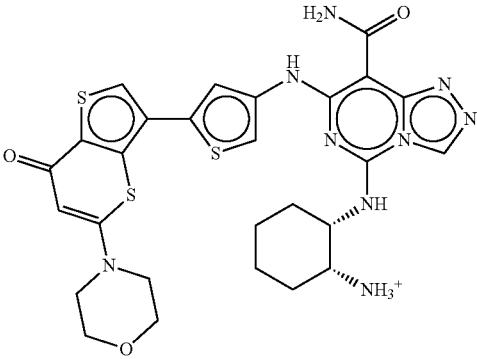 | 624.78 | −53.75 | −46.23 | −30.70 | −45.16 |
| 187 | 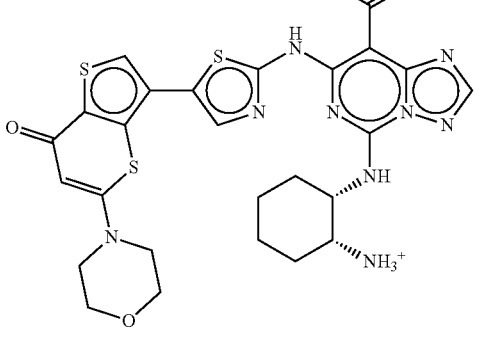 | 625.77 | −53.71 | −39.49 | −32.53 | −44.06 |
| 188 | 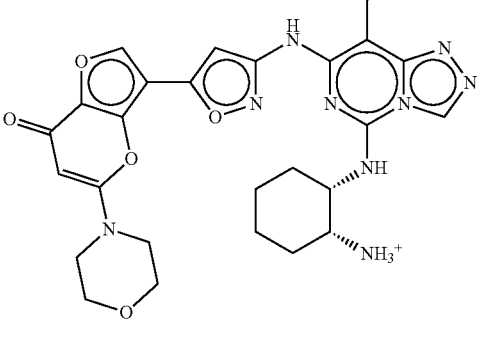 | 577.57 | −53.71 | −30.48 | −36.57 | −49.04 |
| 189 | 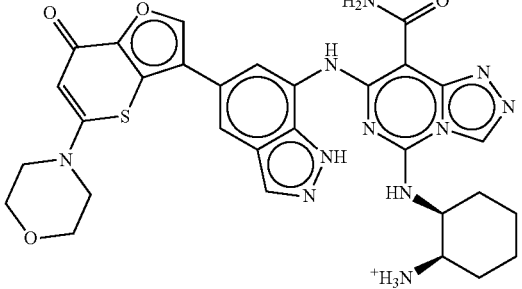 | 642.71 | −53.63 | −47.50 | −30.78 | −57.70 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
| --- | --- | --- | --- | --- | --- | --- |
| 190 | 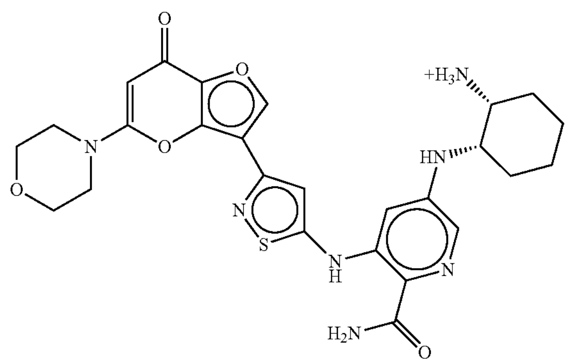 | 552.63 | −53.60 | −37.23 | −41.65 | −52.34 |
| 191 | 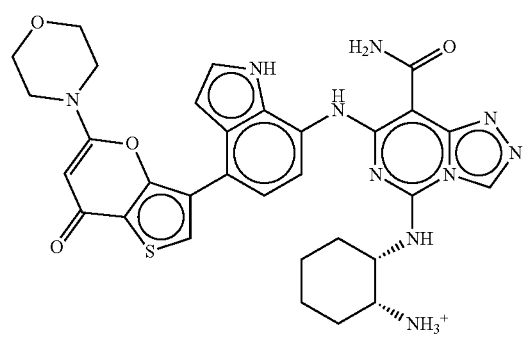 | 641.72 | −53.59 | −41.18 | −21.87 | −16.75 |
| 192 | 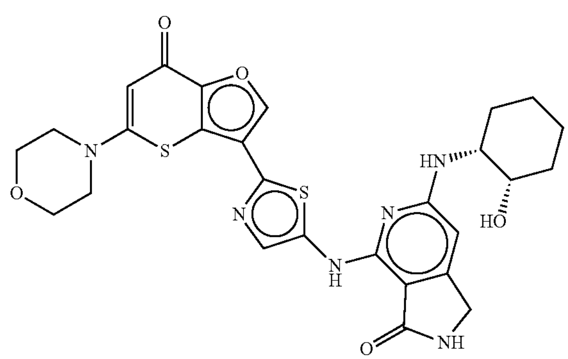 | 580.68 | −53.54 | −49.37 | −40.13 | −32.98 |
| 193 | 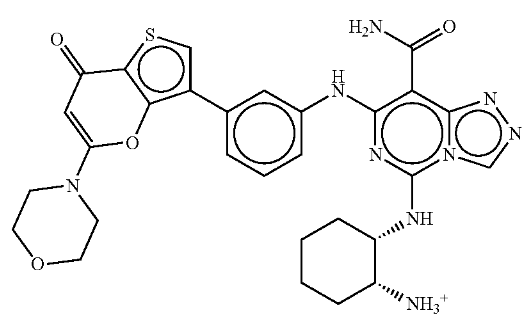 | 602.69 | −53.52 | −38.61 | −32.74 | −33.19 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 194 | 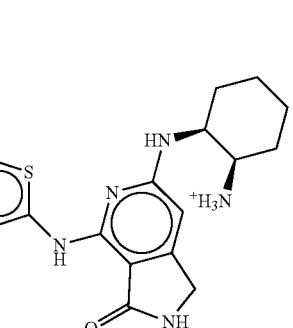 | 580.70 | −53.48 | −47.64 | −47.38 | −42.05 |
| 195 | 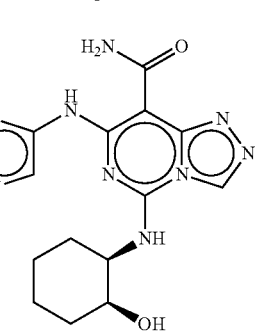 | 593.61 | −53.37 | −43.04 | −50.54 | −44.31 |
| 196 | 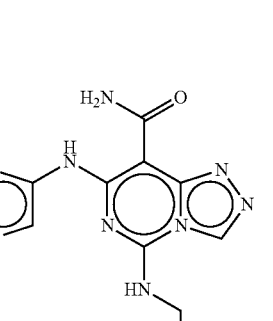 | 555.59 | −53.36 | −41.95 | −42.42 | −31.63 |
| 197 | 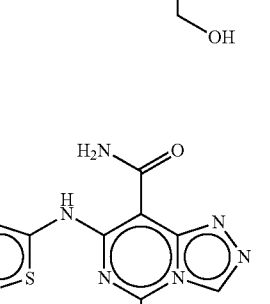 | 609.68 | −53.25 | −30.64 | −30.30 | −15.96 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 198 | 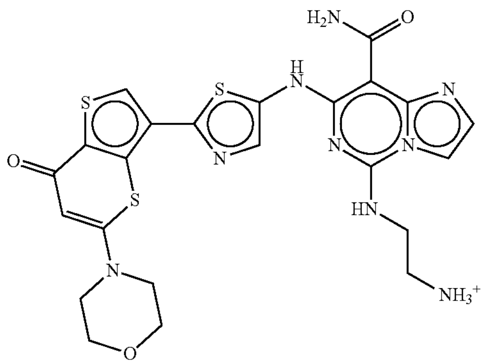 | 570.69 | −53.22 | −43.29 | −28.61 | −42.74 |
| 199 | 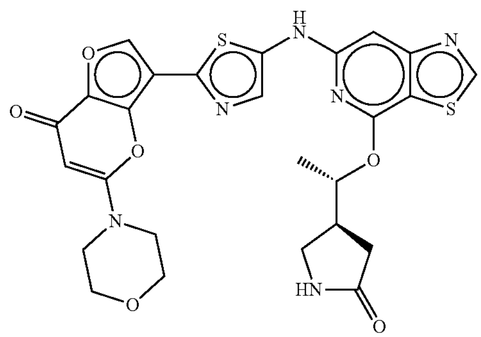 | 580.64 | −53.16 | −45.91 | −36.49 | −51.26 |
| 200 | 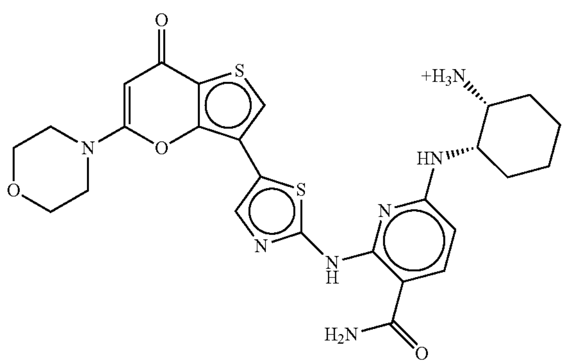 | 568.69 | −53.14 | −36.99 | −29.90 | −44.71 |
| 201 | 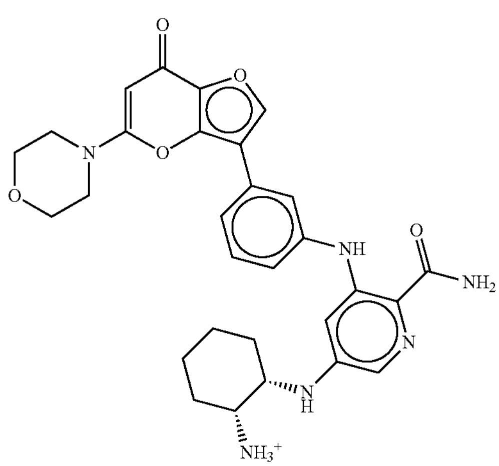 | 545.61 | −53.10 | −32.28 | −35.74 | −38.34 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 202 | 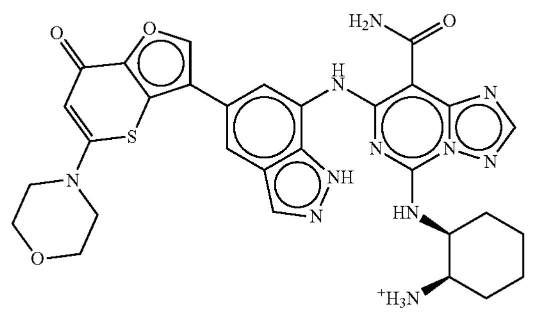 | 642.71 | −53.08 | −41.25 | −31.95 | −37.63 |
| 203 | 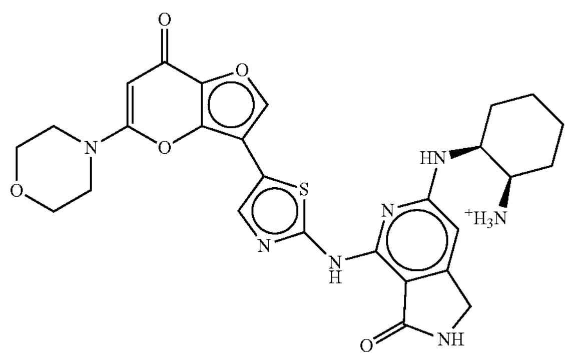 | 564.64 | −52.98 | −47.39 | −41.67 | −53.22 |
| 204 | 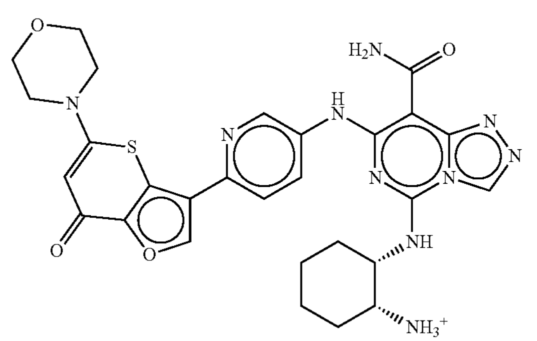 | 603.68 | −52.94 | −40.55 | −35.52 | −35.37 |
| 205 | 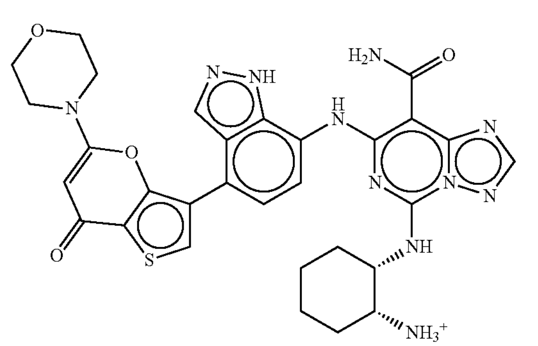 | 642.71 | −52.90 | −33.67 | −32.39 | −29.03 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 206 | 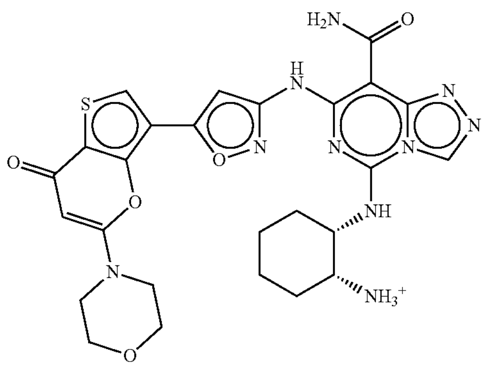 | 593.64 | −52.89 | −39.45 | −39.15 | −42.34 |
| 207 | 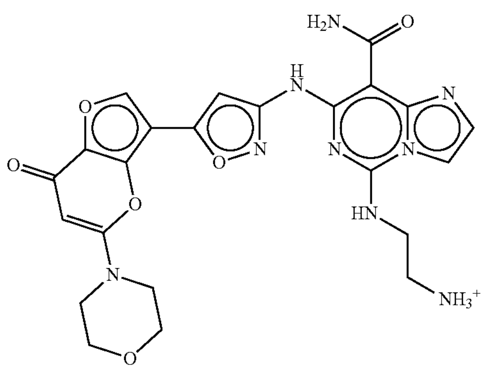 | 522.49 | −52.88 | −50.47 | −35.60 | −42.97 |
| 208 | 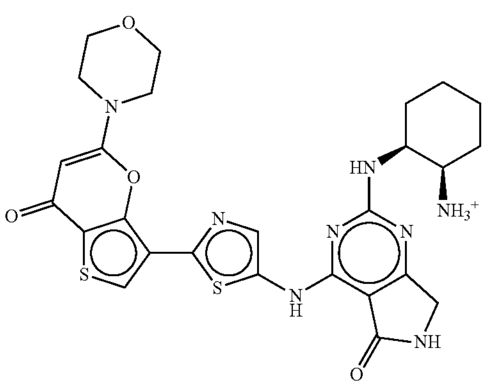 | 581.69 | −52.88 | −46.71 | −35.80 | −45.24 |
| 209 | 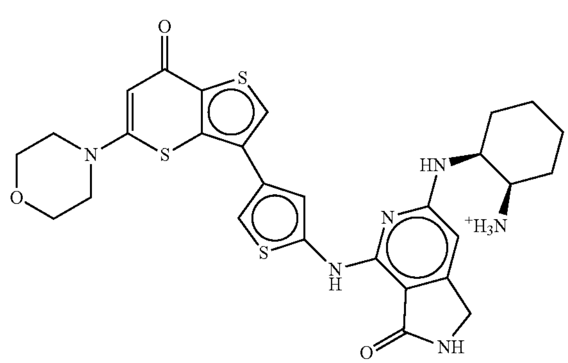 | 595.78 | −52.87 | −35.92 | −47.93 | −50.57 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 210 | 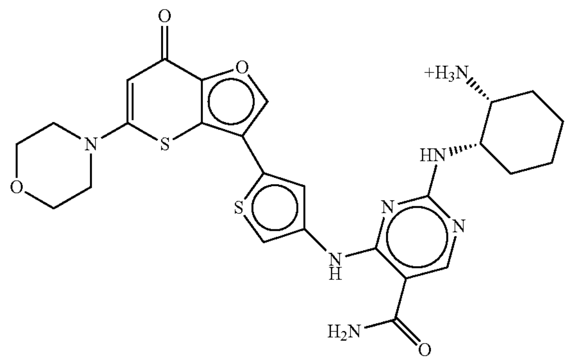 | 568.69 | −52.84 | −46.51 | −28.19 | −43.72 |
| 211 | 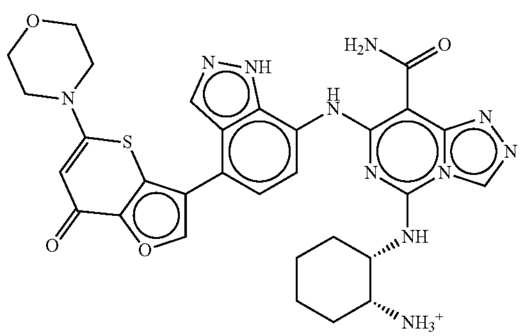 | 642.71 | −52.83 | −38.81 | −13.90 | −32.54 |
| 212 | 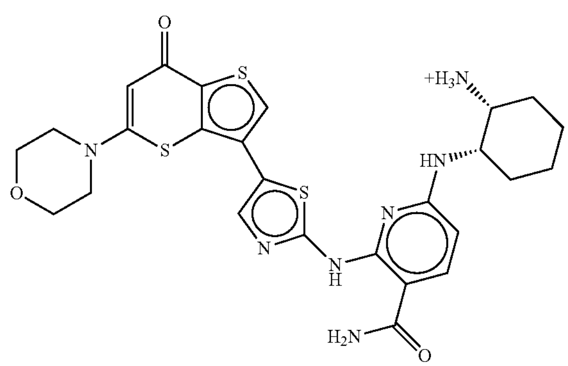 | 584.76 | −52.82 | −37.71 | −38.40 | −40.65 |
| 213 | 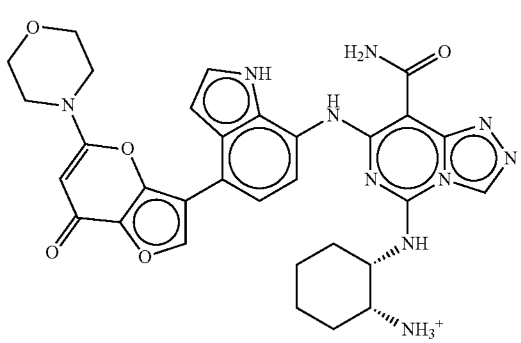 | 625.66 | −52.81 | −36.83 | −32.45 | −38.95 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 214 | 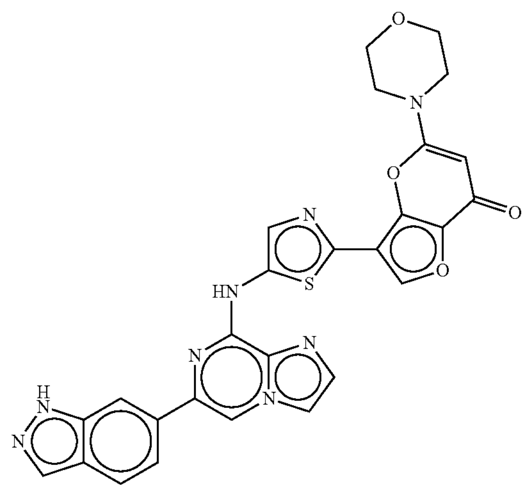 | 552.56 | −52.78 | −36.58 | −34.29 | −40.46 |
| 215 | 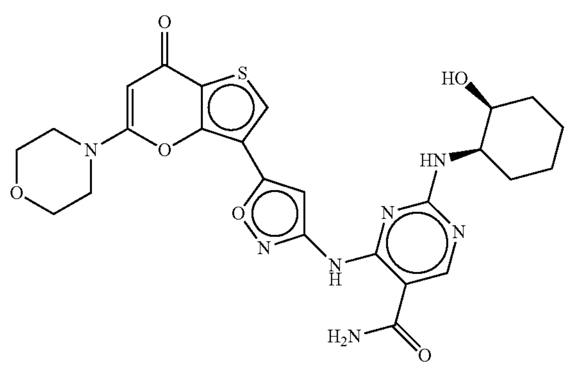 | 553.59 | −52.74 | −33.62 | −43.78 | −42.14 |
| 216 | 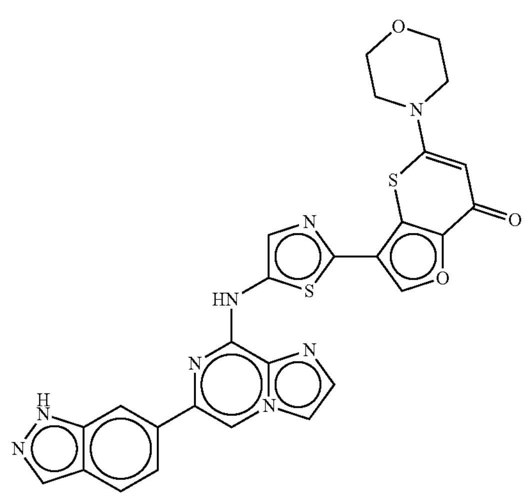 | 568.63 | −52.71 | −50.85 | −46.55 | −38.53 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 217 | 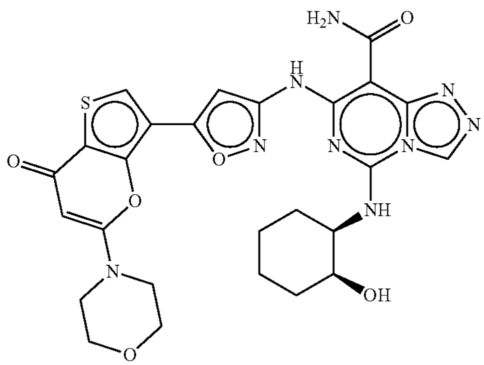 | 593.61 | −52.68 | −36.93 | −33.93 | −40.26 |
| 218 | 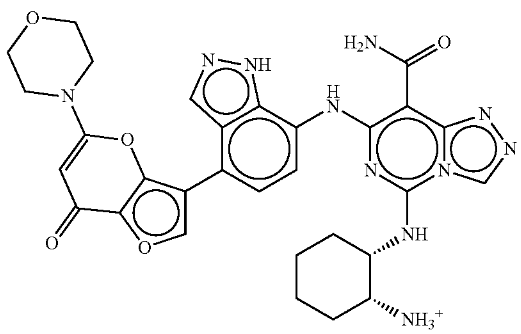 | 626.65 | −52.60 | −34.09 | −25.68 | −31.55 |
| 219 | 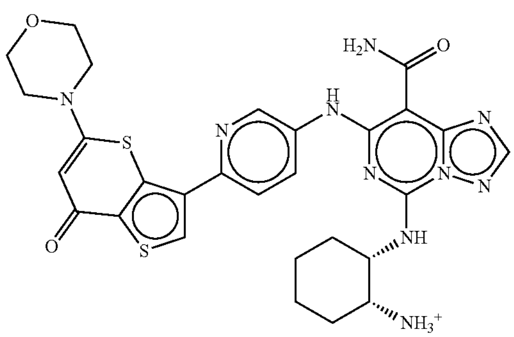 | 619.74 | −52.54 | −37.21 | −32.53 | −43.23 |
| 220 | 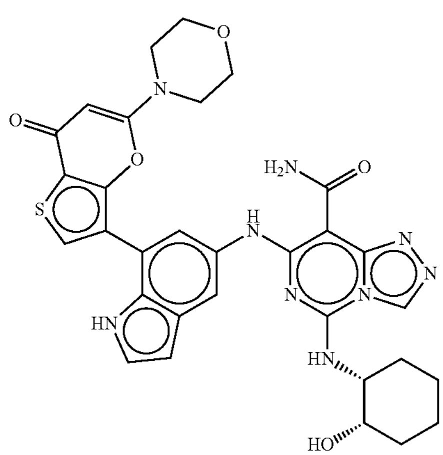 | 641.70 | −52.51 | −32.35 | −26.76 | −21.95 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 221 | 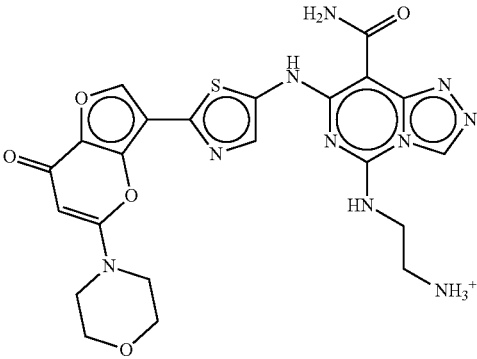 | 539.55 | −52.50 | −35.32 | −48.62 | −51.52 |
| 222 | 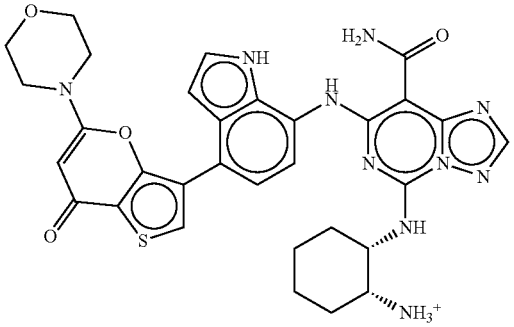 | 641.72 | −52.48 | −20.32 | −23.39 | −33.53 |
| 223 | 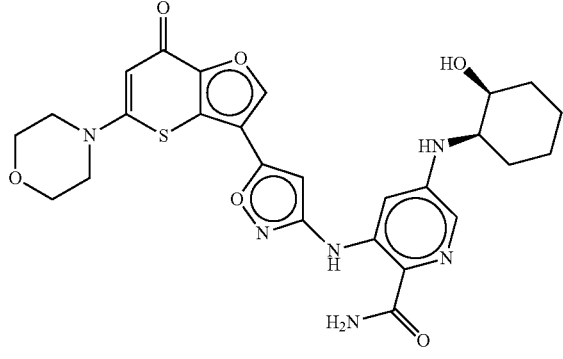 | 552.60 | −52.48 | −41.74 | −32.03 | −44.47 |
| 224 | 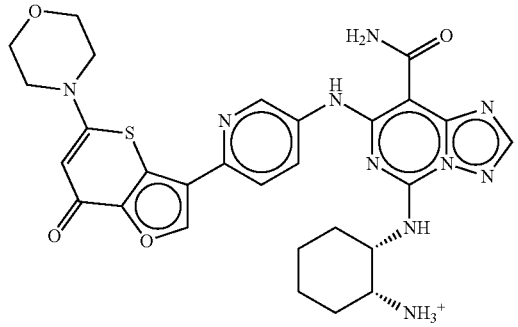 | 603.68 | −52.48 | −41.32 | −32.56 | −29.29 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 225 | 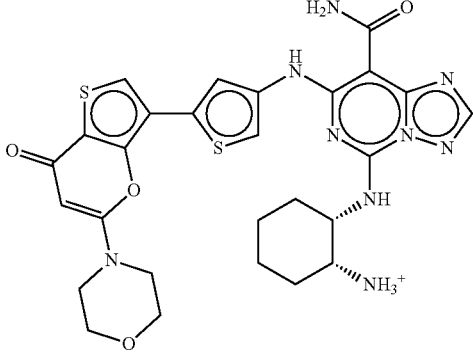 | 608.72 | −52.45 | −32.57 | −33.71 | −39.20 |
| 226 | 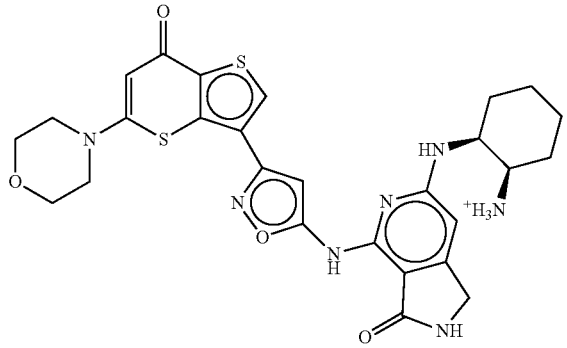 | 580.70 | −52.44 | −53.33 | −48.47 | −53.80 |
| 227 | 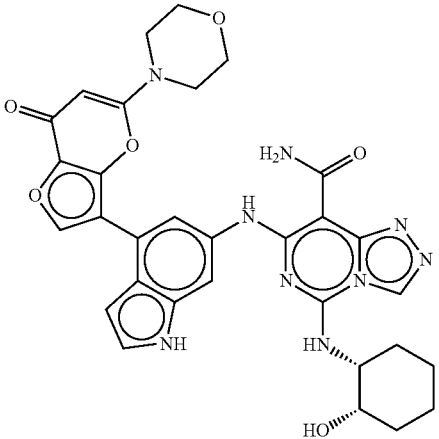 | 625.63 | −52.44 | −32.93 | −18.30 | −37.00 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 228 | 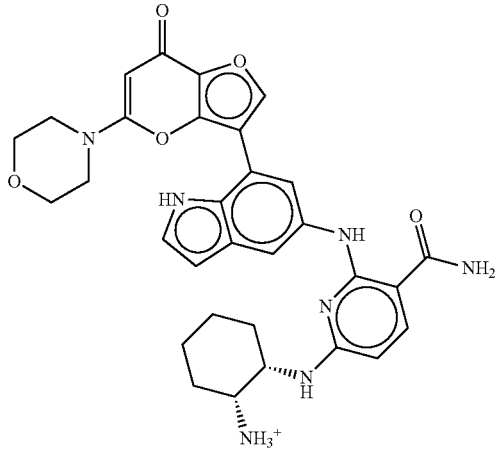 | 584.65 | −52.42 | −24.41 | −21.25 | −26.91 |
| 229 | 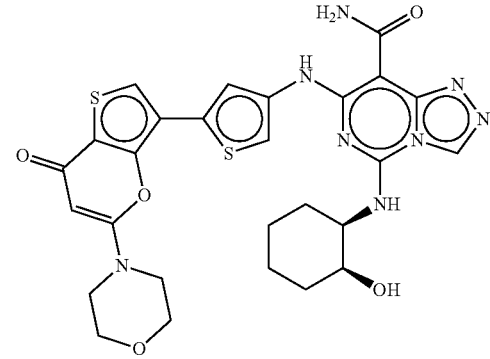 | 608.69 | −52.41 | −39.42 | −37.83 | −43.51 |
| 230 | 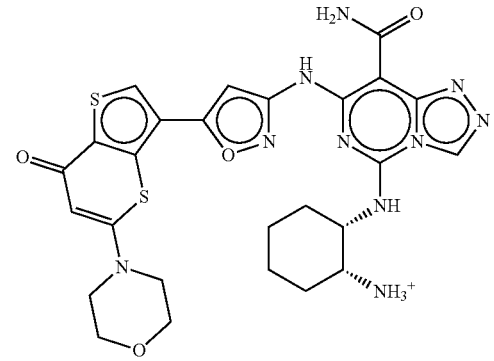 | 609.70 | −52.41 | −33.84 | −31.94 | −45.58 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 231 | 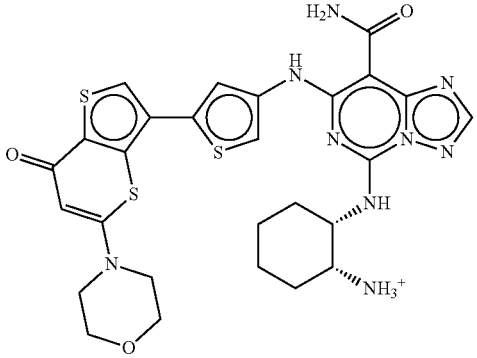 | 624.78 | −52.40 | −44.48 | −29.45 | −23.04 |
| 232 | 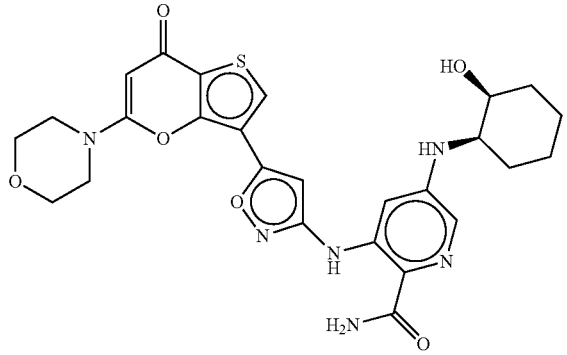 | 552.60 | −52.39 | −41.61 | −42.62 | −28.65 |
| 233 | 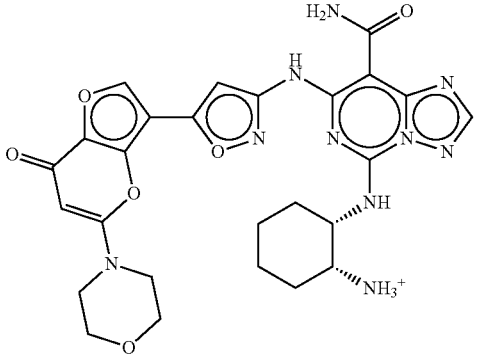 | 577.57 | −52.37 | −32.74 | −37.47 | −36.58 |
| 234 | 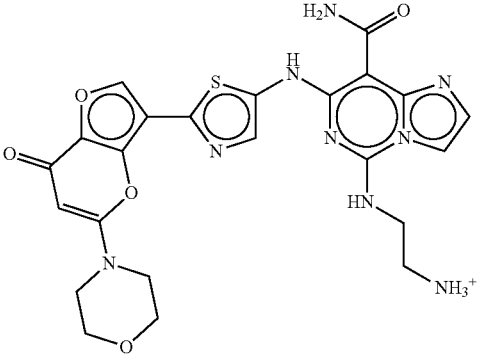 | 538.56 | −52.29 | −45.73 | −26.82 | −41.94 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 235 | 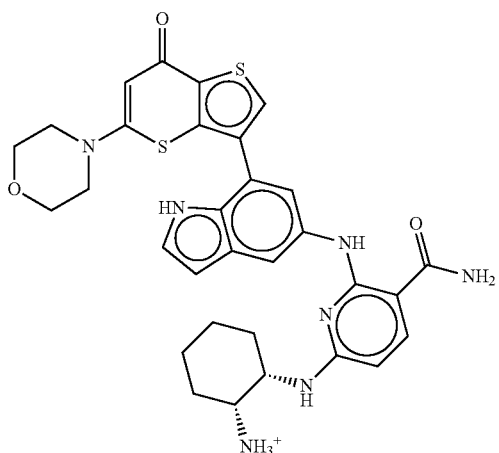 | 616.78 | −52.27 | −37.30 | −24.37 | −40.50 |
| 236 | 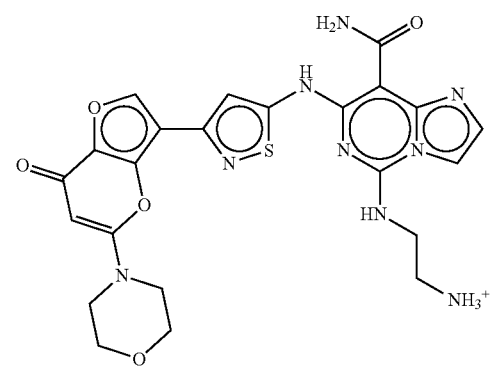 | 538.56 | −52.25 | −37.05 | −24.81 | −44.17 |
| 237 | 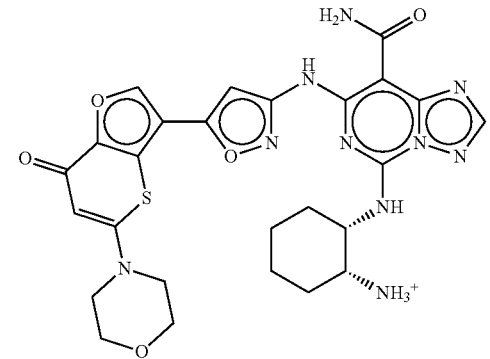 | 593.64 | −52.24 | −40.96 | −35.31 | −27.58 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|------|-----------|------------|-----------|------------------|------------------|------------------|
| 238 | 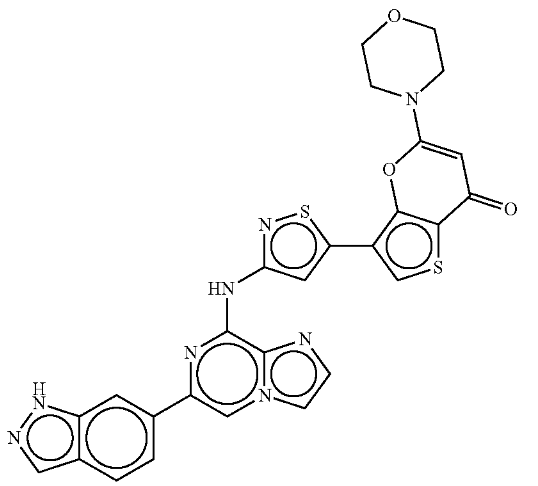 | 568.63 | −52.24 | −29.78 | −34.37 | −24.83 |
| 239 | 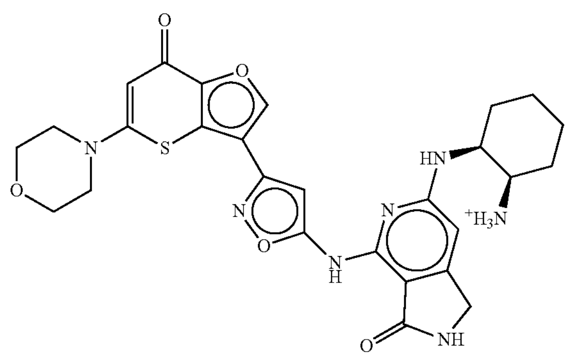 | 564.64 | −52.23 | −39.08 | −34.33 | −36.86 |
| 240 | 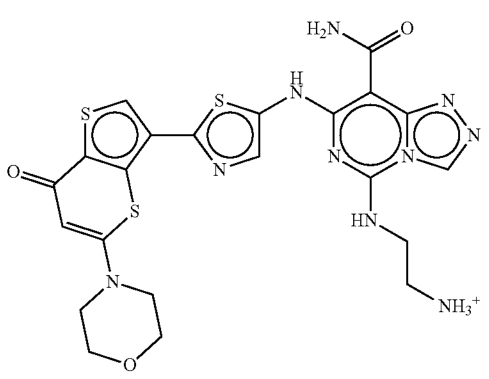 | 571.68 | −52.18 | 252.04 | −26.16 | −47.67 |

TABLE 4-continued
Top 200 SYK and PI3K inhibitors identified by In-Silico Model
| Cmpd | Structure | Mol Weight | SYK SCORE | PI3K-alpha SCORE | PI3K-delta SCORE | PI3K-gamma SCORE |
|---|---|---|---|---|---|---|
| 241 | 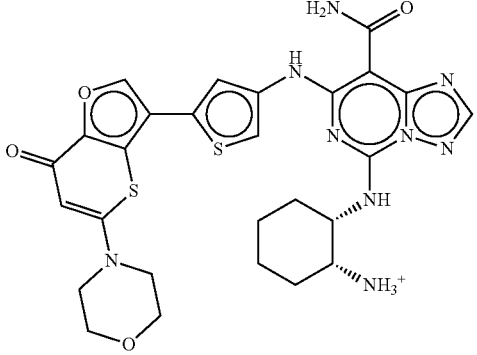 | 608.72 | −52.16 | −42.55 | −26.97 | −43.05 |
| 242 | 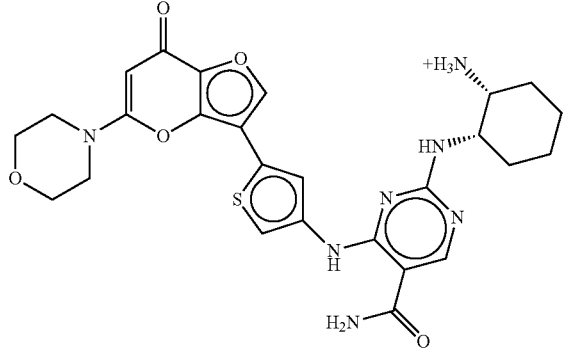 | 552.63 | −52.14 | −33.93 | −25.15 | −39.84 |
| 243 | 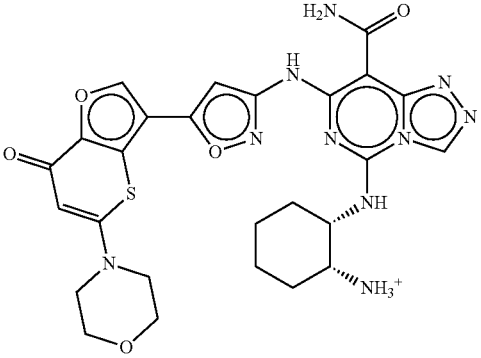 | 593.64 | −52.14 | −40.14 | −29.06 | −37.62 |
| 244 | 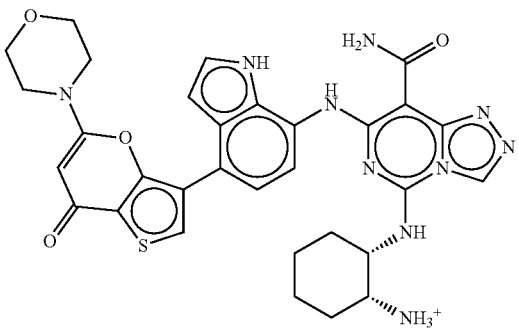 | 657.79 | −52.09 | −27.10 | −38.01 | −27.71 |

TABLE 4-continued

Top 200 SYK and PI3K inhibitors identified by In-Silico Model

| Cmpd | Structure | Mol Weight | SYK SCORE | PI3K-alpha SCORE | PI3K-delta SCORE | PI3K-gamma SCORE |
|---|---|---|---|---|---|---|
| 245 | 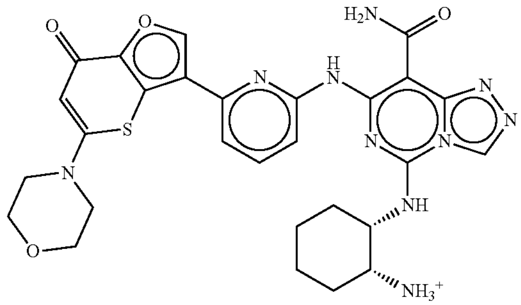 | 603.68 | −52.08 | −30.95 | −48.57 | −44.57 |
| 246 | 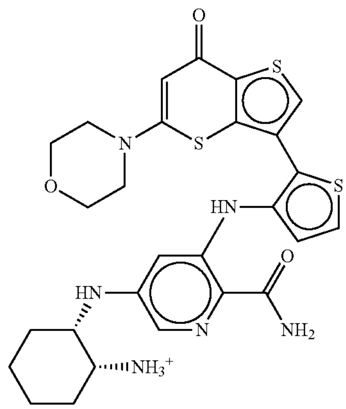 | 583.77 | −52.08 | −48.25 | −36.81 | −51.84 |

Example 5: Preparation of Compound 2

Step 1: Preparation of tert-Butyl 4-[3-(p-aminophenyl)-7-oxo-4-oxa-1-thia-5-indenyl]-1-piperazinecarboxylate tert-Butyl 4-(3-bromo-7-oxo-4-oxa-1-thia-5-indenyl)-1-piperazinecarboxylate (414 mg, 1.0 mmol) (prepared as described in references above) and 4-amino-phenylboronic acid hydrochloride (260 mg, 1.5 mmol, 1.5 eq.) were dissolved in a 2:1 v/v mixture of toluene and ethanol (10 mL). The mixture was treated with $Na_2CO_3$ 2M aqueous solution (3 mL) and deoxygenated by bubbling $N_2$ for 20 minutes. $Pd[PPh_3]_4$ (58 mg, 0.05 mmol) was added and the mixture was heated to 85° C. for 2 hours. LCMS indicated complete conversion to product. The cooled reaction mixture was diluted with $CH_2Cl_2$ (100 mL) and washed with water. The organics were dried over anhydrous $MgSO_4$, filtered and concentrated in vacuo. The crude residue was triturated with MeOH, filtered and air-dried to yield the pure titled product as a tan solid. Yield=160 mg (0.37 mmol, 38%).

LC/MS—HPLC (254 nm)—Rt 2.30 min. MS (ESI) m/z 428.1 [M$^+$+H$^+$]. Purity=95.0% by UV (254 nm).

Step 2: Preparation of 1-{[1-(2-Chloro-4-pyrimidinyl)-3-methyl-1H-pyrazol-4-yl]methyl}-3-azetidinol A stirred suspension of commercially available 1-(2-chloro-4-pyrimidinyl)-3-methyl-1H-pyrazole-4-carbaldehyde (222 mg, 1.0 mmol) and 3-azetidinol hydrochloride (219 mg, 2.0 mmol) in dichloromethane (10 mL) was treated with triethylamine (700 µL, 5.0 mmol) followed by portionwise addition of $Na(OAc)_3BH$ (636 mg, 3.0 mmol). The resulting mixture was stirred at room temperature overnight. After overnight stirring LCMS analysis indicated clean conversion to product. The reaction mixture was transferred to a separatory funnel, diluted with dichloromethane, washed with saturated aqueous $NaHCO_3$ solution. The organic layer was dried over anhydrous $MgSO_4$, filtered and concentrated in vacuo. The crude product was obtained as a white foam (185 mg, 0.66 mmol, 66%) and used directly in the next step.

LC/MS—HPLC (254 nm)—Rt 1.04 min. MS (ESI) m/z 280.5 [M$^+$+H$^+$]. Purity=95% by UV (254 nm).

Step 3: Preparation of tert-Butyl 4-{3-[p-(4-{4-[(3-hydroxy-1-azetidinyl)methyl]-3-methyl-1H-pyrazol-1-yl}-2-pyrimidinylamino)phenyl]-7-oxo-4-oxa-1-thia-5-indenyl}-1-piperazinecarboxylate In a 8 mL vial, 1-{[1-(c-Chloro-4-pyrimidinyl)-3-methyl-1H-pyrazol-4-yl]methyl}-3-azetidinol (72 mg, 0.257 mmol), tert-butyl 4-[3-(p-aminophenyl)-7-oxo-4-oxa-1-thia-5-indenyl]-1-piperazinecarboxylate (100 mg, 0.234 mmol), $Cs_2CO_3$ (152 mg, 0.468 mmol), BINAP (58 mg, 0.094 mmol) and Pd(OAc)$_2$ (11 mg, 0.047 mmol) were degassed under $N_2$ for 10 minutes. Degassed 1,4-dioxane (5 mL) was added and the resulting mixture was stirred at 110° C. for 6 hours. LCMS then indicated approximately 50% conversion to product. At this point, the reaction was cooled and filtered. Solids were rinsed with a 9:1 v/v CH$_2$Cl$_2$/MeOH mixture. The filtrates were concentrated and the crude residue was purified by preparative TLC plate on silica-gel (20×20 cm, 1 m thickness) eluting with a 400:50:2 v/v mixture of CH$_2$Cl$_2$/MeOH/NH$_4$OH. The product was obtained as a yellow film. Yield=15 mg (0.022 mmol, 10%).

LC/MS—HPLC (254 nm)—Rt 2.48 min. MS (ESI) m/z 671.4 [M$^+$+H$^+$]. Purity=85.0% by UV (254 nm).

Step 4: Preparation of 3-[p-(4-{4-[(3-Hydroxy-1-azetidinyl)methyl]-3-methyl-1H-pyrazol-1-yl}-2-pyrimidinylamino)phenyl]-5-(1-piperazinyl)-4-oxa-1-thia-7-indenone dihydrochloride (Compound 2)

A stirred solution of tert-butyl 4-{3-[p-(4-{4-[(3-hydroxy-1-azetidinyl)methyl]-3-methyl-1H-pyrazol-1-yl}-2-pyrimidinylamino)phenyl]-7-oxo-4-oxa-1-thia-5-indenyl}-1-piperazinecarboxylate (10 mg, 0.02 mmol) in dichloromethane (1 mL) was treated with 4N HCl in dioxane solution (0.5 mL). After 1 hour, LCMS analysis indicated clean conversion to product. The reaction mixture was concentrated to dryness and the crude residue was purified by preparative TLC plate on silica-gel (20×20 cm, 1 m thickness) eluting with a 400:50:2 v/v mixture of CH$_2$Cl2/MeOH/NH$_4$OH. The product was obtained as a film. Yield=2 mg (0.004 mmol, 18%).

LC/MS—HPLC (254 nm)—Rt 0.10 min. MS (ESI) m/z 571.1 [M$^+$+H$^+$]. Purity=99.0% by UV (254 nm).

Example 6: Preparation of Compound 3

Step 1: Preparation of 3-(p-Aminophenyl)-5-morpholino-4-oxa-1-thia-7-indenone

3-Bromo-5-morpholino-4-oxa-1-thia-7-indenone (3.16 g, 10.0 mmol) and 4-aminophenylboronic acid hydrochloride (2.00 g, 11.5 mmol, 1.1 eq.) were dissolved in a 2:1 v/v mixture of toluene and ethanol (100 mL). The mixture was treated with Na$_2$CO$_3$ 2M aqueous solution (33 mL) and deoxygenated by bubbling N$_2$ for 30 minutes. Pd[PPh$_3$]$_4$ (578 mg, 0.5 mmol) was added and the mixture was heated to 85° C. for 16 hours. LCMS indicated complete conversion to product. The cooled reaction mixture was diluted with EtOAc (300 mL) washed with water and brine. The organics were dried over anhydrous MgSO$_4$, filtered and concentrated in vacuo. The crude residue was triturated with MeOH/Et$_2$O mixture and filtered to yield the pure title compound as a tan solid. Yield=1.15 g (3.51 mmol, 35%).

LC/MS—HPLC (254 nm)—Rt 2.11 min. MS (ESI) m/z 329.1 [M$^+$+H$^+$]. Purity=98.0% by UV (254 nm).

Step 2: Preparation of 4-[(1-Azetidinyl)methyl]-1-(2-chloro-4-pyrimidinyl)-3-methyl-1H-pyrazole A stirred suspension of 1-(2-chloro-4-pyrimidinyl)-3-methyl-1H-pyrazole-4-carbaldehyde (444 mg, 2.0 mmol) and 3-azetidine hydrochloride (374 mg, 4.0 mmol) in dichloromethane (25 mL) was treated with portionwise addition of Na(OAc)$_3$BH (848 mg, 4.0 mmol). The resulting mixture was stirred at room temperature overnight. Next morning, LCMS analysis indicated clean conversion to product. The reaction was quenched by addition of H$_2$O (20 mL) and 1N NaOH aqueous solution (20 mL). This was transferred to a separatory funnel, the organic layer was separated, dried over anhydrous MgSO$_4$, filtered and concentrated in vacuo. The crude product was obtained as a light yellow solid (556 mg, >2.0 mmol, ~quant.).

LC/MS—HPLC (254 nm)—Rt 0.03 min. MS (ESI) m/z 264.1 [M$^+$+H$^+$]. Purity=85% by UV (254 nm).

Step 3: Preparation of 3-[p-(4-{4-[(1-Azetidinyl)methyl]-3-methyl-1H-pyrazol-1-yl}-2-pyrimidinylamino)phenyl]-5-morpholino-4-oxa-1-thia-7-indenone (Compound 3)

In a 250 mL round bottom flask, 4-[(1-azetidinyl)methyl]-1-(2-chloro-4-pyrimidinyl)-3-methyl-1H-pyrazole (1.03 g, 3.90 mmol), 3-(p-aminophenyl)-5-morpholino-4-oxa-1-thia-7-indenone (1.16 g, 3.54 mmol), Cs$_2$CO$_3$ (2.31 g, 7.08 mmol), BINAP (883 mg, 1.42 mmol) and Pd(OAc)$_2$ (159 mg, 0.71 mmol) were degassed under N$_2$ for 10 minutes. Degassed 1,4-dioxane (60 mL) was added and the resulting mixture was stirred at 110° C. for 18 hours. LCMS indicated clean conversion to product. At this point, the reaction was cooled, diluted with EtOAc (200 mL) and filtered. Solids were rinsed with a 9:1 v/v CH$_2$C12/MeOH mixture. The filtrates were concentrated and the crude residue was purified by silica-gel chromatography eluting with a 400:50:2 v/v mixture of CH$_2$C12/MeOH/NH$_4$OH. The product was obtained as a yellow solid. Yield=570 mg (1.03 mmol, 29%).

LC/MS—HPLC (254 nm)—Rt 2.62 min. MS (ESI) m/z 556.4 [M$^+$+H$^+$]. Purity=99.5% by UV (254 nm).

Example 7. Preparation of Compound 4

Step 1: Preparation of tert-Butyl 4-[3-(p-aminophenyl)-7-oxo-4-oxa-1-thia-5-indenyl]-1-piperazinecarboxylate:

tert-Butyl 4-(3-bromo-7-oxo-4-oxa-1-thia-5-indenyl)-1-piperazinecarboxylate (414 mg, 1.0 mmol) and 4-aminophenylboronic acid hydrochloride (260 mg, 1.5 mmol, 1.5 eq.) were dissolved in a 2:1 v/v mixture of toluene and ethanol (10 mL). The mixture was treated with Na$_2$CO$_3$ 2M aqueous solution (3 mL) and deoxygenated by bubbling N$_2$ for 20 minutes. Pd[PPh$_3$]$_4$(58 mg, 0.05 mmol) was added and the mixture was heated to 85° C. for 2 hours. LCMS indicated complete conversion to product. The cooled reaction mixture was diluted with CH$_2$Cl$_2$ (100 mL) washed with water. The organics were dried over anhydrous MgSO$_4$, filtered and concentrated in vacuo. The crude residue was triturated with MeOH, filtered and air-dried to yield the pure product as a tan solid. Yield=160 mg (0.37 mmol, 38%).

LC/MS—HPLC (254 nm)—Rt 2.30 min. MS (ESI) m/z 428.1 [M$^+$+H$^+$]. Purity=95.0% by UV (254 nm).

Step 2: Preparation of 4-[(1-Azetidinyl)methyl]-1-(2-chloro-4-pyrimidinyl)-3-methyl-1H-pyrazole A stirred suspension of 1-(2-chloro-4-pyrimidinyl)-3-methyl-1H-pyrazole-4-carbaldehyde (444 mg, 2.0 mmol) and 3-azetidine hydrochloride (374 mg, 4.0 mmol) in dichloromethane (25 mL) was treated with portionwise addition of Na(OAc)$_3$BH (848 mg, 4.0 mmol). The resulting mixture was stirred at room temperature overnight. Next morning, LCMS analysis indicated clean conversion to product. The reaction was quenched by addition of H$_2$O (20 mL) and 1N NaOH aqueous solution (20 mL). This was transferred to a separatory funnel, the organic layer was separated, dried over anhydrous MgSO$_4$, filtered and concentrated in vacuo. The crude product was obtained as a light yellow solid (556 mg, >2.0 mmol, ~quant.) and used directly in the next step.

LC/MS—HPLC (254 nm)—Rt 0.08 min. MS (ESI) m/z 264.1 [M$^+$+H$^+$]. Purity=85% by UV (254 nm).

Step 3: Preparation of tert-Butyl 4-{3-[p-(4-{4-[(1-azetidinyl)methyl]-3-methyl-1H-pyrazol-1-yl}-2-pyrimidinylamino)phenyl]-7-oxo-4-oxa-1-thia-5-indenyl}-1-piperazinecarboxylate In an 8 mL vial, 4-[(1-azetidinyl)methyl]-1-(2-chloro-4-pyrimidinyl)-3-methyl-1H-pyrazole (55 mg, 0.21 mmol), tert-butyl 4-[3-(p-aminophenyl)-7-oxo-4-oxa-1-thia-5-indenyl]-1-piperazinecarboxylate (82 mg, 0.19 mmol), $Cs_2CO_3$ (124 mg, 0.38 mmol), BINAP (47 mg, 0.076 mmol) and $Pd(OAc)_2$ (9 mg, 0.038 mmol) were degassed under $N_2$ for 10 minutes. Degassed 1,4-dioxane (3 mL) was added and the resulting mixture was stirred at 110° C. for 16 hours. LCMS analysis indicated clean conversion to product. At this point, the reaction was cooled, diluted with water and extracted with a 9:1 v/v $CH_2Cl_2$/iPrOH mixture. The organic layer was separated, dried over anhydrous $MgSO_4$, filtered and concentrated in vacuo. The crude residue was purified by silica-gel chromatography eluting with EtOAc followed by 1:1 v/v EtOAc/MeOH. The product was obtained as a beige solid. Yield=87 mg (0.13 mmol, 69%).

LC/MS—HPLC (254 nm)—Rt 2.52 min. MS (ESI) m/z 655.9 [$M^+ + H^+$]. Purity=95.3% by UV (254 nm).

Step 4: Preparation of 3-[p-(4-{4-[(1-Azetidinyl)methyl]-3-methyl-1H-pyrazol-1-yl}-2-pyrimidinylamino)phenyl]-5-(1-piperazinyl)-4-oxa-1-thia-7-indenone dihydrochloride (Compound 4)

A stirred solution of tert-butyl 4-{3-[p-(4-{4-[(1-azetidinyl)methyl]-3-methyl-1H-pyrazol-1-yl}-2-pyrimidinylamino)phenyl]-7-oxo-4-oxa-1-thia-5-indenyl}-1-piperazinecarboxylate (87 mg, 0.13 mmol) in dichloromethane (1.3 mL) was treated with 4N HCl in dioxane solution (0.65 mL). After 16 hours, LCMS analysis indicated clean conversion to product. The reaction mixture was concentrated to dryness. The product was obtained as a yellow solid. Yield=55 mg (0.09 mmol, 74%).

LC/MS—HPLC (254 nm)—Rt 1.78 min. MS (ESI) m/z 555.2 [$M^+ + H^+$]. Purity=98.0% by UV (254 nm).

Example 8. Compiled Compound IC50 Data for SYK, BRD4, and PI3K (Values in nM)

Compounds of the invention were characterized for their ability to inhibit target proteins using third party vendors offering such services. PI3K alpha, gamma, and delta inhibition activity was determined by Thermo Fisher Scientific-Biosciences Life Sciences Solutions, Madison, Wis. The bromodomain protein inhibition (binding domain 1 and 2 of BRD4) as well as SYK inhibition was determined at Reaction Biology Corp., Malvern, Pa. Additional information on each of the assays performed and services provided is available at each company's website on the internet (https://www.thermofisher.com/us/en/home/life-science.html and http://www.reactionbiology.com/webapps/site, respectively). The IC50 data (shown below in Table 5) was calculated from a 10-point curve and is expressed in nanomolar concentration (nM) rounded off to the nearest whole number. Where multiple values were obtained the range from lowest to highest values is presented. NI=no inhibition detected up to 50 uM or IC50 not reached at 50 uM.

TABLE 5

| Cmpd # | SYK | BRD4-1 | BRD4-2 | PI3K α | PI3K β | PI3K γ |
|---|---|---|---|---|---|---|
| 1 | * | NI | NI | ** | *** | **** |
| 2 | * | **** | NI | *** | **** | NI |
| 3 | * | *** | *** | ** | ** | **** |
| 4 | ** | **** | NI | **** | **** | NI |

Note:
Compound 0 had SYK inhibition IC50 greater than 50,000 nM
Key for IC50 values:
* = <100 nM
** = 100 nM-1000 nM
*** = >1000 nM-<5000 nM
**** = >5000 nM-50000 nM
NI = >50000 nM Example 9. Effect of Compound 1, a Dual PI3K/SYK Inhibitor and Bay-61-3606 a SYK Inhibitor on Macrophage M2 Differentiation In Vitro Bone marrow derived macrophages (MOs) (BMDMs) were exposed to IL4 or LPS for 24 hours to stimulate the M2 or M1 macrophage transition in presence of Compound 1 and the known SYK inhibitor Bay-61-3606 at 1 µM conc. M2 markers Mmr, Ym1, Fizz1 and Mgl mRNA and M1 markers Il1, Il6 and Tnfa mRNA was quantitated by RT PCR. Values are mean±SEM (n=3-4). Expression of gene of interest is normalized to GAPDH. Table 6 below shows gene expression in LPS or IL4 stimulated BMDMs relative to control samples treated with agonist LPS or IL4. Control stimulated cells are ascribed a value of 1, hence a change of less than 1 indicates suppression of this mRNA below control, and a value of greater than 1 reflects an increase in mRNA for this gene. The data provide direct evidence that Compound 1 can block the immunosuppressive macrophage M2 gene expression and activate the M1 gene expression and therefore activate antitumor innate immune cell differentiation in vitro. Compound 1 augments M1 inflammatory gene expression and blocks immunosuppressive M2 gene expression in macrophages in vitro.

TABLE 6

Effect of Compound 1 on macrophage M2 gene expression.

| Samples | Il1 | Il6 | Tnfa | Mmr | Ym1 | Fizz1 | Arg | Mgl |
|---|---|---|---|---|---|---|---|---|
| Control | 1 | 1 | 1 | 1 | 1 | 1 | 1 | 1 |
| 200 nM Compound 1 | 1.1 | 1.7 | 0.88 | 0.41 | 0.37 | 0.44 | 0.5 | 0.31 |
| 500 nM Compound 1 | 1.1 | 1.29 | 1.23 | 0.18 | 0.21 | 0.31 | 0.45 | 0.41 |
| 1 µM Compound 1 | 1.2 | 3.15 | 1.70 | 0.19 | 0.10 | 0.11 | 0.39 | 0.30 |
| 2 µM Compound 1 | 1.25 | 1.59 | 1.99 | 0.14 | 0.11 | 0.22 | 0.14 | 0.40 |
| 5 µM Compound 1 | 0.69 | 0.97 | 0.90 | 0.18 | 0.04 | 0.06 | 0.22 | 0.24 |
| 500 nM Bay 61-3606 | 0.66 | 0.79 | 0.88 | 0.12 | 0.07 | 0.05 | 0.35 | 0.33 |
| 1 µM Bay 61-3606 | 0.22 | 0.31 | 0.69 | 0.12 | 0.07 | 0.005 | 0.33 | 0.34 |
| 5 µM Bay 61-3606 | 0.11 | 1.63 | 2.25 | 0.15 | 0.04 | 0.0013 | 0.06 | 0.36 |

Example 10

We investigated the effect of Compound 3 on immune cell in vitro and on tumor growth in in vivo in immunocompetent syngeneic tumor models and the effects on the macrophage and T cell immune compartment in vivo by this compound. Compound 3 blocked tumor growth, immunosuppressive macrophage polarization and increased infiltration of CD8+ T cells in LLC and MC38 tumors, and we observed an increased expression of the inflammatory cytokines, Ifng and GzmB in Compound 3-treated LLC tumor. In order to distinguish whether Compound 3 blocks tumor growth due to its effect on immune cell compartment and not on tumor compartment, we tested the effect of this chemotype on CT26 tumor growth in immunodeficient NSG mice vs immunocompetent Balb/c mice. Compound 3 administration did not reduce CT26 tumor growth in NSG mice. In contrast, Compound 3 blocked CT26 tumor growth in immunocompetent Balb/c mice (58% inhibition), validating our results that Compound 3 blocks tumor growth due to its effect on immune activation in vivo. Furthermore, Compound 3 didn't show any effect on viability of CT26 tumor cells in vitro. In CT26 model, an anti-tumor immune response was generated in combination with anti-PDL1 antibody as evident by a decrease in tumor growth and increase in CD8+ T cells. These results provide direct evidence of the efficacy of Compound 3, a dual SYK/PI3K inhibitor in blocking immune suppression and activating the adaptive T cell immune response and opened new opportunities to explore it in combination with check point inhibitors. Conclusion: These data provide direct evidence that Compound 3 has the capacity to activate the innate and adaptive immune response against cancer cells in vitro and in vivo. Compound 3 has combinatorial immune-oncologic activity in vivo to stimulate anti-cancer innate and adaptive immunity in well-defined accepted immune competent murine models for cancer immunotherapy.

Relative mRNA expression of IL4 or LPS polarized genes in murine bone marrow derived macrophages (BMDMs) treated with various concentrations of inhibitors in vitro. Conclusion: Compound 3 suppressed in vitro macrophage specific immunosuppressive M2 gene expression markers and augmented macrophage stimulatory immune response M1 genes respectively.

TABLE 7

Effect of Compound 3 on macrophage M2 genes:

| Samples | Arg | Tgfb | Il10 | Mmr | Vegf |
| --- | --- | --- | --- | --- | --- |
| Control | 1 ± 0.127 | 1 ± 0.025 | 1 ± 0.039 | 1 ± 0.029 | 1 ± 0.064 |
| 500 nM R788 | 0.352 ± 0.07 | 0.771 ± .007 | 0.35 ± 0.026 | 0.31 ± 031 | 0.58 ± 0.065 |
|  | p value ≤ 0.05 | p value ≤ 0.05 | p value ≤ 0.001 | p value ≤ 0.001 | p value ≤ 0.01 |
| 500 nM IPI549 | 0.62 ± 0.08 | 0.568 ± 0.05 | 0.081 ± .002 | 0.324 ± 0.049 | 0.374 ± .132 |
|  | p value ≤ 0.05 | p value ≤ 0.05 | p value ≤ 0.001 | p value ≤ 0.001 | p value ≤ 0.01 |
| 200 nM Compound 3 | 0.107 ± 0.01 | 0.458 ± 0.01 | 0.058 ± 0.01 | 0.143 ± 0.03 | 0.294 ± 0.04 |
|  | p value ≤ 0.05 | p value ≤ 0.05 | p value ≤ 0.001 | p value ≤ 0.001 | p value ≤ 0.01 |

TABLE 8

Effect of Compound 3 on macrophage M1 gene expression:

| Samples | Il1 | Il6 | Nos2 | Ifng | Tnfa |
| --- | --- | --- | --- | --- | --- |
| Control | 1 ± 0.19 | 1 ± 0.125 | 1 ± 0.11 | 1 ± 0.05 | 1 ± 0.13 |
| 500 nM R788 | 1.4 ± 0.003 | 1.8 ± 0.05 | 0.6 ± 0.014 | 3.2 ± 0.09 | 1.4 ± 0.13 |
|  | p value ≤ 0.05 | p value ≤ 0.05 | NS | p value ≤ 0.05 | NS |
| 500 nM IPI549 | 3.9 ± 0.003 | 1.8 ± 0.05 | 0.83 ± .04 | 1.9 ± 0.249 | 0.984 ± .16 |
|  | p value ≤ 0.05 | p value ≤ 0.05 | NS | p value ≤ 0.05 | NS |
| 200 nM Compound 3 | 7.19 ± 0.9 | 2.5 ± 0.2 | 2.458 ± 0.31 | 5.043 ± 1.9 | 2.2 ± 0.3 |
|  | p value ≤ 0.05 | p value ≤ 0.05 | p value ≤ 0.05 | p value ≤ 0.05 | p value ≤ 0.05 |

RT-PCR analysis of cDNAs generated from mRNAs reflecting tumor associated macrophages (TAMs) isolated from LLC tumors grown in WT animals and treated with Compound 3. *p<0.001p<0.01 and *p<0.05, t test. Conclusion: Compound 3 suppressed the expression of macrophage M2 immunosuppressive genes in LLC and activated the expression of immune response genes in this immunocompetent immune-oncology model system as compared to vehicle control treated mice. Expression of gene of interest is normalized to GAPDH. Table 9 shows gene expression in macrophages sorted from LLC tumors implanted in WT mice and treated with 3207. Statistical significance is accessed by t test. For example, Compound 3 augmented IL1 gene expression in TAMs 8-fold and suppressed Arginase (Arg) 98% in TAMs isolated from LLC tumors in vivo.

TABLE 9

Gene expression in macrophage sorted from LLC tumors.

| Samples | Il1 | Il6 | Ifng | Nos2 | Arg | Tgfb | Vegf |
|---|---|---|---|---|---|---|---|
| Macrophages sorted from Vehicle LLC tumors | 1.0 ± 0.04 | 1.0 ± 0.3 | 1 ± 0.3 | 0.95 ± 0.06 | 1 ± 0.9 | 1 ± 0.7 | 0.995 ± 0.06 |
| Macrophages sorted from Compound 3 Treated LLC tumors | 8.3 ± 1.43 p value ≤ 0.001 | 1.8 ± 0.16 p value ≤ 0.05 | 3.26 ± 1.04 p value ≤ 0.05 | 21 ± 0.19 p value ≤ 0.05 | 0.08 ± 0.004 p value ≤ 0.05 | 0.35 ± 0.014 p value ≤ 0.01 | 0.56 ± 0.05 p value ≤ 0.01 |

Compound 3: a novel dual Syk/PI3K inhibitory chemotype: Combinatorial inhibition of Syk and PI3K increases anti-tumor innate and adaptive T cell immune response in vivo. Tumor volume of LLC inoculated subcutaneously in WT mice treated with 10 mg/Kg Compound 3 (n=9, ***p<0.0001, t test). Conclusion: Compound 3 suppressed tumor growth of LLC by 68% in this immunocompetent immune-oncology model system as compared to vehicle control treated mice.

TABLE 10

| Tumor Type | % Growth inhibition in Compound 3 treated tumor compared to control |
|---|---|
| LLC | 68 ± 27%, p value ≤ 0.001 |

Quantification of CD3+, CD4+ and CD8+ T cells in the LLC tumors treated with Compound 3 (n=3, *p<0.05, t test). Conclusion: Compound 3 decreased CD4+ cells by 50% and increased CD8+ T cells in the tumor compartment by 7% in vivo as compared to vehicle control treated mice.

TABLE 11

| LLC Tumor Type | CD4+ T cells (% of CD3+ T cells) | CD8+ T cells (% of CD3+ T cells) |
|---|---|---|
| Vehicle | 47 ± 9 | 27 ± 3.0 |
| Compound 3 | 23 ± 7, p value ≤ 0.05, compared to control | 34 ± 1.1, p value ≤ 0.05, compared to control |

Effect of Compound 3 treatment in vivo at 10 mg/kg dose on mRNA expression of interferon (Ifng) gamma and granzyme b (Gzmb) in LLC tumors implanted in vehicle vs Compound 3 treated mice (n=3, biological replicates, p<0.05, t test). Relative gene expression is normalized to a house keeping gene, GAPDH for comparison. Conclusion: Compound 3 treatment of tumor bearing mice in vivo increased the expression of immunostimulatory T cell immune effectors in vivo as compared to vehicle control mice.

TABLE 12

| LLC Tumor Type | Ifng | Gzmb |
|---|---|---|
| Vehicle | 0.8 ± 0.18 | 0.87 ± 0.27 |
| Compound 3 | 1.4 ± 0.27, p value ≤ 0.05 compared to vehicle | 1.87 ± 0.5 p value ≤ 0.05 compared to vehicle |

Tumor volumes of CT26 inoculated subcutaneously in Balb/c mice treated with 3 mg/Kg Compound 3, or 200 ug anti-PDL1 or both. Conclusion: Compound 3 has greater antitumor immune activating activity as compared to anti-PDL1 monoclonal antibody treatment in this in vivo immune-oncology model. Compound 3 suppressed tumor growth by 88% in this model (n=6, p<0.001, t test) as compared to vehicle control treated mice.

TABLE 13

| CT26 Tumor Type | % Growth inhibition compared to control | p value |
|---|---|---|
| PDL1 | 65 ± 14% | ≤0.001 |
| Compound 3 | 88 ± 10% | ≤0.001 |
| Compound 3 + PDL1 | 89 ± 6% | ≤0.001 |

Effect of Compound 3 treatment of CT26 tumor bearing mice in vivo 3 mg/kg by intraperitoneal injection QD (IP) for 14 days on number of CD3+/CD8+ T cells infiltrating the tumor tissue. Conclusion: Compound 3 increased CD8+ T cells in the tumor compartment by 800% in vivo. (n=6, p<0.001, t test) as compared to vehicle control treated mice.

TABLE 14

| CT26 Tumor Type | CD3+ T cells (% of live cells) | p value compared to control |
|---|---|---|
| Vehicle | 1.1 ± 0.29 | |
| PDL1 | 3.6 ± 2.2 | ≤0.05 |
| Compound 3 | 8 ± 0.46 | ≤0.001 |
| Compound 3 + PDL 1 | 8.7 ± 0.8 | ≤0.001 |

Table shows flow cytometric quantification of CD3+ and CD4+ and CD8+ T cells respectively from the tumors CT26 treated with Compound 3 vs anti-PDL1 mAB (n=3; p<0.0001, analyzed by t test). Values represent mean±SEM. Conclusion: Compound 3 decreased CD4+ T cells by 5.6-fold and increased CD8+ T cells in the tumor compartment by 6% in vivo as compared to vehicle control treated mice.

TABLE 15

| CT26 Tumor Type | CD4+ T cells (% of CD3+ T cells) | CD8+ T cells (% of CD3+ T cells) | p value compared to control |
|---|---|---|---|
| Vehicle | 56 ± 5.29 | 56 ± 3.9 | |
| PDL1 | 38 ± 9.0 | 46 ± 9.0 | ≤0.001 |
| Compound 3 | 9.5 ± 0.7 | 62 ± 2.0 | ≤0.001 |

TABLE 15-continued

| CT26 Tumor Type | CD4+ T cells (% of CD3+ T cells) | CD8+ T cells (% of CD3+ T cells) | p value compared to control |
|---|---|---|---|
| Compound 3 + PDL1 | 9.2 ± 1.48% | 72 ± 7.0 | ≤0.001 |

Compound 3 has no effect on the in vitro viability of CT26 tumor cells.

TABLE 16

| Log Inhibitor (Compound 3) conc. | % Cell Viability |
|---|---|
| 0 | 100 |
| 1.68867 | 96.5 ± 5.3 |
| 1.9897 | 96 ± 8.0 |
| 2.29073 | 91.6 + 8.9 |
| 2.59176 | 91.3 ± 5.13 |
| 2.89279 | 89.8 ± 6.7 |
| 3.19382 | 87.3 ± 4.1 |
| 3.49485 | 87.1 ± 9.6 |
| 3.79588 | 84.3 ± 4.3 |
| 4.09691 | 83.9 ± 6.27 |
| 4.39794 | 83.6 ± 5.1 |
| 4.69897 | 77.4 ± 5.0 |

Compound 3 treatment at 3 mg/kg has no significant effect on CT26 tumor growth in immunodeficient (nod/scid/IL2 gamma k/o) mice (NSG) mice. Conclusion: this establishes effect of Compound 3 as immune-oncologically active agent in cancer immunotherapy. In immunocompetent mice with same tumor cell ino kculum Compound 3 inhibited CT26 tumor growth by 58% decrease in tumor volume. (n=x, p<0.001, t test).

TABLE 17

| Tumor type | % Growth inhibition |
|---|---|
| CT26 NSG | −33 ± 27<br>33% increase in tumor growth in immunodeficient NSG mice |

In contrast to above data, Compound 3 has a marked significant inhibitory effect on CT26, LLC and MC38 tumor growth in immunocompetent murine models. Conclusion: this establishes effect of Compound 3 as immune-oncologically active agent in cancer immunotherapy. In immunocompetent mice with same tumor cell inoculum Compound 3 inhibited tumor growth by from 58-68%. p<0.001 in all experiments compared to vehicle control.

TABLE 18

| Tumor Type | % Growth Inhibition |
|---|---|
| LLC | 68 +/− 27 |
| CT26 | 58 +/− 10 |
| MC38 | 62 +/− 24 |

What is claimed is:

1. A compound or a pharmaceutically acceptable salt thereof selected from the group consisting of Formula II-V,

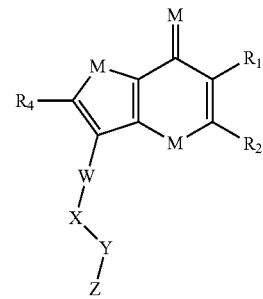

Formula II

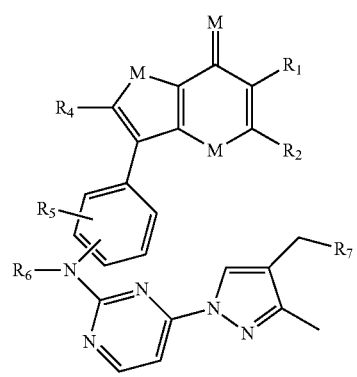

Formula III

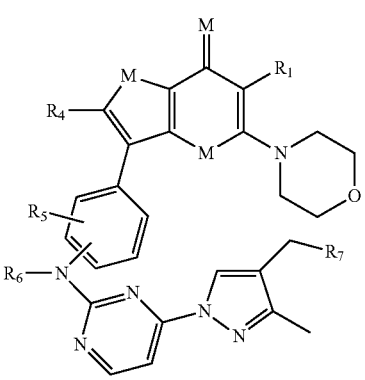

Formula IV

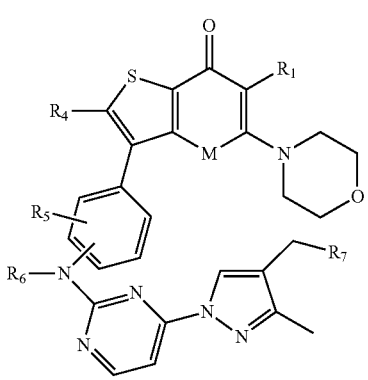

Formula V wherein M is independently oxygen (O) or sulfur (S);
R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1 or morpholine, or thiomorpholine or piperazine;

R3 is selected from R1;

R4 is selected from R1;

R5 is present in 1, 2, 3, or 4 points of substitution on the aryl ring and is independently selected from R1;

R6 is independently selected from R1;

R7 is independently selected from R1;

W is null, aryl, heteroaryl, or heterocyclic;

X is oxygen or amino wherein the amino group is either a secondary nitrogen or substituted tertiary nitrogen;

Y is a heteroaryl;

Z is a heteroaryl containing one or two amino groups in the ring.

2. A compound or a pharmaceutically acceptable salt thereof selected from the group consisting of

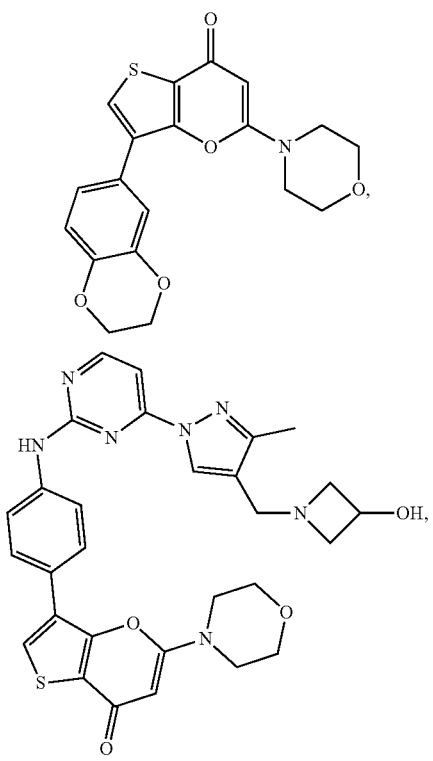

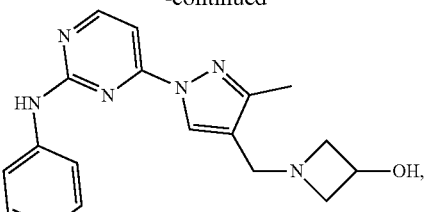

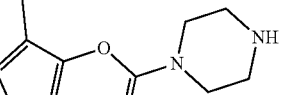

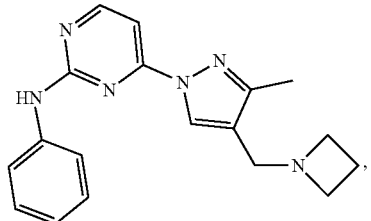

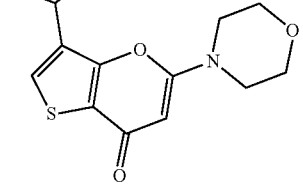

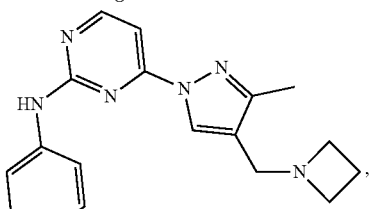

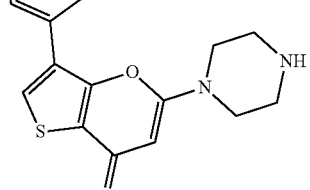

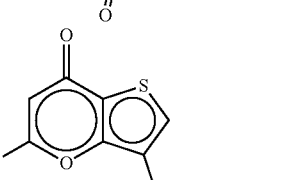

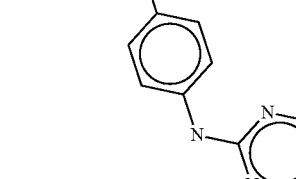

221
-continued
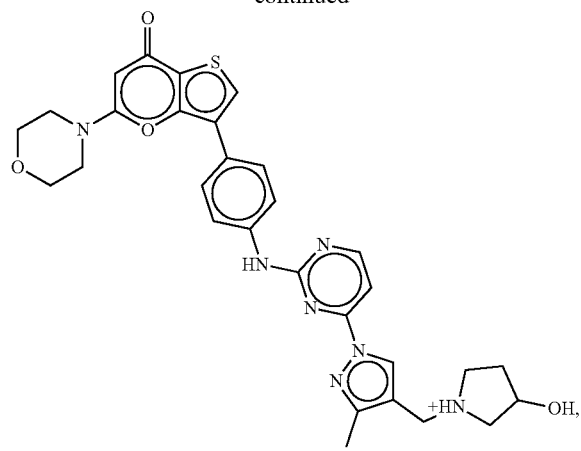
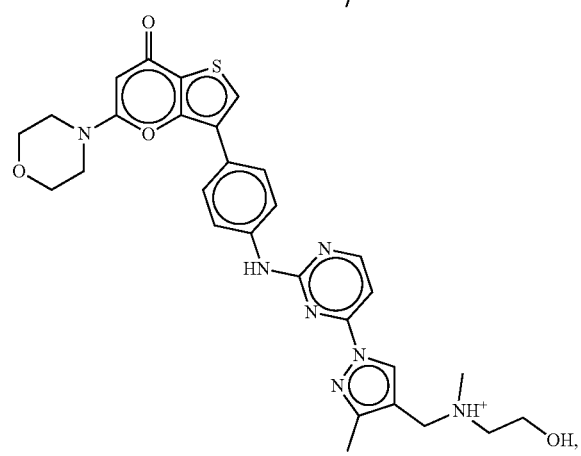
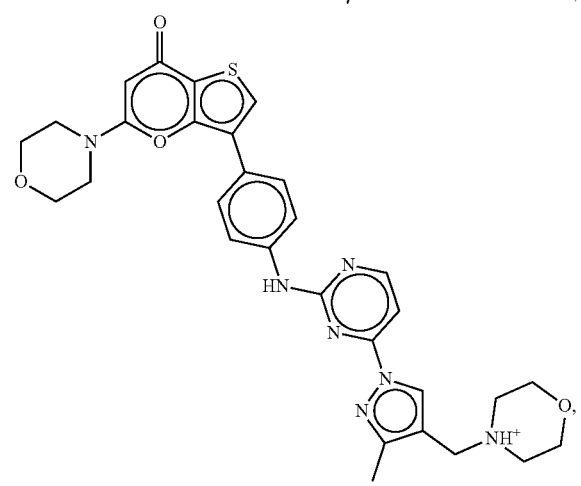
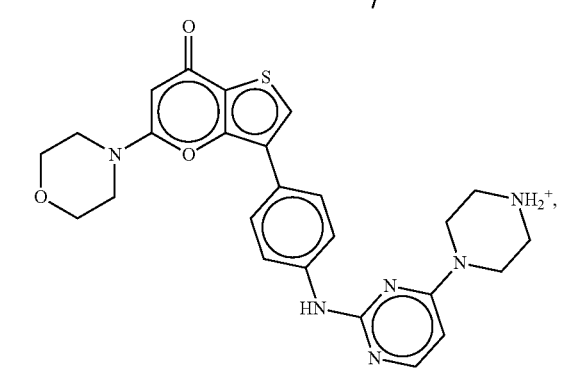
222
-continued
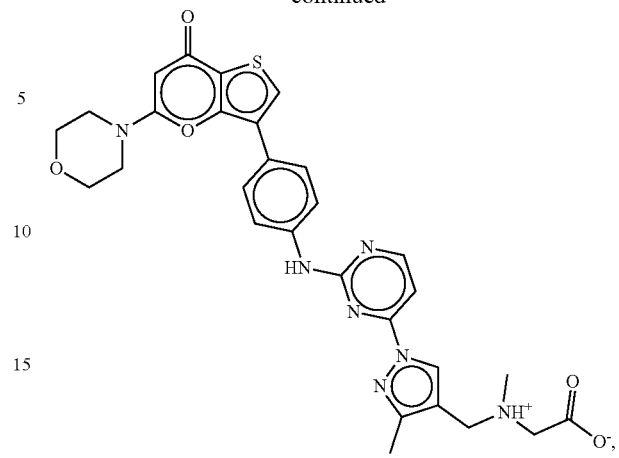
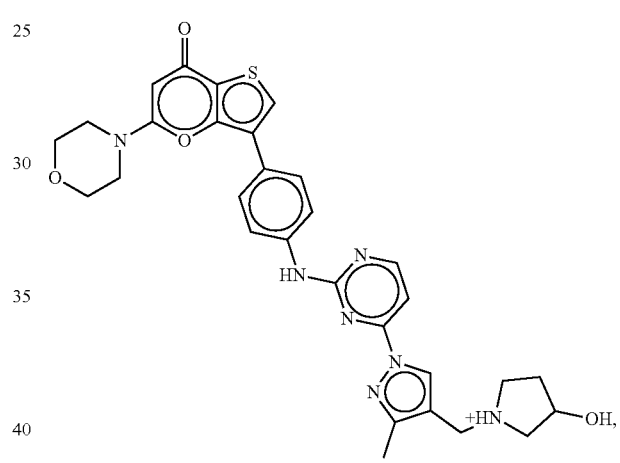
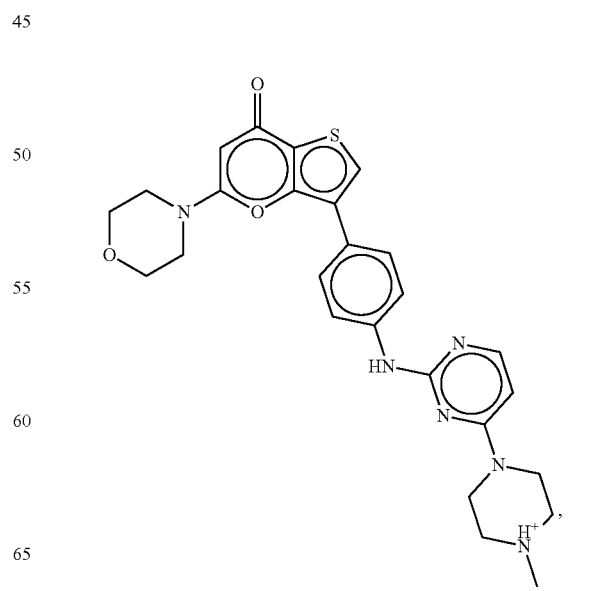

223
-continued
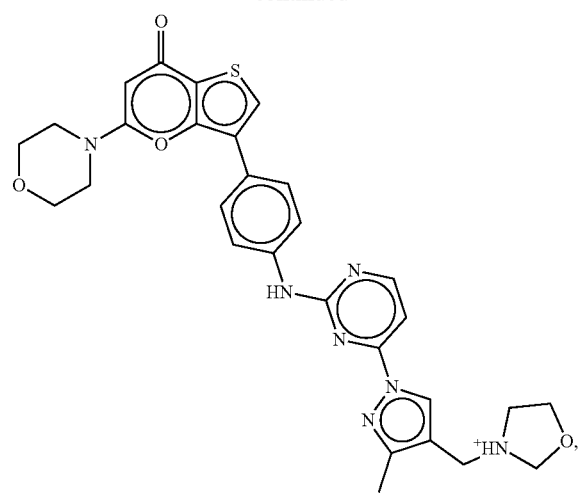
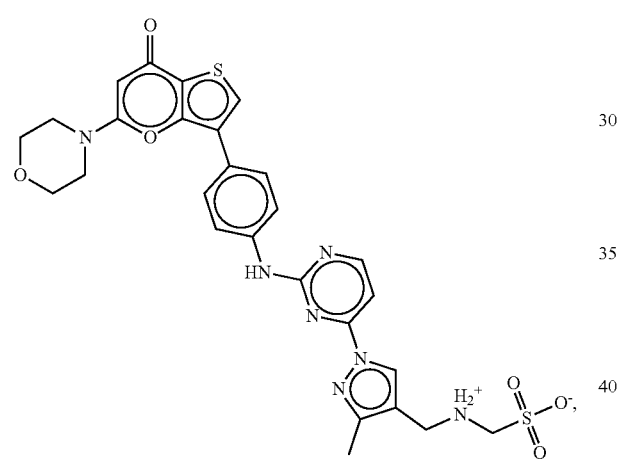
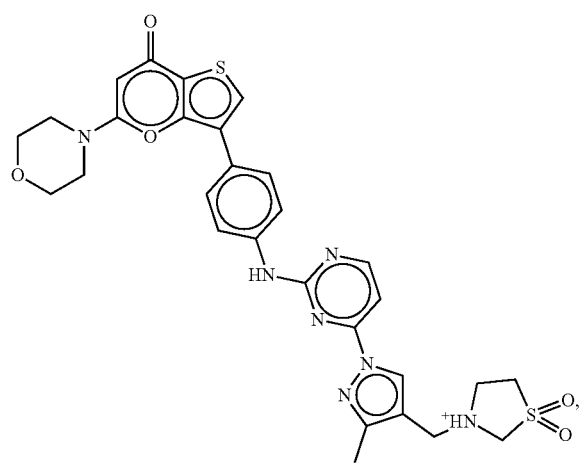
224
-continued
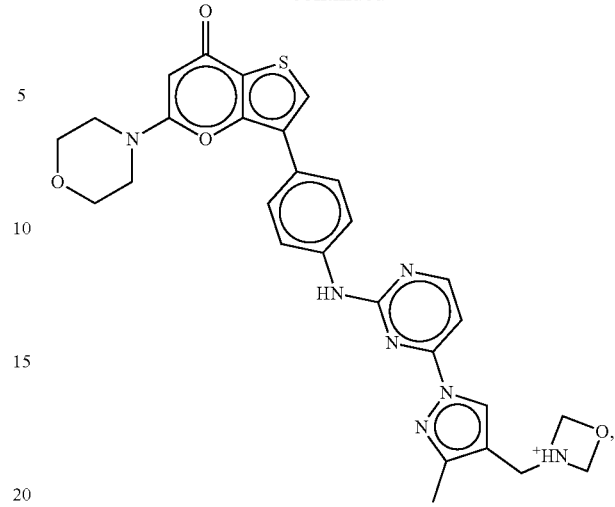
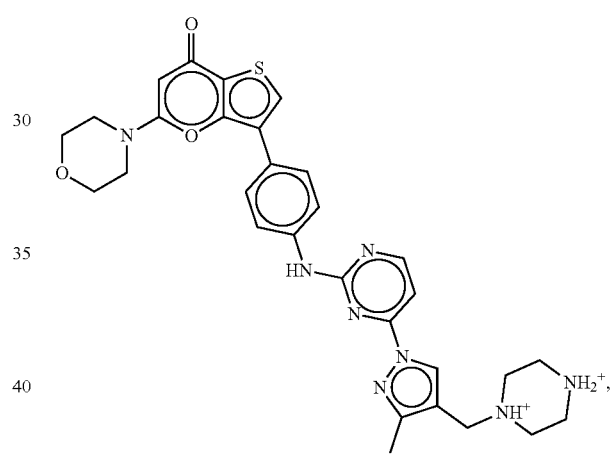
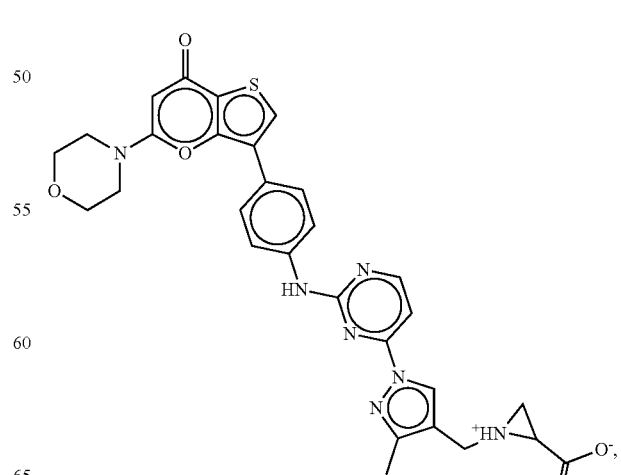

225
-continued
226
-continued
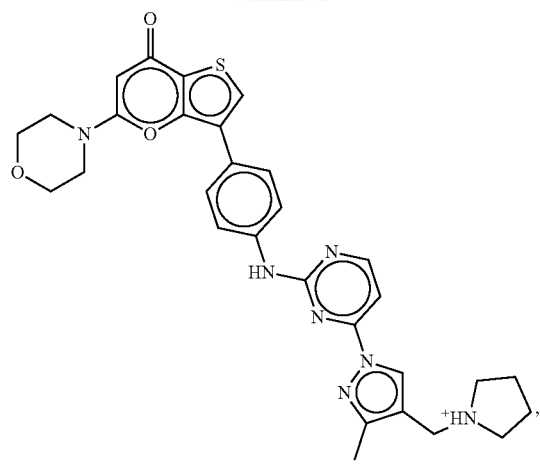
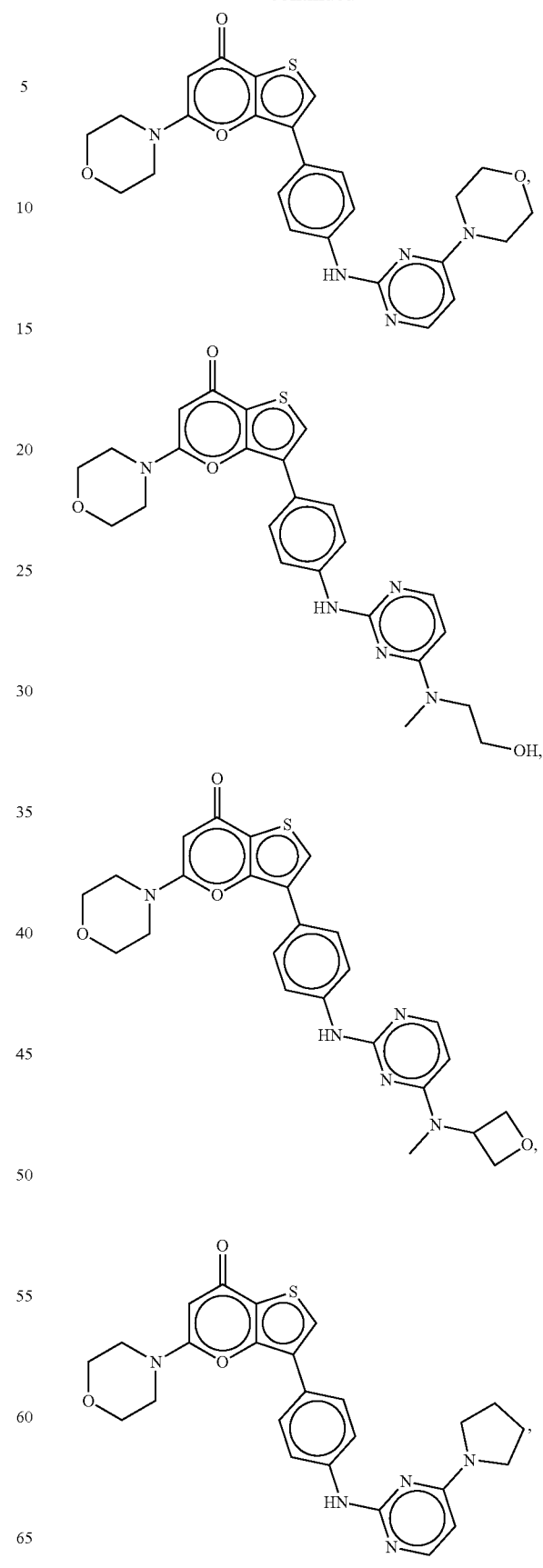

227
-continued
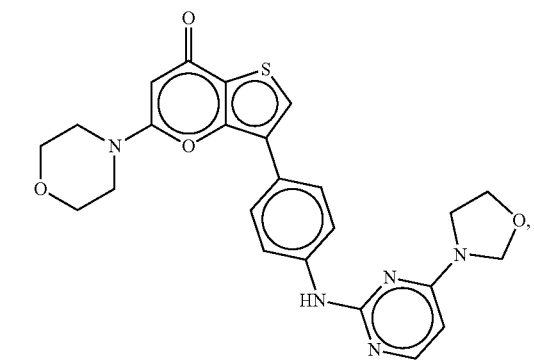
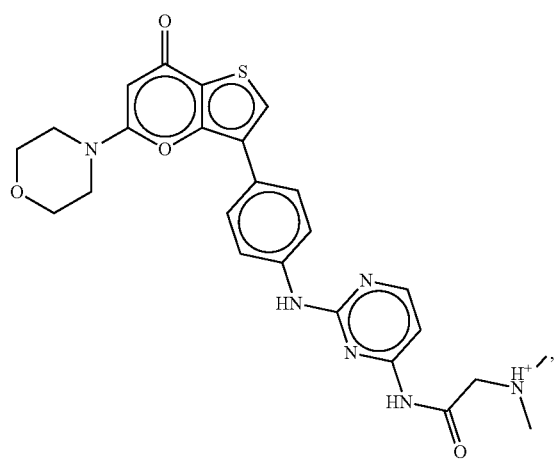
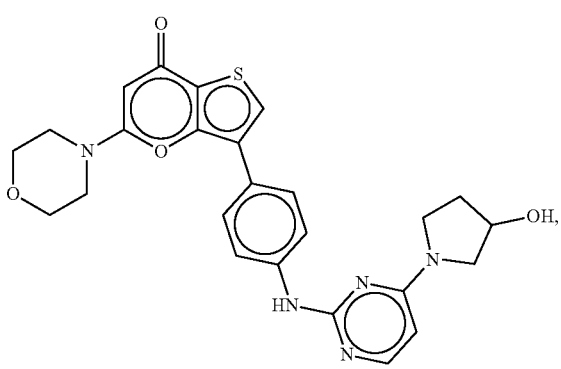
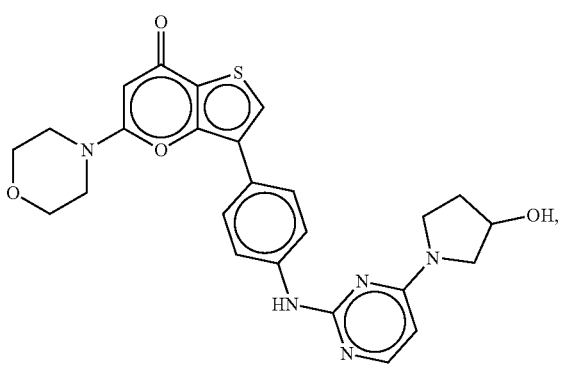
228
-continued
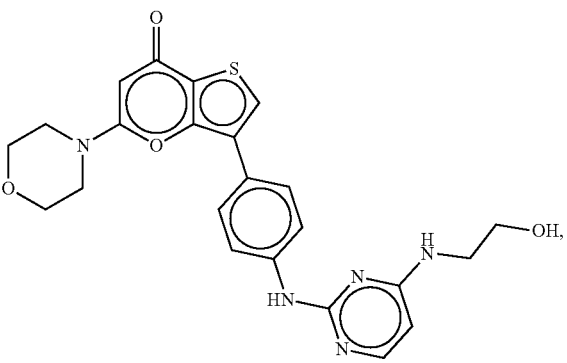
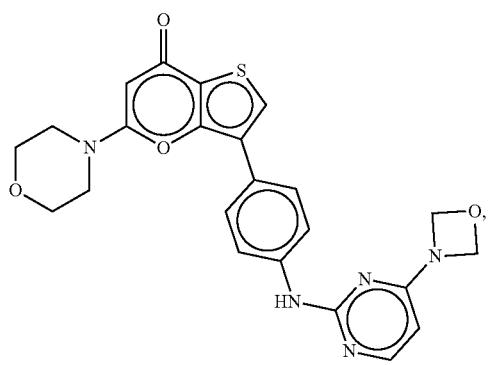
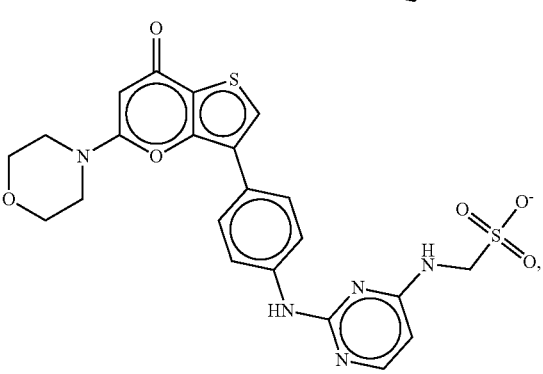
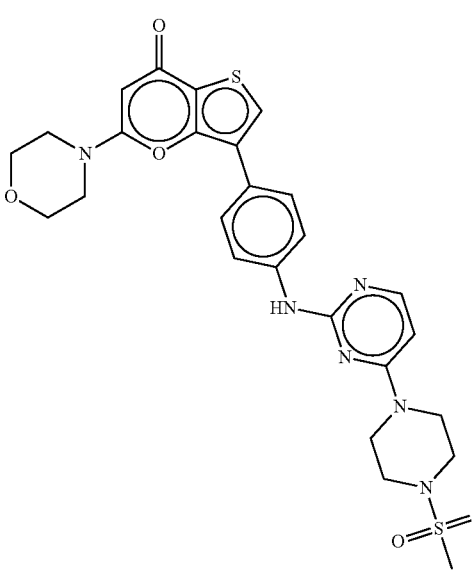

229
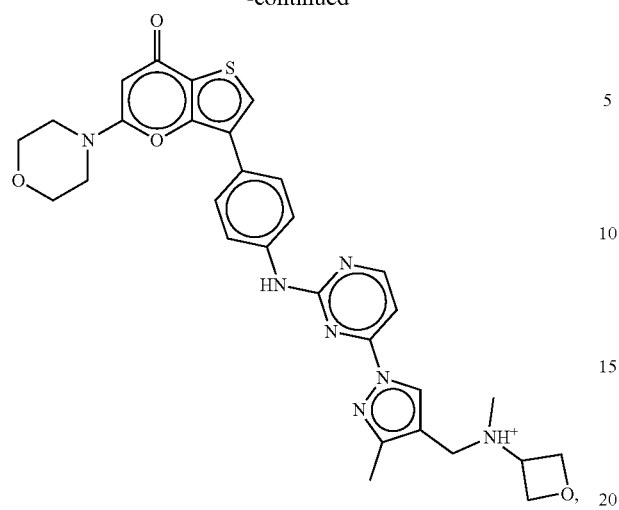
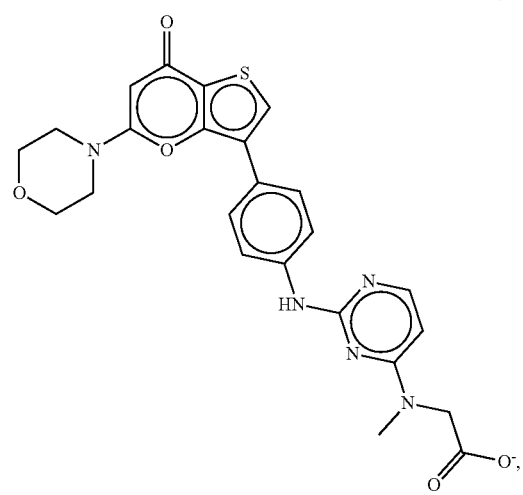
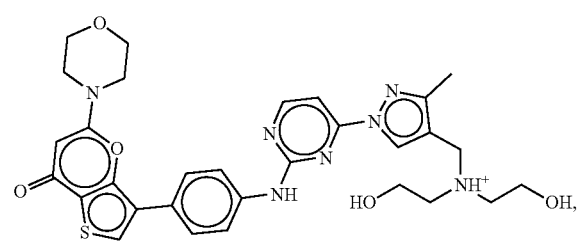
230
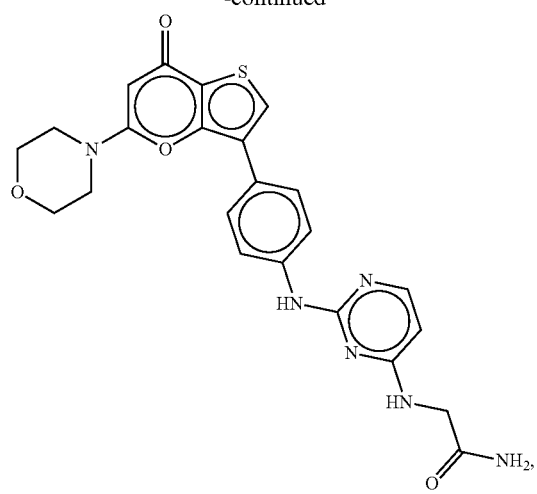
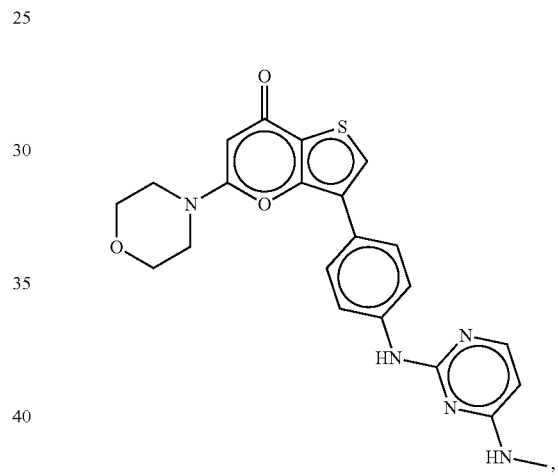
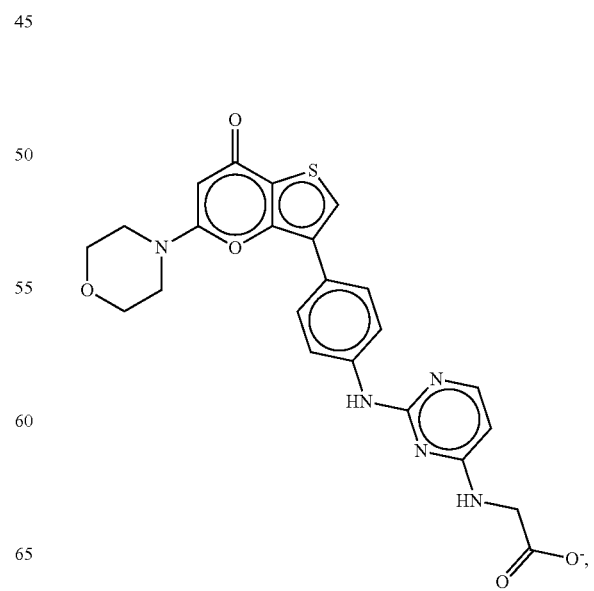

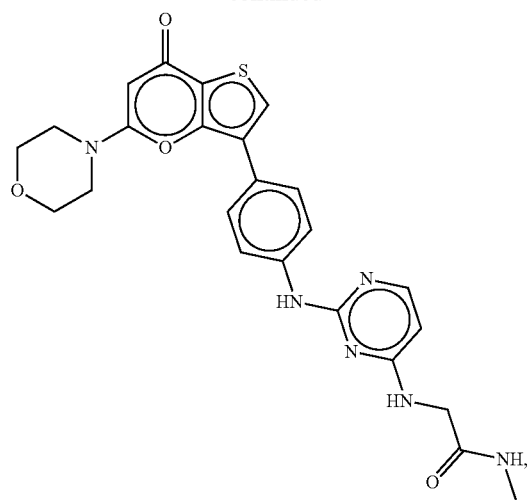
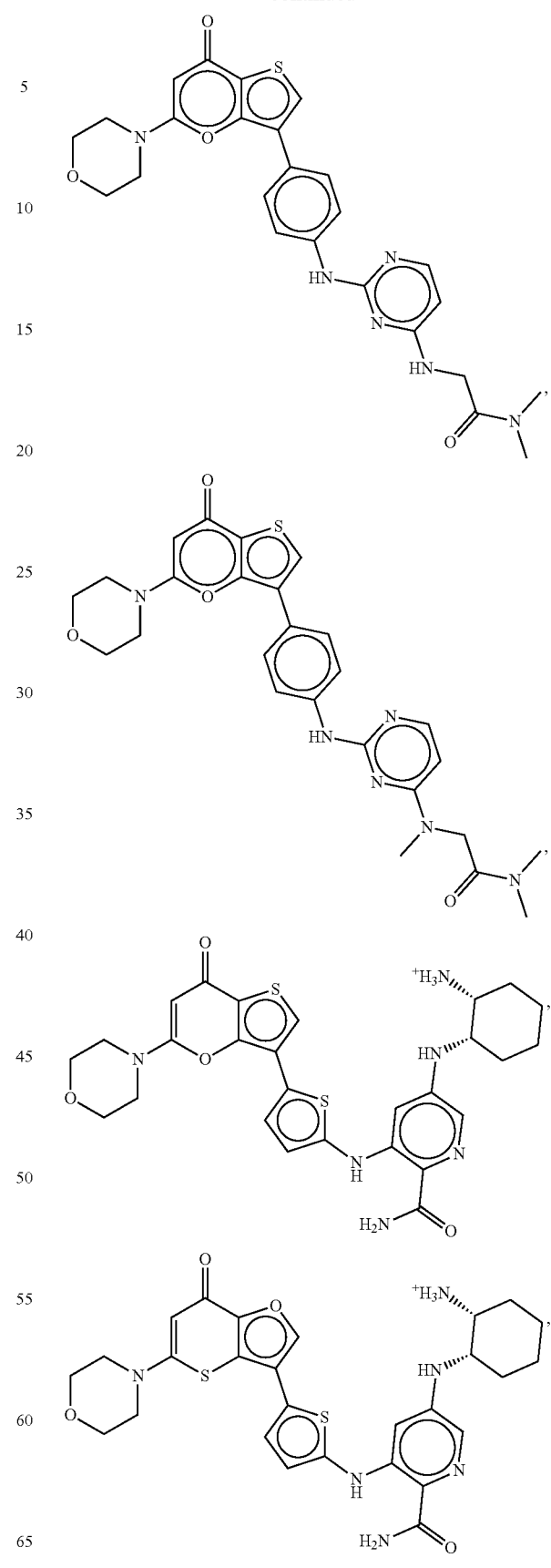

233
-continued
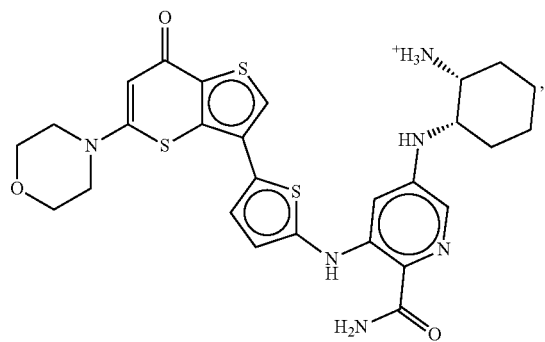
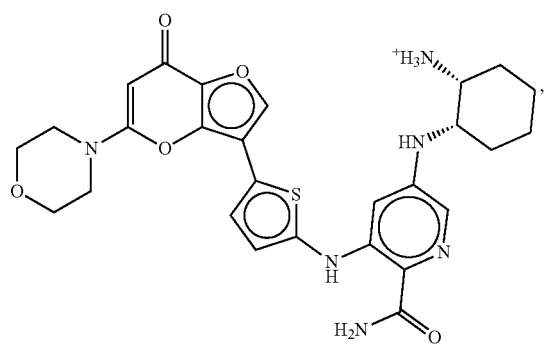
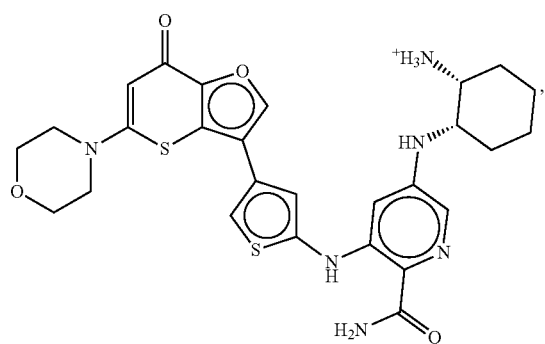
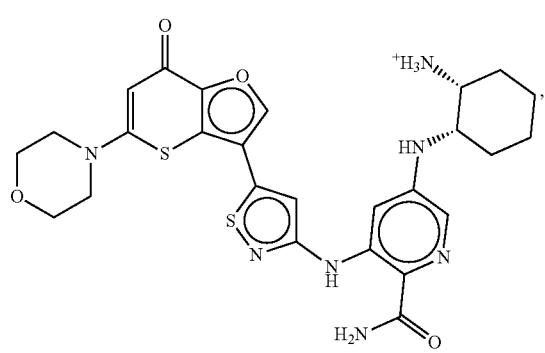
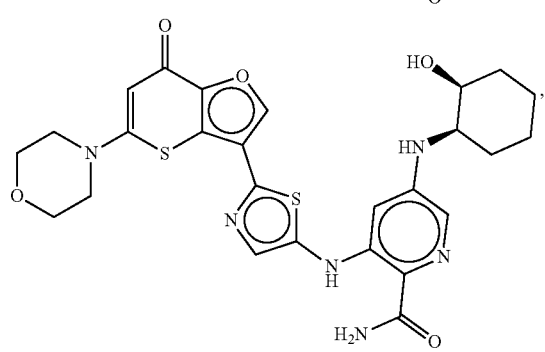
234
-continued
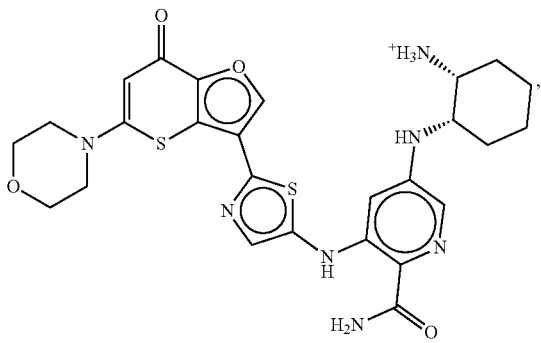
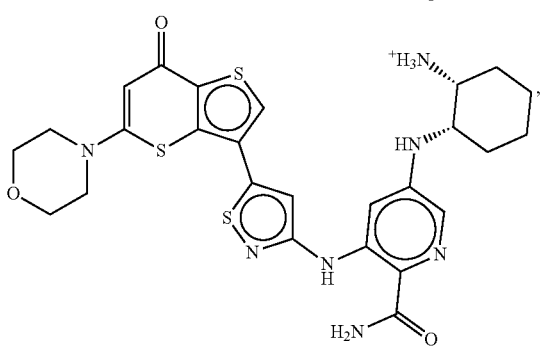
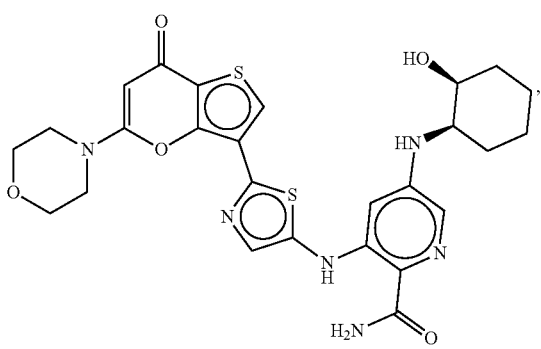
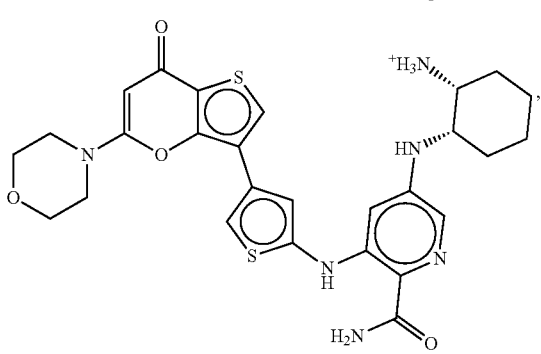
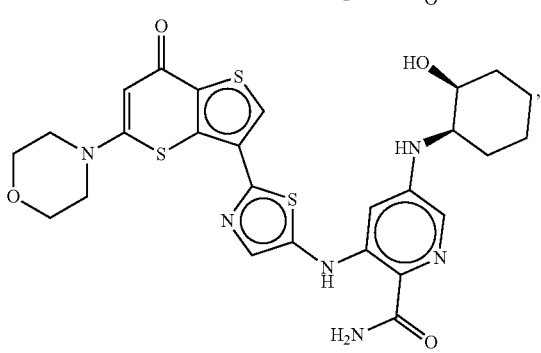

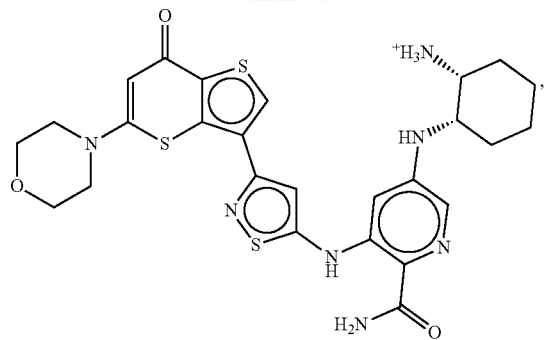
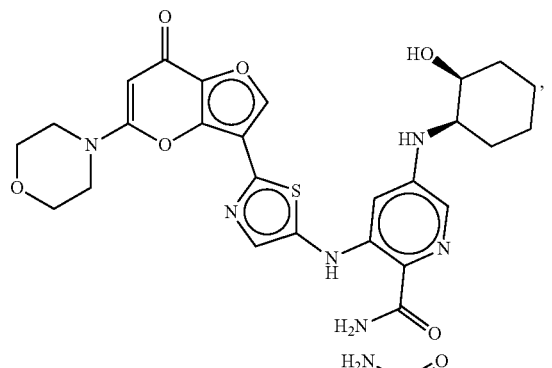
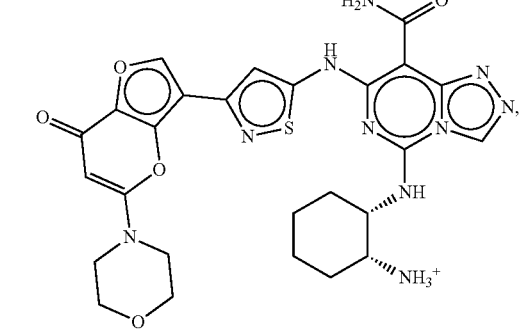
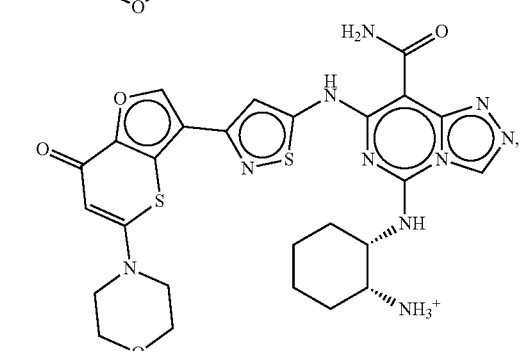
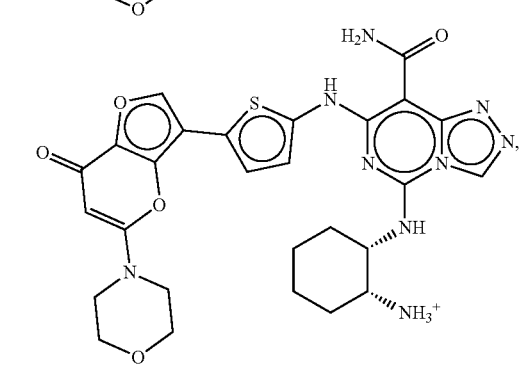
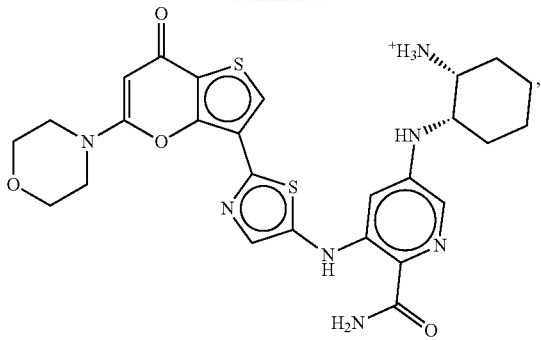
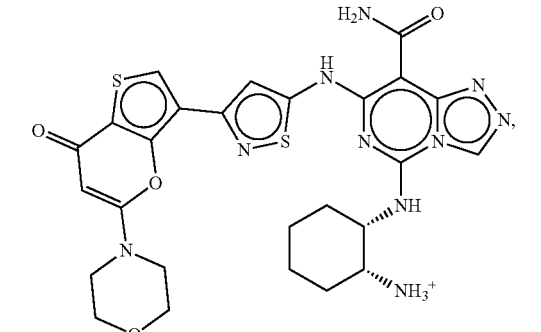
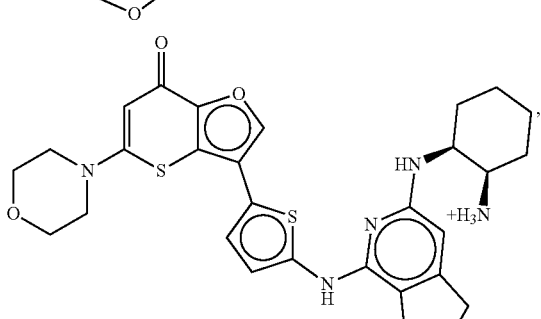
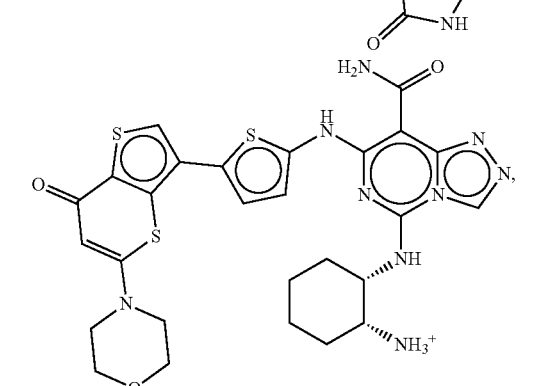
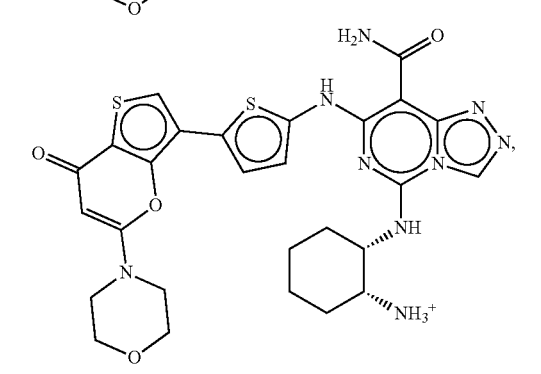

237
-continued
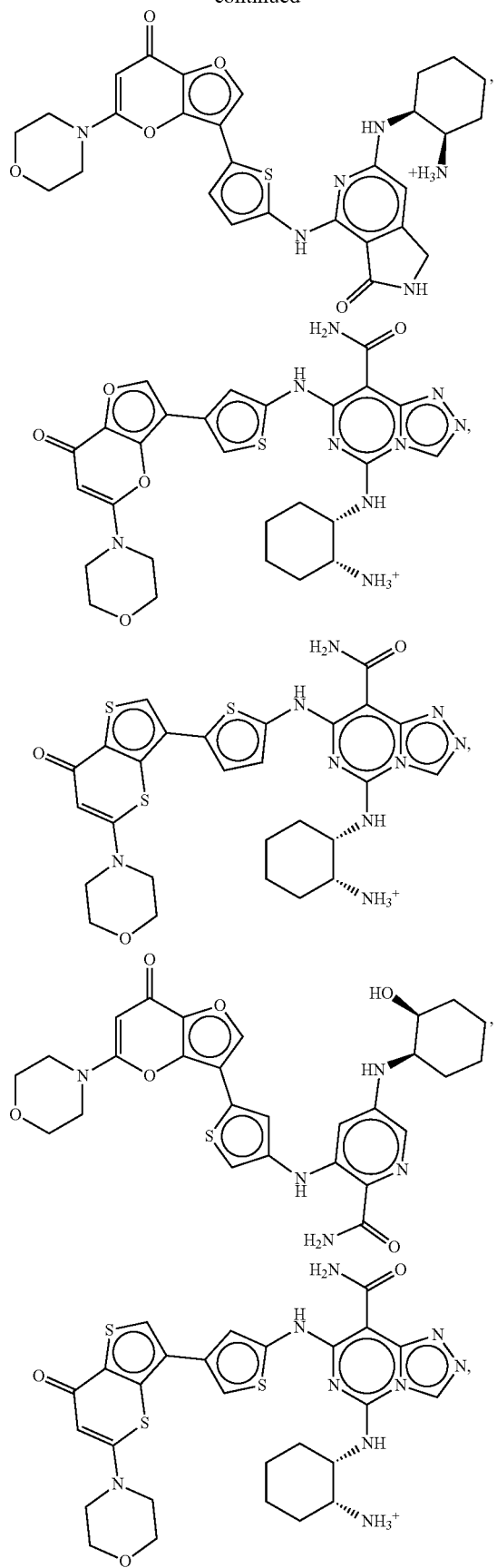
238
-continued
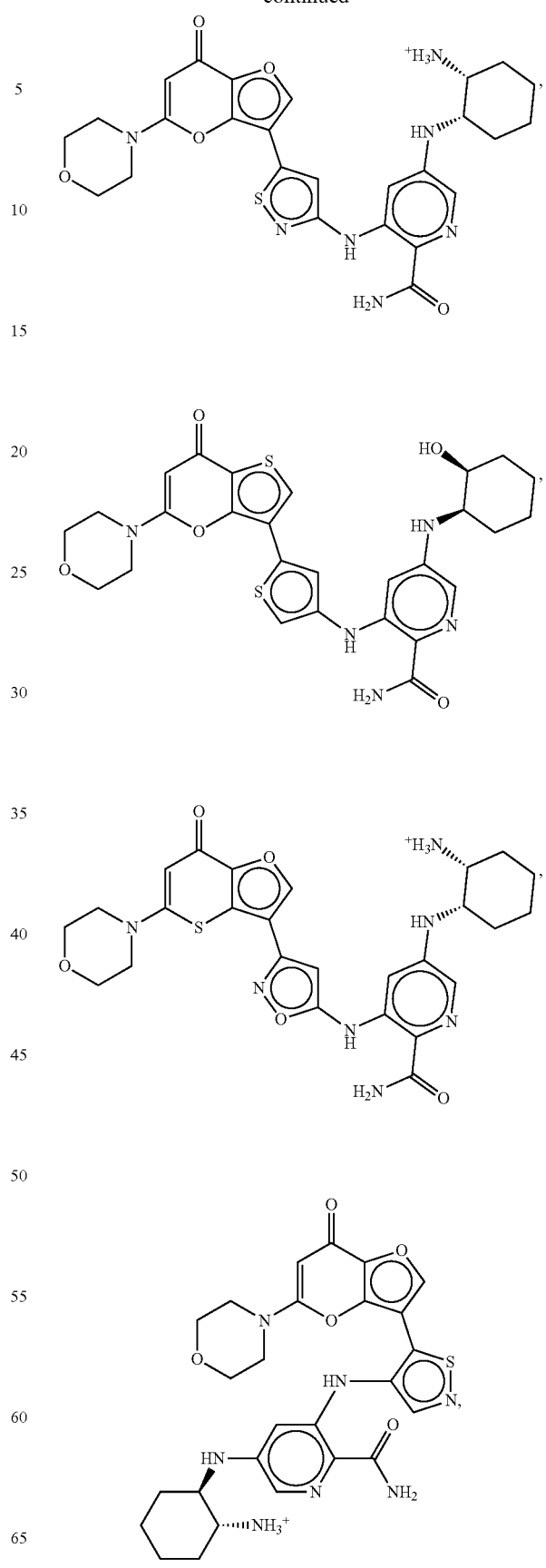

239
-continued
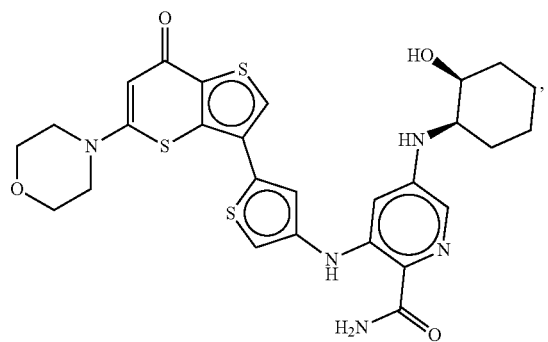
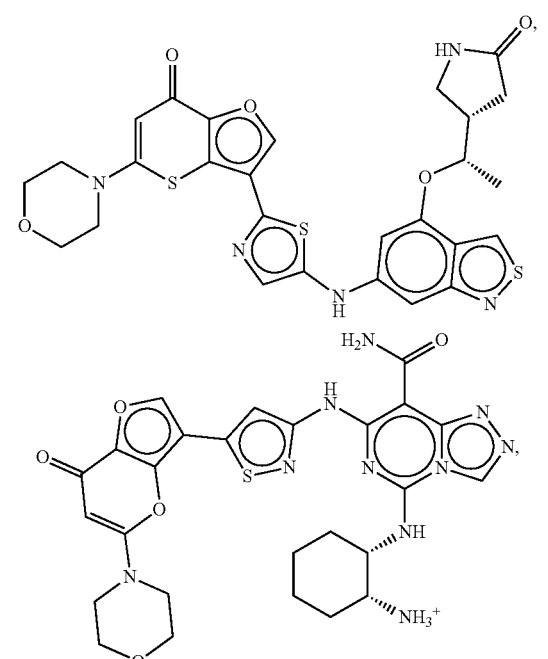
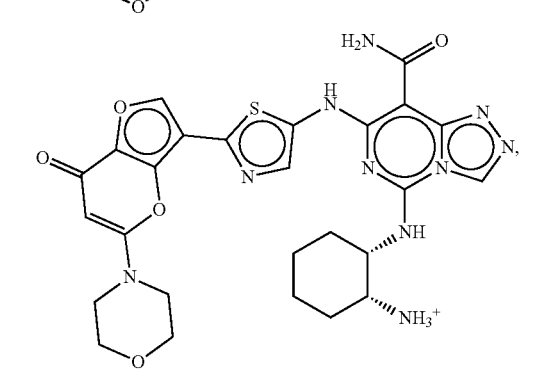
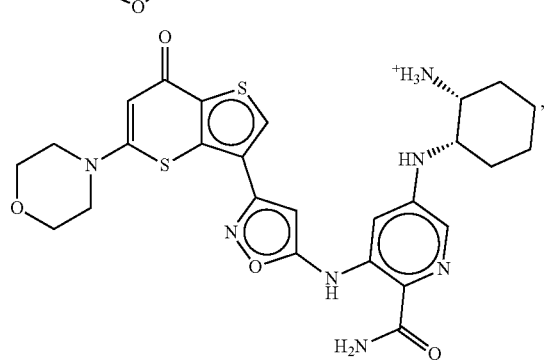
240
-continued
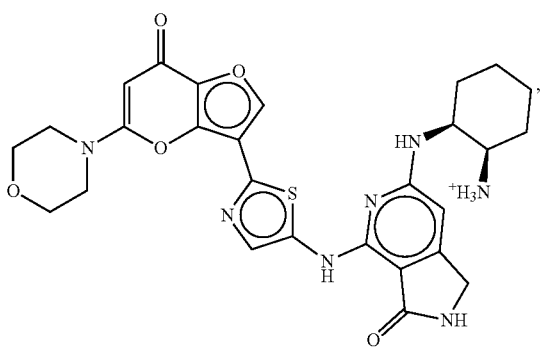
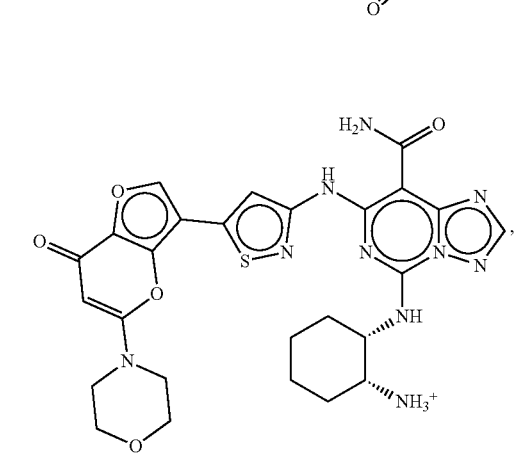
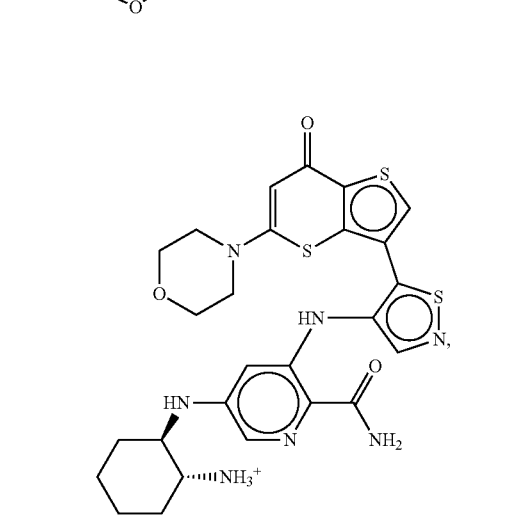
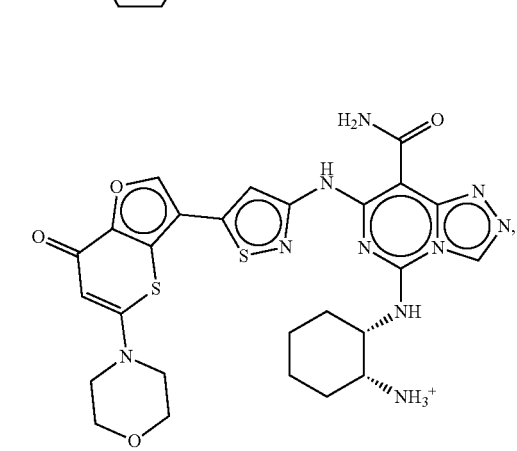

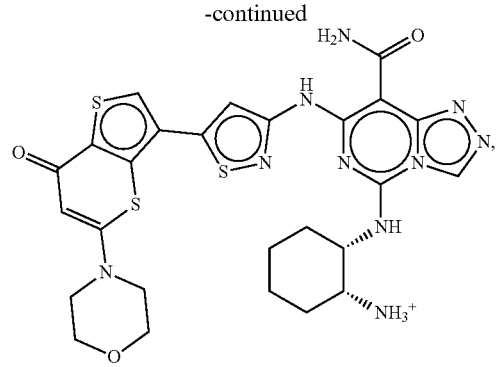
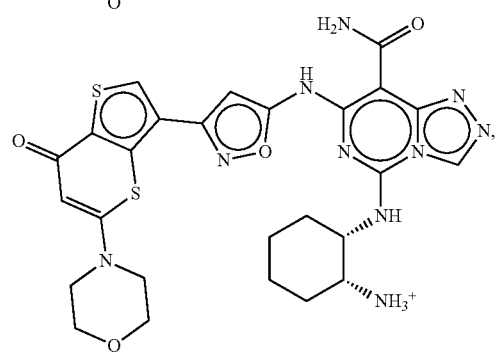
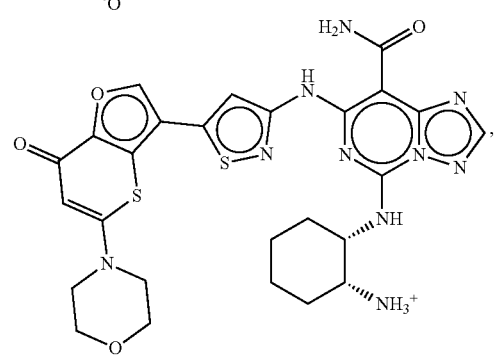
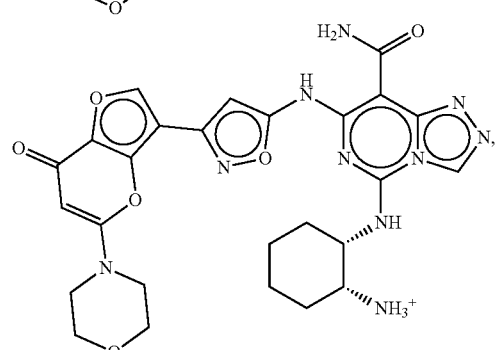
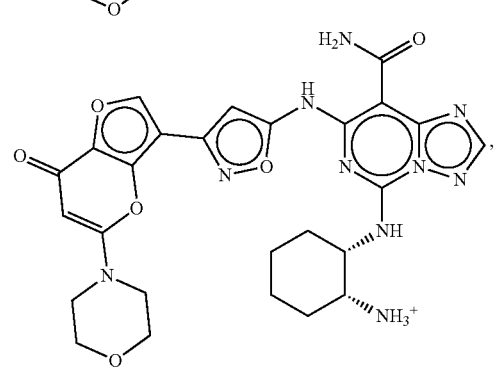
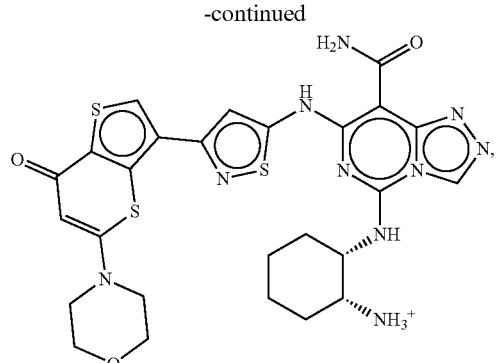
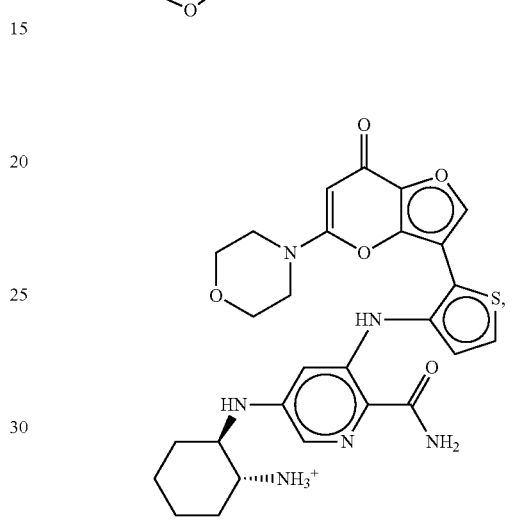
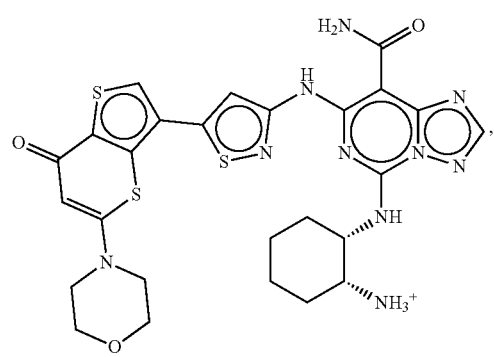
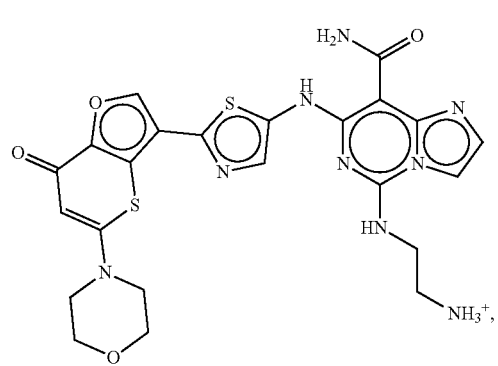

243
-continued
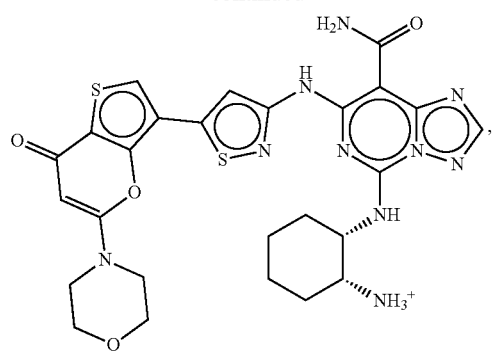
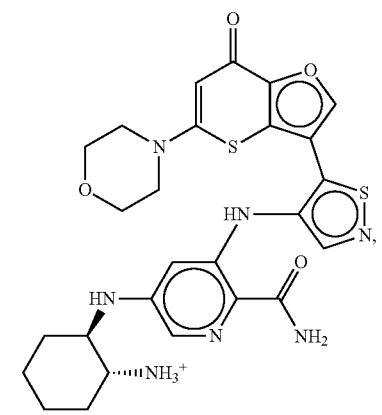
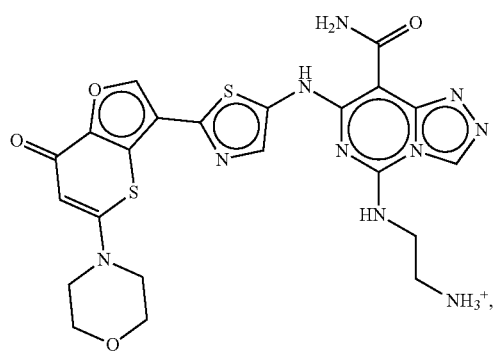
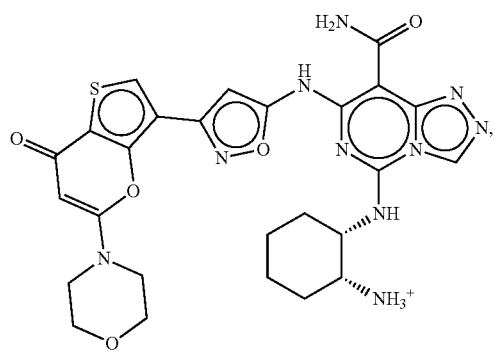
244
-continued
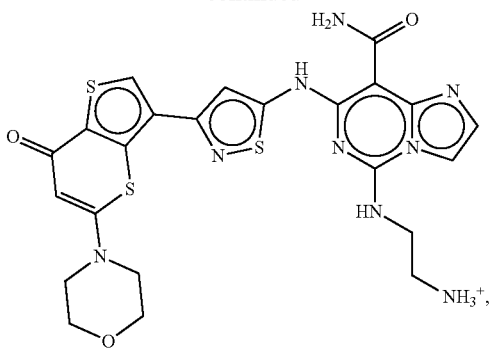
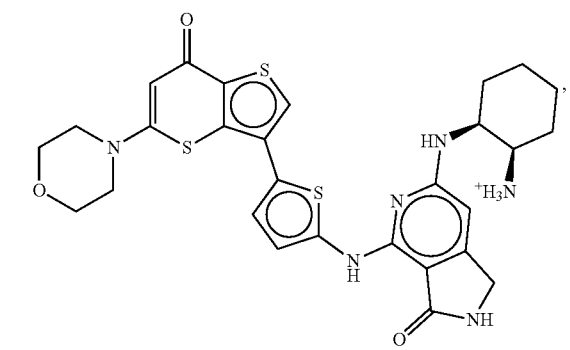
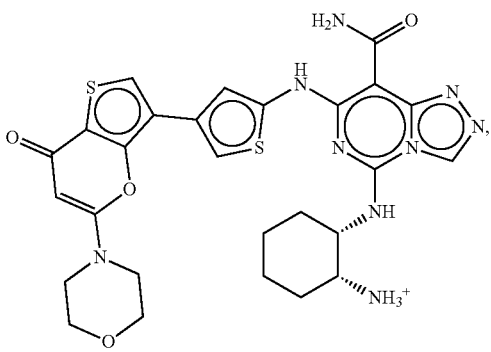
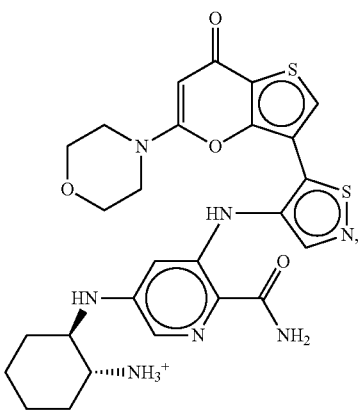

245
-continued
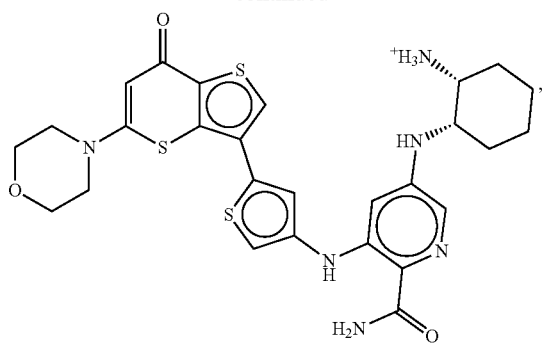
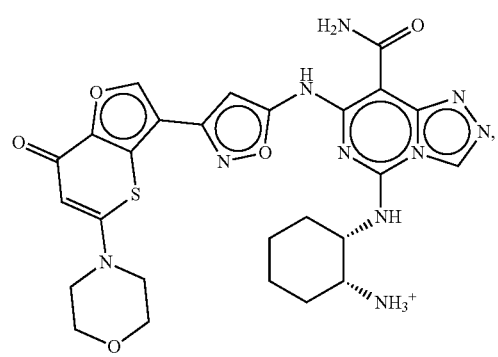
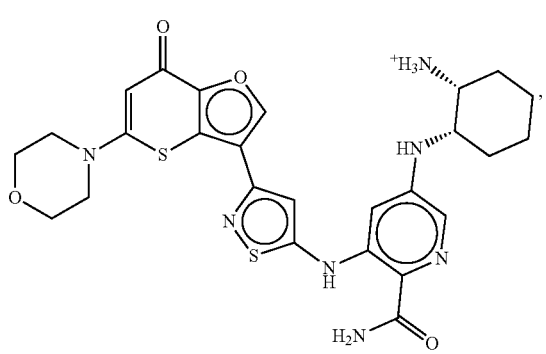
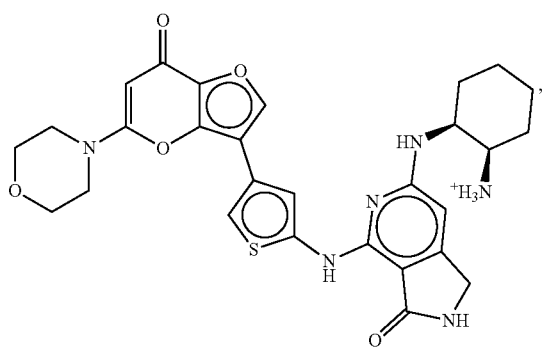
246
-continued
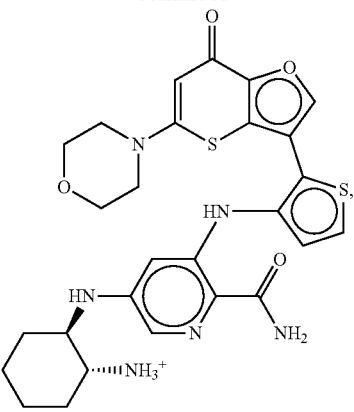
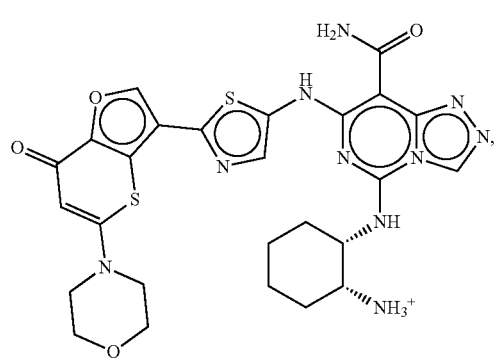
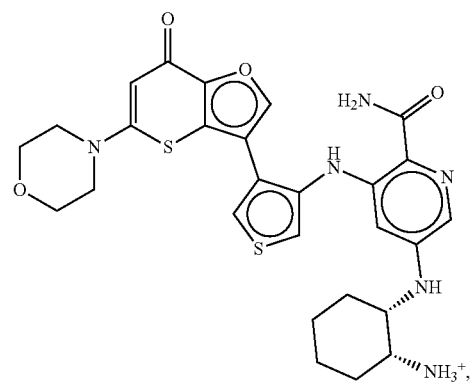
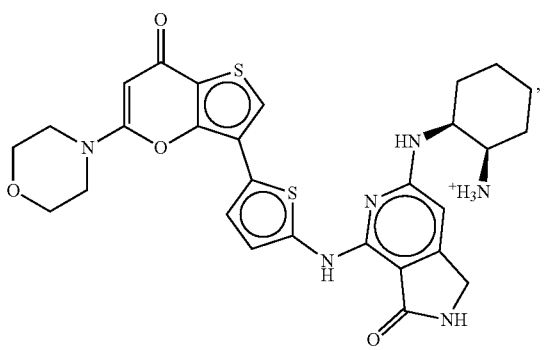

247
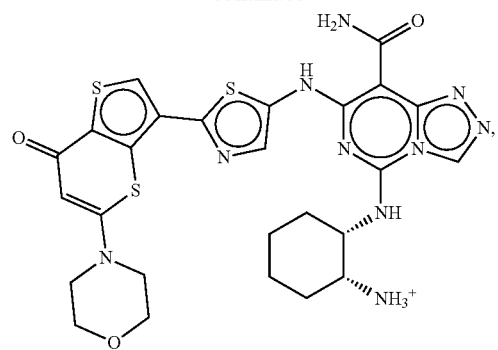
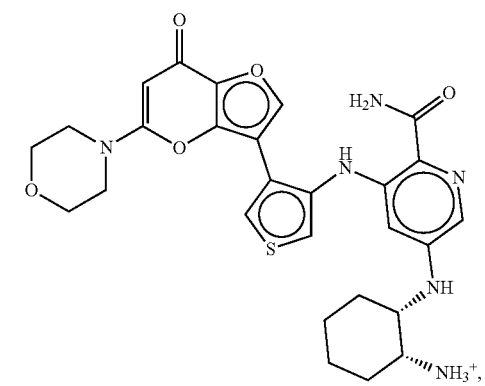
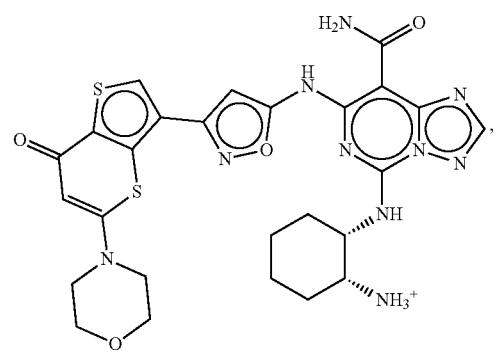
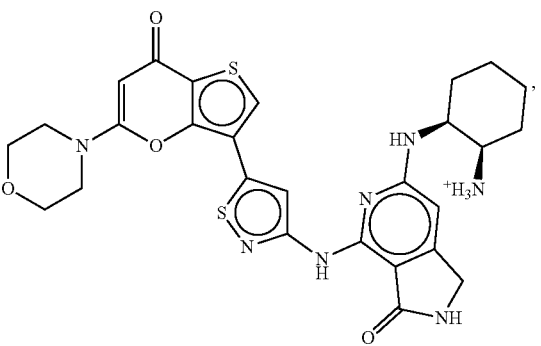
248
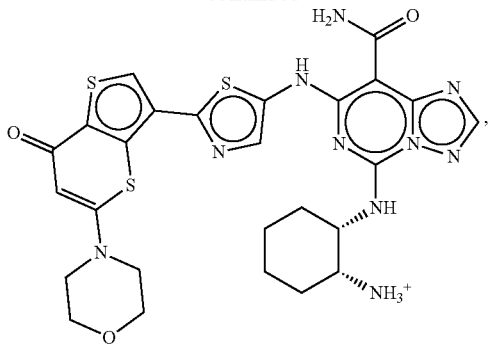
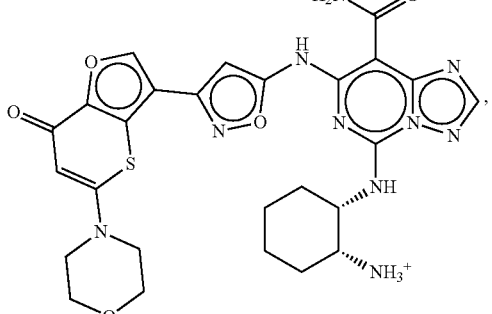
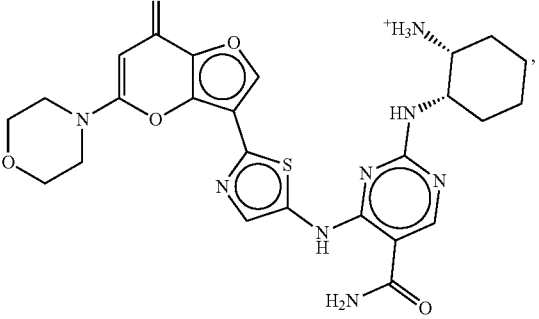
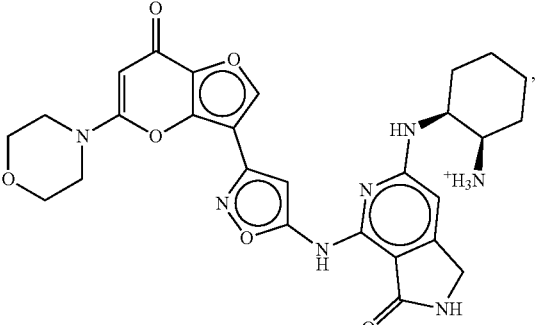
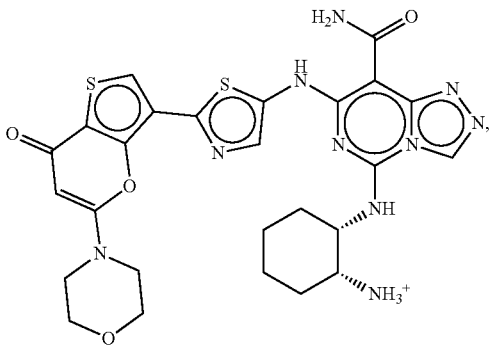

249
-continued
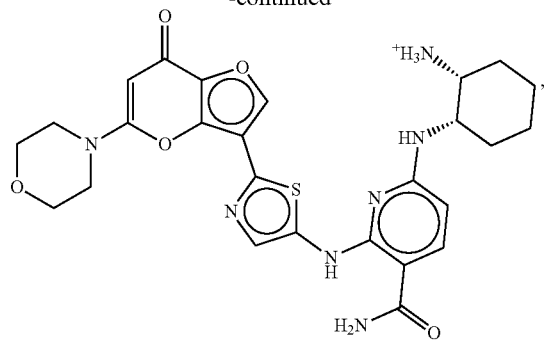
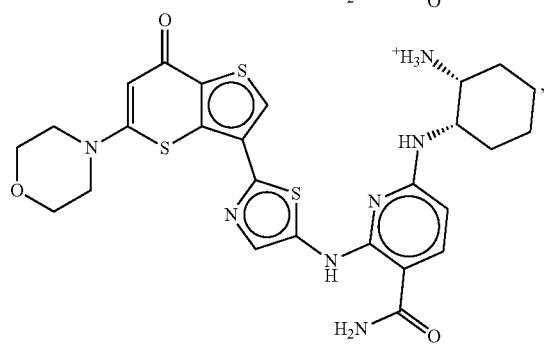
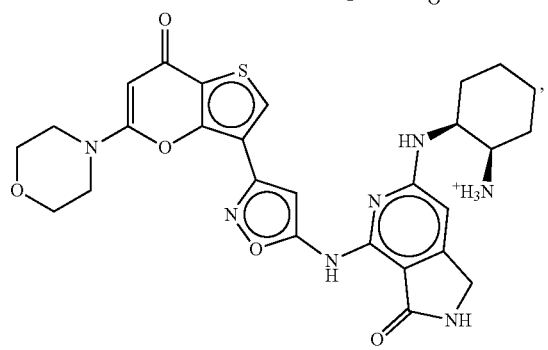
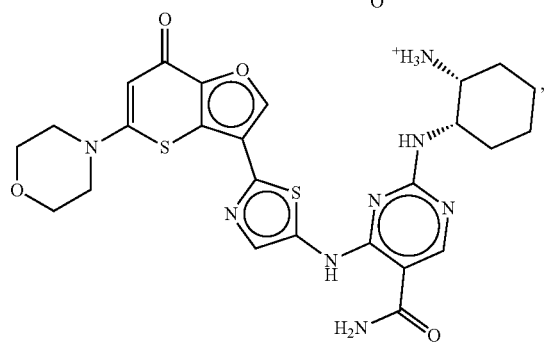
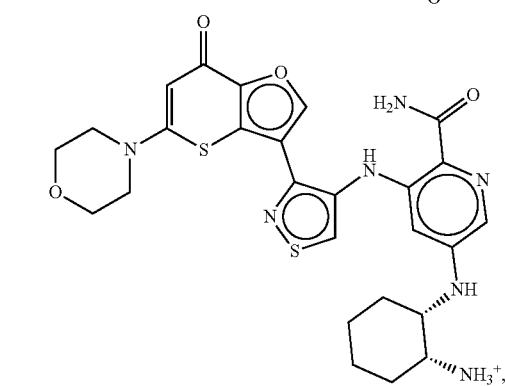
250
-continued
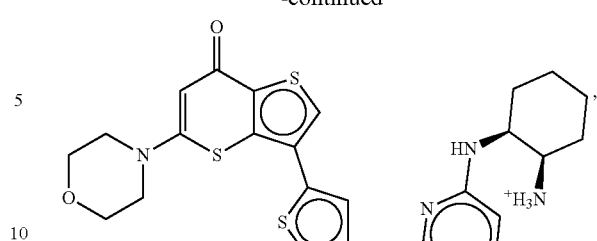
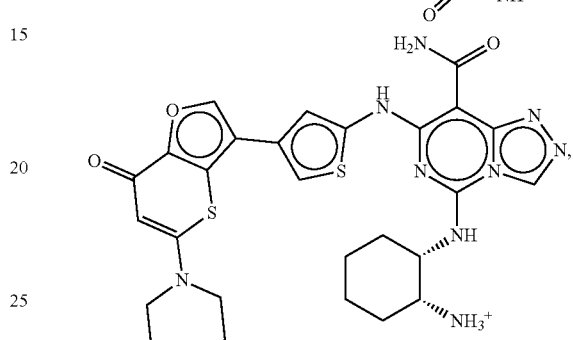
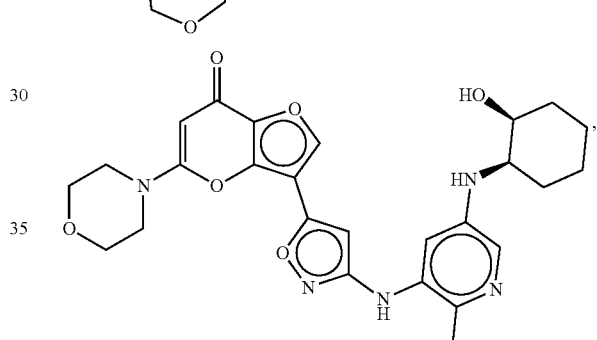
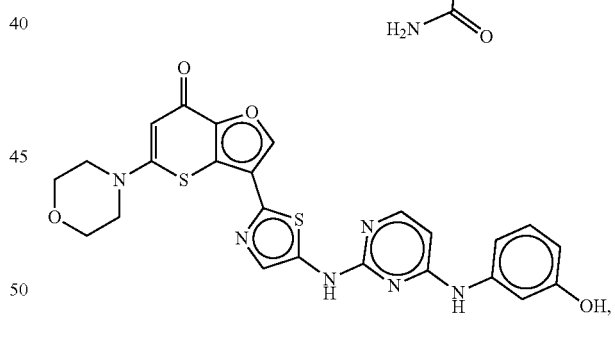
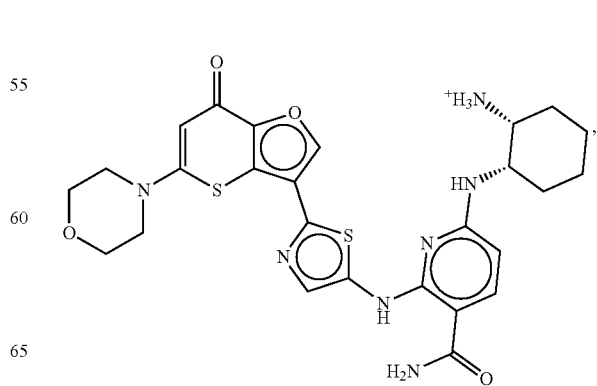

251
-continued
252
-continued
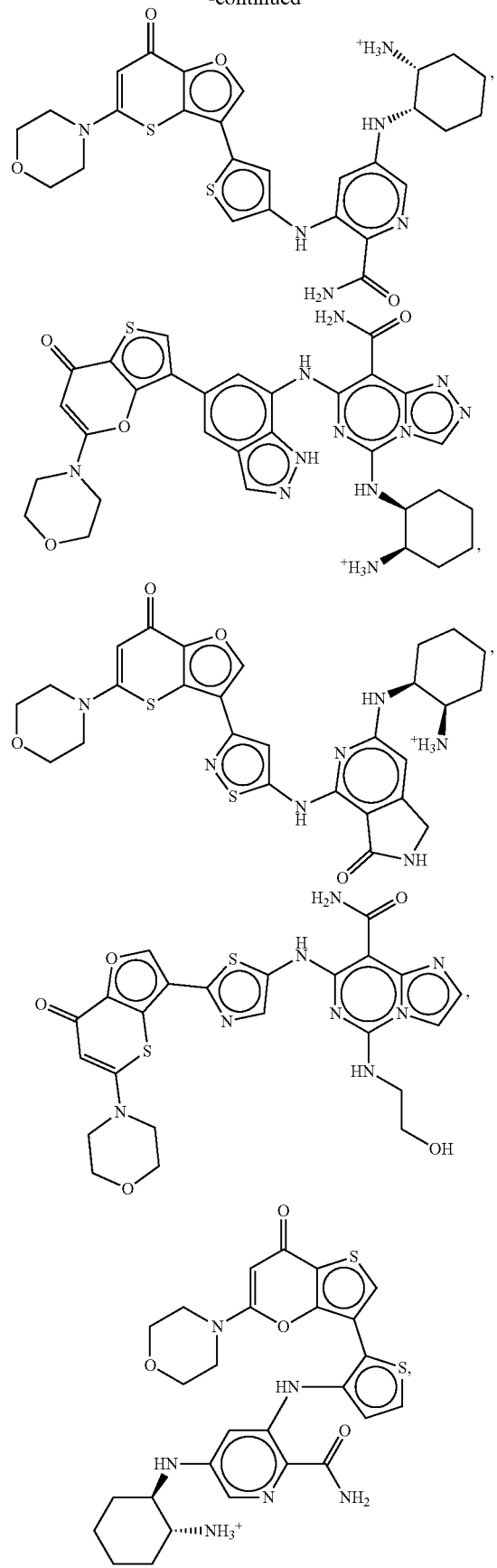
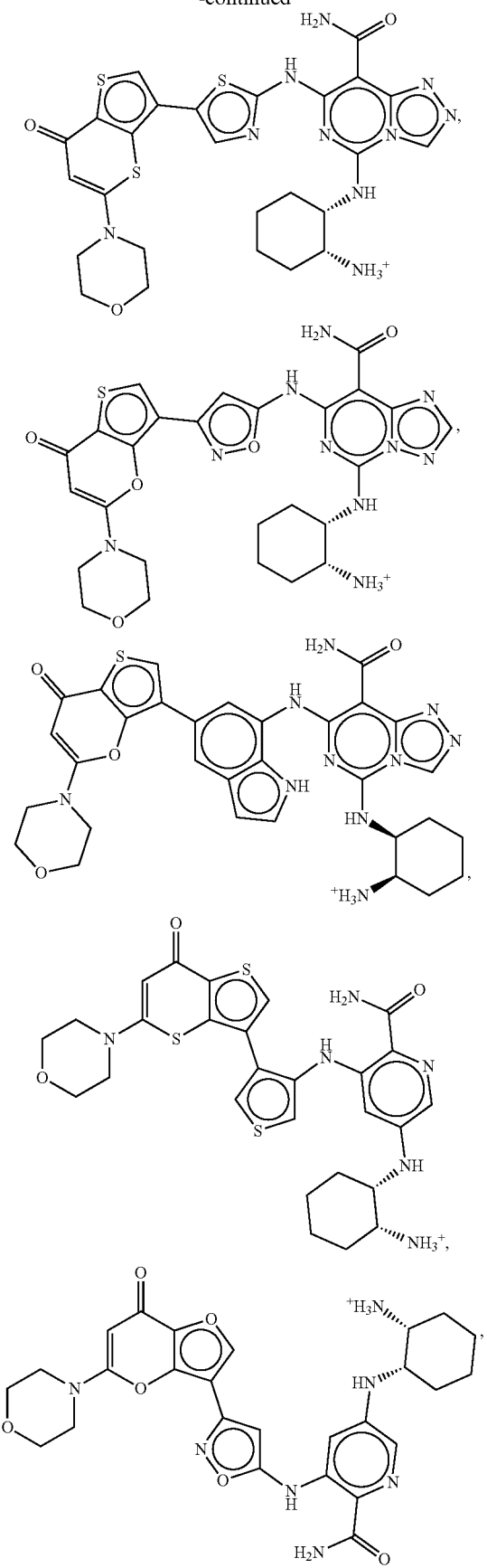

253
-continued
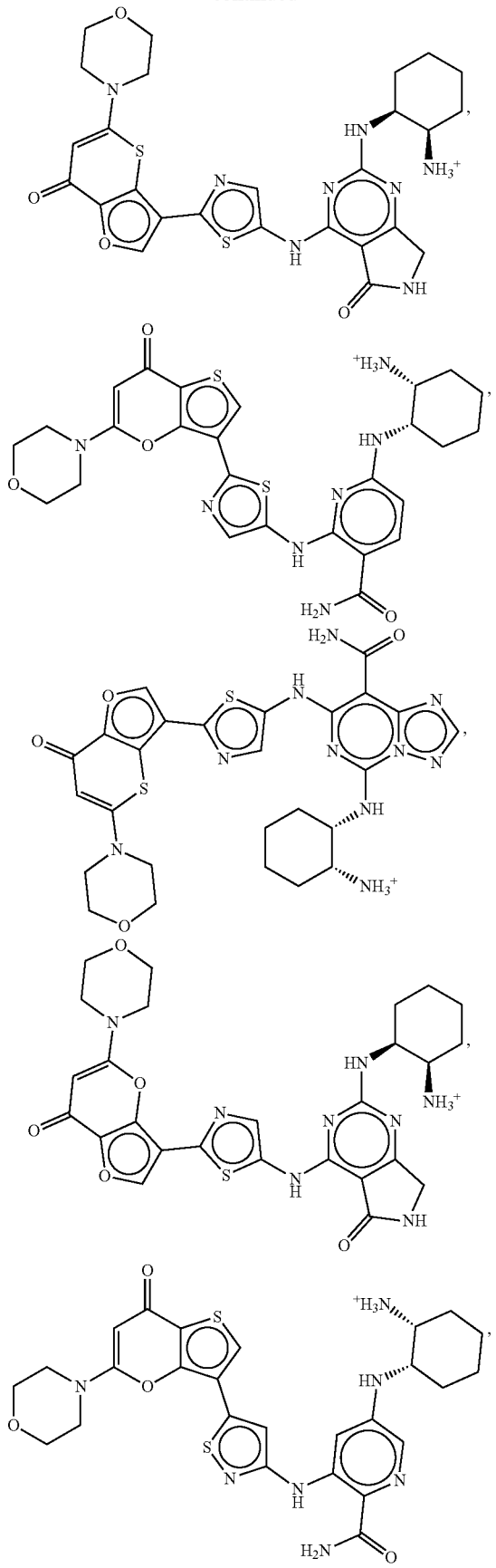
254
-continued
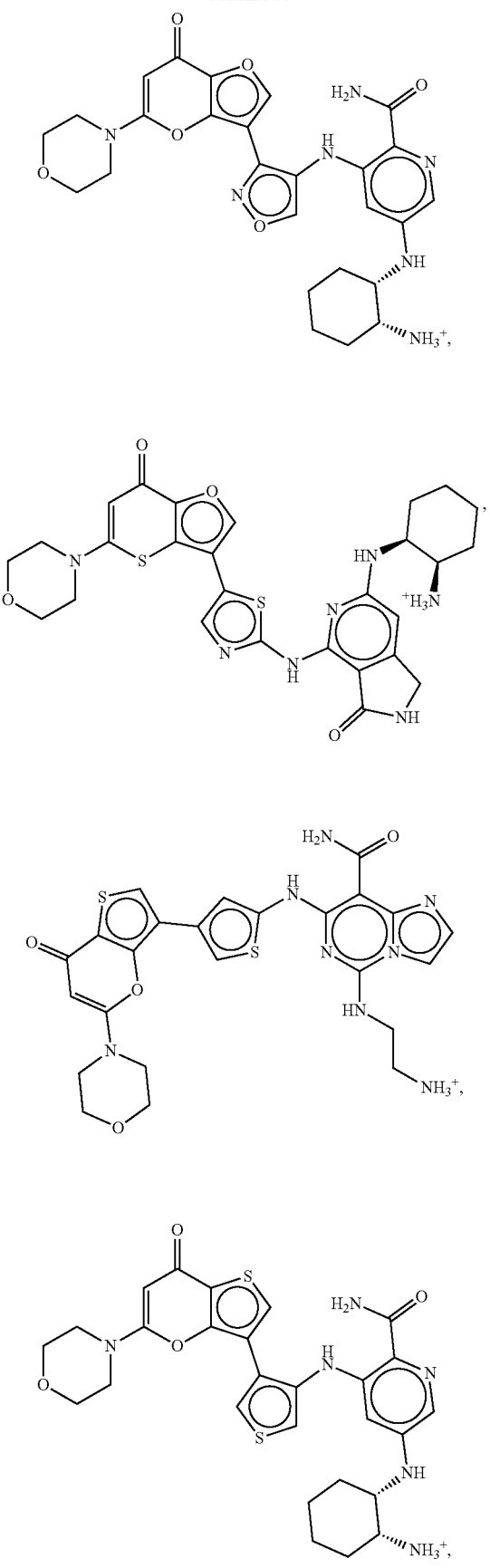

255
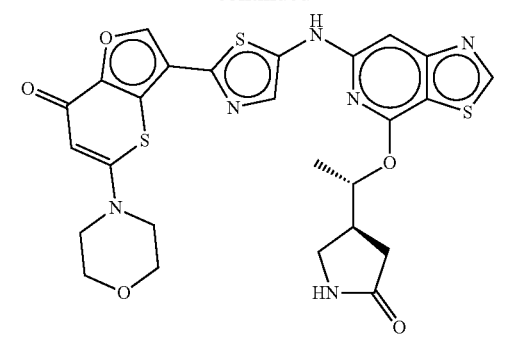
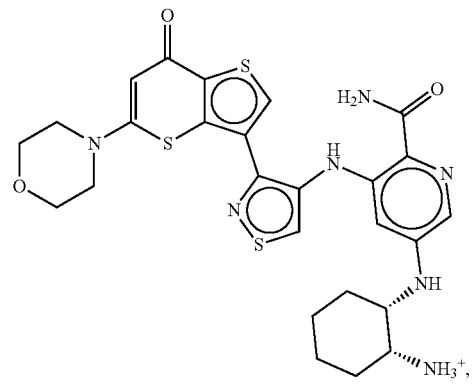
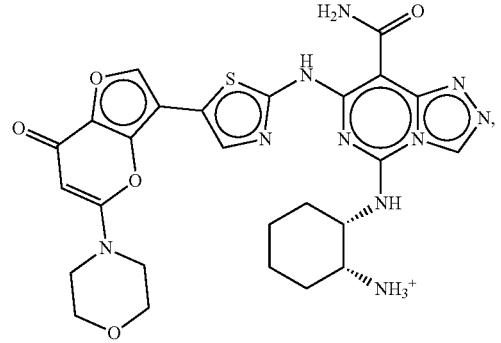
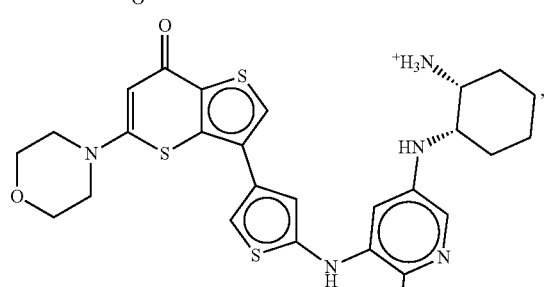
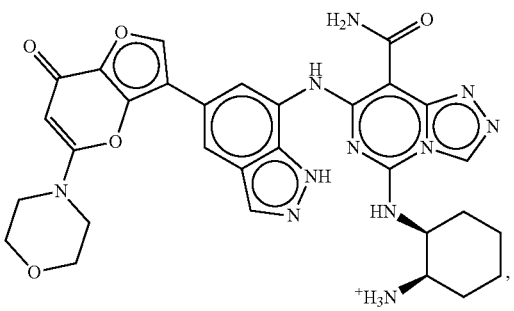
256
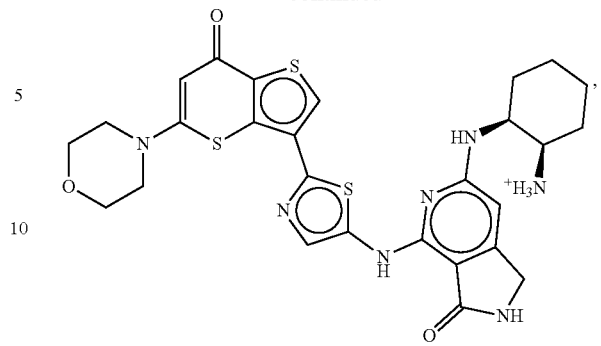
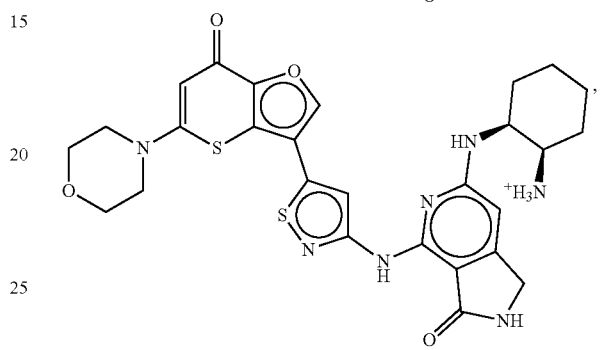
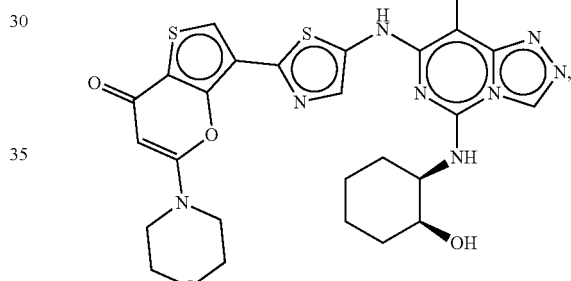
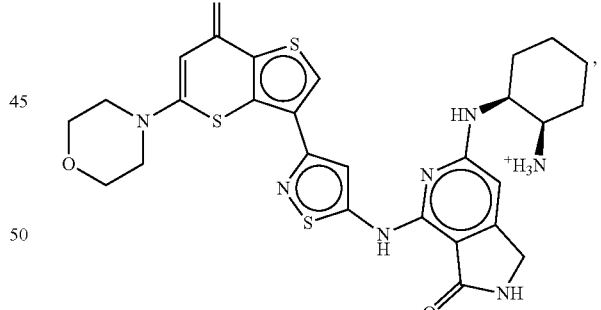
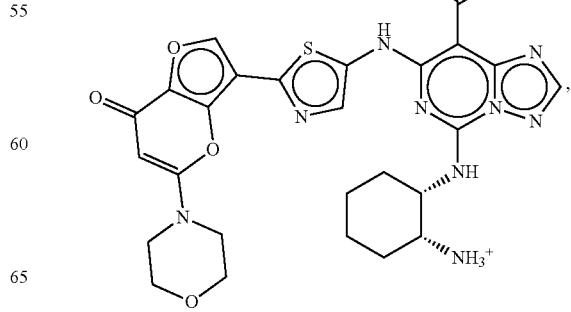

257
-continued
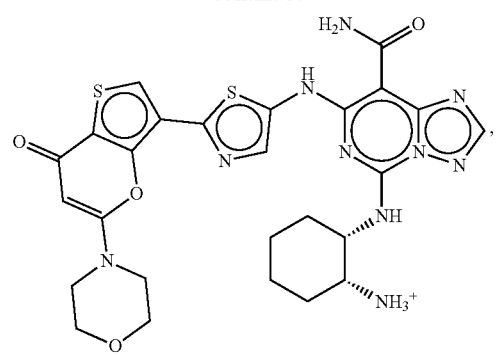
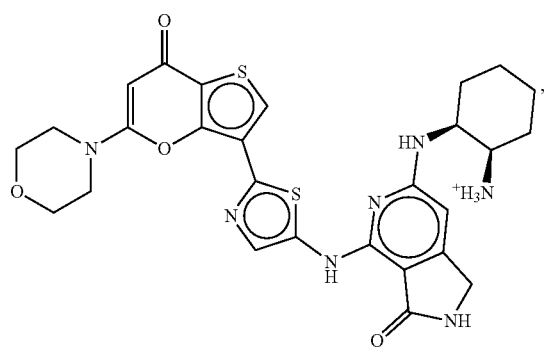
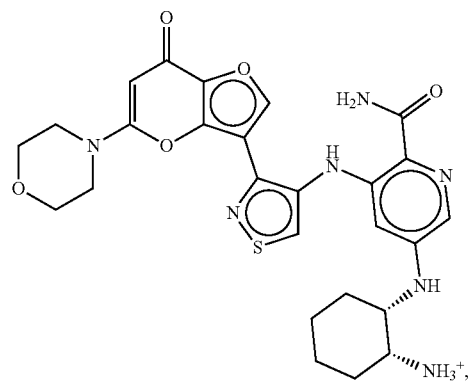
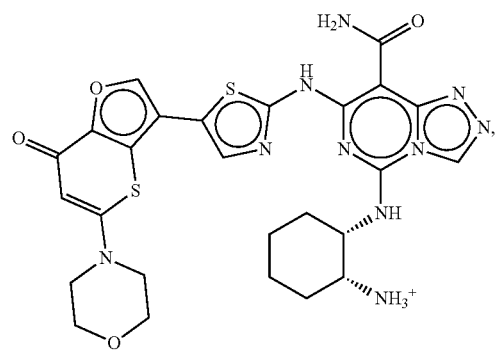
258
-continued
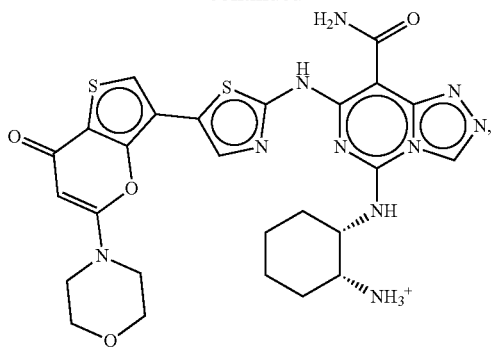
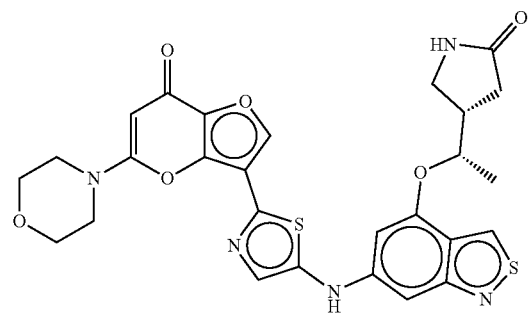
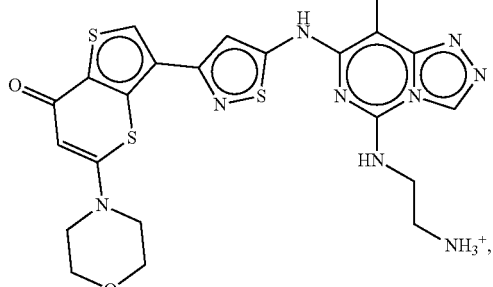
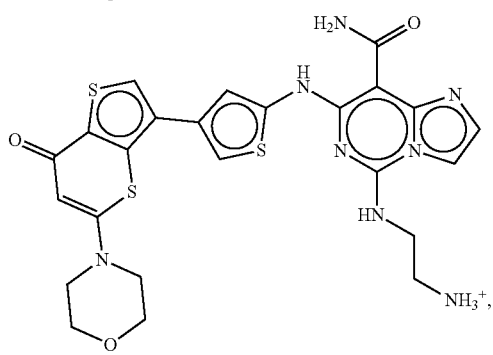
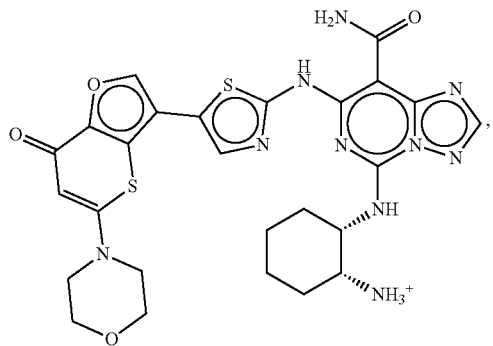

259
-continued
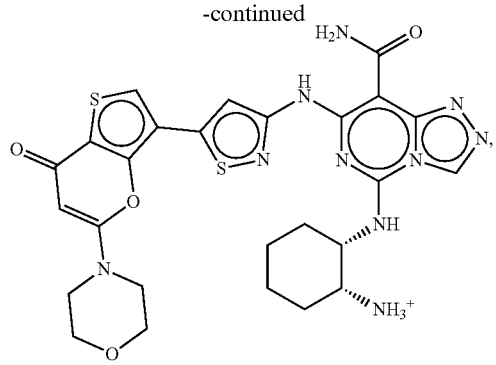
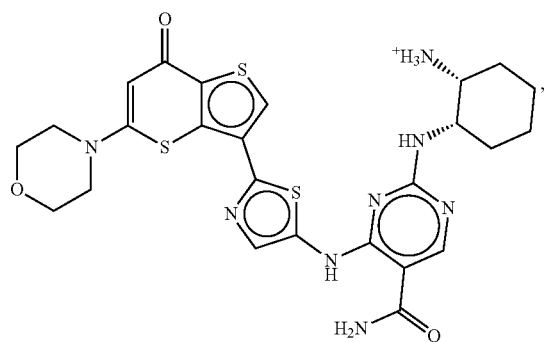
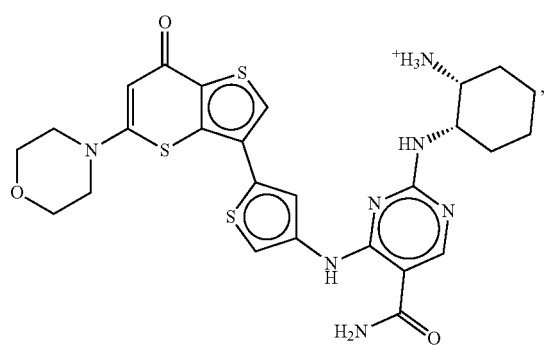
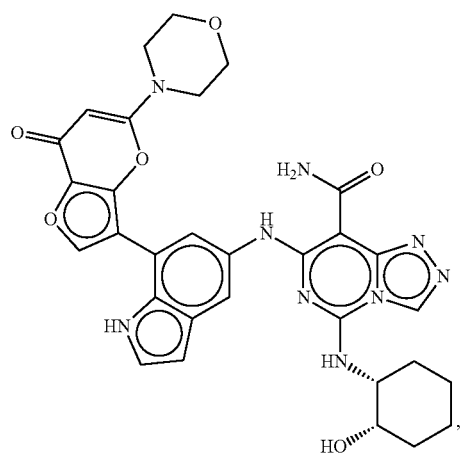
260
-continued
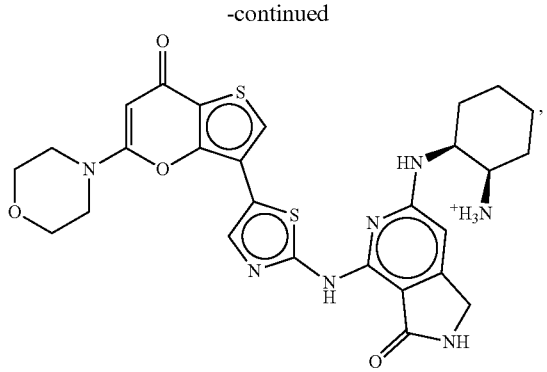
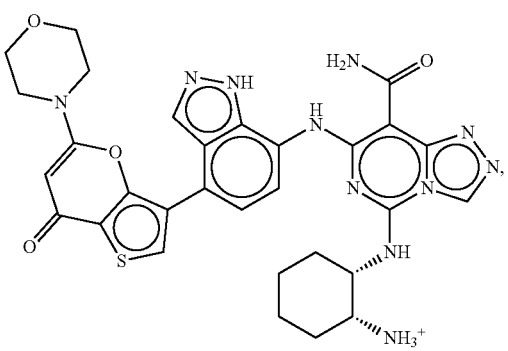
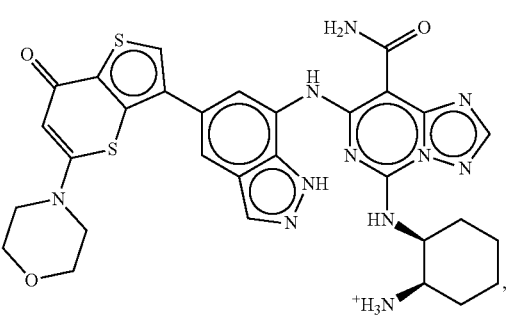
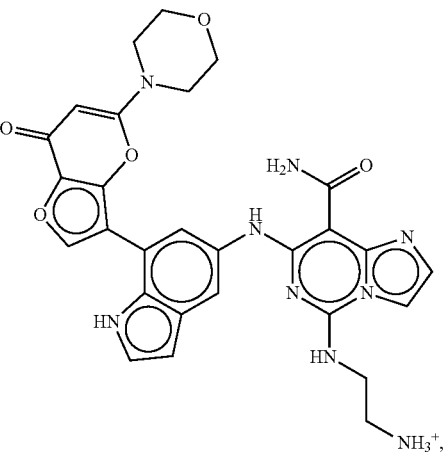

261
-continued
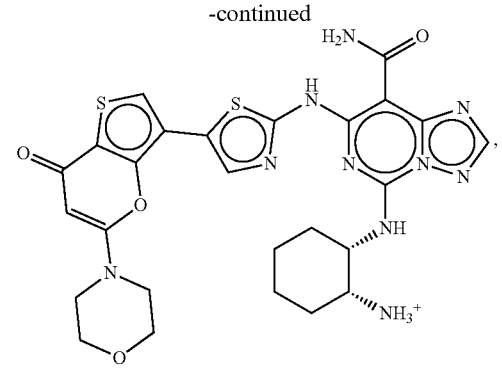
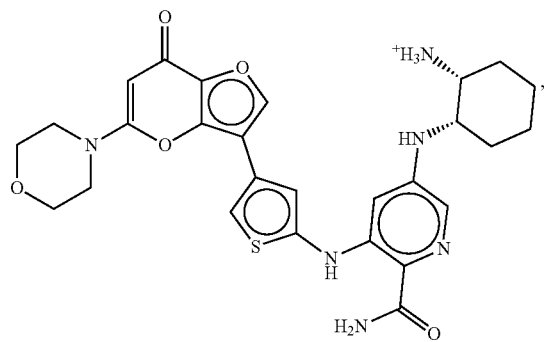
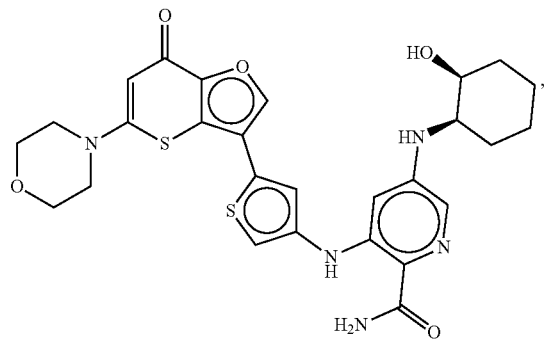
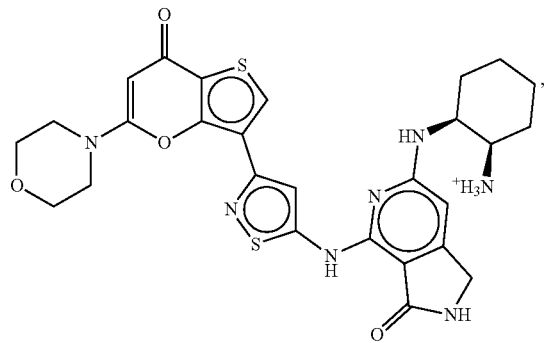
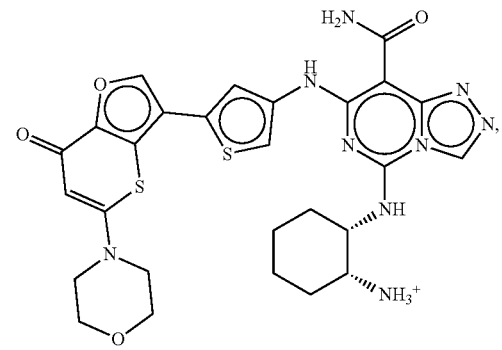
262
-continued
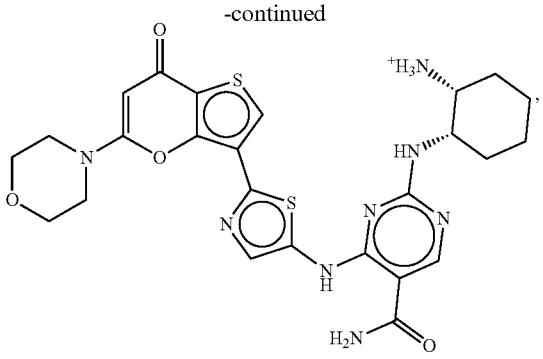
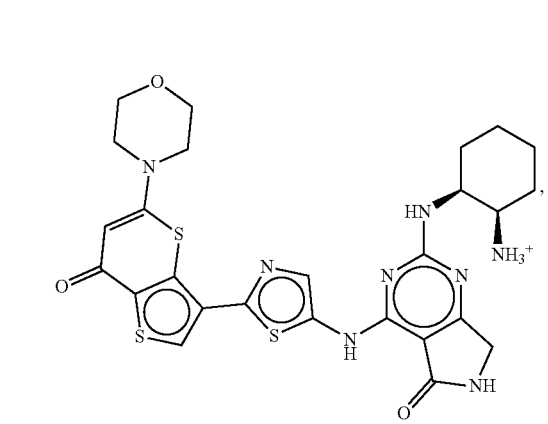
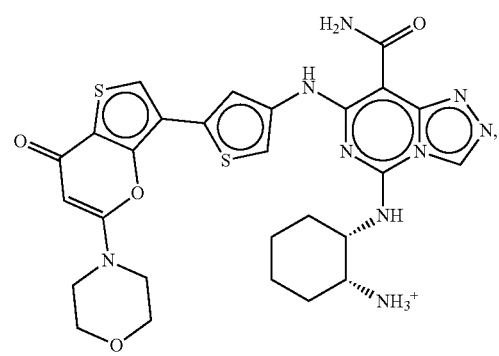
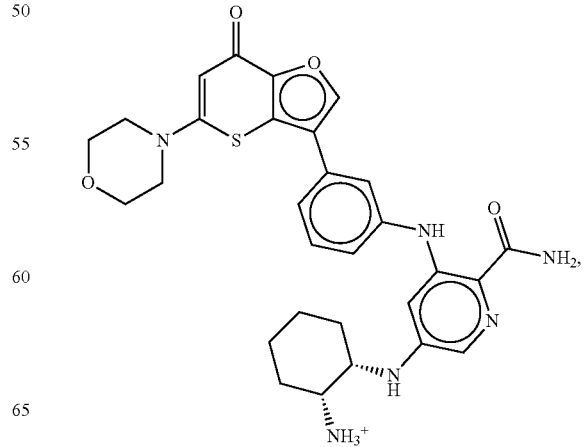

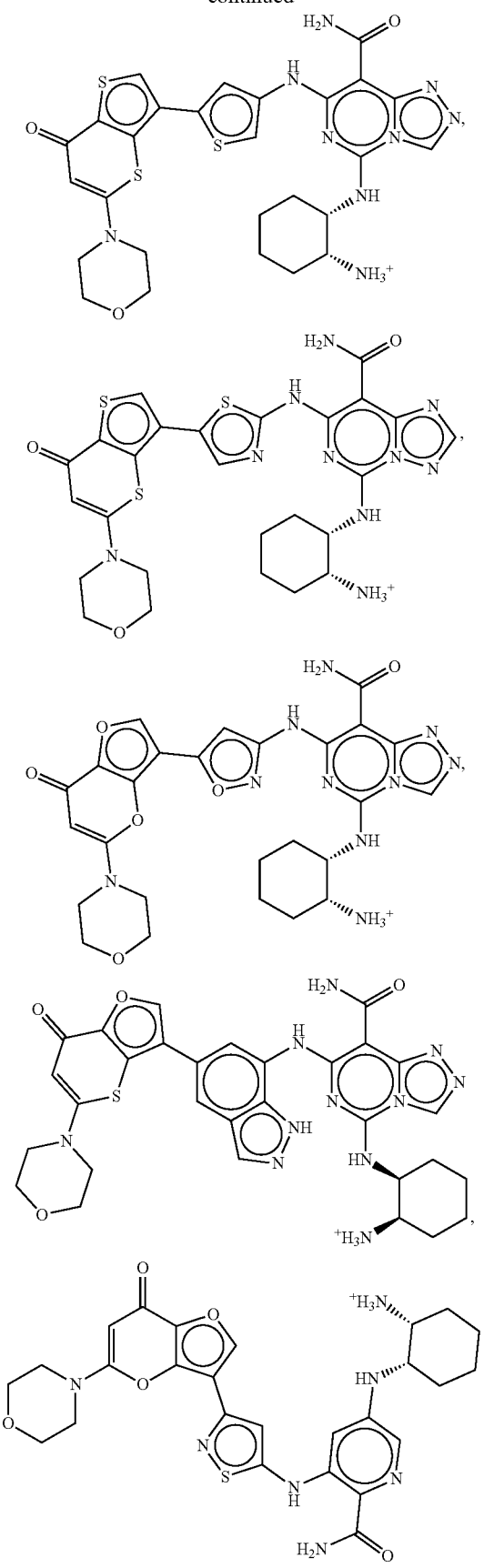
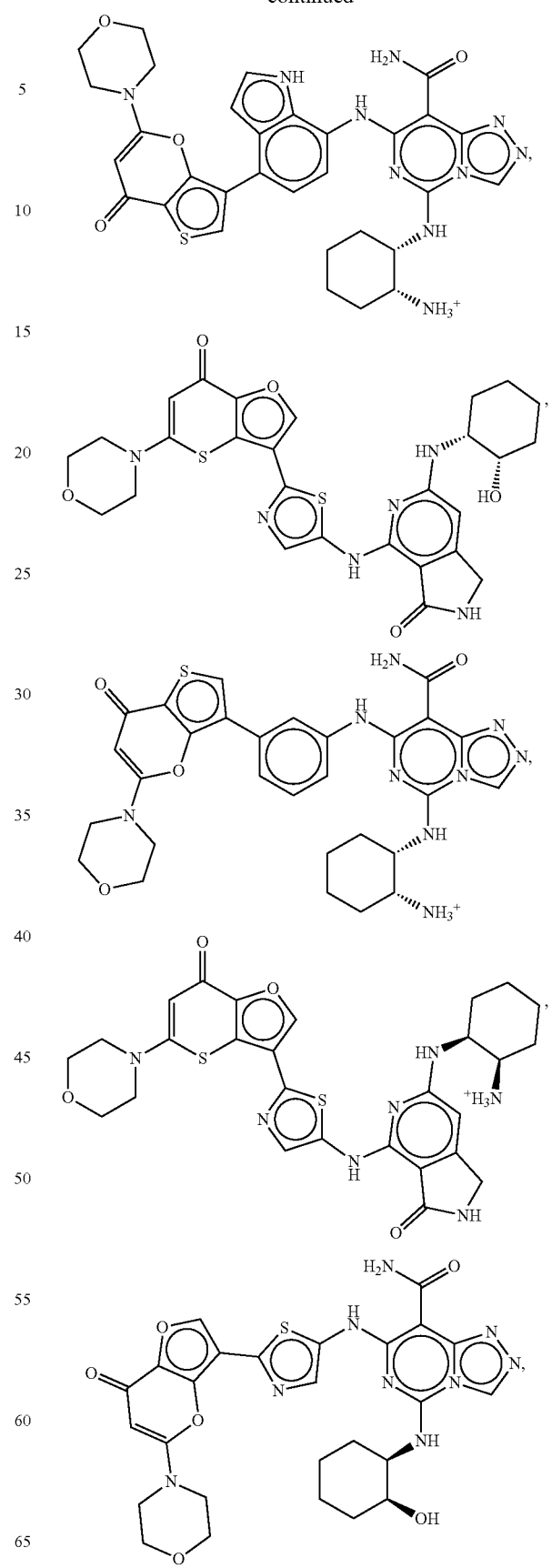

265
-continued
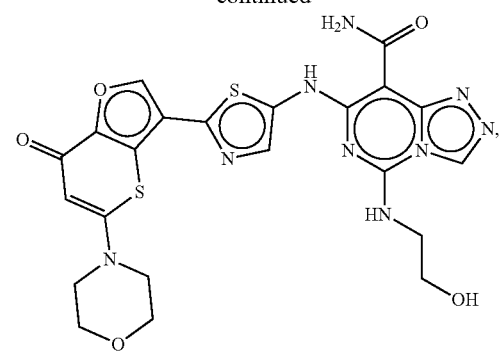
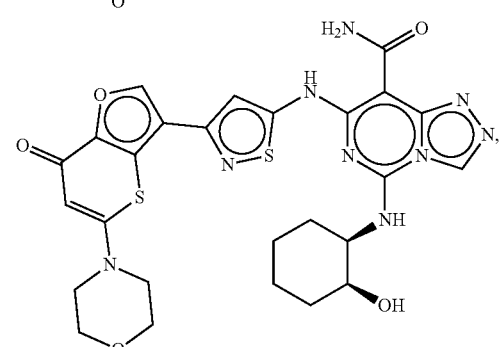
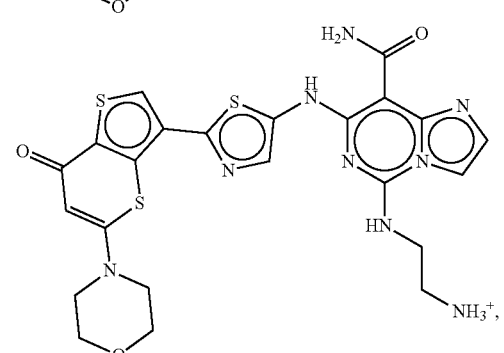
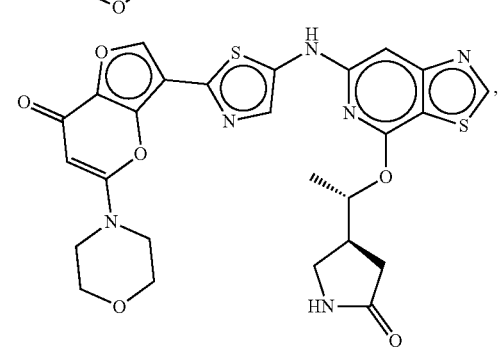
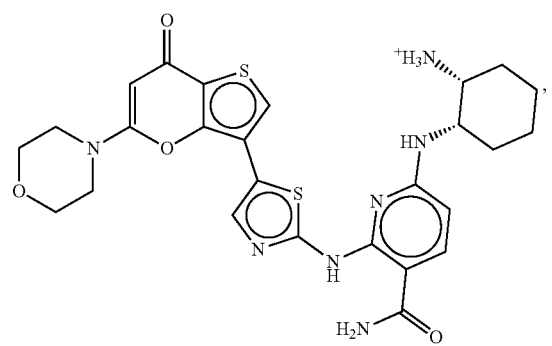
266
-continued
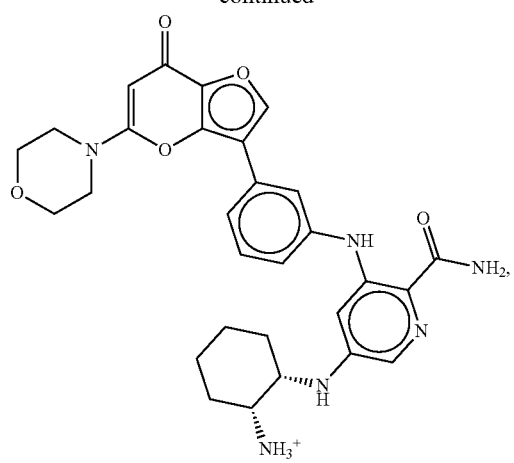
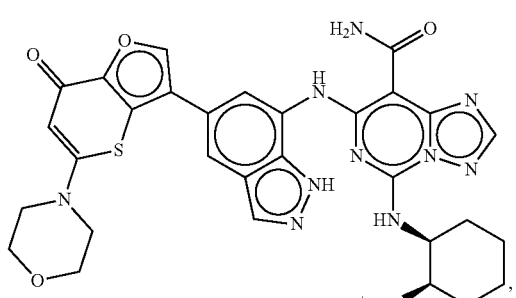
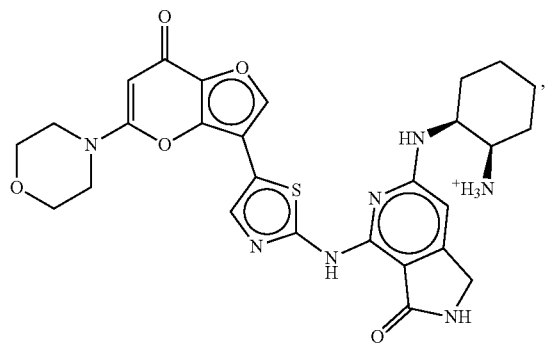
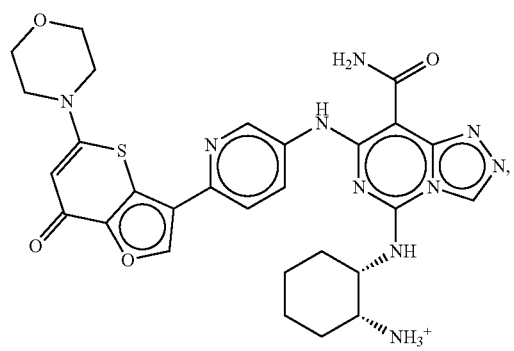

267
-continued
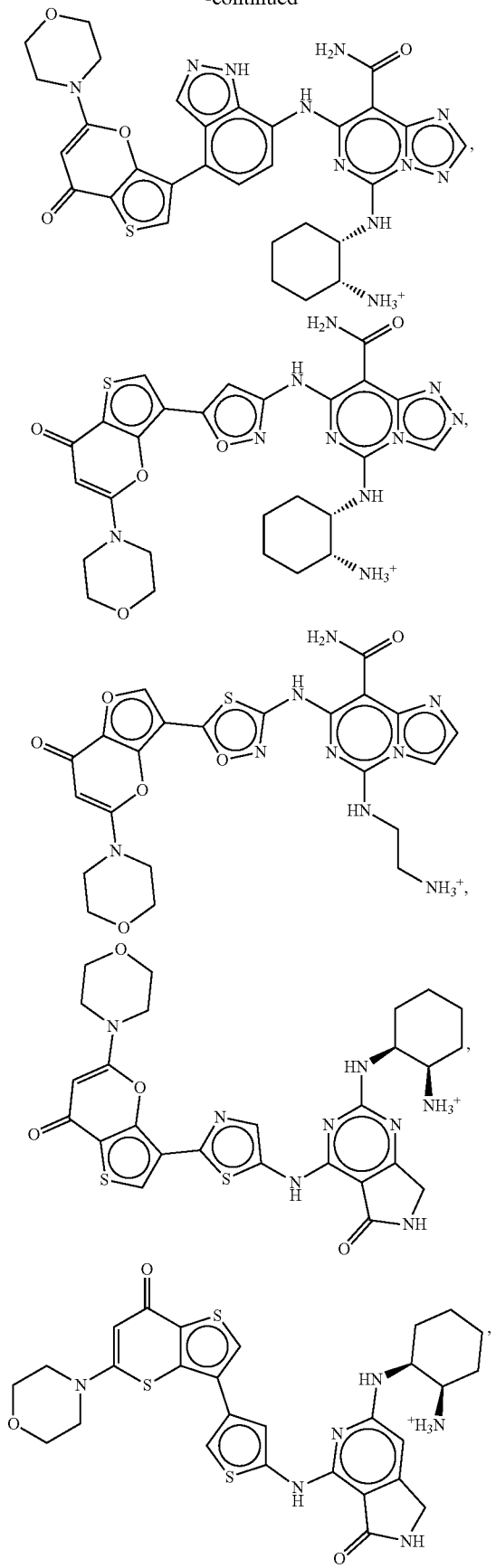
268
-continued
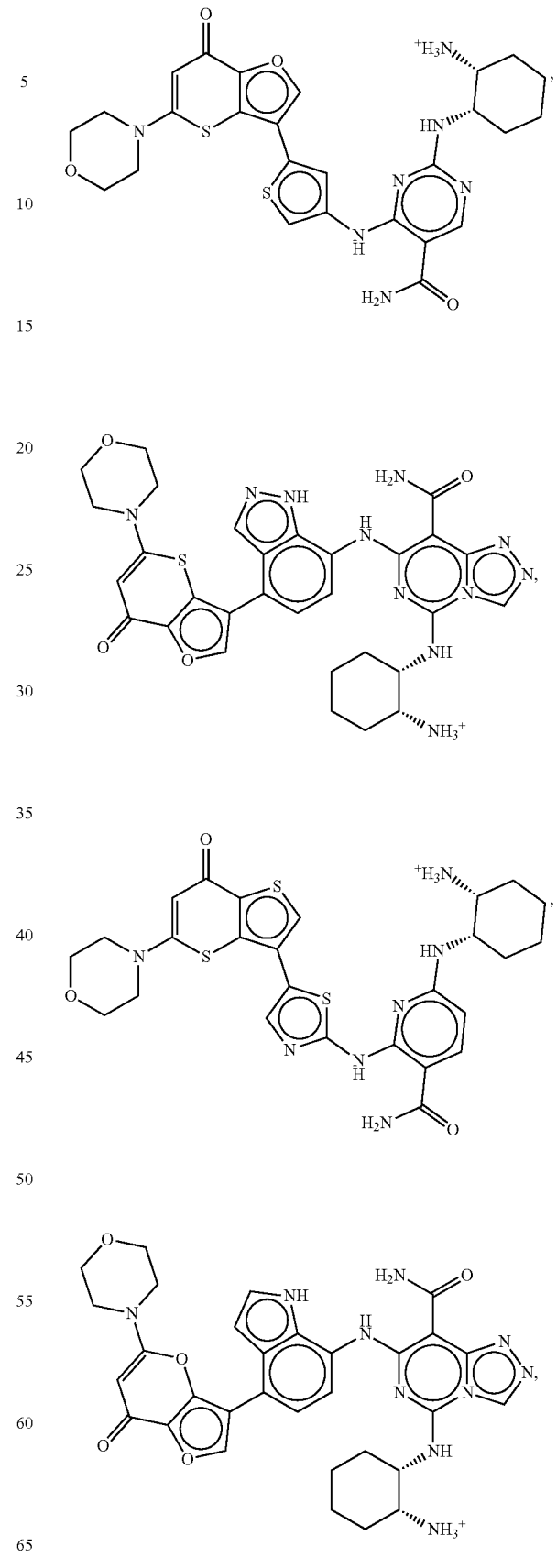

269
-continued
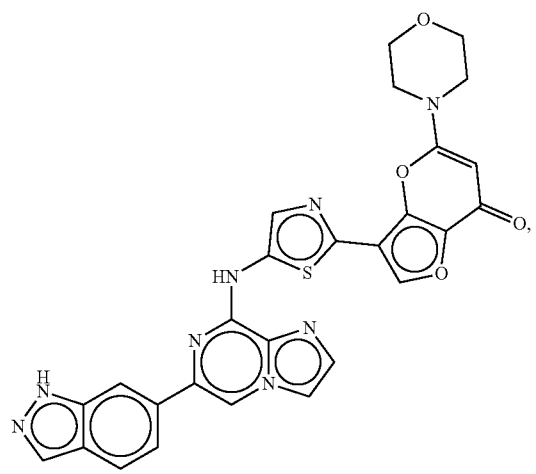
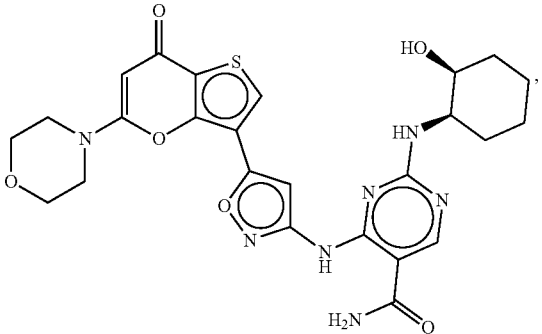
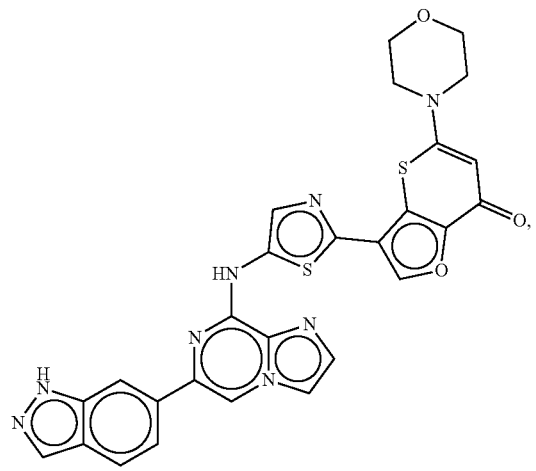
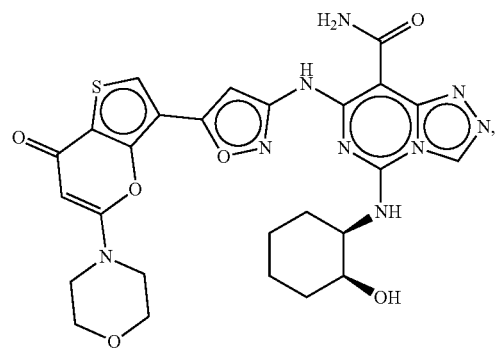
270
-continued
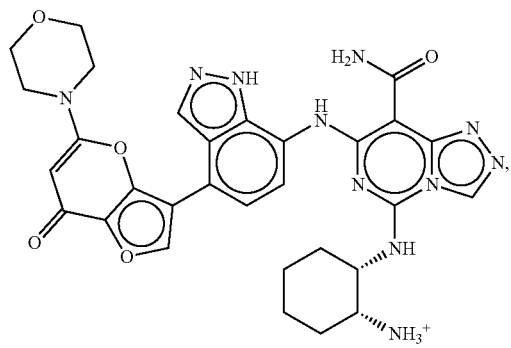
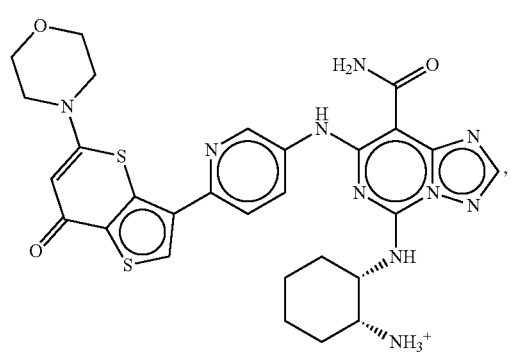
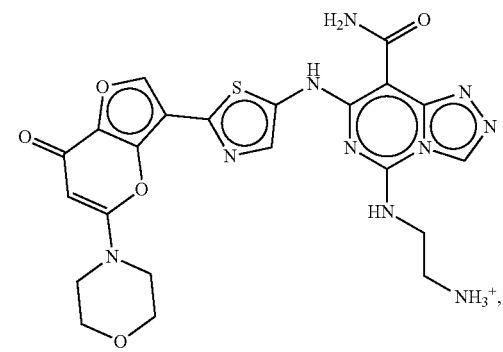

271
-continued
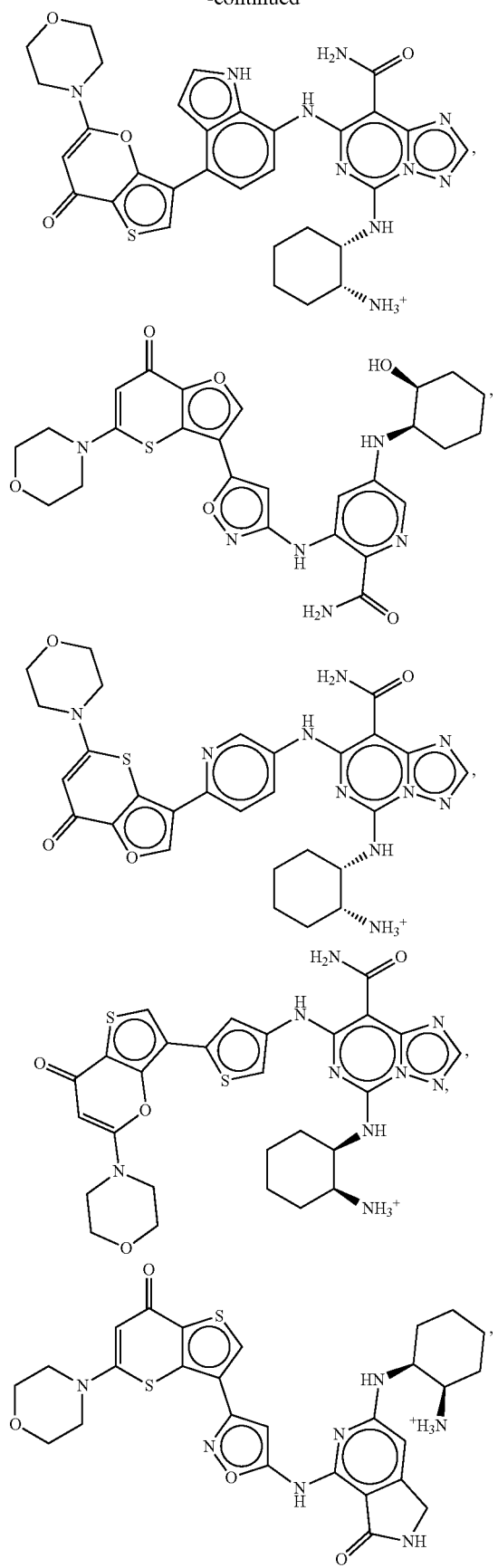
272
-continued
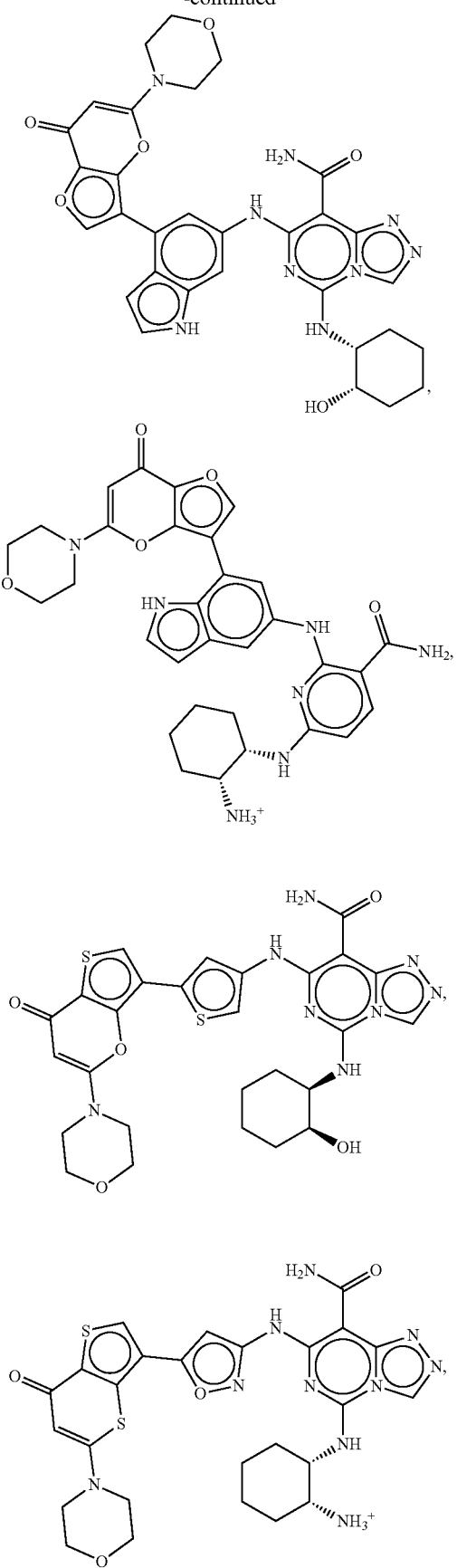

273
-continued
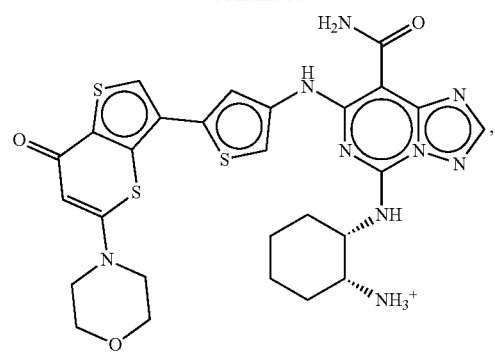
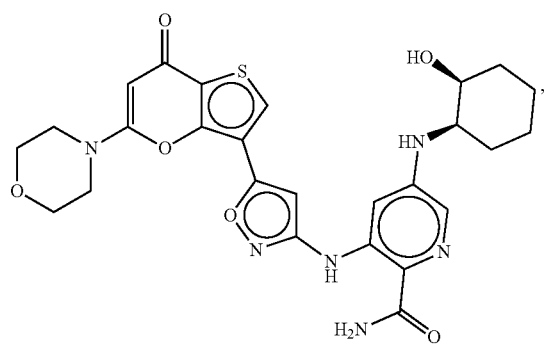
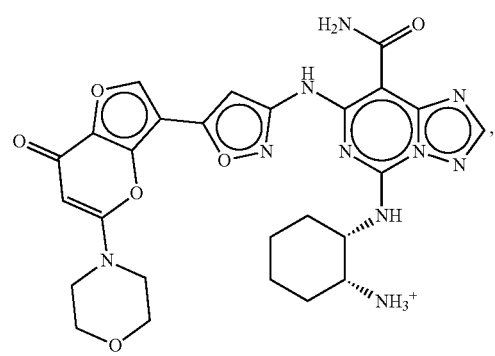
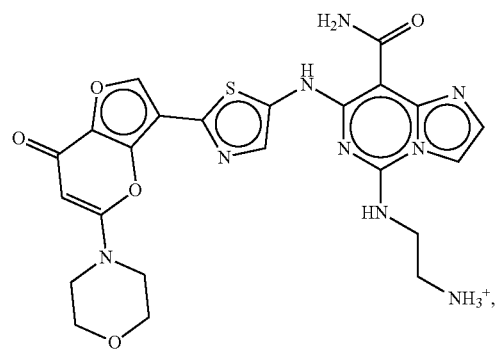
274
-continued
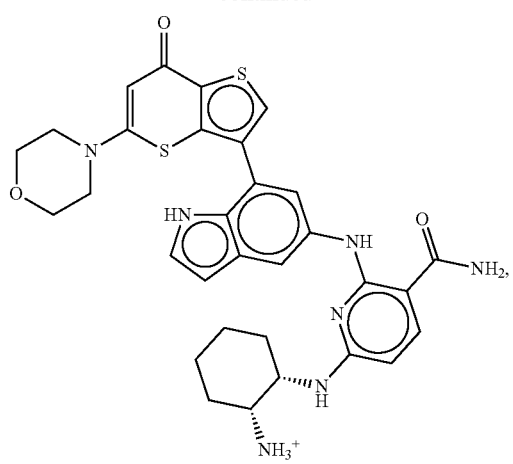
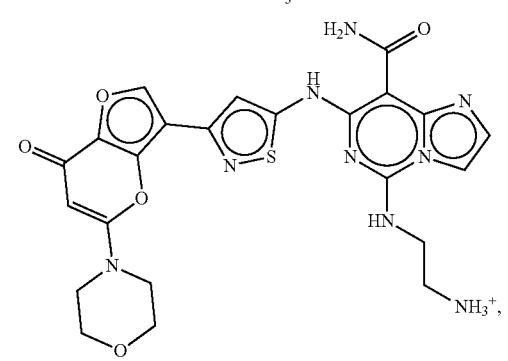
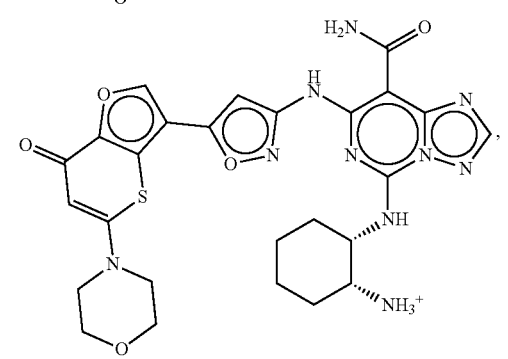
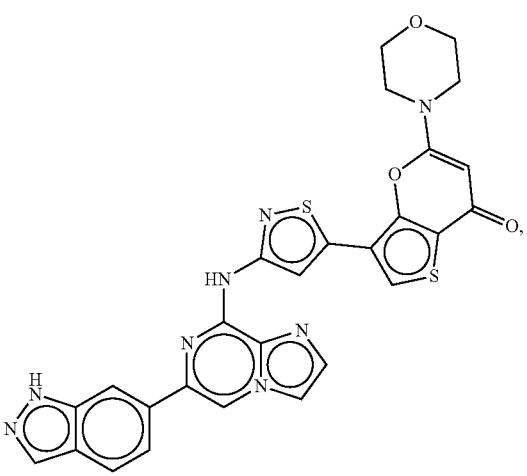

275
-continued

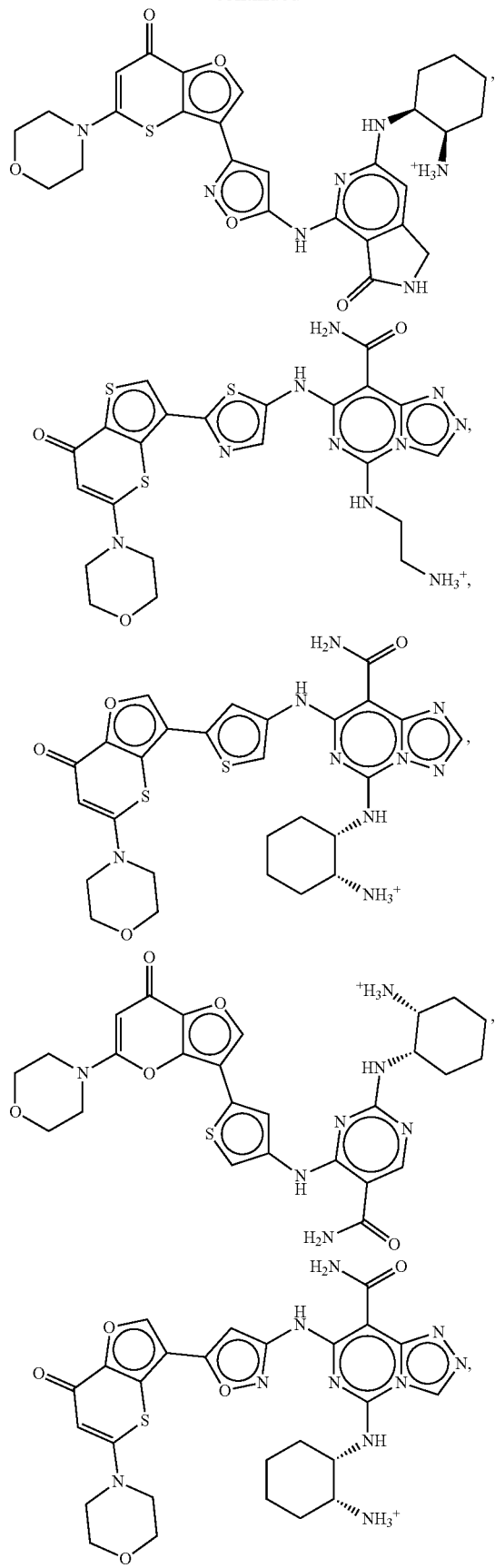

276
-continued

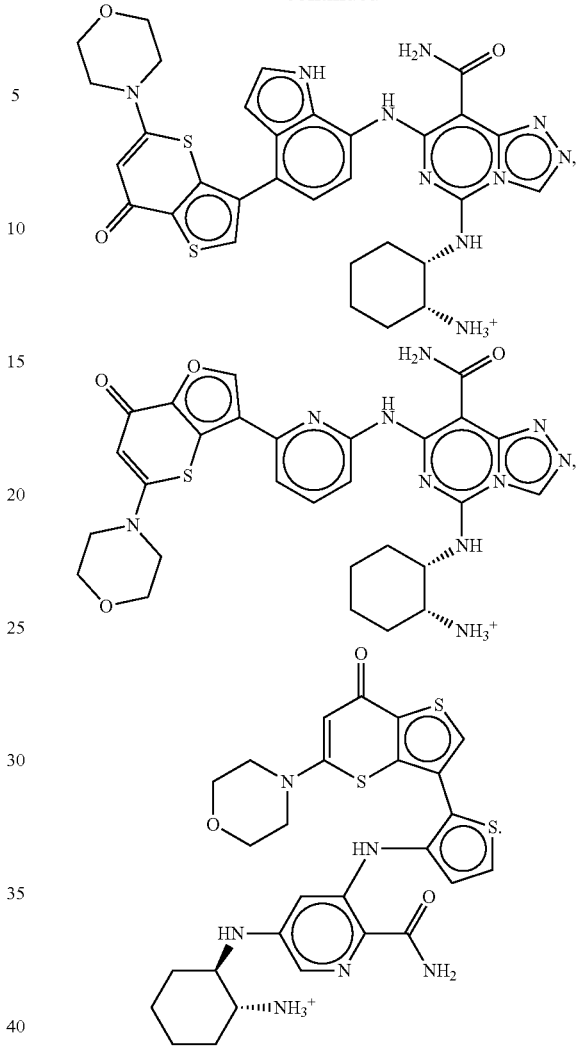

3. A pharmaceutical formulation comprising a compound of claim 1 in association with a pharmaceutically acceptable carrier, diluent, or excipient.

4. A method for reversing, alleviating, delaying the onset of, or inhibiting the progress of a disease in a human selected from hematologic cancer, lung cancer, colon cancer, retinoblastoma, glioma, non-cancer proliferative disease, sepsis, autoimmune disease, infection, atherosclerosis, Type I or 2 diabetes, obesity, inflammatory disease, fibrotic disease, neurodegenerative disease, organ system degenerative disease, aberrant transcriptome/epigenetic disease, metabolic or Myc-dependent disorder comprising administering a compound of Formulas II-V, as in claim 1.

5. The method of claim 4 wherein said disease is associated with aberrant SYK and/or PI3K activity, tumor-induced microenvironment immunity, and/or M1-M2 macrophage transition dependent conditions, including metastatic processes.

6. The method of claim 4 wherein said disease is non-cancer proliferative disease selected from meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

7. The method of claim 4 wherein said disease is inflammatory disease selected from appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis, Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus, rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierma, mycosis fungoides, graft versus host disease, irritable bowel syndrome, psoriasis, acute respiratory distress syndrome and ischemia/reperfusion injury.

8. The method of claim 4 wherein said disease is a Myc-dependent disorder selected from CLL, multiple myeloma, neuroblastoma, pancreatic, breast, prostate cancer, lymphoid malignancy, myeloid malignancy, medulloblastoma or any other Myc-dependent cancer or disease process.

9. The method of claim 4 wherein the administration of a compound of Formula II-V is in combination with one or more additional anticancer agents or therapeutic agents.

10. The method of claim 9 wherein the additional anticancer agent is a checkpoint inhibitor.

11. The method of claim 4 wherein the compound inhibits SYK and at least one of PI3K and BRD4.

12. The method of claim 4 wherein said disease is fibrotic disease.

13. The method of claim 4 wherein said disease is related to one or more of autoimmunity, immunosuppression, hypertrophy, metabolic syndromes, apoptosis, autophagy, cell death, and inflammation.

14. The method of claim 4 wherein the disease is associated with aberrant angiogenesis, including eye diseases, macular degeneration, and retinopathy.

15. The method of claim 11 wherein said disease is associated with aberrant angiogenesis or vasculogenesis.

16. The method of claim 11 further including administering a cell-based immunotherapy.

17. The method of claim 11 wherein the disease is cancer selected from hematologic cancer, lung cancer, colon cancer, retinoblastoma, and glioma, associated with metastasis driven by activation of immunosuppressive macrophages and/or M2 macrophages.

18. The method of claim 11 wherein the disease is an eye or skin related disorder associated with autoimmunity, immune suppression, fibrosis, proliferation, inflammation, angiogenesis or thrombosis.

* * * * *